US012755829B2

(12) United States Patent
Hong

(10) Patent No.: US 12,755,829 B2
(45) Date of Patent: Oct. 6, 2026

(54) PSYCHOLOGICAL COUNSEL PROVISION SYSTEM AND METHOD THEREFOR

(71) Applicant: ANOTHER SIGHT CO., LTD., Seoul (KR)

(72) Inventor: Yeon Ju Hong, Seoul (KR)

(73) Assignee: ANOTHER SIGHT CO., LTD., Seoul (KR)

( * ) Notice: Subject to any disclaimer, the term of this patent is extended or adjusted under 35 U.S.C. 154(b) by 260 days.

(21) Appl. No.: 18/725,880

(22) PCT Filed: Jan. 9, 2023

(86) PCT No.: PCT/KR2023/000365
§ 371 (c)(1),
(2) Date: Sep. 13, 2024

(87) PCT Pub. No.: WO2023/136566
PCT Pub. Date: Jul. 20, 2023

(65) Prior Publication Data

US 2026/0171214 A1 Jun. 18, 2026

(30) Foreign Application Priority Data

Jan. 13, 2022 (KR) ........................ 10-2022-0004975
Jan. 13, 2022 (KR) ........................ 10-2022-0004976
(Continued)

(51) Int. Cl.
*G16H 20/70* (2018.01)
*G16H 10/20* (2018.01)
(Continued)

(52) U.S. Cl.
CPC ............. *G16H 20/70* (2018.01); *G16H 10/20* (2018.01); *G16H 10/60* (2018.01); *G16H 50/20* (2018.01); *G16H 50/30* (2018.01)

(58) Field of Classification Search
CPC ........ G16H 20/70; G16H 10/60; G16H 50/30; G16H 50/20; G16H 10/20
See application file for complete search history.

(56) References Cited

U.S. PATENT DOCUMENTS 6,425,764 B1 * 7/2002 Lamson ................. G16H 30/40
434/236
9,690,784 B1 * 6/2017 Hughes ................... G06F 3/011
(Continued)

FOREIGN PATENT DOCUMENTS

KR 10-2012-0087492 A 8/2012
KR 10-2017-0118470 A 10/2017
(Continued)

OTHER PUBLICATIONS

Rehm, Imogen C., "What Role Can avatars play in e-mental health interventions? Exploring New Models of Client-Therapist Interaction", Frontiers in Psychiatry, 2016, pp. 1-6 (Year: 2016).*
(Continued)

*Primary Examiner* — Terrell M Robinson
(74) *Attorney, Agent, or Firm* — Sughrue Mion, PLLC

(57) ABSTRACT

Disclosed are a system for providing psychological counseling and a method therefor. According to the present invention, when a preset extended reality (XR) room-creation menu is selected from a website screen, an expert of an expert terminal performs a psychological counseling function in a metaverse chat room with a specific user under management, and a user of a terminal and the expert of the expert terminal may participate in another metaverse chat room together while performing a counseling function to perform a chat function, so that the expert may perform the psychological counseling function with the user in real-time and accordingly identify the user's psychological state and provide appropriate coping measures, and may accurately
(Continued)

identify the user's state as the user performs the chat function with another user in a metaverse chat room.

10 Claims, 72 Drawing Sheets

(30) Foreign Application Priority Data

| | | |
|---|---|---|
| Jan. 13, 2022 | (KR) | 10-2022-0004977 |
| Nov. 29, 2022 | (KR) | 10-2022-0162510 |
| Nov. 29, 2022 | (KR) | 10-2022-0162512 |
| Nov. 29, 2022 | (KR) | 10-2022-0162513 |
| Nov. 29, 2022 | (KR) | 10-2022-0162514 |
| Nov. 29, 2022 | (KR) | 10-2022-0162515 |

(51) Int. Cl.

| | |
|---|---|
| ***G16H 10/60*** | (2018.01) |
| ***G16H 50/20*** | (2018.01) |
| ***G16H 50/30*** | (2018.01) |

(56) References Cited

U.S. PATENT DOCUMENTS

| | | | | |
|---|---|---|---|---|
| 10,325,066 | B2 * | 6/2019 | Yeh | G16H 50/30 |
| 2023/0047622 | A1 * | 2/2023 | Lax | A61B 5/165 |
| 2024/0149008 | A1 * | 5/2024 | Robinson | G09B 19/00 |

FOREIGN PATENT DOCUMENTS

| | | | |
|---|---|---|---|
| KR | 10-2018-0097947 | A | 9/2018 |
| KR | 10-1911516 | B1 | 10/2018 |
| KR | 10-2020-0017138 | A | 2/2020 |
| KR | 10-2020-0076183 | A | 6/2020 |
| KR | 10-2130750 | B1 | 7/2020 |
| KR | 10-2193656 | B1 | 12/2020 |
| KR | 10-2021-0064472 | A | 6/2021 |
| KR | 10-2257427 | B1 | 6/2021 |

OTHER PUBLICATIONS

Liu, Tian, "Application of virtual reality technology in clinical psychology", 2020, International Conference on Computer Information and Big Data Applications (CIBDA), pp. 400-402 (Year: 2020).*

Parsons, Thomas D., Extended Reality for the Clinical, Affective, and Social Neurosciences, Nov. 2020, MDPI, pp. 1-22 (Year: 2020).*

Jehyun Kim, et al., "Metaverse Based Virtual Reality Space Consulting Service Platform Research and Development", Journal of the Semiconductor & Display Technology, vol. 20, No. 4, 2021, pp. 130-133.

International Search Report for PCT/KR2023/000365 dated Apr. 14, 2023.

* cited by examiner

FIG. 48

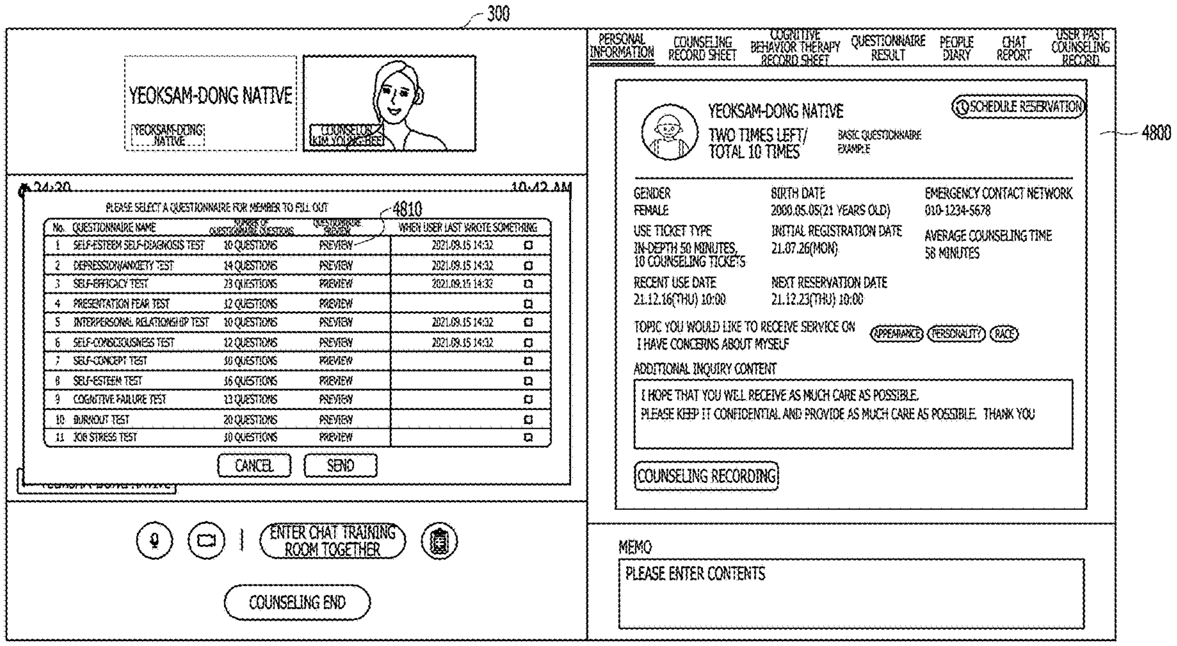

| No. | QUESTIONNAIRE NAME | NUMBER OF QUESTIONNAIRE QUESTIONS | QUESTIONNAIRE PREVIEW | WHEN USER LAST WROTE SOMETHING | |
|---|---|---|---|---|---|
| 1 | SELF-ESTEEM SELF-DIAGNOSIS TEST | 10 QUESTIONS | PREVIEW | 2021.09.15 14:32 | ☐ |
| 2 | DEPRESSION/ANXIETY TEST | 14 QUESTIONS | PREVIEW | 2021.09.15 14:32 | ☐ |
| 3 | SELF-EFFICACY TEST | 23 QUESTIONS | PREVIEW | 2021.09.15 14:32 | ☐ |
| 4 | PRESENTATION FEAR TEST | 12 QUESTIONS | PREVIEW | | ☐ |
| 5 | INTERPERSONAL RELATIONSHIP TEST | 10 QUESTIONS | PREVIEW | 2021.09.15 14:32 | ☐ |
| 6 | SELF-CONSCIOUSNESS TEST | 12 QUESTIONS | PREVIEW | 2021.09.15 14:32 | ☐ |
| 7 | SELF-CONCEPT TEST | 10 QUESTIONS | PREVIEW | | ☐ |
| 8 | SELF-ESTEEM TEST | 16 QUESTIONS | PREVIEW | | ☐ |
| 9 | COGNITIVE FAILURE TEST | 13 QUESTIONS | PREVIEW | | ☐ |
| 10 | BURNOUT TEST | 20 QUESTIONS | PREVIEW | | ☐ |
| 11 | JOB STRESS TEST | 10 QUESTIONS | PREVIEW | | ☐ |

PSYCHOLOGICAL COUNSEL PROVISION SYSTEM AND METHOD THEREFOR

CROSS REFERENCE TO RELATED APPLICATIONS

This application is a National Stage of International Application No. PCT/KR2023/000365 filed Jan. 9, 2023, claiming priority based on Korean Patent Application No. 10-2022-0004975 filed Jan. 13, 2022, Korean Patent Application No. 10-2022-0004976 filed Jan. 13, 2022, Korean Patent Application No. 10-2022-0004977 filed Jan. 13, 2022, Korean Patent Application No. 10-2022-0162510 filed Nov. 29, 2022, Korean Patent Application No. 10-2022-0162512 filed Nov. 29, 2022, Korean Patent Application No. 10-2022-0162513 filed Nov. 29, 2022, Korean Patent Application No. 10-2022-0162514 filed Nov. 29, 2022 and Korean Patent Application No. 10-2022-0162515 filed Nov. 29, 2022, the entire disclosures of which are incorporated herein by reference.

TECHNICAL FIELD

The present invention relates to a system for providing psychological counseling and a method therefor, and more particularly, to a system for providing psychological counseling in which, when a preset extended reality (XR) room-creation menu is selected from a website screen, an expert using an expert terminal performs a psychological counseling function in a metaverse chat room with a specific user under management, and a user of a terminal and the expert of the expert terminal participate in another metaverse chat room together while performing a counseling function to perform a chat function, and a method therefor.

BACKGROUND ART

Social anxiety refers to the vague feeling of anxiety that instability in social order has on all members of society.

Approximately 70% of the total population experiences mild social anxiety symptoms such as presentation anxiety, social phobia, and gaze phobia, and 1 out of 10 people have social anxiety disorder (SAD). If SAD is taken lightly and not actively treated, it develops into chronic conditions and causes more and more difficulties in social life.

DISCLOSURE

Technical Problem

An object of the present invention is to provide a system for providing psychological counseling in which, when a preset XR room-creation menu is selected from a website screen, an expert of an expert terminal performs a psychological counseling function in a metaverse chat room with a specific user under management, and a user of a terminal and the expert of the expert terminal participate in another metaverse chat room together while performing a counseling function to perform a chat function, and a method therefor.

Another object of the present invention is to provide a system for providing psychological counseling that provides a user-related questionnaire or counseling record sheet while a user of a terminal and an expert of an expert terminal perform a counseling function through a metaverse chat room, and a method therefor.

Still another object of the present invention is to provide a system for providing psychological counseling that provides a user-related cognitive behavior therapy record sheet while a user of a terminal and an expert of an expert terminal perform a counseling function through a metaverse chat room, and a method therefor.

Yet another object of the present invention is to provide a system for providing psychological counseling that provides information on a user-related chat report or people diary while a user of a terminal and an expert of an expert terminal perform a counseling function through a metaverse chat room, and a method therefor.

Yet another object of the present invention is to provide a system for providing psychological counseling that provides a user-related past counseling record while a user of a terminal and an expert of an expert terminal perform a counseling function through a metaverse chat room, and a method therefor.

Yet another object of the present invention is to provide a system for providing psychological counseling in which, when a preset people diary menu is selected from a website screen, an expert of an expert terminal confirms information on an emotional state by date recorded by a specific user in a diary format in relation to the specific user under management, and a method therefor.

Yet another object of the present invention is to provide a system for providing psychological counseling in which, when a preset chat report menu is selected from a website screen, an expert of an expert terminal provides a free expression index, an anxiety index, etc., corresponding to a comprehensive psychological state of a specific user in relation to the specific user under management, and a method therefor.

Yet another object of the present invention is to provide a system for providing psychological counseling in which, when a preset XR room-creation menu is selected from a website screen, an expert of an expert terminal performs a psychological counseling function in an XR room with a specific user under management, and a method therefor.

Technical Solution

According to one aspect of the present invention, a system for providing psychological counseling includes: when a preset extended reality (XR) room-creation menu is selected from an initial screen displayed on an expert terminal, a server providing an XR counseling room invitation client selection screen corresponding to the selected XR room-creation menu to the expert terminal; and the expert terminal that is linked with the server and a terminal owned by a selected specific user to display an XR counseling room screen when the XR counseling room invitation client selection screen is displayed and the specific user is selected from the displayed XR counseling room invitation client selection screen, selects a specific metaverse chat room when an entry item with a chat training room displayed on one side of the XR counseling room screen is selected while a counseling function with an expert of the expert terminal and the specific user is performed through the XR counseling room screen displayed on the expert terminal, displays an expert's position selection screen to select whether the expert enters as a spectator or as chatter, and when a spectator item or a chatter item is selected from the expert's position selection screen displayed on the expert terminal according to the expert's selection, enters the metaverse chat room as a spectator corresponding to the selected spectator item or as chatter corresponding to the selected chatter item.

The XR counseling room screen may include a counseling screen area for displaying a counseling function performance state with the specific user of the terminal and a detailed member information display area for displaying detailed information on the specific user, the counseling screen area may include at least one of a video information display area for displaying video information related to the expert and the specific user, a counseling time display item for displaying a counseling time, a current time display item for displaying a current time, a microphone item for setting whether to output voice, a video item for setting whether to output the video information, the entry item with a chat training room for a counselor and the specific user to enter a new metaverse chat room related to a specific theme to perform a chat function, a questionnaire writing request item for requesting the specific user in counseling to fill out a questionnaire, a file item for sharing a file during the counseling, and a counseling end item for ending the counseling function, and the detailed member information display area may include at least one of a personal information item for displaying personal information on the specific user in counseling, a counseling record sheet item for displaying a counseling record sheet related to one or more counseling sessions performed by the specific user in counseling, a cognitive behavior therapy record sheet item for displaying a cognitive behavior therapy record sheet related to one or more counseling sessions performed by the specific user in counseling, a questionnaire result item for displaying a questionnaire result related to the questionnaire performed by the specific user in counseling, a people diary item for displaying an emotional state written by the specific user by date, a chat report item for displaying a chat report related to the specific user, a past counseling record item for displaying past counseling record performed by the specific user, and an additional detailed information display area for providing detailed information on a specific item selected from a plurality of items.

When a room leader who opens the metaverse chat room selects a preset start menu while the number of people set in the metaverse chat room is satisfied, the expert terminal may be the spectator or the chatter and may be linked with the terminal, one or more other terminals owned by each of one or more other users who entered the metaverse chat room, and the server to perform or monitor a chat function related to a specific topic in the metaverse chat room, generate feedback information related to the specific user when the chat function in the metaverse chat room ends, and provide the generated feedback information to the terminal through the server.

According to another aspect of the present invention, a method of providing psychological counseling includes: when a preset extended reality (XR) room-creation menu is selected from an initial screen displayed on an expert terminal, displaying, by the expert terminal linked with a server, an XR counseling room invitation client selection screen corresponding to the selected XR room-creation menu to select a client to be invited to the XR counseling room; when a specific user is selected from the XR counseling room invitation client selection screen displayed on the expert terminal, displaying, by the expert terminal linked with the server and a terminal owned by the selected specific user, an XR counseling room screen; while a counseling function with an expert of the expert terminal and the specific user is performed through the XR counseling room screen displayed on the expert terminal, to perform a monitoring function for the specific user through a chat function by participating in a metaverse chat room related to a specific theme, selecting, by the expert terminal, a specific metaverse chat room when an entry item with a chat training room displayed on one side of the XR counseling room screen is selected; displaying, by the expert terminal, an expert's position selection screen for selecting whether the expert enters as a spectator or as a chatter; and when a spectator item or a chatter item is selected from the expert's position selection screen displayed on the expert terminal according to the expert's selection, entering, by the expert terminal linked with the server, the metaverse chat room as a spectator corresponding to the selected spectator item or as chatter corresponding to the selected chatter item.

The selecting of the specific metaverse chat room may include any one of: creating, by the expert terminal, a new metaverse chat room and selecting the created new metaverse chat room as the specific metaverse chat room; and selecting a specific metaverse chat room as the specific metaverse chat room according to the expert selection from one or more pre-created metaverse chat rooms.

In the entering of the metaverse chat room as the spectator corresponding to the selected spectator item or as the chatter corresponding to the selected chatter item, when the spectator item is selected from the expert's position selection screen displayed on the expert terminal according to the expert's selection, the expert terminal may be linked with the server to enter the metaverse chat room as the spectator corresponding to the selected spectator item.

In the entering of the metaverse chat room as the spectator corresponding to the selected spectator item or as the chatter corresponding to the selected chatter item, when entering the metaverse chat room as the spectator from the expert terminal, an image or an emoticon indicating that the expert of the expert terminal is participating as the spectator may be displayed on one side of the screen of the expert terminal and the terminal related to the specific user entering the metaverse chat room together.

In the entering of the metaverse chat room as the spectator corresponding to the selected spectator item or as the chatter corresponding to the selected chatter item, when the chatter item is selected from the expert's position selection screen displayed on the expert terminal according to the expert's selection, the expert terminal may be linked with the server to enter the metaverse chat room as the spectator corresponding to the selected chatter item.

In the entering of the metaverse chat room as the spectator corresponding to the selected spectator item or as the chatter corresponding to the selected chatter item, the terminal corresponding to the specific user in counseling may also be linked with the server to enter the metaverse chat room together with the expert terminal as the chatter.

The method may further include: when a room leader who opens the metaverse chat room selects a preset start menu while the number of people set in the metaverse chat room is satisfied, performing or monitoring, by the expert as the spectator or the chatter linked with the terminal, one or more other terminals owned by each of one or more other users who entered the metaverse chat room, and the server, a chat function related to a specific topic of the metaverse chat room; when the chat function in the metaverse chat room ends, generating, by the expert terminal, feedback information related to the specific user; and providing, by the expert terminal, the generated feedback information to the terminal through the server.

Advantageous Effects

According to the present invention, when a preset extended reality (XR) room-creation menu is selected from a website screen, an expert of an expert terminal performs a psychological counseling function in a metaverse chat room with a specific user under management and a user of a terminal and the expert of the expert terminal participate in another metaverse chat room together while performing a counseling function to perform a chat function, so that it is possible for the expert to perform a psychological counseling function with the user in real time, identify a user's psychological state and provide appropriate coping measures, and accurately identify a user's state as the user performs the chat function with other users in the metaverse chat room.

In addition, according to the present invention, by providing a user-related questionnaire or counseling record sheet while a user of a terminal and an expert of an expert terminal perform a counseling function through a metaverse chat room, it is possible for the expert to perform a psychological counseling function with the user in real time, identify a user's psychological state and provide appropriate coping measures, and specifically confirm the user's state through the questionnaire or counseling record sheet.

In addition, according to the present invention, by providing a user-related cognitive behavior therapy record sheet while a user of a terminal and an expert of an expert terminal perform a counseling function through a metaverse chat room, it is possible for the expert to perform a psychological counseling function with the user in real time, identify a user's psychological state and provide appropriate coping measures, and specifically confirm the user's state through the cognitive behavior therapy record sheet.

In addition, according to the present invention, by providing a user-related chat report or people diary while a user of a terminal and an expert of an expert terminal perform a counseling function through a metaverse chat room, it is possible for the expert to perform a psychological counseling function with the user in real time, identify a user's psychological state and provide appropriate coping measures, and comprehensively confirm a user's state by considering user-related data together.

In addition, according to the present invention, by providing a user-related past counseling record while a user of a terminal and an expert of an expert terminal perform a counseling function through a metaverse chat room, it is possible for the expert to perform a psychological counseling function with the user in real time, identify a user's psychological state and provide appropriate coping measures, and comprehensively confirm a user's state by considering the user's past counseling record data together.

In addition, according to the present invention, when a preset people diary menu is selected from a website screen, an expert of an expert terminal confirms information on an emotional state by date recorded by a specific user in a diary format in relation to the specific user under management, so that it is possible for the expert to conveniently confirm a change in the user's emotional state by date.

In addition, according to the present invention, when a preset chat report menu is selected from a website screen, an expert of an expert terminal provides a free expression index, an anxiety index, etc., corresponding to a comprehensive psychological state of a specific user in relation to the specific user under management, so that it is possible for the expert to conveniently confirm information on the user's psychological state.

In addition, according to the present invention, when a preset XR room-creation menu is selected from a website screen, an expert of an expert terminal performs a psychological counseling function in an XR room with a specific user under management to perform a psychological counseling function with the user in real time, so that it is possible to identify the user's psychological state and provide appropriate coping measures.

BEST MODE

Figure 1:
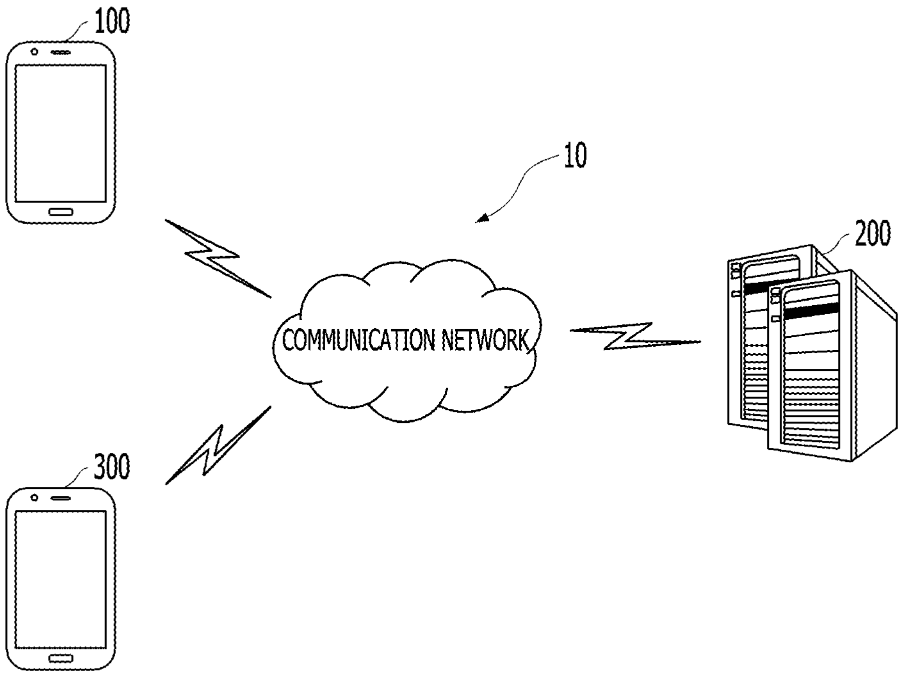
FIG. 1 is a block diagram illustrating a configuration of a system for providing psychological counseling according to an embodiment of the present invention.
Figure 2:
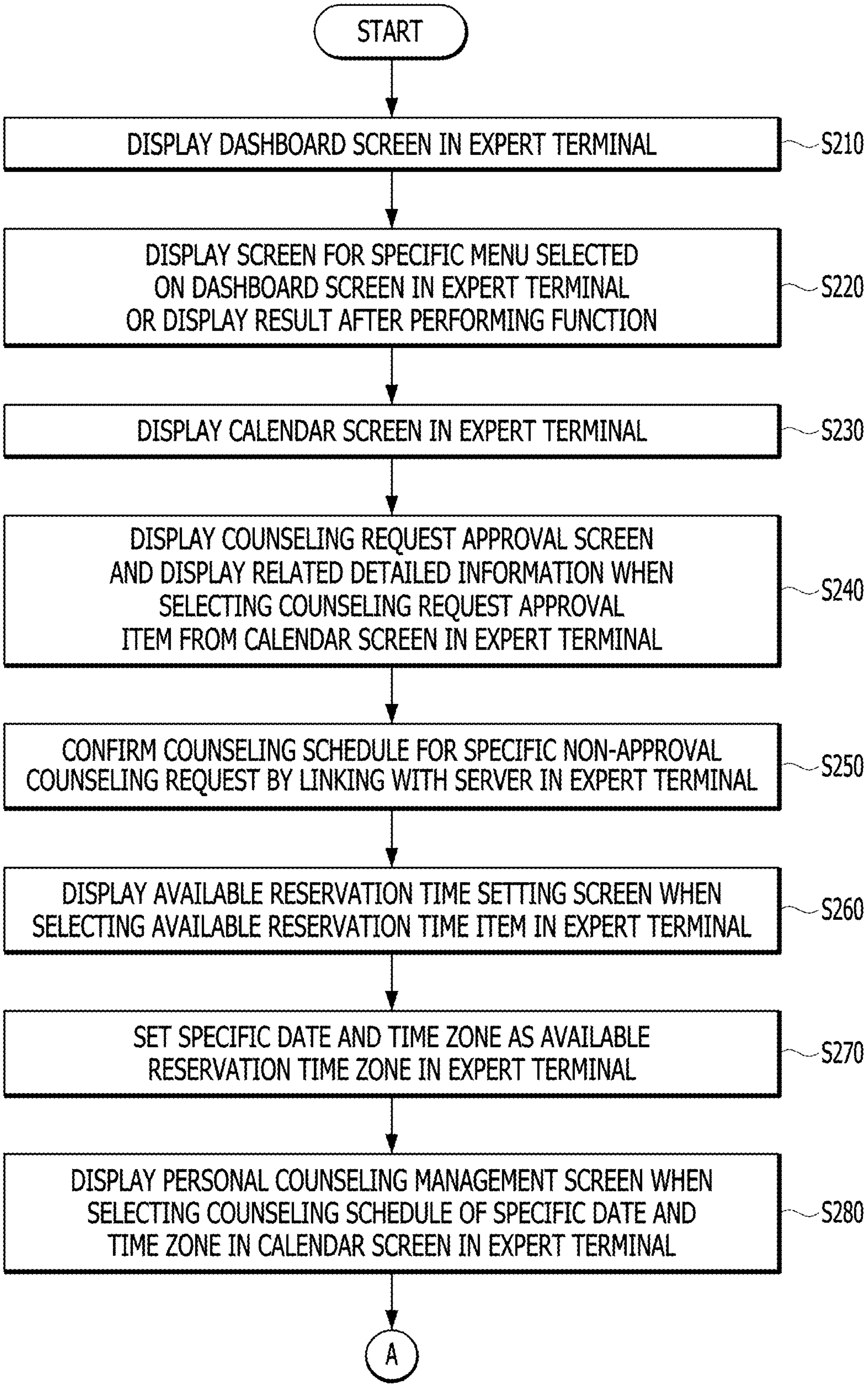
FIGS. 2 to 8 are flowcharts illustrating a method of providing psychological counseling according to an embodiment of the present invention.
Figure 3:
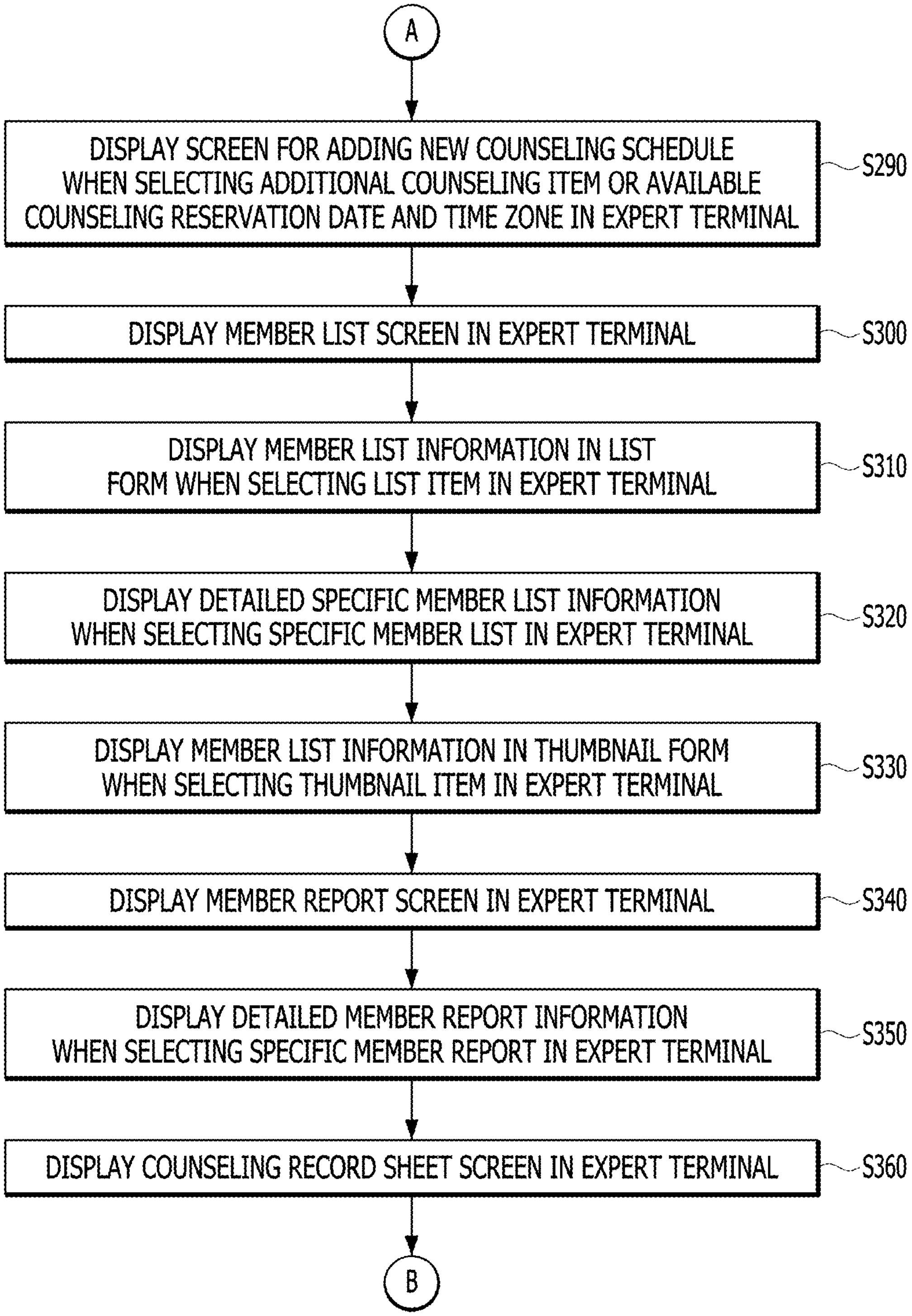
Figure 4:
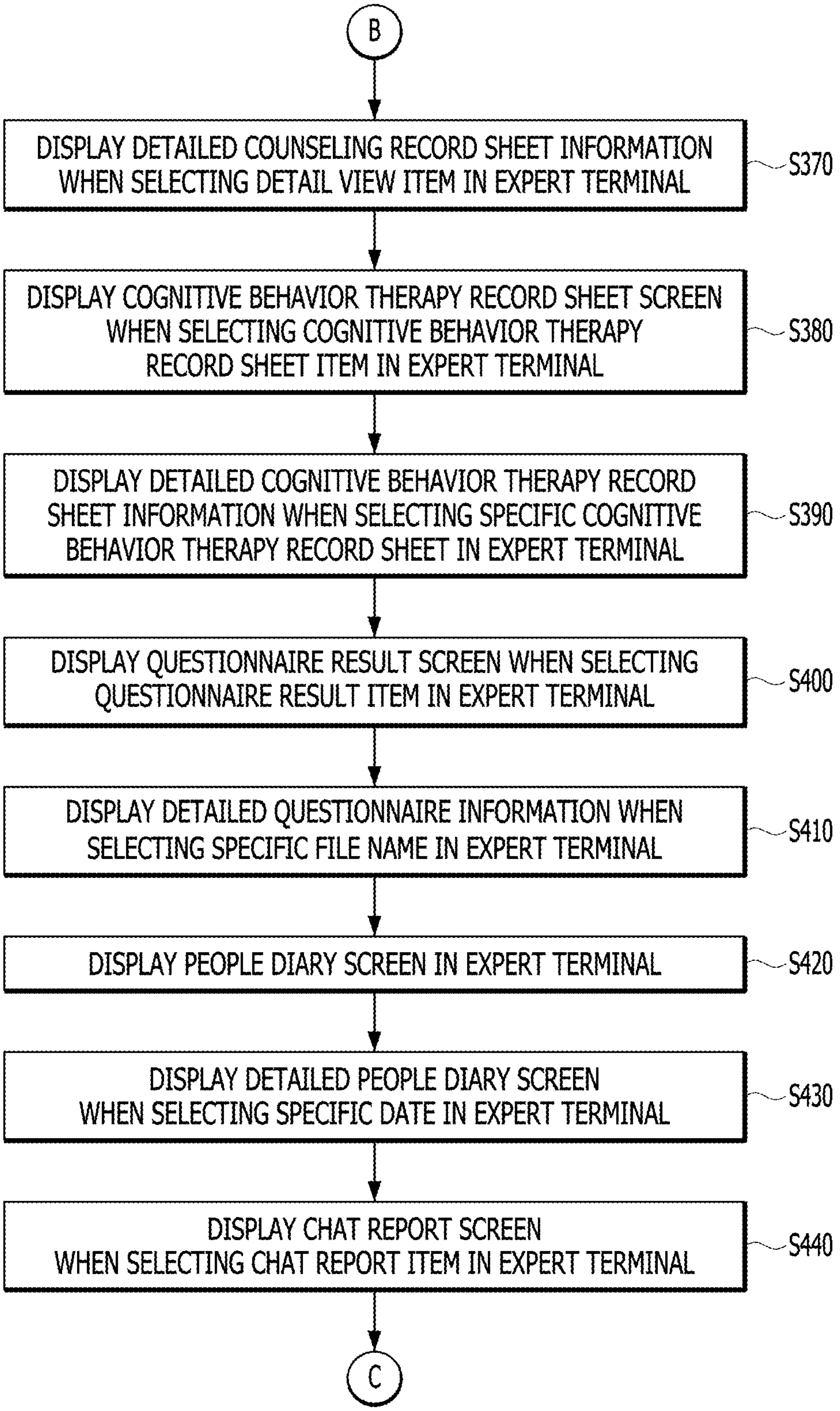
Figure 5:
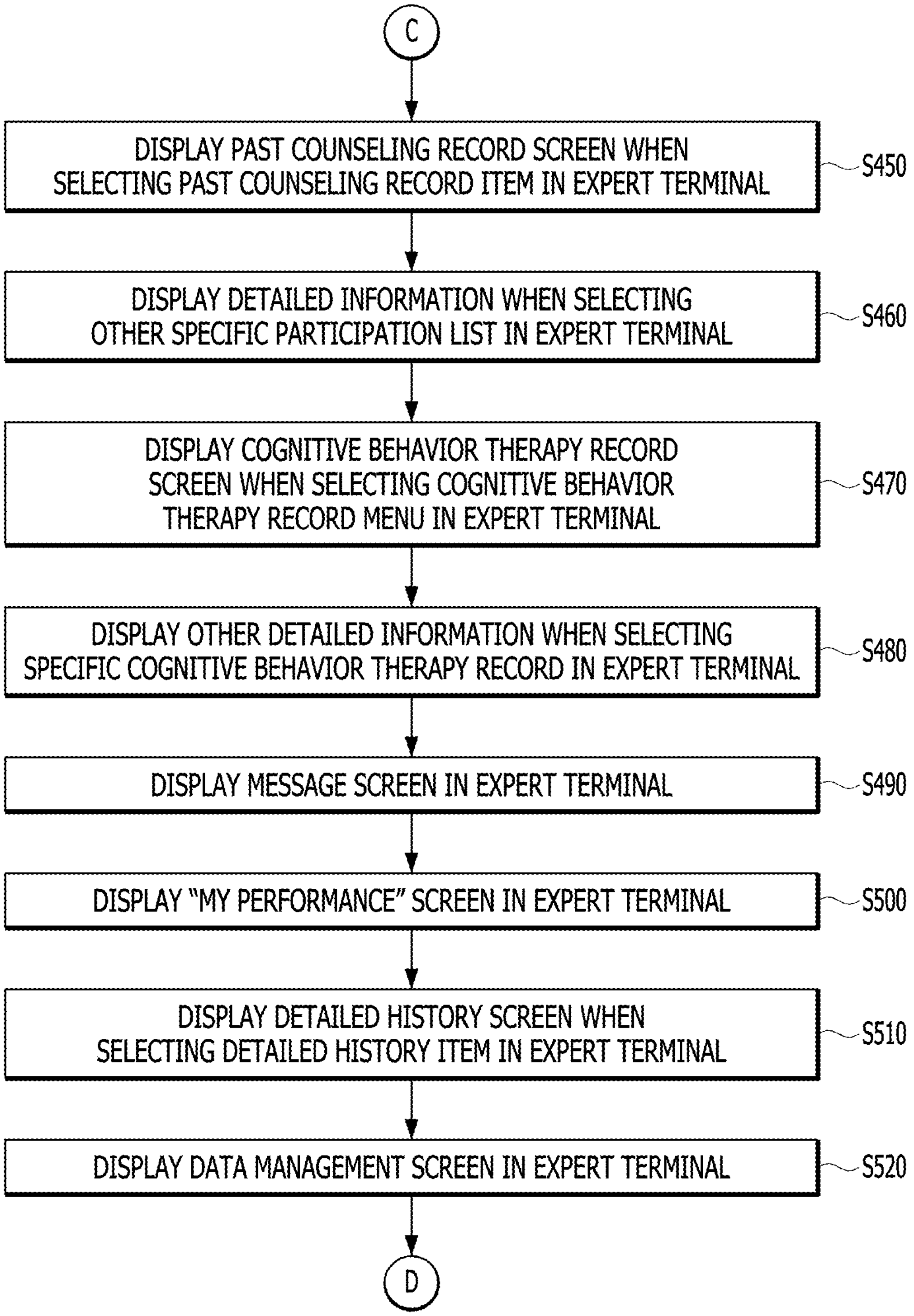
Figure 6:
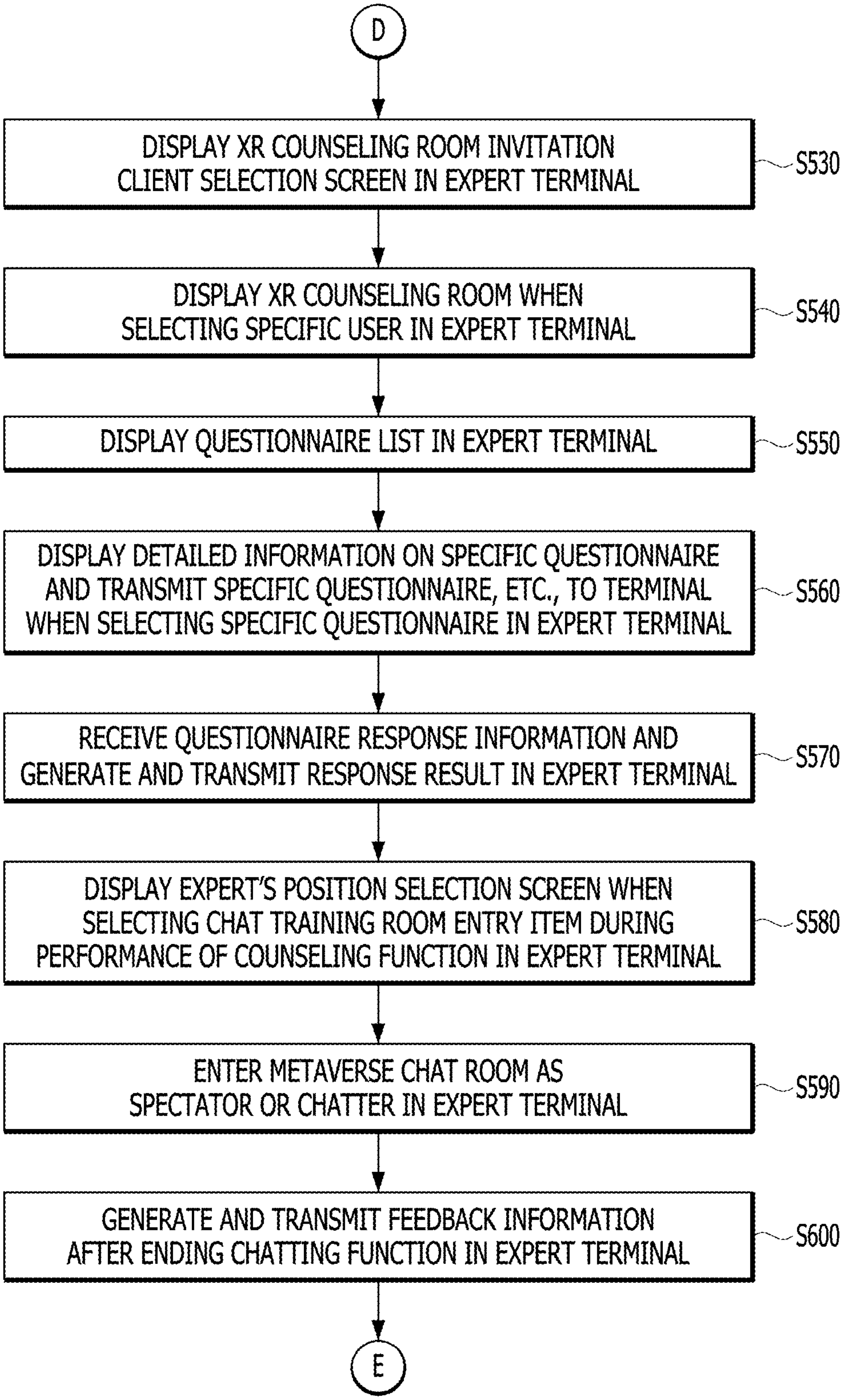
Figure 7:
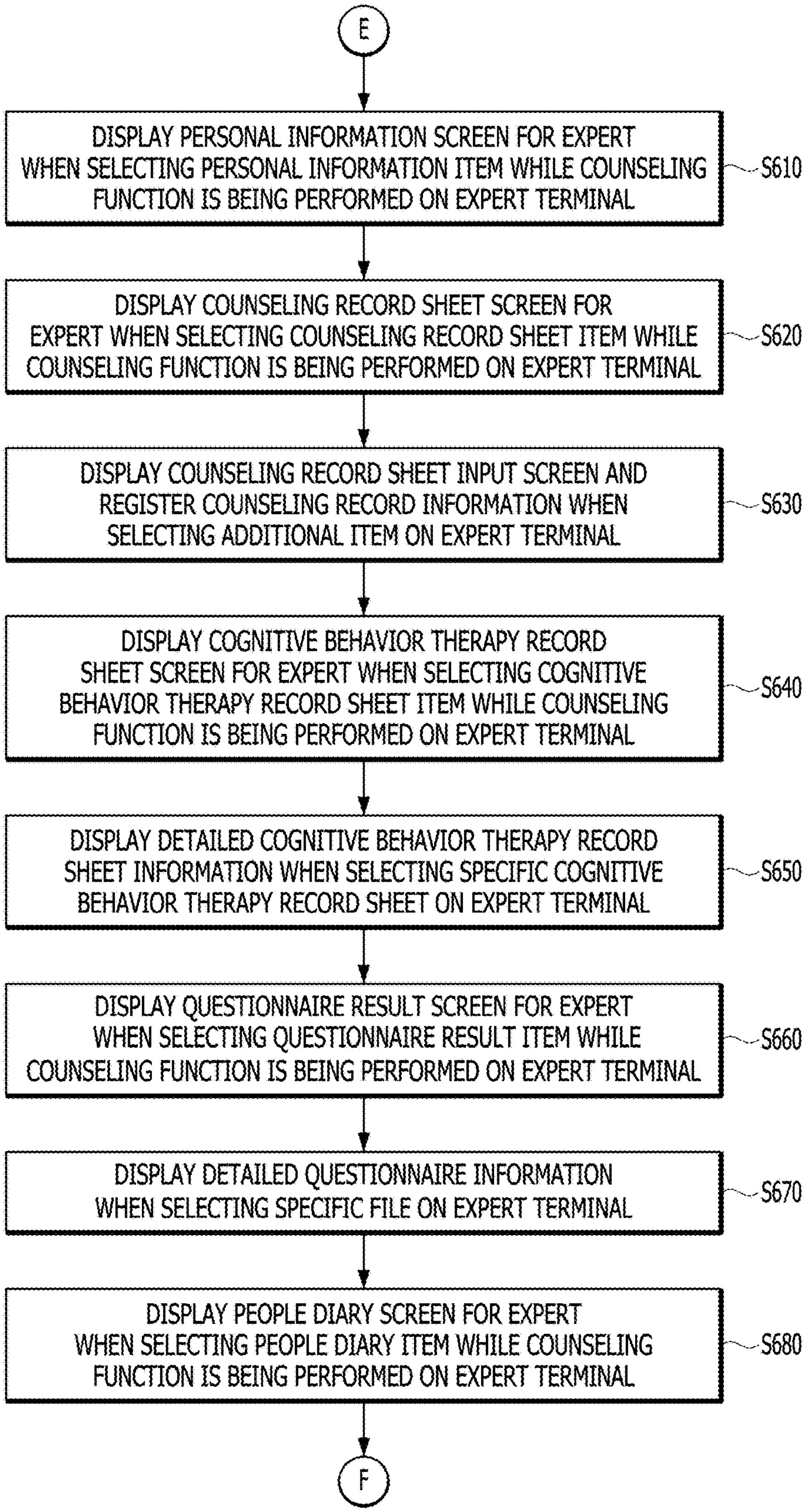
Figure 8:
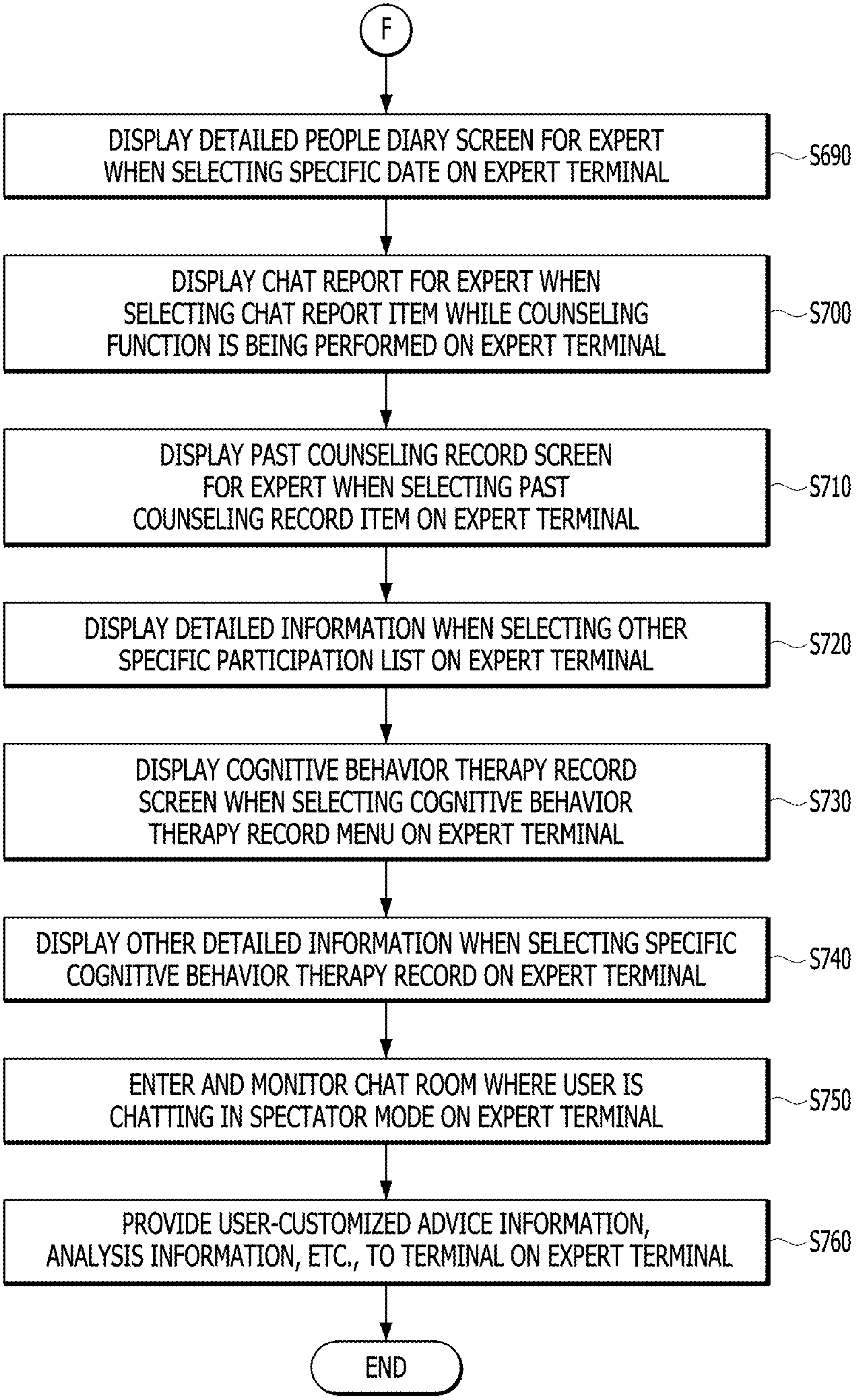

It is to be noted that technical terms used in the present invention are used in order to describe only specific exemplary embodiments rather than restricting the present invention. In addition, unless indicated otherwise in the present invention, it is to be understood that all the technical terms used in the present invention are construed with meanings that are generally understood by those skilled in the art rather than with excessively comprehensive meanings or excessively reduced meanings. In addition, when the technical terms used in the present invention are wrongly technical terms that do not accurately indicate the technical spirit of the present invention, it is to be understood that the terms can be replaced with the technical terms understood by those skilled in the art. Further, the general terms used in the present invention should be understood according to the terms defined by the dictionary or according to the context and should not have excessively reduced meanings.

In addition, singular forms used in the present invention are intended to include plural forms unless the context clearly indicates otherwise. In the present invention, it is to be noted that the terms "configured of," "including," or the like, are not to be construed as necessarily including several components or several steps described in the present invention and some of the above components or steps may not be included or additional components or steps may be construed as being further included.

Terms including an ordinal number such as "first," "second," or the like, used in the present invention may be used to describe various components. However, these components are not limited to these terms. These terms are used only in order to distinguish one component from another component. For example, a "first" component may be named a "second" component, and vice versa, without departing from the scope of the present invention.

Hereinafter, exemplary embodiments of the present invention will be described in detail with reference to the accompanying drawings. The same reference numerals will be used to describe the same or like components throughout the drawings, and overlapping description of the same components will be omitted.

Further, when it is decided that the detailed description of the known art related to the present invention may obscure the gist of the present invention, the detailed description thereof will be omitted. In addition, it is to be noted that the accompanying drawings are provided only in order to allow the spirit of the present invention to be easily understood and are not to be interpreted as limiting the spirit of the present invention.

FIG. 1 is a block diagram illustrating a configuration of a system 10 for providing psychological counseling according to an embodiment of the present invention.

As illustrated in FIG. 1, a system 10 for providing psychological counseling includes a terminal 100, a server 200, and an expert terminal 300. Not all of the components of the system 10 for providing psychological counseling illustrated in FIG. 1 are essential components, and the system 10 for providing psychological counseling may be implemented with more components than those illustrated in FIG. 1, or may be implemented with fewer components.

The terminal 100 and the expert terminal 300 may be applied to various terminals such as a smart phone, a portable terminal, a mobile terminal, a foldable terminal, a personal digital assistant (PDA), a portable multimedia player (PMP) terminal, a telematics terminal, a navigation terminal, a personal computer, a laptop computer, a slate PC, a tablet PC, an ultrabook, wearable devices (e.g., including a smartwatch, a smart glass, a head mounted display (HMD), etc.), a Wibro terminal, an Internet protocol television (IPTV) terminal, a smart TV, a digital broadcasting terminal, an audio video navigation (AVN) terminal, an audio/video (A/V) system, a flexible terminal, a digital signage device, etc.

The server 200 may be implemented in the form of a web server, a database server, a proxy server, etc. In addition, the server 200 may be equipped with a network load balancing mechanism or one or more of various types of software that allows the server 200 to operate on the Internet or other networks, and thus may be implemented as a computerized system. In addition, the network may be an http network, a private line, an Intranet, or any other network. Furthermore, the connection between the terminal 100, the server 200, and the expert terminal 300 may be connected to a secure network to prevent data from being attacked by any hacker or other third party. In addition, the server 200 may include a plurality of database servers, and these database servers may be implemented in such a way that they are separately connected to the server 200 through any type of network connections, including distributed database server architecture.

The terminal 100, the server 200, and the expert terminal 300 may each include a communication unit (not illustrated) for performing a communication function with other terminals, a storage unit (not illustrated) for storing various types of information and programs (or applications), a display unit (not illustrated) for displaying various types of information and program execution results, an audio output unit (not illustrated) for outputting voice information corresponding to the various types of information and program execution results, a control unit (not illustrated) for controlling various components and functions of each terminal, etc.

The terminal 100 communicates with the server 200, the expert terminal 300, etc. In this case, the terminal 100 may be a terminal owned by a user who uses the chat room related to topic talk, role-playing (or role play), theme practice, etc., provided by the server 200 to anonymously perform chat functions with other users or perform counseling functions with experts.

In addition, the terminal 100 is linked with the server 200 to register as a user (or client) who receives, through a dedicated app and/or website provided by the server 200, a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc., and register personal information, etc., in the server 200. In this case, the personal information includes an ID, an email address, a password (or passcode), a name, a gender, a date of birth, contact information, an address (or address information), etc.

In addition, the terminal 100 may subscribe a user as a member on the server 200 using SNS account information to which the user of the terminal 100 subscribes or other site account information. Here, the SNS account may be information related to Facebook, Twitter, Instagram, Kakao Story, Naver Blog, etc. In addition, other site accounts may be information related to YouTube, Kakao, Naver, etc. In this case, the dedicated app may be configured as different user interfaces according to a user who receives a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc., and an expert (or counselor) who performs a counseling function for a user, a people diary/"my report" check function for a specific user while performing the counseling function, a counseling result writing and management function, a speech lesson function, a mentor function (or mentoring function), a psychological counseling function, an extended reality (XR) chat room (or metaverse chat room) creation and management function, etc.

In addition, when performing the member subscription process, the terminal 100 should complete an authentication function through an identity authentication method (e.g., including a mobile phone, a credit card, an i-PIN, etc.) to complete the member subscription process for the server 200 normally.

In addition, after the member subscription is completed, to use the service provided by the server 200, the terminal 100 installs a dedicated app (or application/application/specific app) provided from the server 200 on the corresponding terminal 100. At this time, examples of the dedicated app include a native app, a mobile web app, a mobile webapp design (RWD), an adaptive web design (AWD), a hybrid app, etc., and may be an app for performing a chat room search function, a chat function/user-to-user chat function, a counseling with expert function/expert search function, a room creation function, a topic talk chat room function, a role-playing chat room function, a theme practice chat room function, a people diary creation and/or management function, a "my report" management function, a user community function for information exchange between users, an expert community function for information exchange between experts, etc.

In addition, after the member subscription is completed, the terminal 100 may display a discount coupon provided by the server 200 through the corresponding dedicated app. In this case, the discount coupon may be a discount coupon including discount information of a certain percentage when using the chat room function, etc., provided by the server 200.

In addition, the terminal 100 executes a dedicated app pre-installed on the terminal 100 and displays an app execution result screen according to the execution of the dedicated app. In this case, the app execution result screen includes an edit menu (or button/item) for screen editing, a search menu (or expert search menu) for searching for the chat room corresponding to the search word or searching for an expert, a notification menu for confirming notices or notification messages, etc., a "my page" menu (or setting menu) for setting a user information or dedicated app function, etc., an advertising display area (or advertising/event display menu) where advertising content or event content is displayed, a subscription menu for regular subscription to chat room service, a user-to-user menu for performing chat functions corresponding to topic talk, role-playing, theme practice, etc. with other users related to a specific topic or situation, an expert interaction menu for performing psychological counseling or speech lesson functions with an expert, a chat room display area (or chat room display menu) for displaying a list of chat rooms opened in relation to a preset category, a filter menu for providing a filter function for the list of opened chat rooms, a view only waiting rooms menu for providing a list of waiting chat rooms, a random participation menu for randomly participating in a chat room among the opened chat rooms, a room creation menu for creating a new chat room of one's choice, a home menu for moving to a home screen/home screen, a people diary menu for writing an emotional state by date related to a user, a "my report" menu for providing analysis results based on performance of a user's chat function, participation list, and cognitive behavior therapy record (or cognitive behavior record), etc. In this case, the user-to-user menu (or user-to-user tab) includes an analysis result item for providing analysis results according to the performance of functions such as topic talk, role-playing, and theme practice in relation to the user of the terminal 100, a participation list item for providing a participation list related to the chat list in which the user participates, etc. In addition, the expert interaction menu (or expert interaction tab) includes a participation list menu for providing a list of people who have performed a psychological counseling function, a speech lesson function, or a mentoring function with an expert in relation to a specific topic or situation, a cognitive behavior therapy record menu for providing expert feedback based on performance of a training function on appropriate chat room methods in relation to the specific topic or situation, etc. In addition, the filter screen includes a topic talk filter item (e.g., interpersonal relationship, daily life, employment/workplace, knowledge sharing, well-being, psychology/MBTI, travel, art, sports, other, etc.) related to topic talk, a role-playing filter item (e.g., including work, dating, daily life, other, etc.) related to role-playing, a theme practice filter item (e.g., including blind dates, phone situations, interview situations, work reports, small-scale presentations, large-scale presentations, professional discussions, pros and cons discussion, other, etc.) related to theme practice, etc. Here, the terminal 100 performs a login procedure when running the dedicated app using the ID and password according to the membership subscription, a barcode or a QR code including the ID, etc., while subscribing as a member in the server 200 that provides the dedicated app to perform one or more functions of the dedicated app (e.g., including a chat room search function, a chat function/user-to-user chat function, a counseling with expert function/expert search function, a room creation function, a people diary writing function, a "my report" checking function, etc.). In this case, the dedicated app may be configured as different user interfaces according to a user who receives a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc., and an expert (or counselor) who receives a counseling function for a user, a people diary/"my report" check function for a specific user while performing the counseling function, a counseling result writing and management function, a speech lesson function, a mentor function (or mentoring function), a psychological counseling function, a psychological counseling function, an XR chat room (or metaverse chat room) creation and management function, etc.

In addition, when a preset search menu is selected from the app execution result screen displayed on the terminal 100, the terminal 100 displays a search screen corresponding to the selected search menu to provide a list of chat rooms for each category that are in a standby state (or in which chat is in progress) to perform the chat functions. Here, the search screen includes a search word input item for receiving search words (e.g., including topic, keyword, etc.) according to the user input, a category item for searching for chat rooms opened for each category (e.g., including topic talk, role-playing, theme practice, etc.), a popular search word display item for displaying popular search words, etc.

In addition, when the search word according to the user input of the terminal 100 is received on the search screen displayed on the terminal 100, the terminal 100 is linked with the server 200 to display one or more chat room lists corresponding to the corresponding search word.

That is, when the search word according to the user input of the terminal 100 is received on the search screen displayed on the terminal 100, the terminal 100 transmits the received search word, the identification information of the terminal 100, etc., to the server 200. Here, the identification information of the terminal 100 includes a mobile directory number (MDN), mobile Internet protocol (IP), mobile media access control (MAC), subscriber identification module (SIM) card unique information, a serial number, etc.

In addition, when the chat room corresponding to the search word is found among one or more chat rooms opened in the server 200, the terminal 100 receives the chat room list corresponding to the search word transmitted from the server 200 in response to the previously transmitted search word, etc., and displays (or outputs) the received chat room list. Here, the chat room list includes the number of searched chat rooms, a type of chat room, a topic, a chat room name, a keyword, a nickname (or screen name) of a user who has entered the corresponding chat room, the number of people currently inside compared to the total number of people, and whether the chat is in progress (e.g., waiting, chatting, chat over, etc.), an entry menu (or no entry menu), etc.

In addition, when the corresponding chat room is not found with the search word among one or more chat rooms opened on the server 200, the terminal 100 receives information indicating that the chat room corresponding to the search word transmitted from the server 200 in response to the previously transmitted search word or the like does not exist (or information indicating that the registered chat room corresponding to the corresponding search word does not exist) and displays (or outputs) information indicating that the chat room corresponding to the received search word does not exist (or information indicating that the registered chat room corresponding to the search word does not exist).

In addition, when one chat room is selected from one or more displayed chat room lists, the terminal 100 is linked with the server 200 and other terminals (not illustrated) participating in the chat room to perform the chat function.

Further, the terminal 100 is linked with the server 200 to perform a self-evaluation function and a counterpart evaluation function after the chat function ends.

In addition, when a preset notification menu is selected from the app execution result screen displayed on the terminal 100, the terminal 100 displays a notification screen corresponding to the selected notification menu to provide notices or notification messages provided from the server 200, messages (or post message content) transmitted from other users, etc. Here, the notification screen includes information on a sender who transmits notices, messages, etc., a title, content, transmission time information (e.g., including 5 minutes ago, 1 hour ago, 2 hours ago, etc.), deletion items, etc.

In addition, when one message is selected from among one or more messages included in the notification screen displayed on the terminal 100, the terminal 100 displays detailed content on the selected message.

In addition, when a preset "my page" menu (or setting menu) is selected from the app execution result screen displayed on the terminal 100, to set user information, a dedicated app function, etc., the terminal 100 displays a "my page" screen corresponding to the selected "my page" menu. Here, the my page screen includes an image item (or character item), a nickname item, an identification (ID) (or email address) item, a self-introduction item, a chat temperature item, a "my badges" item, a "my psychological test results" item, a "my keywords" item, a chosen expert item, a payment means management item, a notice item, a frequently asked questions item, a 1:1 inquiry item, a stipulation and policy item, a setting item, etc. In this case, the chat temperature item may be calculated based on the number of chats, the received evaluation results, etc.

For example, the chat temperature may increase by 0.5° C. per chat to a preset standard value (e.g., 36.5° C.), and when the received evaluation result is affirmative evaluation/satisfactory, the chat temperature may increase by 0.5° C., and when the received evaluation result is negative/not good, the chat temperature may decrease by 0.5·C.

In addition, the concept of level or points may be applied instead of the chat temperature. That is, for the level or points, the level or the preset number of points may be calculated according to a plurality of preset grades based on the number of chats, the received evaluation results, etc.

In addition, the "my badges" item is provided when other users confirm the personal information of the user of the terminal 100, and includes a preset number of (e.g. 3) badges (or badge information) according to user selection among the badges acquired when the user of the terminal 100 participates in a chat room related to various topics and keywords and performs the chat function normally. Here, the types of badges include topic talk rookie (e.g., participation in topic talk chat room less than 30 times), topic talk intermediate (e.g., participation in topic talk chat room 30 to 90 times), topic talk expert (e.g., participation in topic talk chat room exceeding 90 times), role-playing rookie (e.g., participation in role-playing chat room less than 30 times), role-playing intermediate (e.g., participation in role-playing chat room 30 to 90 times), role-playing expert (e.g., participation in role-playing chat room exceeding 90 times), theme practice rookie (e.g., participation in theme practice chat room less than 30 times), theme practice intermediate (e.g., participation in theme practice chat room 30 to 90 times), theme practice expert (e.g., participation in theme practice chat room exceeding 90 times), confidence/assertiveness rookie (e.g., confident and assertive or confidence/assertiveness score exceeding 80 points and 10 times or more based on evaluation results), confidence/assertiveness intermediate (e.g., confident and assertive or confidence/assertiveness exceeding 80 points and 25 times or more based on evaluation results), confidence/assertiveness expert (e.g., confident and assertive or confidence/assertiveness points exceeding 80 points based on evaluation results), mind control rookie (e.g., good emotion control or emotion control exceeding 80 points and 10 times or more based on the evaluation results), mind control intermediate (e.g., good emotion control or emotion control exceeding 80 points and 25 times or more based on evaluation results), mind control expert (e.g., good emotion control or emotion control exceeding 80 points and 50 times or more based on evaluation results), communication skills/logic/persuasive power rookie (e.g., good at communicating logically or accurate communication exceeding 80 points and 10 times or more), communication skills/logic/persuasive power intermediate (e.g., good at communicating logically or accurate communication exceeding 80 points and 25 times or more), communication skills/logic/persuasive power expert (e.g., good communication or accurate communication exceeding 80 points and 50 times or more), immersion rookie (e.g., good immersion in a situation or immersion exceeding 80 points and 10 times or more based on evaluation results), immersion intermediate (e.g., good immersion in a situation or immersion exceeding 80 points more and 25 times or more based on evaluation results), immersion expert (e.g., good immersion in a situation or immersion exceeding 80 points and 50 times or more based on evaluation results), empathy/listening rookie (e.g., good listening and good empathy, or empathy/listening exceeding 80 points and 10 times or more based on evaluation results), empathy/listening intermediate (e.g., good listening and good empathy, or empathy/listening exceeding 80 points and 25 times or more based on evaluation results), empathy/listening expert (e.g., good listening and good empathy, or empathy/listening exceeding 80 points and 50 times or more based on evaluation results), etc.

In addition, the "my keywords" item is an item for pre-registering keywords that the user of the terminal 100 is mainly interested in, and may use one or more keywords stored in the my keyword item when inputting the search word or searching for an expert.

In addition, the chosen expert item is an item for pre-registering an expert in whom the user of the terminal 100 is interested, and may use one or more experts stored in the chosen expert item when searching for an expert.

In addition, when a preset subscription menu (or pro subscription menu) is selected from the app execution result screen displayed on the terminal 100, the terminal 100 displays a subscription application screen corresponding to the selected subscription menu for regular subscription of the chat room service. Here, the subscription application screen (or subscription screen) includes a subscription period selection item (e.g., including a payment amount for each subscription period, etc.), a payment means selection item (e.g., Kakao Pay, a credit/check card, etc.), a payment amount item, a subscription item, etc.

In addition, after receiving a plurality of input values corresponding to a plurality of input items included in a subscription application screen displayed on the terminal 100, when a subscription item displayed on one side of the subscription application screen is selected, the terminal 100 is linked with the server 200 and a payment server (not illustrated) for performing a payment function for a subscription fee (or cost) corresponding to a subscription period selected by the terminal 100, and after the payment function is performed normally, the terminal 100 participates in various chat rooms provided by the server 200 in the subscription period according to the execution of the subscription function to perform the chat function, the expert counseling function, etc. In this case, the terminal 100 may participate in a chat room of a preset category (e.g., theme practice) only while the subscription function is being performed.

In addition, when a preset chat menu is selected from the app execution result screen displayed on the terminal 100, the terminal 100 is linked with the server 200 to perform functions such as creating a new chat room corresponding to the selected chat menu or participating in the existing chat room so that the terminal 100 performs chat functions corresponding to topic talk, role-playing, theme practice, etc., in relation to a specific topic or situation, and perform a chat function with other users in the chat room in which the user is participating.

In addition, when the preset expert search menu is selected from the app execution result screen displayed on the terminal 100, the terminal 100 displays the expert search screen corresponding to the selected expert search menu to perform the psychological counseling, the speech lesson, or the mentor function with an expert. Here, the expert search screen includes a sorting menu for sorting functions in specialized fields related to all, psychological counseling, speech lessons, mentoring, etc., an expert count display menu for displaying the number of registered (or active) experts, an immediately available item for providing a list of specialists who are immediately available for counseling, an expert display item for providing information on an expert, a smart filter application menu for searching for an expert according to detailed conditions, desired counseling date and time information, etc. Here, examples of the expert display item include an expert name, a counseling field (or specialty field) (e.g., psychological counseling, speech lesson, mentoring, etc.), a brief introduction, a photo (or image), a fee per session, a rating (or star rating), review information, immediate counseling availability, popularity (or number of likes), etc. In addition, the smart filter application menu includes an expert type item (e.g., including all, psychological counseling, speech lesson, mentoring, etc.), an expert gender item (e.g., including all, male, female, etc.), an expert level (or badge) item (e.g. including all, general with less than 30 sessions, specialty for whom the number of counseling sessions is 30 to 90, master for whom the number of counseling sessions is 90 or more, etc.), a "Please select the topic you would like to discuss together" item (e.g., including "I have concerns about myself" (e.g., including self-esteem, personality/disposition, value, interest, religion, background, marriage, etc.), "Social life is difficult," "Interpersonal relationships are difficult," "I need dream/career advice," "I want to know about my emotions/psychology," "I need expert advice," etc.), a "Please select the situation in which you want to say something well" item (e.g., including a situation of expressing oneself, a work situation, a situation of presenting in front of others, a situation of dealing with a difficult subject, a situation that promotes friendship, a situation where there is conflict with others, a situation of having to express honest feelings, a discussion/persuasion situation, etc.), a "Please select the mentoring field you would like to receive mentoring in" item (e.g., including mentoring about oneself, mentoring for social life, mentoring for dream/careers, etc.) etc. Here, the "Please select the topic you would like to discuss together" item may include "me," social life, interpersonal relationships, dreams/career, emotions/psychology, experts, etc., and the "Please select the situation in which you want to say something well" item may include "expressing myself," work situation, presentation situation, difficult object, friendship, conflict situation, emotion expression, discussion/persuasion, etc.

In addition, the terminal 100 receives expert search information including a plurality of other input values corresponding to a plurality of other input items according to the user input of the terminal 100 from the expert search screen displayed on the terminal 100. Here, the expert search information includes an expert type, an expert gender, an expert level, "Please select a topic you would like to talk about (or topic you would like to receive psychological counseling on)," "Please select a situation in which you want to say something well (or speech lesson topic)," "Please select a mentoring field you would like to receive mentoring in (or mentoring topic)," desired counseling date and visual information, etc.

In addition, the terminal 100 is linked with the server 200 to display one or more pieces of expert information corresponding to the received expert search information. Here, the expert information includes an expert name, a counseling field (or specialty field) (e.g., psychological counseling, speech lessons, mentorship, etc.), a brief introduction, a photo (or image), a fee per session, a rating (or star rating), review information, whether immediate counseling is possible, popularity (or number of likes), etc.

In addition, when the specific expert information is selected from one or more pieces of expert information displayed on the terminal 100, the terminal 100 is linked with the server 200 to display the detailed expert information corresponding to the selected specific expert information. Here, the detailed expert information includes an expert name item, a counseling field (or specialty) item (e.g., including psychological counseling, speech lesson, mentoring, etc.), a rating (or star rating) item, a photo (or image) item, a brief introduction item, a usage fee per counseling session, a re-use desire rate of users who received counseling item, a total number of counseling sessions item, a counseling information item, a counselor information item, a review item, etc. In addition, the counseling information item includes a price option item (e.g., including a basic counseling item, a severe anxiety counseling item, etc.), a detailed description item, a location item, a popularity (or number of likes) item, a counseling application item, etc. In addition, the basic counseling item, the severe anxiety counseling item, etc., include the number of counseling sessions, additional composition (e.g., XR chat room training 40%, data analysis 60%, etc.), time (e.g., including 1 hour, etc.), price (e.g., 50,000 won/time), etc. In addition, the counselor information item includes a counselor introduction, a career introduction, a certification introduction, etc. In addition, the review item includes an overall star rating, ratings for each category (e.g., including use of XR, friendliness, analytical skills, empathy and comfort, appropriate advice, etc.), the total review, etc.

In addition, the terminal 100 is linked with the server 200 to perform a counseling reservation function for a specific expert corresponding to the corresponding specific expert information.

That is, when the preset counseling reservation menu displayed on one side of the expert detailed information of the terminal 100 is selected, the terminal 100 is linked with the server 200 and the payment server (not illustrated) to perform the payment function for the preset counseling cost related to the expert. In this case, the server 200 may perform card payment, an automatic transfer function through linkage with a bank payment account, payment using cash points or cash remaining in the account of the terminal 100 that is subscribed as a member of the server 200, and a payment function through simple payments including Kakao Pay, Naver Pay, etc. Here, before/after performing the payment function for the counseling fee, the terminal 100 may schedule the counseling with the corresponding expert, or may automatically reserve (or confirm) the counseling schedule with the expert according to the desired counseling date and time information included in the expert search information.

In addition, the terminal 100 receives the information indicating that the counseling schedule with the corresponding expert transmitted from the server 200 is confirmed, and displays (or outputs) the information indicating that the counseling schedule with the received corresponding expert has been confirmed.

In addition, the terminal 100 is linked with the server 200 to perform a final confirmation function (or final acceptance/confirmation function) for the counseling schedule case newly registered in the expert terminal 300 so that the counseling schedule for the counseling schedule case newly registered in the expert terminal 300 is finally confirmed.

In addition, when a preset expert search menu is selected from the app execution result screen displayed on the terminal 100, the terminal 100 is linked with the server 200 and allows the user of the terminal 100 to confirm whether to perform the preset counseling questionnaire writing function.

In addition, when the user of the terminal 100 does not perform the counseling questionnaire writing function, the terminal 100 displays a preset counseling questionnaire screen before displaying the expert search screen corresponding to the selected expert search menu. Here, the counseling questionnaire screen is for the purpose of confirming the psychological state related to the user of the terminal 100 and may be provided to experts performing the counseling function in the future, and includes a plurality of questions and view items that include “I have difficulty dealing with extreme anxiety right before a presentation,” “If I improve my personality, I will be able to communicate better with others,” “When I speak, others seem to secretly ignore me,” “I want to gain the courage to be honest about myself and my feelings,” “I want to increase the persuasive power of my words when presenting or speaking,” “I feel like my voice or the way I speak is unattractive,” “I want to know how to react well to what my counterpart says when chatting,” “I find it difficult to speak calmly when I am embarrassed during presentations and interviews,” “I am worried that I may be doing a job that is not suitable for me,” “I need someone to have fun chats about topics I like,” “My confidence is low because I know less than other people,” “I am thirsty for productive self-improvement chat,” etc.

In addition, the terminal 100 receives a plurality of answers according to the user selection of the terminal 100 for the plurality of questions included in the counseling questionnaire screen displayed on the terminal 100, and then transmits the plurality of received answers, the identification information of the terminal 100, etc., to the server 200.

In addition, the terminal 100 transmits the plurality of received answers, etc., to the server 200 and then displays an expert search screen corresponding to the selected expert search menu.

In addition, the terminal 100 is linked with the server 200 to perform the psychological test function.

In addition, when a specific category (e.g., including all, topic talk, role-playing, theme practice, etc.) within the preset conversation menu is selected from the app execution result screen displayed on the terminal 100, the terminal 100 is linked with the server 200 to filter one or more chat rooms corresponding to the selected specific category among the plurality of chat rooms created in the corresponding server 200 and display the filtered one or more chat rooms (or information on the corresponding chat rooms) in the chat room display area.

In addition, when a preset filter menu is selected from the app execution result screen displayed on the terminal 100, the terminal 100 displays a filter screen corresponding to the selected filter menu to provide a filter function for the list of opened chat rooms. Here, the filter screen includes a topic talk filter item (e.g., interpersonal relationship, daily life, employment/workplace, knowledge sharing, well-being, psychology/MBTI, travel, art, sports, other, etc.) related to topic talk, a role-playing filter item (e.g., including work, dating, daily life, other, etc.) related to role-playing, a theme practice filter item (e.g., including blind date, phone situation, interview situation, 1:1 meeting/work report, small-scale presentation, large-scale presentation, professional discussion, other, etc.) related to theme practice, etc.

In addition, after receiving the filter information including the plurality of input values corresponding to the plurality of input items included in the filter screen displayed on the terminal 100, when the applying menu (or confirmation menu) displayed on one side of the filter screen is selected, the terminal 100 is linked with the server 200 to filter the plurality of chat rooms created in the server 200 according to the received filter information and display one or more filtered chat rooms (or information on the corresponding chat room) in the chat room display area.

In addition, when the preset only waiting room view menu is selected from the app execution result screen displayed on the terminal 100, the terminal 100 is linked with the server 200 to filter at least one chat room in which the chat function is not yet being performed (or a waiting state/in waiting) among the plurality of chat rooms created in the server 200 and display at least one filtered chat room (or information on the corresponding chat room) in the chat room display area.

In addition, when a preset random participation menu is selected from the app execution result screen displayed on the terminal 100, the terminal 100 is linked with the server 200 to participate in any one randomly selected chat room among one or more category-specific chat rooms created by one or more other terminals (not illustrated) and perform the chat function related to the corresponding category.

In addition, when a preset room creation menu is selected from the app execution result screen displayed on the terminal 100, to create a new chat room in relation to the category the user wants, the terminal 100 displays the room creation screen corresponding to the selected room creation menu. Here, the room creation screen includes a room type selection menu for selecting a room type, etc. In addition, the room type selection menu includes the topic talk item for free chat between users with similar interests, a role-playing item for practicing expressing emotions and opinions by setting up situations, a theme practice item for developing (or practicing) adaptability and appropriate responsiveness by creating the theme that may cause tension, etc. In this case, the room creation menu may be activated and displayed only on the terminal 100 of a pre-registered (or set) expert terminal 300 or a paid member (or subscription member) for whom chat room creation rights are set.

In addition, when a preset topic talk item is selected from the room creation screen displayed on the terminal 100, the terminal 100 displays a topic talk chat room creation screen corresponding to the selected topic talk item to communicate freely with users with similar interests. Here, the topic talk chat room creation screen includes a topic selection menu (e.g., including interpersonal relationships, daily life, employment/workplace, knowledge sharing, well-being, psychology/MBTI, travel, art, sports, etc.), a keyword selection menu for selecting keywords related to a specific topic selected from the topic selection menu, a room title input menu for selecting a room title, an answer time selection menu for setting an answer time per person (e.g., including 45 seconds, 60 seconds, 90 seconds, etc.), the maximum number of people menu for setting the maximum number of people (e.g., including 2, 3, 4, etc.), etc.

In addition, after receiving a plurality of input values corresponding to the plurality of input items included in the topic talk chat room creation screen displayed on the terminal 100, when the room creation menu (or creation menu) displayed on one side of the topic talk chat room creation screen is selected, the terminal 100 is linked with the server 200 to create (or open) a new topic talk chat room corresponding to the plurality of received input values. Here, the plurality of input values include a topic, a keyword, a room title, an answer time, the maximum number of people, etc. In this case, the topic talk chat room creation may be performed in the terminal 100 that is performing a subscription function in advance or in the terminal 100 that has paid a preset usage amount for each topic to create the topic talk chat room. Here, when the keyword related to the specific topic included in the plurality of input values is used by a plurality of users more than the preset number of times (for example, 10 times), the server 200 may preferentially provide the corresponding keyword (or hashtag) according to an auto-complete function so that other users may easily use the corresponding keyword (or hashtag).

In this way, the terminal 100 may be used for various personal purposes, such as overcoming speaking anxiety by speaking in front of others, relieving isolation and depression by having enjoyable chats and feeling empathy and solidarity with other people, and practicing various presentations, reading discussions, and speaking English, through the topic talk chat room, which allows for maximum free chat between individuals, like real chat, with minimal intervention.

In addition, when a preset role-playing item is selected from the room creation screen displayed on the terminal 100, the terminal 100 displays a role-playing chat room creation screen corresponding to the selected role-playing item to practice expressing emotions and opinions by setting up situations. Here, the role-playing chat room creation screen includes a context setting menu (e.g., including work, dating, daily life, etc.), a room title input menu for selecting a room title, an answer time selection menu for setting an answer time per person (e.g., including 45 seconds, 60 seconds, 90 seconds, etc.), and a maximum number of people menu for setting the maximum number of people (e.g., including 2, 3, 4, etc.).

In addition, after receiving a plurality of other input values corresponding to the plurality of other input items included in the role-playing talk chat room creation screen displayed on the terminal 100, when the room creation menu (or creation menu) displayed on one side of the role-playing chat room creation screen is selected, the terminal 100 is linked with the server 200 to create (or open) a new role playing chat room corresponding to the plurality of received other input values. Here, the plurality of other input values include situation information, a room title, an answer time, the maximum number of people, etc. In this case, the role-playing chat room creation may be performed in the terminal 100 that is performing a subscription function in advance or in the terminal 100 that has paid a preset usage amount for each case to create the role-playing chat room.

In this way, the terminal 100 may allow participants to receive roles and scripts and perform short chats, uses the role-playing chat room in which users, who are response targets, should spontaneously and appropriately respond in turn to allow people who are not good at expressing their emotions (or opinions) due to fear of the gaze and evaluation of others to overcome their anxiety and express themselves appropriately, and help train context understanding through role-playing based on real situations since patients with social anxiety disorder tend to be slow in understanding social context.

In addition, when the preset theme practice item is selected from the room creation screen displayed on the corresponding terminal 100, to develop (or practice) adaptability and appropriate responsiveness by creating the theme that may cause tension, the terminal 100 displays a spectator type setting screen corresponding to the selected theme practice item. Here, the spectator type setting screen includes a no spectator item, a spectator item, etc., for selecting the theme type according to the presence or absence of a spectator.

In addition, when a preset no spectator item is selected from the spectator type setting screen displayed on the terminal 100, to create a theme practice chat room for performing the chat function with the question-and-answer, the terminal 100 displays a theme setting screen corresponding to the selected no spectator item. Here, the theme setting screen (or question theme setting screen) includes a question-and-answer item, a next item, etc. In this case, the chat room without a spectator (or theme practice chat room without a spectator) may be configured to be created in the pre-registered (or set) expert terminal 300 or the terminal 100 of a paid member (or subscription member) where the chat room creation permission is set.

In addition, when the preset question-and-answer item is selected from the theme setting screen displayed on the terminal 100, the terminal 100 displays the questionnaire setting screen for receiving the self-introduction or question content. Here, the questionnaire setting screen may be configured in different forms (or formats) from the perspective of a general user or an expert/trainer, and includes a simple self-introduction/question purpose section, one or more questionnaire items the user would like to ask other participants, a questionnaire addition item, a registration item, etc. Here, the one or more questionnaire items may include at least one basic question (e.g., "Briefly introduce yourself," "Have you ever participated in outside activities or clubs?" "What kind of work you would like to do at the company?" etc.) that is preset by default. Here, the registration item remains deactivated by default, and may be displayed by switching from the deactivated state to the activated state when the input values for the simple self-introduction/question purpose item, the questionnaire item, etc., are input (or received).

In addition, the terminal 100 receives questionnaire setting information including the plurality of input values corresponding to the plurality of input items included in the questionnaire setting screen displayed on the terminal 100 according to the user input. Here, the questionnaire setting information includes a brief self-introduction/purpose of the question, content of one or more questionnaires to be asked to other participants, etc.

In addition, after receiving the questionnaire setting information from the questionnaire setting screen, when the registration item displayed on one side of the questionnaire setting screen is selected, the terminal 100 displays the detailed theme setting screen to which the received questionnaire setting information is applied (or reflected). Here, the detailed theme setting screens (or other theme practice chat room creation screen/question-and-answer theme setting screens) include a category item (e.g., including blind date practice without a spectator, etc.), a brief self-introduction/question purpose item, one or more questionnaire content items, a room title input item for selecting the room title, a "number of general users who can participate in training" input item (e.g., no, 1, 2, 3, 4 people, etc., male/female) for selecting the number of general users who can participate in training, a "number of experts who can participate in feedback" input item (for example, include 1, 2, 3, etc.) for selecting the number of experts who can participate in feedback, a room creation item, etc. Here, the room creation item remains deactivated by default, and may be displayed by switching from the deactivated state to the activated state when the input values for the category item, the brief self-introduction/question purpose item, the one or more questionnaire content items, the room title input item, the "number of general users who can participate in training" input item, the "number of experts that can participate in feedback" input item, etc., are input (or received).

In addition, the terminal 100 receives other detailed theme setting information including the plurality of other input values corresponding to the plurality of other input items included in the detailed theme setting screen displayed on the terminal 100 according to the user input. Here, the detailed theme setting information includes the category (e.g., question-and-answer without a spectator), brief self-introduction/question purpose, content of one or more questions the user wants to ask other participants, a room title, and the number of general users who can participate in training, the number of experts who can participate in feedback, etc.

In addition, after receiving the detailed theme setting information on the detailed theme setting screen displayed on the terminal 100, when the room creation item (or creation item) displayed on one side of the detailed theme setting screen is selected, the terminal 100 is linked with the server 200 to create (or open) a new theme practice chat room (or question-and-answer theme practice chat room) corresponding to the received detailed theme setting information. In this case, the theme practice chat room creation may be performed in the terminal 100 that is performing a subscription function in advance or in the terminal 100 that has paid a preset usage amount for each topic to create the theme practice chat room. In addition, the terminal 100 displays the waiting screen according to the entry into the chat room. Here, the waiting screen includes the type of the corresponding chat room, the topic, the chat room name, the keyword, the nickname (or chat name) of the user in the corresponding chat room, the chat temperature, and the number of chats (or the number of times the user has participated in the chat room), etc. In this case, the chat temperature may be calculated based on the number of chats, the received evaluation results, etc., and the concept of level or points may be applied instead of the chat temperature. That is, for the level or points, the level or the preset number of points may be calculated according to a plurality of preset grades based on the number of chats, the received evaluation results, etc.

The embodiment of the present invention mainly describes the creation of the question-and-answer theme practice chat room in the terminal 100, but is not limited thereto. The expert terminal 300 may also create the question-and-answer theme practice chat room and invite the corresponding terminal 100.

In addition, when a preset spectator item is selected from the spectator type setting screen displayed on the terminal 100, to create a theme practice chat room in the form of a free theme or discussion theme, the terminal 100 displays other theme setting screens corresponding to the selected spectator item. Here, the other theme setting screen (or free/discussion theme setting screen) includes a free theme item (e.g., including blind date practice item, phone practice item, interview practice item, business report practice item, small-scale presentation practice item, large-scale presentation practice item, singing practice item, etc.), a discussion theme item (e.g., including professional discussion item, pros and cons discussion item, etc.), a registration item, etc.

The embodiment of the present invention mainly describes performing the creation of the chat room with a spectator (or theme practice chat room with a spectator) in the terminal 100, but is not limited thereto, and the chat room with a spectator may also be configured to be created only in the pre-registered (or set) expert terminal 300 where the chat room creation right is set.

In addition, when any one theme item is selected from other theme setting screens displayed on the terminal 100, the terminal 100 displays other detailed theme setting screens for receiving the room title, the number of participants in training, or the maximum number of spectators. Here, the other detailed theme setting screens (or other theme practice chat room creation screens/free/discussion theme setting screen) include a category item (e.g., including blind date practice with a spectator, phone practice with a spectator, etc.), a room title input item for selecting the room title, a "number of general users who can participate in training" input item (e.g., 1, 2, 3, 4 people, etc., male/female) for selecting the number of general users who can participate in training, a "maximum number of spectators" input item (e.g., 5, 10, 20 people, etc.) for selecting the number of users who can be spectate, a room creation item, etc. In this case, when a professional discussion item or pros and cons discussion item included in the discussion theme item in the other theme setting screens is selected, before displaying the other detailed theme setting screens, the terminal 100 may first display a discussion topic setting screen, receive one or more discussion topics (or discussion topic information/content) according to the user input, and then display the other detailed theme setting screens to which one or more discussion topics are applied. Here, when the room creation item is kept in a deactivated state by default, and input values for the category item, the room title input item, the "number of general users who can participate in training" input item, and the "maximum number of spectators" input item, etc., are input (or received), the room creation item may be displayed by switching from a deactivated state to an activated state.

In addition, the terminal 100 receives other detailed theme setting information including a plurality of additional input values corresponding to a plurality of additional input items included in other detailed theme setting screens displayed on the terminal 100 according to the user input. Here, the other detailed theme setting information includes categories (e.g., blind date practice with spectators, phone practice, interview practice, work reporting practice, small-scale presentation practice, large-scale presentation practice, professional discussion, pros and cons discussion, etc.), a discussion topic, a room title, the number of general users who can participate in training, the maximum number of spectators, etc.

In addition, after receiving other theme detailed setting information on other theme detailed setting screens displayed on the terminal 100, when the room creation item (or creation item) displayed on one side of other theme detailed setting screens is selected, the terminal 100 is linked with the server 200 to create (or open) a new theme practice chat room (or free theme practice chat room/discussion theme practice chat room) corresponding to the received other detailed theme setting information and enter the created new theme practice chat room. In this case, the theme practice chat room creation may be performed in the terminal 100 that is performing a subscription function in advance or in the terminal 100 that has paid a preset usage amount for each topic to create the theme practice chat room. In addition, the terminal 100 displays the waiting screen according to the entry into the chat room. Here, the waiting screen includes the type of the corresponding chat room, the topic, the chat room name, the keyword, the nickname (or chat name) of the user in the corresponding chat room, the chat temperature, and the number of chats (or the number of times the user has participated in the chat room), etc. In this case, the chat temperature may be calculated based on the number of chats, the received evaluation results, etc., and the concept of level or points may be applied instead of the chat temperature. That is, for the level or points, the level or the preset number of points may be calculated according to a plurality of preset grades based on the number of chats, the received evaluation results, etc.

The embodiment of the present invention mainly describes the creation of the corresponding free theme practice chat room or discussion theme practice chat room in the terminal 100, but is not limited thereto. The expert terminal 300 may also create the free theme practice chat room or the discussion theme practice chat room and invite the corresponding terminal 100.

In this way, the terminal 100 may provide a place to practice for people who are particularly nervous in specific situations to overcome anxiety and to respond quickly and flexibly through the theme practice chat room to intensively create the specific situations (e.g., including interviews, company dinners, blind dates, etc.) and practice quick and appropriate responses.

In addition, in this way, the terminal 100 may create the topic talk chat room, the role-playing chat room, the theme practice chat room, etc., according to the user request of the terminal 100.

When the chat function is being performed in the chat room created in this way, other general users cannot use the spectator mode for the chat room in which the chat function is being performed, and only an expert who has set up the counseling function in advance in relation to the specific user participating in the corresponding chat room may be allowed to use the spectator mode to perform the monitoring functions for that specific user.

That is, the present invention is intended to provide a service with the purpose of exposure training, which may be said to be the most important cognitive behavior therapy program for social anxiety disorder, and is configured to give all users the right to participate in a chat room and share their thoughts or opinions with anonymous others and disable a spectator mode for general users in order to provide an opportunity to actively participate in the chat. This prevents people from just watching what other users do and talk about in the chat room, allows them to participate directly, and enables users who feel anxious about giving presentations or talking to people to perform chats through an anonymous avatar so that they may overcome this anxiety as much as possible.

However, when the psychological counselor, the speech lesson expert, or the mentor (or mentor expert) is performing the counseling with the client (or user), the state of being able to spectate the chat may only be allowed when the client needs to observe, diagnose, and train the appearance of the chat through the chat with other users.

In addition, when the terminal 100 participates in the topic talk chat room, the role-playing chat room, the theme practice chat room, etc., the terminal 100 performs the chat function with other users in a similar state (or at a similar level) as the user based on the self-diagnosis results for the user of the terminal 100 according to the artificial intelligence in the server 200.

In addition, when a preset home menu is selected from the app execution result screen displayed on the terminal 100, the terminal 100 displays a preset home screen (or initial screen).

In addition, when the preset people diary menu is selected from the app execution result screen displayed on the terminal 100, the terminal 100 displays the people diary screen corresponding to the selected people diary menu to write the emotional state by date related to the user. Here, the people diary screen includes a date selection menu for selecting a date, when there is a pre-stored memo (or diary/emotional record content) corresponding to the activated (or selected) date, a memo content display area (or memo content display menu) for displaying the corresponding memo content, a detailed emotional record menu for recording detailed emotions, a simple record menu for simply recording emotions, a calendar menu for confirming an emotional record state by date, etc. In this case, the current date (or today's date) in the corresponding terminal 100 may be displayed by default in the date selection item.

In this way, in the case of a general user who does not have social anxiety disorder, the terminal 100 may be configured to write his or her normal schedule (e.g., including time, location, activity details, etc.) and to be used for scheduler purposes through the corresponding people diary (or people diary function/people screen).

In this case, there are in-session exposure and cognitive reconstruction among the most important treatment protocols when treating people with social anxiety disorder, and in the case of the in-session exposure, the terminal 100 may be configured to enable treatment and training using the chat function of the present invention.

In addition, the cognitive reconstruction process explores how users (or patients) cope with situations they face in reality, what automatic thoughts they have, and what cognitive errors they make, and represents leading to new rational responses with the help of experts, and since people with social anxiety usually have characteristics such as negative thinking, behavior that causes errors in thinking, distorted thinking and anxiety, may record "How you behaved in situations you faced in real life," "What emotions you had and how you expressed them," activities, emotional state, etc., so they can apply it themselves as a cognitive reconstruction activity.

For example, the terminal 100 may perform recording so that a user can think once more about what automatic thoughts they have about a situation, whether they understood their emotions and expressed them or not, and what their rational response is through questions such as "Where have you been?" "With whom? "What activities?" "How did you feel? "What emotions did you feel?" "How much emotion did you express?" recording emotions, and "How much emotions were expressed." Above all, when the client later receives counseling with an expert based on people diary records, with the expert's permission, it may be organized so that the expert may explore negative automatic thoughts together and help the client with cognitive reconstruction training to enable the rational thinking.

In addition, the cognitive reconstruction process of the present invention may be performed (or managed) for each user by the learning through the artificial intelligence.

In addition, after a specific date is selected from the people diary screen displayed on the terminal 100 according to the user input (or user selection/touch/control) of the terminal 100, when the preset detailed emotional record menu is selected, the terminal 100 displays a detailed emotional record screen corresponding to the selected detailed emotional record menu. Here, the detailed emotional record screen includes a date selection item for selecting a date, a situation selection item for selecting a specific situation, an emotion selection item for selecting an emotional state felt by a user in relation to the specific situation, a review selection item related to a user's regrets and future resolutions in relation to the specific situation, etc. In addition, examples of the situation selection item include a "Who were you with today?" item (e.g., including family, a date/lover, a friend, work/a coworker, school, a senior/junior, others, etc.) for selecting who on was with, a "What did they do?" item (e.g., including affirmative items such as "They complimented me," "They empathized with me," "They comforted me," "They gave me advice, and "They respected me," negative items such as "They ignored me, "They were annoyed, "They were upset, "They were angry, and "We argued," etc.) for selecting what action the counterpart did, a "What action did I take?" item for selecting what action one took oneself (e.g., including affirmative items such as "I were considerate," "I apologized," "I acknowledged it," "I supported them," and "I helped them," negative items such as "I was embarrassed," "I was rambling," "I was having a hard time," "I was silent," "I could not do anything," and "I forced a smile," etc.), etc. In addition, examples of the emotion selection item include a "How did I feel at that time?" item (e.g., including happiness, joy, vitality, confidence, courage, spirit, gratitude, appreciation, passion, inspiration, ecstasy, love, anger/fury, irritation, disbelief, displeasure, disappointment, sadness/depression, anxiety, exhausted, fatigue, frustration, nothingness, etc.) for selecting how the user felt in a corresponding situation, a "Did you express that feeling?" item (e.g., including not expressed, expressed a little, expressed actively, etc.) for selecting whether the user expressed the emotion they felt, a "OO is currently a '~~~' person to me" item (e.g., including affirmative items such as reliable, cute, lovely, and kind, neutral items such as mediocre and average, and negative items such as bad and disgusting, etc.) for selecting how one currently feel about one's counterpart, etc. In addition, the review selection item includes a "Did you feel comfortable talking to that person?" item (e.g., including very uncomfortable, uncomfortable, average, comfortable, very comfortable, etc.) for selecting one's comfort level when talking to a counterpart, a "What do you want to do in the future?" item for selecting one's regrets or future resolutions, a "Please write your own memo to record the situation in more detail at that time," item, etc.

In this case, when there is detailed emotional record information or simple emotional record information pre-stored in relation to the selected specific date, the terminal 100 may display a detailed emotional record screen including the pre-stored detailed emotional record information in relation to the specific date, or a simple emotional record screen including pre-stored simple emotional record information in relation to the corresponding specific date. Here, when there is simple emotional record information in relation to the selected specific date, the terminal 100 may display an emotional record status screen that further includes a detailed emotional record menu so that the detailed emotions may be recorded for the simple emotional record information along with the simple emotional record information pre-stored in relation to the specific date. In addition, when the detailed emotional record menu displayed on the emotional record status screen is selected, the terminal 100 may display the detailed emotional record screen instead of the simple emotional record information pre-stored in relation to the specific date so that detailed emotion may be recorded, and receive the detailed emotional record information according to the user input.

The embodiment of the present invention describes that, after the date is selected on the people diary screen, when the detailed emotional record menu is selected, the terminal 100 displays the detailed emotional record screen corresponding to the selected detailed emotional record menu in relation to the selected date, but is not limited thereto. When the detailed emotional record menu is selected from the people diary screen, the terminal 100 may display the detailed emotional record screen corresponding to the selected detailed emotional record menu with the current date as the default. In this case, the date displayed on the detailed emotional record screen may be modified to a different date depending on the user input.

In addition, the terminal 100 receives detailed emotional record information including a plurality of input values corresponding to the plurality of input items related to the emotion felt by the user in a specific situation on the previously selected specific date (or specific date) according to the user input of the terminal 100 from the detailed emotional record screen displayed on the terminal 100. Here, the detailed emotional record information includes date information, situation information (e.g., including who else was there, other people's behaviors, one's own behaviors, etc.), and emotional information (e.g., including one's emotional state, whether emotions were expressed, one's current emotions, etc.), review information (e.g., level of comfort in chat, future resolutions, memos for oneself, etc.), etc.

In addition, the terminal 100 is linked with the server 200 to map (or match/link) the received detailed emotional record information with the user information of the terminal 100 and stores (or registers/manages) the mapped information in the corresponding server 200.

That is, the terminal 100 transmits the received detailed emotional record information, the emotional record storage request information, the identification information of the terminal 100, etc., to the server 200. Here, the identification information of the terminal 100 includes a mobile directory number (MDN), mobile Internet protocol (IP), mobile media access control (MAC), subscriber identification module (SIM) card unique information, a serial number, etc.

In addition, the terminal 100 updates and displays the people diary screen related to the corresponding specific date.

That is, the terminal 100 displays the people diary screen to which the detailed emotional record information is applied (or reflected) on the corresponding specific date.

In addition, after a specific date is selected from the people diary screen displayed on the terminal 100 according to the user input (or user selection/touch/control) of the terminal 100, when the preset simple record menu is selected, the terminal 100 displays a simple emotional record screen corresponding to the selected simple record menu. Here, the simple emotional record screen includes a date selection item for selecting a date, a situation description input item for inputting information about who did what and with whom, a mental state item (e.g., uncomfortable, average, comfortable, other, etc.) for selecting what one's state of mind was, etc.

The embodiment of the present invention describes that, after the date is selected on the people diary screen, when the simple record menu is selected, the terminal 100 displays the simple emotional recording screen corresponding to the selected simple record menu in relation to the selected date, but is not limited thereto. When the simple record menu is selected on the people diary screen, the terminal 100 may display the simple emotional recording screen corresponding to the selected simple recording menu with the current date as the default. In this case, the date displayed on the simple emotional record screen may be modified to another date according to the user input.

In addition, the simple emotional record information including a plurality of other input values corresponding to the plurality of other input items related to the emotions felt by the user in a specific situation on the specific date (or specific date) previously selected according to the user input of the terminal 100 on the simple emotional recording screen displayed on the terminal 100 is received. Here, the simple emotional record information includes date information, situation description information (e.g., including who else was there, activity details, etc.), mental state information, etc.

In addition, the terminal 100 is linked with the server 200 to map (or match/link) the received simple emotional record information with the user information of the terminal 100 and stores the mapped information in the corresponding server 200 (or registration/management).

That is, the terminal 100 transmits the received simple emotional record information, the other emotional record storage request information, the identification information of the terminal 100, etc., to the server 200.

In addition, the terminal 100 updates and displays the people diary screen related to the specific date.

That is, the terminal 100 displays the people diary screen to which the simple emotional record information is applied (or reflected) on the corresponding specific date.

An embodiment of the present invention describes that, when the people diary menu is selected from the app execution result screen displayed on the terminal 100, the terminal 100 displays the people diary screen including the detailed emotional record menu and the simple record menu in response to the selected people diary menu, but is not limited thereto. When the people diary menu is selected from the app execution result screen, the terminal 100 may display the detailed emotional record screen corresponding to the detailed emotional record menu set by default in response to the selected people diary menu.

In addition, the embodiment of the present invention mainly describes registering one piece of detailed emotional record information or simple emotional record information on the same date, but is not limited thereto, and the terminal 100 may register a plurality of pieces of detailed emotional record information and simple emotional record information on the same date.

In addition, when a preset calendar menu is selected from the people diary screen displayed on the terminal 100, the terminal 100 displays a calendar screen including an emotional record state by date corresponding to the selected calendar menu to display an emotional record state by date. Here, when the emotional record information (including detailed emotional record information, simple emotional record information, etc.) has been stored on the specific date, the calendar screen includes emotional record states such as images (or emoticons/avatars) representing feeling comfortable, normal, uncomfortable, etc., corresponding to mental state information, which is some of the information within the corresponding emotional record information on the corresponding specific date.

In addition, when a preset "my report" menu is selected from the app execution result screen displayed on the terminal 100, to provide the analysis results and participation list related to the chat room in which the user of the terminal 100 participates or provide the participation list and cognitive behavior therapy record related to the chat room in which the user of the terminal 100 participates with the expert, the terminal 100 displays the "my report" screen corresponding to the selected "my report" menu. Here, the "my report" screen includes an edit item for screen editing, a search item for searching for the chat room corresponding to the search word, a notification item for confirming notices or notification messages, etc., a "my page" item (or setting item) for setting user information or dedicated app functions, etc., a user-to-user item for providing analysis results based on the performance of functions such as topic talk, role-playing, and theme practice in relation to the user of the terminal or a participation list related to the chat list in which the user participates, an expert interaction item for providing a cognitive behavior therapy record, which is a list or feedback from the expert performing the psychological counseling function, the speech lesson function, or the mentoring function with an expert in relation to a specific topic or situation, a content display item (or content display area) for displaying the detailed information according to the user-to-user item or expert interaction item selection, etc. In addition, the user-to-user item (or user-to-user tab) includes an analysis result item for providing analysis results according to the performance of functions such as topic talk, role-playing, and theme practice in relation to the user of the terminal 100, a participation list item for providing a participation list related to the chat list in which the user participates, etc. In addition, the expert interaction item (or expert interaction tab) includes a participation list item for providing a list of people who have performed a psychological counseling function, a speech lesson function, or a mentoring function with an expert in relation to a specific topic or situation, a cognitive behavior therapy record item for providing expert feedback based on performance of a training function on appropriate chat room methods in relation to the specific topic or situation, etc.

In addition, when an analysis result item within a preset user-to-user item is selected from the "my report" screen displayed on the terminal 100, the terminal 100 displays the detailed information corresponding to the selected analysis result menu in the content display area to provide analysis results according to the performance of chat functions such as topic talk, role-playing, and theme practice in relation to the user of the terminal 100. In this case, when the preset "my report" menu is selected from the app execution result screen displayed on the corresponding terminal 100, the terminal 100 may display, by default, an analysis result screen (or the detailed information) corresponding to the analysis result item within the item among users set as default in response to the selected "my report" menu in the content display area. Here, the analysis result item (or the analysis result screen/detailed information) includes a sort item for sorting functions related to all, topic talk, role-playing, theme practice, etc., a "number of times you've participated in the chat room" display item for displaying the number of times the user has participated in the chat room within a preset period, a period display item for displaying the corresponding preset period, a "number of times you've participated in the chat room by category" display item for displaying the number of times the user has participated in the chat room by category, a "free expression" index display item for displaying the "free expression" index calculated in relation to the user, an anxiety index display item for displaying the anxiety index calculated in relation to the user, a detailed score view item for displaying additional detailed information in relation to the "free expression" index or the anxiety index, a relative evaluation display item for displaying information on oneself as evaluated by other users who performed the chat function together, a "my 'free expression' score aspect" display item for displaying the "free expression" score aspect, a "my anxiety score pattern" display item for displaying the user's anxiety score pattern, a "my confidence/assertiveness, mind control, communication skills/logic/persuasive power, immersion, empathy/listening skills score aspect" display item for displaying the user's confidence/assertiveness, mind control, communication skills/logic/persuasive power, immersion, empathy/listening skills score aspect, a "topic I have practiced a lot" display item for displaying a topic that the user has practiced a lot in relation to the topic talk, a "keyword that I have practiced a lot" display item for displaying keywords that the user has practiced a lot in relation to the topic talk, a "target I've practiced a lot" display item for displaying what the user has practiced a lot in relation to role-playing, a "situation I've practiced a lot" display item for displaying situations in which the user has practiced a lot in relation to role-playing, a "What emotions am I sensitive to?" display item for displaying what emotions the user is sensitive to in relation to role-playing, a "Which experts I have practiced with a lot?" display item for a displaying indicating with which experts the user has practiced a lot in relation to the theme, a "theme I practiced a lot" display item for displaying a theme that the user has practiced a lot in relation to theme practice, etc. Here, the "free expression" index display item includes an overall rating display item, a "free expression" index overall average display item, a satisfaction graph display item for overall average, a "free expression" index change graph display item by day of the week, a score display item for each item (e.g., including confidence/assertiveness, mind control, communication skills/logic/persuasive power, immersion, empathy/listening skills, etc.), a graph display item of a score change for each item by day of the week, an exponential distribution display item for each topic and situation, a detailed score view item, etc. In addition, the anxiety index display item includes a total rating display item, an anxiety index overall average display item, an anxiety graph display item for the overall average, a graph display item of an anxiety index change by day of the week, etc. In this case, the "free expression" index can be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates. In addition, the anxiety index represents the average value of the anxiety self-evaluated by the user after performing the chat function in the chat room (e.g., including the topic talk chat room, the role-playing chat room, the theme practice chat room, etc.) in which the user participates in relation to one or more chat rooms in which the user of the corresponding terminal 100 participates for a preset period or all chat rooms in which the user of the corresponding terminal 100 participates. In addition, examples of the relative evaluation display item include the reason for receiving a good evaluation, the reason for receiving a bad evaluation, and the satisfaction of chat evaluated by others. In addition, examples of the "my 'free expression' score aspect" display item include a "How many people am I with when my free expression score gets high?" item, a "What age group of people am I talking with when I have a high score in 'free expression'?" item, a "What MBTI type am I talking with when I have a high score in 'free expression'?" item, a "What gender is the person I'm talking with when I have a high score in 'free expression'?" item, a "When I talk in a certain place, do I have a high score in free expression?" item, etc. In addition, the "my anxiety score aspect" display item includes a "How many people am I with when my anxiety score gets high?" item, a "What age group of people am I talking with when I have a high score in anxiety?" item, a "What MBTI type am I talking with when I have a high score in anxiety?" item, a "What gender is the person I'm talking with when I have a high score in anxiety?" item, a "When I talk in a certain place, do I have a high score in anxiety?" item, etc. In addition, examples of the "topic that I have practiced a lot" display item include an interpersonal relationship item, a daily life item, an employment/workplace item, a knowledge sharing item, a well-being item, other items, etc. In addition, examples of the "keyword that I have practiced a lot" display item include a boss item, a soccer item, a job preparation item, a presentation preparation item, a health item, other items, etc. In addition, examples of the "target that I have practiced a lot" display item include a husband item, a boss item, a coworker item, a chairman item, a stranger item, other items, etc. In addition, examples of the "situation that I have practiced a lot" display item include a rejection expression item, an affection expression item, an opinion expression item, a gratitude/sorry expression item, a conflict item, other items, etc. In addition, examples of the "What emotions am I sensitive to?" display item include a joy/pleasure item, an empathy item, an appreciation item, a sorry item, a grief/hurt item, an anger/annoyance/rage item, etc. In addition, examples of the "Which experts I have practiced with a lot?" display item include a psychological counselor item, a speech trainer item, a mentor item, etc. In addition, examples of the "theme that I practiced a lot" display item include a blind date item, a phone item, an interview item, a business report item, a small-scale presentation item, a large-scale presentation item, a professional discussion item, a pros and cons discussion item, etc.

In addition, when a preset detailed score view item is selected from the detailed information included in the content display area displayed on the terminal 100, the terminal 100 is linked with the server 200 to display detailed score information corresponding to the selected detailed score view item. Here, the detailed score information (or detailed score screen) includes the sort items for sorting functions related to all, topic talk, role-playing, theme practice, etc., the "number of times you've participated in the chat room" display item, the period display item for displaying the corresponding preset period, the "number of times you've participated in the chat room for each category" display item, the "free expression" index display item, the anxiety index display item, the relative evaluation display item, the "my 'free expression' score aspect" display item, the "my anxiety score aspect" display item, the "my confidence/assertiveness, mind control, communication skills/logic/persuasive power, immersion, empathy/listening skills score pattern" display item, the "topic I have practiced a lot" display item, the "keyword that I have practiced a lot" display item, the "target that I have practiced a lot" display item, the "situation that I have practiced a lot" display item, the "Which emotions I am sensitive to?" display item, the "Which experts have I practiced with a lot?" display item, the "theme which I have practiced a lot" display item, etc. In this case, when the detailed score view item related to the "free expression" index is selected, the terminal 100 may display one or more pieces of information related to the "free expression" index among the information included in the detailed score information, and when the detailed score view item related to the anxiety index is selected, the terminal 100 may mainly display one or more other pieces of information related to the anxiety index among the information included in the detailed score information.

That is, when a preset detailed score view item is selected from the detailed information included in the content display area displayed on the terminal 100, the terminal 100 is linked with the server 200 to display the detailed score information corresponding to the selected detailed score view item instead of the "free expression" index display item or anxiety index display item displayed previously.

In addition, when a preset period display item (or date selection item/calendar item) is selected from the "my report" screen displayed on the terminal 100, the terminal 100 displays a calendar screen corresponding to the selected period. Here, the calendar screen includes information on the presence or absence of chat records by date recorded by the user of the terminal 100 within the corresponding period (or corresponding month).

In addition, when a specific date within the calendar screen is selected, if the chat record exists on the corresponding specific date, the terminal 100 displays detailed score information related to the chat record, and if no chat record exists on the corresponding specific date, the terminal 100 displays information indicating that no chat record exists.

In addition, when the participation list item in the preset user-to-user item is selected from the my report screen displayed on the terminal 100, the terminal 100 displays a participation list screen corresponding to the selected participation list item to provide a participation list related to the chat list in which the user of the terminal 100 participates. Here, the participation list screen includes a sort item for sorting functions related to all, topic talk, role-playing, theme practice, etc., a change information display item for providing information on changes in self-evaluation results or other's evaluation results compared to a preset period (or last week), a "number of times you've participated in the chat room" display item for displaying the number of times the user has participated in the chat room within a preset period, an information display item for each chat participation case for providing information related to topic talk, role-playing, theme practice, etc., in which the user participates, etc. In this case, the information display item for each chat participation includes a date information display item of participation in the chat room, a detail view item for displaying the detailed information, a chat room type (or chat room category) display item (e.g., including topic talk, role-playing, theme practice, etc.) for displaying the type of chat room in which the user participates, a chat room topic display item for displaying the topic of the chat room, a chat room name display item for displaying the room title (or chat room name) of the chat room, a keyword display item for displaying the main keywords/hashtags related to the corresponding chat room, a self-evaluation information display item for displaying the self-evaluation results, a received evaluation information display item for displaying the evaluation information received from other users participating in the corresponding chat room, a chat recording display item for the re-listening function of chat content from the chat room, etc.

In addition, when a specific participation list (or a detail view item displayed on one side of the corresponding specific participation list) is selected from one or more participation lists displayed in the information display items for each chat participation in the participation list screen displayed on the terminal 100, the terminal 100 is linked with the server 200 to display the detailed view information related to the selected specific participation list. Here, the detailed view information includes a date information display item of participation in the chat room corresponding to the selected specific participation list, a chat room type (or chat room category) display item for displaying the type of chat room in which the user participates (e.g., including a topic talk chat room, a role-playing chat room, a theme practice chat room, etc.), a chat room topic display item for displaying the topic of the chat room, a chat room name display item for displaying the room title of the chat room, a keyword display item for displaying main keywords/hashtags related to the chat room, a chat participant information display item for displaying information (e.g., including nicknames) of other users participating in the corresponding chat room, a self-evaluation result display item (or self-evaluation information display item) for displaying self-evaluation results, a received evaluation result display item (or a received evaluation information display item) for displaying evaluation results received from other users participating in the chat room, a chat recording display item for re-listening to chat content from the chat room, etc.

In addition, when the participation list item (or other participation list items) in the preset expert interaction item is selected from the "my report" screen displayed on the terminal 100, the terminal 100 displays other participation list screens corresponding to the selected participation list item to provide other participation lists in which the user of the terminal 100 performs a counseling function, a speech lesson function, a mentoring function, etc., with an expert. Here, the other participation list screens include other sort items for sorting functions related to all, psychological counseling, speech, mentoring, etc., other change information display items for providing information on changes in the number of counseling sessions or the number of chat training sessions with an expert or changes of a cognitive behavior therapy record compared to a preset period (or last week), other "number of times you've participated in the chat room" display items for displaying the number of times the user has participated in the chat room within a preset period, an information display item for each expert chat participation case for providing information related to psychological counseling, speech, mentoring, etc. in which the user participates, etc. In this case, examples of the information display item for each expert chat participation case include other chat room type (or chat room category) display items for displaying the type of chat room in which the user participates (e.g., including psychological counseling, speech, mentoring, etc.), another chat room topic display item for displaying the topic of the chat room, a detail view item for displaying detailed information, an expert information display item for displaying an expert's photo and name, a counseling date display item for displaying a counseling date, other keyword display items for displaying main keywords/hashtags related to the corresponding chat room, an expert feedback item for providing expert feedback, a cognitive behavior therapy record sheet item for providing a cognitive behavior therapy record sheet, a written questionnaire item for providing questionnaire content written by a user, a chat room training display item for displaying chat room training content, etc.

In addition, when other specific participation lists (or detail view item displayed on one side of the corresponding other specific participation lists) are selected from one or more other participation lists being displayed in the information display items for each expert participation in other participation list screens displayed on the terminal 100, the terminal 100 is linked with the server 200 to display the detailed information related to the selected other specific participation lists. Here, the detailed information (or detailed counseling result item screen) includes other chat room type (or chat room categories) display items for displaying the types of chat rooms (e.g., including psychological counseling, speech, mentoring, etc.) in relation to the other specific participation lists, other chat room topic display items for displaying the topic of the chat room, an expert information display item for displaying the expert's photo and name, a counseling date display item for displaying the counseling date, other keyword display items for displaying the main keywords/hashtags related to the corresponding chat room, an expert feedback display item for displaying the expert feedback, a cognitive behavior therapy record sheet item for providing the cognitive behavior therapy record sheet before and after training, a questionnaire item written during counseling for providing the type and results of the questionnaire written by the user, a chat room participation record display item for providing the chat room participation record, etc. In this case, the questionnaire item written during counseling may include various types of tests (or questionnaires) such as a self-esteem self-diagnosis test, a communication type test, an anxiety test, etc. In addition, examples of the chat room participation record display item include a date information display item of participation in the chat room, an expert state item for displaying whether the expert is participating in training or observing the expert, a chat room type (or chat room category) display item for displaying the type of chat rooms (e.g., including a topic talk chat room, a role-playing chat room, a theme practice chat room, etc.) in which the user participates, a chat room topic display item for displaying the topic of the chat room, a chat room name display item for displaying the room title of the chat room, a chat participant information display item for displaying information (e.g., including nicknames) of other users participating in the corresponding chat room, a self-evaluation result display item (or self-evaluation information display item) for displaying the self-evaluation results, a received evaluation result display item (or received evaluation information display item) for displaying the evaluation results received from other users participating in the corresponding chat room, a chat recording display item for the re-listening function of the chat content from the chat room, etc.

In addition, when the cognitive behavior therapy record item in the preset expert interaction item is selected from the "my report" screen displayed on the terminal 100, to provide expert feedback according to the user of the terminal 100 performing a training function on an appropriate chat room type in relation to a specific topic or situation, the terminal 100 displays the cognitive behavior therapy record screen corresponding to the selected cognitive behavior therapy record item. Here, the cognitive behavior therapy record screen (or cognitive behavior therapy record sheet screen) includes a cognitive behavior therapy record information display item for each chat participation for writing (or providing) a cognitive behavior therapy record before and after training in relation to a specific topic or situation in which the user participates, a new cognitive behavior therapy record sheet writing item for writing a new cognitive behavior therapy record sheet, etc. In addition, examples of the cognitive behavior therapy record information display item for each chat participation include a cognitive behavior therapy record sheet title display item for displaying a title, a writing and modification item for writing or editing a non-written cognitive behavior therapy record, a result view item for displaying the written cognitive behavior therapy record results, a record date display item for displaying a date the cognitive behavior therapy record is written, a record sheet progress display item for displaying record sheet progress before/after training, a confirmed expert display item for displaying an expert who has confirmed a cognitive behavior therapy record sheet written by a user, etc.

The cognitive behavior therapy record sheet (or "free expression" cognitive behavior therapy record sheet) described in the present invention is self-recorded by the user for the period of counseling and/or training with the psychological counselor, and is a record sheet that aims to help better understand one's own and others' actions and motivations, learn professional problem-solving skills to deal with them, and develop confidence in oneself and one's abilities, and may be written (or recorded/edited/created) both before and after training.

In addition, when the writing and modification item displayed on one side of the specific cognitive behavior therapy record is selected from among one or more cognitive behavior therapy record items displayed in the cognitive behavior therapy record information display item for each chat participation in the cognitive behavior therapy record screen displayed on the terminal 100, the terminal 100 is linked with the server 200 to display the cognitive behavior therapy record input screen corresponding to the selected writing and modification item to edit the cognitive behavior therapy record information related to the selected specific cognitive behavior therapy record. Here, in the case of the pre-training, the cognitive behavior therapy record input screen includes the "What are situations that make you anxious?" item, the "How are you feeling at this time" item (e.g., including anger/fury, irritation, disbelief, discomfort, disappointment, sadness/depression, anxiety, tiredness, fatigue, frustration, bitterness, remorse, jealousy, shame, embarrassment, despondence, outrage, panic, isolation, loneliness, boredom, etc.), the "What are your thoughts in that situation?" item (e.g., including a confidence level, a cognitive error, etc.), the "please correct my wrong thoughts" item (or reasonable response finding item), the behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, the cognitive behavior therapy record input screen after training includes a "Please display any area that has improved slightly through training" item (e.g., an improvement-related item, an anxiety-related item, etc.), a "What actually happened related to an area I was worried about before training?" item, a "Please re-evaluate your thoughts before training" item, a "how I feel now" selection item (e.g. happiness, joy, vitality, confidence, courage, spirit, gratitude, appreciation, passion, inspiration, ecstasy, love, anger/rage, irritation, disbelief, displeasure, disappointment, sadness/depression, anxiety, tiredness, fatigue, frustration, etc.), a "What did you learn?" item, etc.

In addition, the terminal 100 receives a plurality of input values corresponding to the plurality of input items included in the cognitive behavior therapy record input screen displayed on the terminal 100 according to the user input. Here, the plurality of input values include the input values before training (e.g., including "What are situations that make you anxious?" content, "How are you feeling at this time" content, "What are your thoughts in that situation?" content, "Please correct my wrong thoughts" content, behavioral goal setting content etc.), the input values after training (e.g., "Please display any area that has improved slightly through training" content, "What actually happened related to an area I was worried about before training?" content, "Please re-evaluate your thoughts before training" content, "how I feel now" content, "What did you learn?" content, etc.).

In addition, the terminal 100 is linked with the server 200 to apply the plurality of received input values to the user information of the terminal 100 and the cognitive behavior therapy record information related to the specific cognitive behavior therapy record case and display the cognitive behavior therapy record screen in the state in which the plurality of input values are applied (or updated).

In addition, when the item for writing a new cognitive behavior therapy record sheet in the cognitive behavior therapy record screen displayed on the terminal 100 is selected, the terminal 100 is linked with the server 200 to display a new cognitive behavior therapy record sheet writing screen corresponding to the selected new cognitive behavior therapy record sheet writing item. Here, the new cognitive behavior therapy record sheet creation screen includes a cognitive behavior therapy record sheet title input item for inputting the cognitive behavior therapy record sheet title, a pre-training or post-training item for selecting pre/post-training, a pre-training input item (e.g., including "What are situations that make you anxious?" "How are you feeling at this time?" "What are your thoughts in that situation?" "Please correct my wrong thoughts," "Please set action goal," etc.), a post-training input item (e.g., including "Please display any area that has improved slightly through training," "What actually happened in relation to an area I was worried about before training?" "Please re-evaluate your thoughts before training," "How do you feel now?" "What have you learned?" etc.) etc.

In addition, the terminal 100 receives a plurality of other input values corresponding to the plurality of other input items included in the new cognitive behavior therapy record input screen displayed on the terminal 100 according to the user input. Here, the plurality of other input values include the cognitive behavior therapy record sheet title, the input values before training (e.g., including "What are situations that make you anxious?" content, "How are you feeling at this time" content, "What are your thoughts in that situation?" content, "Please correct my wrong thoughts" content, behavioral goal setting content, etc.), the input values after training (e.g., "Please display any area that has improved slightly through training" content, "What actually happened related to an area I was worried about before training" content, "Please re-evaluate your thoughts before training" content, "how I feel now" content, "What did you learn?" content, etc.).

In addition, the terminal 100 is linked with the server 200 to generate the new cognitive behavior therapy record related to the user (or user information) of the terminal 100 based on the plurality of received different input values, apply the plurality of received different input values to the cognitive behavior therapy record information related to the generated new cognitive behavior therapy record case, and display the cognitive behavior therapy record screen in the state in which the plurality of different input values are applied.

In addition, when a chat room related to any one topic talk is selected from one or more chat rooms related to the topic talk displayed in the preset chat room display area among the app execution result screen displayed on the corresponding terminal 100, the terminal 100 is linked with the server 200 to enter (or participate in) the chat room related to the selected topic talk. In this case, the terminal 100 displays the waiting screen according to the entry into the chat room. Here, the waiting screen includes the type of the corresponding chat room, the topic, the chat room name, the keyword (or hashtag), the nickname (or chat name) of the user who enters the corresponding chat room, the chat temperature, and the number of chats (or the number of times the user has participated in the chat room), etc. In this case, the chat temperature may be calculated based on the number of chats, the received evaluation results, etc., and the concept of level or points may be applied instead of the chat temperature. That is, for the level or point, the level or the preset number of points may be calculated according to a plurality of preset grades based on the number of chats, the received evaluation results, etc.

For example, the chat temperature may increase by 0.5° C. per chat to a preset standard value (e.g., 36.5° C.), and when the received evaluation result is affirmative evaluation/satisfactory, the chat temperature may increase by 0.5° C., and when the received evaluation result is negative/not good, the chat temperature may decrease by 0.5·C.

In addition, the concept of level or points may be applied instead of the chat temperature. That is, for the level or point, the level or the preset number of points may be calculated according to a plurality of preset grades based on the number of chats, the received evaluation results, etc.

In addition, when the room leader who opens the corresponding chat room selects the preset start menu while the number of people (or number of participants) set in the chat room related to the topic talk is met, the terminal 100 selects one or more keywords the user wants to say, one or more keywords the user wants to hear, one or more additional keywords, etc., according to the user selection of the terminal 100 from the screen for selecting the keyword that the user of the terminal 100 wants to say or hear.

People with social anxiety vary depending on the situation, but when most of these people talk to others, even if it is something that they know well, they may feel anxious just from chatting with others. However, people with social anxiety feel extreme anxiety about their own ignorance, how their stories will be viewed by others, and whether what they say will be evaluated negatively by others especially when talking about topics they do not know much about. Accordingly, if anxiety about chat persists, these people may become passive in everyday chat with other people, and if it gets worse, they may become isolated and unable to socialize with people at all.

Therefore, through the function provided by the present invention, it is possible to encourage these people to actively participate in chat with anonymous people as much as possible using characters (or avatars) without their faces being exposed.

In particular, when most people chat with others about a topic, to encourage participation and leadership in chat on topics they can speak about as much as possible, such as confidently showing off their knowledge or feeling the joy of sharing knowledge when it comes to topics these people know, the present invention provides "keywords I want to say."

In addition, by allowing people with social anxiety to choose keywords that they may say with as much confidence as possible to encourage participation and leadership in chat, the present invention provides "keywords I want to say."

In addition, in the case of "keyword I want to hear," it is "A topic you think is interesting, but you don't know anything about" or "A topic about which you have knowledge but are not sure about it and cannot speak confidently about it yourself." By selecting keywords about which one would like to hear the opinions and thoughts of others rather than one's own, they can naturally participate in the chat and ultimately be encouraged to share their thoughts and knowledge with others.

In addition, the terminal 100 is linked with the server 200 and one or more other terminals (not illustrated) owned by one or more other users in the chat room related to the topic talk, to perform the chat function related to the specific topic. In this case, the terminal 100 is linked with the server 200 and uses the avatar (or character) preset in the terminal 100 to change (or apply/reflect) and display the expression (e.g., including happiness, joy, excitement, passion, pleasure, frustration, outrage, sadness, surprise, pain, rage, etc.) of the corresponding avatar according to the analysis (e.g., including a change in a user's gaze, a change in facial expression, a voice tremor, a change in heart rate, etc.) of the psychological state of the corresponding user's voice and/or facial expression while the user of the terminal 100 is chatting.

That is, the terminal 100 sequentially targets a plurality of users (e.g., including the user of the terminal 100, other users of terminals, etc.) in the chat room related to the corresponding topic talk, and performs the chat function related to the topic and keyword of the corresponding chat room once sequentially (or under the control of the room leader).

In addition, the terminal 100 performs free talking (or a free talking chat function) with a plurality of users participating in the corresponding chat room for a preset time (e.g., including 2 minutes) according to the keywords (e.g., interpersonal relationships, junior management, company life, boss, career, office worker, company, stress, other/adding keyword, etc.) set by the room leader who creates the chat room related to the topic talk.

In this way, the terminal 100 may freely perform the chat function with other users in relation to the topic, the keyword, etc., in which the user of the terminal 100 is interested.

In addition, in relation to the chat room in which the terminal 100 is participating, when the subject or keyword of the corresponding chat room is not permitted according to social norms (e.g., including drugs, human trafficking, etc.), the reporting function for the corresponding chat room may also be performed.

The embodiment of the present invention mainly describes participating in the chat room related to the topic talk that has already been generated (or opened) in the terminal 100 and performing a chat function with other users, but is not limited thereto. When a preset room creation menu is selected from the app execution result screen displayed on the terminal 100, the terminal 100 may display the room creation screen corresponding to the selected room creation menu, receive room creation information including at least one input value corresponding to at least one other input item according to the user selection (or user input/touch/control) of the corresponding terminal 100 on the displayed room creation screen, and may be linked with the server 200 based on the received room creation information to create a new chat room related to the topic talk set by the user, and linked with other terminals owned by other users participating in the created chat room and the server 200 to perform chat functions for topic talk related to a specific topic.

In addition, when the topic talk (or topic talk chat function) related to the chat room ends, the terminal 100 is linked with the server 200 to perform a self-evaluation function for the user of the corresponding terminal 100 and a counterpart evaluation function for one or more other users participating in the corresponding chat room. Here, examples of the self-evaluation function include an evaluation function for an overall satisfaction item (e.g., including disappointed, average, satisfied, other, etc.) with one's chat, an anxiety item, a confidence/assertiveness item, a mind control item, a communication skills/logic/persuasive power item, an immersion item, an empathy/listening skills item, etc. In this case, the anxiety item, the confidence/assertiveness item, the mind control item, the communication skills/logic/persuasive power item, the immersion item, the empathy/listening skills item, etc., may be selected in a preset range (e.g., 0 to 100 points) depending on the user's selection. In addition, the counterpart evaluation function includes an evaluation function for a satisfaction item (e.g., including disappointed, average, satisfied, etc.) of overall chats by different users, other user-specific chat evaluation items (e.g., including "He doesn't seem anxious at all, he's confident and assertive," "He's good at controlling his emotions," "He's good at communicating logically," "He's good at immersing himself in the situation," "He listens well and has good empathy," etc.), etc.

That is, when the topic talk (or topic talk chat function) related to the chat room ends, the terminal 100 transmits the information related to the self-evaluation according to the user input of the terminal 100, receives the information, etc., related to counterpart evaluation of other users, and transmits the information related to the received self-evaluation, the information related to the received counterpart evaluation of other users, the identification information of the terminal 100, etc., to the server 200.

In addition, the terminal 100 receives the chat results related to the user of the corresponding terminal 100 according to the self-evaluation function and the counterpart evaluation function transmitted from the server 200 in response to information related to self-evaluation related to the previously transmitted topic talk, information related to counterpart evaluation, etc. Here, the chat result (or chat result information) includes a total average score item according to self-evaluation, an overall rating display item, an item for displaying scores (e.g., including an anxiety score, a confidence/assertiveness score, a mind control score, a communication skills/logic/persuasive power score, an immersion score, an empathy/listening skills score, etc.) for each self-evaluation item and an average score display item related to the topic talk, an evaluation item received according to the counterpart's evaluation, the number saves display item for displaying the number of times the chat content from the corresponding chat room can be saved (or downloaded), a chat recording storing item for storing the chat content, a chat time display item for displaying the total chat time in the corresponding chat room and the time the corresponding user spoke, a chat content output item for re-listening to the chat content in the corresponding chat room, etc. In addition, examples of the received evaluation item include the number of votes item received for each chat satisfaction item, the number of votes item received for each chat evaluation item, etc.

In addition, the terminal 100 displays (or outputs) the received chat results.

In addition, when a chat room related to any one role-playing is selected from one or more chat rooms related to the role-playing for the specific role (or situation) displayed in the preset chat room display area among the app execution result screen displayed on the corresponding terminal 100, the terminal 100 is linked with the server 200 to enter (or participate in) the chat room related to the selected role-playing. In this case, the terminal 100 displays the waiting screen according to the entry into the chat room. Here, the waiting screen includes the type of the corresponding chat room, the topic, the chat room name, the keyword (or hashtag), the nickname (or chat name) of the user in the corresponding chat room, the chat temperature, and the number of chats (or the number of times the user has participated in the chat room), etc. In this case, the chat temperature may be calculated based on the number of chats, the received evaluation results, etc., and the concept of level or points may be applied instead of the chat temperature. That is, for the level or points, the level or the preset number of points may be calculated according to a plurality of preset grades based on the number of chats, the received evaluation results, etc.

In addition, when the room leader who opened the corresponding chat room selects the preset start menu while the number of people (or the number of participants) set in the chat room related to the corresponding role-playing is met, the terminal 100 displays the my role description screen for confirming the description of the role of the user of the terminal 100 in the chat room related to the corresponding role-playing and the emotions felt by the user.

In addition, the terminal 100 is linked with one or more other terminals (not shown) owned by one or more other users in the chat room related to the role-playing and the server 200 to perform the chat function according to the role-playing while alternately performing the main and sub roles with the user and other users. In this case, when the chat view menu displayed on one side of the screen of the terminal 100 is selected to confirm the appropriate chat for the role while performing the chat function according to the performance of the main role or sub-role, the terminal 100 may display information (or lines/tips) on the related main role or sub-role on one side of the screen. In addition, the terminal 100 is linked with the server 200 and uses the avatar (or character) preset in the terminal 100 to change (or apply/reflect) and display the expression (e.g., including happiness, joy, excitement, passion, pleasure, frustration, outrage, sadness, surprise, pain, rage, etc.) of the corresponding avatar according to the analysis (e.g., including a change in a user's gaze, a change in facial expression, a voice tremor, a change in heart rate, etc.) of the psychological state of the corresponding user's voice and/or facial expression while the user of the terminal 100 is chatting.

That is, the terminal 100 sequentially targets a plurality of users (e.g., including the user of the terminal 100, other users of terminals, etc.) in the chat room related to the role-playing, and performs the chat function according to the main role and sub role of the corresponding chat room once sequentially (or under the control of the room leader). Here, the main role should directly answer (or deal with/respond to) to a given situation spontaneously without any set chat, and the sub-role is responsible for describing the corresponding situation description, confirming the answer of the user performing the main role, etc. In this case, the user performing the main role should answer questions on the "my role" description screen (e.g., including questions such as "How do you feel in this situation?" etc.) for confirming the description of the role and the emotion felt by the user, and the answer to this question may be used to identify the automatic thoughts in the cognitive reconstruction therapy, one of the cognitive behavior therapy programs, to evaluate the automatic thought. Here, the automatic thoughts represent (or mean) thoughts, ideas, etc., for interpreting the situation when suddenly faced with a certain situation.

In this way, the terminal 100 may freely perform the chat function with other users according to the role-playing in relation to the topic, the keyword, etc., in which the user of the terminal 100 is interested.

The embodiment of the present invention mainly describes participating in the chat room related to the role-playing that has already been generated (or opened) in the terminal 100 and performing a chat function with other users, but is not limited thereto. When a preset room creation menu is selected from the app execution result screen displayed on the terminal 100, the terminal 100 may display the room creation screen corresponding to the selected room creation menu, receive other room creation information including at least one other input value corresponding to at least one other input item according to the user selection (or user input/touch/control) of the corresponding terminal 100 on the displayed room creation screen, may be linked with the server 200 based on the received other room creation information to create a new chat room related to the role-playing set by the user, and linked with other terminals owned by other users participating in the created chat room and the server 200 to perform chat functions for role-playing related to specific roles.

In addition, when the chat room related to the role-playing is selected, after displaying the waiting screen including the type of chat room, the topic, the chat room name, the keyword, the nickname of the user entering the corresponding chat room, the chat temperature, the number of chats, etc., in the case where the start menu is selected while the number of people set in the chat room related to the role-playing is met, the embodiment of the present invention mainly describes that a "my role" description screen for confirming a description of the role of the user of the terminal 100 in the chat room related to the role-playing and the emotions felt by the user is displayed and the terminal 100 is linked with the server 200 and one or more other terminals owned by one or more other users entering the chat room related to the role-playing to perform the chat function according to the role playing while alternately performing main roles and sub roles with the user and other users, but is not limited thereto. After selecting the chat room related to the role-playing on the terminal 100 and displaying the waiting screen, the terminal 100 may be configured to set (or designate) a main role and a sub role for the user and one or more other users participating in the chat room related to the role-playing, respectively, under the control of the room leader (or other terminals owned by the room leader) who opens the chat room related to the corresponding role-playing, display a character introduction screen according to the set main role and sub role on the terminal 100 and the other terminals, respectively, display a short (or simple) situation description, and confirm the emotions of each user and then perform the chat function according to the role-playing according to the set main role and sub-role. In addition, after performing the chat function according to the role-playing according to the set main role and sub-role, the terminal 100 and the other terminals may be configured to perform the chat function according to the role-playing while alternately performing the main role and sub-role (or modifying the role) under the control of the room leader (or other terminals owned by the corresponding room leader).

In addition, when the role-playing (or role-playing chat function) related to the chat room ends, the terminal 100 is linked with the server 200 to perform a self-evaluation function for the user of the corresponding terminal 100 and a counterpart evaluation function for one or more other users participating in the corresponding chat room. Here, the self-evaluation function includes an evaluation function for overall satisfaction item (e.g., including disappointed, average, satisfied, other, etc.) with the user's chat, an anxiety item, a confidence/assertiveness item, a mind control item, a communication skills/logic/persuasive power item, an immersion item, an empathy/listening skills item, etc. In this case, the anxiety item, the confidence/assertiveness item, the mind control item, the communication skills/logic/persuasive power item, the immersion item, the empathy/listening skills item, etc., may be selected in a preset range (e.g., 0 to 100 points) depending on the user's selection. In addition, the counterpart evaluation function includes an evaluation function for a satisfaction item (e.g., including disappointed, average, satisfied, etc.) of overall chats by different users, other user-specific chat evaluation item (e.g., including "He doesn't seem anxious at all, he's confident and assertive, "He's good at controlling his emotions," "He's good at communicating logically," "He's good at immersing himself in the situation," "He listens well and has good empathy," etc.), etc.

That is, when the role-playing (or role-playing chat function) related to the chat room ends, the terminal 100 transmits the information related to the self-evaluation according to the user input of the terminal 100, receives the information, etc., related to counterpart evaluation of other users, and transmits the information related to the received self-evaluation, the information related to the received counterpart evaluation of other users, the identification information of the terminal 100, etc., to the server 200.

In addition, the terminal 100 receives other chat results related to the user according to the self-evaluation function and the counterpart evaluation function transmitted from the server 200 in response to information related to self-evaluation related to the previously transmitted role-playing, information related to counterpart evaluation, etc. Here, the other chat results (or other chat result information) include a situation description and scoring item for displaying one's initial feelings about the situation, a "my first emotion of how I felt about the situation" display item, a total average score item according to self-evaluation, an overall rating display item, an item for displaying scores (e.g., including an anxiety score, a confidence/assertiveness score, a mind control score, a communication skills/logic/persuasive power score, an immersion score, an empathy/listening skills score, etc.) for each self-evaluation item and an average score related to the corresponding role-playing, an evaluation item received according to the counterpart's evaluation, the number saves display item for displaying the number of times content from the corresponding chat room can be saved (or downloaded), a chat recording storing item for storing the corresponding chat content, a chat time display item for displaying a total chat time in the corresponding chat room and the time the user spoke, a chat content output item for re-listening to the chat content from the corresponding chat room, etc. In addition, the received evaluation item includes a number of votes item for each chat satisfaction item, a number of votes item for each chat evaluation item, etc.

In addition, the terminal 100 displays (or outputs) the other received chat results.

In addition, regarding the chat room related to the theme practice created in the terminal 100 in relation to the theme practice for a specific theme displayed in the preset chat room display area among the app execution result screen displayed on the terminal 100, when the room leader who opens the corresponding chat room selects the preset start menu while the number of people (or number of participants) set in the chat room related to the theme practice is met, the terminal 100 is linked with one or more other terminals (not shown) owned by one or more other users who have entered a chat room related to the theme practice and the server 200 to perform the chat function related to the specific theme (or topic) of the corresponding chat room. In this case, in the case where it is difficult to give an answer related to the theme while performing the chat function for the theme, when the tip menu displayed on one side of the screen of the terminal 100 is selected to check the tip, and the terminal 100 may display information (or a tip) on related themes on one side of the screen. In addition, the terminal 100 is linked with the server 200 and uses the avatar (or character) preset in the terminal 100 to change (or apply/reflect) and display the expression (e.g., including happiness, joy, excitement, passion, pleasure, frustration, outrage, sadness, surprise, pain, rage, etc.) of the corresponding avatar according to the analysis (e.g., including a change in a user's gaze, a change in facial expression, a voice tremor, a change in heart rate, etc.) of the psychological state of the corresponding user's voice and/or facial expression while the user of the terminal 100 is chatting.

That is, the terminal 100 sequentially targets a plurality of users (e.g., including the user of the terminal 100, other users of terminals, etc.) in the chat room related to the corresponding theme practice, and performs the chat function related to the theme of the corresponding chat room once sequentially (or under the control of the room leader). In this case, the terminal 100 may perform the chat function related to the corresponding theme without a spectator (or in a state without a spectator) on the chat room set as no spectator, or perform the chat function related to the corresponding theme with a spectator (or in a state having a spectator) on the chat room set as spectator according to the preset maximum number of spectators.

In this way, the terminal 100 may freely perform the chat function alone or with other users in relation to a specific theme in which the user of the terminal 100 appears to be interested.

The embodiment of the present invention mainly describes performing the chat function with other users participating in the chat room related to the theme practice generated (or opened) in the terminal 100, but is not limited thereto. When the chat room related to the theme practice is selected from one or more chat rooms related to the theme practice that has already been generated (or opened) displayed in the preset chat room display area within the app execution result screen displayed on the terminal 100, the terminal link may be linked with the server 200 to enter the chat room related to the selected theme practice and may be linked with other terminals (not illustrated) owned by other users entering the chat room related to the theme practice to perform the chat function.

In addition, when the theme practice (or theme practice chat function) related to the question-and-answer chat room ends, the terminal 100 is linked with the server 200 to perform the self-evaluation function for the user of the terminal 100. Here, the self-evaluation function includes an evaluation function for overall satisfaction item (e.g., including disappointed, average, satisfied, other, etc.) with the user's chat, an anxiety item, a confidence/assertiveness item, a mind control item, a communication skills/logic/persuasive power item, an immersion item, an empathy/listening skills item, etc. In this case, the anxiety item, the confidence/assertiveness item, the communication skills/logic/persuasive power item, the immersion item, the empathy/listening skills item, etc., may be selected in a preset range (e.g., 0 to 100 points) depending on the user's selection.

That is, when the theme practice (or theme practice chat function) related to the question-and-answer chat room ends, the terminal 100 receives the information related to the self-evaluation, etc., according to the user input of the terminal 100, and transmits the received information related to the self-evaluation, the identification information of the terminal 100, etc., to the server 200.

In addition, after the user of the terminal 100 performs the chat function through the theme practice with other users, when the theme practice (or theme practice chat function) related to the free theme chat room or the discussion theme chat room ends, the terminal 100 is linked with the server 200 to perform the self-evaluation function for the user of the terminal 100 and the counterpart evaluation function for one or more other users participating in the corresponding chat room. Here, the self-evaluation function includes an evaluation function for overall satisfaction item (e.g., including disappointed, average, satisfied, others, etc.) with the user's chat, an anxiety item, a confidence/assertiveness item, a mind control item, a communication skills/logic/persuasive power item, an immersion item, an empathy/listening skills item, etc. In this case, the anxiety item, the confidence/assertiveness item, the mind control item, the communication skills/logic/persuasive power item, the immersion item, the empathy/listening skills item, etc., may be selected in a preset range (e.g., 0 to 100 points) depending on the user's selection. In addition, the counterpart evaluation function performs a feedback (or feedback evaluation/feedback information) function on the counterpart that participates in the corresponding chat, or includes evaluation functions for chat evaluation items for each user (e.g., including "He doesn't seem anxious at all," "He's confident and assertive, "He's good at controlling his emotions," "He's good at communicating logically," "He's good at immersing himself in the situation," "He listens well and has good empathy," etc.), etc. In this case, the terminal 100 may be configured to allow the user to directly input content into the counterpart evaluation function.

That is, when the theme practice (or theme practice chat function) related to the free theme chat room or the discussion theme chat room ends, the terminal 100 transmits the information related to the self-evaluation according to the user input of the terminal 100, receives the information, etc., related to counterpart evaluation of other users, and transmits the information related to the received self-evaluation, the information related to the received counterpart evaluation of other users, the identification information of the terminal 100, etc., to the server 200.

In addition, when the chat function is performed in the question-and-answer chat room, the terminal 100 receives the chat result related to the user of the terminal 100 according to the performance of the self-evaluation function transmitted from the server 200.

In addition, the terminal 100 displays (or outputs) the received chat results.

In addition, when the user of the terminal 100 performs the chat function through theme practice with other users (or performs the chat function in the free theme chat room or the discussion theme chat room), the terminal 100 receives another chat result related to the user of the terminal 100 according to the performance of the self-evaluation function and the counterpart evaluation function transmitted from the server 200.

In addition, the terminal 100 displays (or outputs) another received chat result.

In addition Thereafter, according to the corresponding reserved counseling schedule for the expert terminal 300, when the terminal 100 is invited to the metaverse chat room (or XR counseling room/XR chat room) created by the expert terminal 300, the terminal 100 enters (or participates in) the metaverse chat room (or XR counseling room/XR chat room) created by the corresponding expert terminal 300. In this case, the terminal 100 displays the metaverse waiting screen according to the entry into the metaverse chat room. Here, the metaverse waiting screen includes the type of the corresponding metaverse chat room, the topic, the chat room name, the keyword, the nickname (or chat name) of the user in the corresponding metaverse chat room, the chat temperature, and the number of chats (or the number of times the user has participated in the chat room), etc. In this case, the chat temperature may be calculated based on the number of chats, the received evaluation results, etc., and the concept of level or points may be applied instead of the chat temperature. That is, for the level or points, the level or the preset number of points may be calculated according to a plurality of preset grades based on the number of chats, the received evaluation results, etc.

In addition, the terminal 100 is linked with the server 200 and the expert terminal 300 to receive the questionnaire transmitted (or provided) from the expert terminal 300 via the server 200. Here, the questionnaire includes one or more multiple-choice/subject questions related to a specific situation (or specific topic).

In addition, the terminal 100 displays the received questionnaire.

In addition, the terminal 100 receives questionnaire response information including a plurality of input values corresponding to the plurality of input items included in the questionnaire displayed on the terminal 100. Here, the questionnaire response information includes response information (e.g., not at all, no, average, yes, very much, etc.) for each question.

In addition, the terminal 100 transmits the received questionnaire response information, the identification information of the terminal 100, etc., to the expert terminal 300 via the server 200.

In addition, the terminal 100 receives the response results to the questionnaire related to the corresponding questionnaire response information transmitted (or provided) from the expert terminal 300 in response to the questionnaire response information related to the previously transmitted questionnaire. Here, the response results include the user's response information for each question, correct answer information for each question, and the user's earned score compared to the total points, etc.

In addition, the terminal 100 displays (or outputs) the response results to the received questionnaire.

In addition, the terminal 100 is linked with the server 200 and the expert terminal 300 to perform the psychological counseling function, the speech lesson, the mentor function, etc., with the expert through the metaverse chat room (or counseling room/XR chat room) generated from the corresponding expert terminal 300.

In addition, after the chat function ends, the terminal 200 receives the feedback information transmitted from the expert terminal 300, and displays (or outputs) the received feedback information. Here, the feedback information includes information such as an expert's view (or opinion) regarding the psychological counseling function, the speech lesson function, the mentor function, etc., performed in the metaverse chat room.

In addition, when the terminal 100 receives a request from the expert terminal 300 to participate in the metaverse chat room (or XR counseling room/XR chat room), the terminal 100 enters the metaverse chat room (or XR counseling room/XR chat room) created by the expert terminal 300 through the mediation of the server 200 or enters a specific metaverse chat room (or XR counseling room/XR chat room) selected by the expert terminal 300 from the plurality of pre-created metaverse chat rooms (or XR counseling rooms/XR chat rooms).

That is, when the terminal 100 transmits an affirmative response to the expert terminal 300 after receiving a request from the expert terminal 300 to participate in the metaverse chat room (or XR counseling room/XR chat room), the terminal 100 enters the metaverse chat room (or XR counseling room/XR chat room) created by the expert terminal 300 through the mediation of the server 200 to perform the chat function.

In addition, when the terminal 100 transmits an affirmative response to the expert terminal 300 after receiving a request from the expert terminal 300 to participate in the metaverse chat room (or XR counseling room/XR chat room), the terminal 100 enters a specific metaverse chat room (or XR counseling room/XR chat room) selected by the expert terminal 300 from among the plurality of pre-created metaverse chat rooms (or XR counseling room/XR chat room) through the mediation of the server 200.

In this case, the terminal 100 displays information indicating that the expert terminal 300 is participating in the chat as a spectator on one side of the screen of the terminal 100. Here, the terminal 100 may display icons or emoticons indicating that the expert terminal 300 is participating in the chat as a spectator on one side of the screen of the terminal 100.

In addition, the terminal 100 is linked with the expert terminal 300 owned by a specific expert selected from the plurality of located experts and the server 200 to perform the counseling function, the speech lesson function, the mentor function (or mentor-mentee function/mentoring function), etc. In this case, when the subscription function is being performed on the terminal 100, the counseling function, the speech lesson function, the mentor function, etc., with the corresponding expert may be performed free of charge, a free usage ticket assigned in advance depending on the performance of the subscription function may be deducted (or processed for use) according to the performance of the counseling function, the speech lesson function, or the mentor function, or the corresponding expert may perform and use a per-case payment function for a pre-set usage fee depending on the corresponding counseling function case, speech lesson function case, or mentor function case.

In addition, when the terminal 100 performs the counseling function, speech lesson function, mentor function, etc., with an expert, the terminal 100 may provide the personal information related to the user, the counseling record sheet (or counseling record information), the people diary (or people diary information), the chat report (or "my report" information), the psychological test results, etc., to the expert terminal 300 owned by the corresponding expert depending on the personal information use agreement in the form of an electronic document preset by the terminal 100. In this case, the digital rights management (DRM) function may be set so that the personal information related to the user provided to the expert terminal 300, the counseling record sheet (or counseling record information), the people diary (or people diary information), the chat report (or my report information), the psychological test results, etc., may not be stored, but can only be viewed.

In addition, when various types of information related to the user of the terminal 100 are provided to the expert terminal 300 or when the terminal 100 downloads the chat content according to the chat function performed by the user of the terminal 100 in the form of a file, the server 200 manages (or stores) log records in which the corresponding information is provided, log records in which the corresponding chat content is downloaded, etc. Here, the log record includes the type of information/chat content provided, date and time information on when it was provided/downloaded, information on the user/terminal that received/downloaded it, etc.

In this way, the terminal 100 may perform a topic talk chat room function, a role-playing chat room function, a theme practice chat room function, a people diary writing and/or management function, a "my report" management function, etc.

The embodiment of the present invention describes that the terminal 100 performs a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc., in the form of the dedicated app, but is not limited thereto, and it may perform the chat room search function, the chat function/user-to-user chat function, the counseling with expert function/expert search function, the room creation function, the topic talk chat room function, the role-playing chat room function, the theme practice chat room function, the people diary writing and/or management function, the "my report" management function, etc., through the website provided on the server 200, etc., in addition to the dedicated app.

The server 200 communicates with the terminal 100, the expert terminal 300, etc.

In addition, the server 200 performs a member subscription process for a user of the terminal 100, the expert terminal 300, etc.

In addition, the server 200 registers personal information related to the user of the terminal 100, the expert terminal 300, etc. In this case, the server 200 registers (or manages) the corresponding personal information, etc., in a DB server (not shown), and may be provided with a personal information use consent form in advance in the form of an electronic document from the user of the corresponding terminal 100, the expert of the expert terminal 300, etc.

In addition, the server 200 performs a member management function for a user of the terminal 100, the expert terminal 300, etc.

In this case, the server 200 provides the terminal 100, the expert terminal 300, etc., with the dedicated app and/or website providing a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, a counseling function for a user, a people diary/"my report" check function for a specific user while performing the counseling function, a counseling result writing and management function, a speech lesson function, a mentor function (or mentoring function), a psychological counseling function, an XR chat room (or metaverse chat room) creation and management function, etc. In this case, the dedicated app may be configured as different user interfaces (UIs) according to a user who receives a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc., and an expert (or counselor) who receives a counseling function for a user, a people diary/"my report" check function for a specific user while performing the counseling function, a counseling result writing and management function, a speech lesson function, a mentor function (or mentoring function), a psychological counseling function, an XR chat room (or metaverse chat room) creation and management function, etc.

In addition, the server 200 provides a bulletin board function for notices, events, etc.

In addition, the server 200 is linked with the terminal 100 to provide a topic talk chat room function, a role-playing chat room function, a theme practice chat room, a people diary (or patient diary) writing and/or management function, a "my report" management function, etc., to the terminal 100 according to the request from the terminal 100.

In addition, the server 200 analyzes the content spoken by the user of the terminal 100 and other users of terminals, and changes (or applies/reflects) and provides the avatar (or character) related to the user of the terminal 100 and the facial expression (e.g., including happiness, joy, excitement, passion, pleasure, frustration, outrage, sadness, surprise, pain, rage, etc.) of the avatar related to the other users of terminals according to the psychological state analysis (e.g., including a change in a user's gaze, a change in facial expression, a voice tremor, a change in heart rate, etc.).

In addition, when the chat function is performed (or ends) through the chat room in the terminal 100, the server 200 is linked with the terminal 100 to perform a self-evaluation function for the user of the corresponding terminal 100 and a counterpart evaluation function for one or more other users participating in the corresponding chat room. Here, the self-evaluation function includes an evaluation function for overall satisfaction item (e.g., including disappointed, average, satisfied, other, etc.) with "my chat," an anxiety item, a confidence/assertiveness item, a mind control item, a communication skills/logic/persuasive power item, an immersion item, an empathy/listening skills item, etc. In this case, the anxiety item, the confidence/assertiveness item, the mind control item, the communication skills/logic/persuasive power item, the immersion item, the empathy/listening skills item, etc., may be selected in a preset range (e.g., 0 to 100 points) depending on the user's selection. In addition, the counterpart evaluation function includes an evaluation function for a satisfaction item (e.g., including disappointed, average, satisfied, etc.) of overall chats by different users, other user-specific chat evaluation items (e.g., including "He doesn't seem anxious at all," "He's confident and assertive," "He's good at controlling his emotions," "He's good at communicating logically," "He's good at immersing in the situation," "He listens well and has good empathy," etc.), etc.

In addition, the server 200 generates chat results for each user participating in the corresponding chat room according to the performance of the self-evaluation function and counterpart evaluation function performed by each of the plurality of terminals participating in the corresponding chat room. In this case, the server 200 may generate different chat results according to each type of chat room (e.g., a topic talk chat room, a role-playing chat room, a theme practice chat room, etc.).

That is, the server 200 generates chat results for each user in relation to the topic talk chat room, generates other chat results for each user in relation to the role-playing chat room, and generates still other chat results for each user in relation to the theme practice chat room. Here, the chat result (or chat result information) includes a total average score item according to self-evaluation, an overall rating display item, an item for displaying scores (e.g., including an anxiety score, a confidence/assertiveness score, a mind control score, a communication skills/logic/persuasive power score, an immersion score, an empathy/listening skills score, etc.) for each self-evaluation item and an average score display item related to the topic talk, an evaluation item received according to the counterpart's evaluation, the number saves display item for displaying the number of times the chat content from the corresponding chat room can be saved (or downloaded), a chat recording storing item for storing the chat content, a chat time display item for displaying the total chat time in the corresponding chat room and the time the corresponding user spoke, a chat content output item for re-listening to the chat content in the corresponding chat room, etc. In addition, examples of the received evaluation item include the number of votes item received for each chat satisfaction item, the number of votes item received for each chat evaluation item, etc. In addition, the other chat results (or other chat result information) include a situation description and scoring item for displaying one's initial feelings about the situation, a "my first emotion of how I felt about the situation" display item, a total average score item according to self-evaluation, an overall rating display item, an item for displaying scores (e.g., including an anxiety score, a confidence/assertiveness score, a mind control score, a communication skills/logic/persuasive power score, an immersion score, an empathy/listening skills score, etc.) for each self-evaluation item and an average score related to the corresponding role-playing, an evaluation item received according to the counterpart's evaluation, the number saves display item for displaying the number of times content from the corresponding chat room can be saved (or downloaded), a chat recording storing item for storing the corresponding chat content, a chat time display item for displaying a total chat time in the corresponding chat room and the time the user spoke, a chat content output item for re-listening to the chat content from the corresponding chat room, etc. In addition, the received evaluation item includes a number of votes item for each chat satisfaction item, a number of votes item for each chat evaluation item, etc. In addition, the other chat result (or other chat result information) includes total average score items according to self-evaluation, an overall rating display item, an item for displaying scores (e.g., including an anxiety score, a confidence/assertiveness score, a mind control score, a communication skills/logic/persuasive power score, an immersion score, an empathy/listening skills score, etc.) for each self-evaluation item and an average score related to the theme practice display item, an evaluation item received according to the counterpart's evaluation, the number of saves display item for displaying the number of times chat content from the corresponding chat room can be saved (or downloaded), a chat recording storing item for storing the chat content, a chat time display item for displaying the total chat time in the corresponding chat room and the time the corresponding user spoke, a chat content output item for re-listening to the chat content in the corresponding chat room, etc. In addition, the received evaluation item includes the number of votes item for each chat satisfaction item, the number of votes item for each chat evaluation item, an evaluation content item input directly by the counterpart, etc.

In addition, the server 200 transmits the generated chat results for each user, the other chat results for each user, the still other chat results for each user, etc., to the terminal 100 owned by each user.

In addition, the server 200 updates (or calculates/computes) the free expression index, the anxiety index, the chat temperature, etc., related to the user based on the chat results generated in relation to the user of the terminal 100, the other chat results, the still other chat results, etc.

In this way, when the chat functions such as topic talk, role-playing, and theme practice are performed on the terminal 100, the server 200 uses the results (e.g., including self-evaluation information, received evaluation information, etc.) of performing the corresponding chat function to update the "free expression" index, the anxiety index, the chat temperature (or level/points), etc., related to the user.

In addition, the server 200 may not only apply the results (e.g., including self-evaluation information, received evaluation information, etc.) of performing the corresponding chat function, but also apply (or reflect) the detailed emotional record information, the simple emotional record information, etc., recorded by the corresponding terminal 100 along with the results of executing the corresponding chat function to update the "free expression" index, the anxiety index, the chat temperature (or level/points), etc., related to the user.

When a specific menu is selected from the dashboard screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform a function corresponding to the selected specific menu and provide function performance results according to the performance of the corresponding function to the expert terminal 300.

In addition, when an expert search result screen is displayed on any terminal 100 that is connected to the server 200 to search for and confirm experts, to indicate that an expert who has set the immediate counseling function among the experts in the search is available for immediate counseling, the server 200 is configured to display preset marks (e.g., including immediate counseling availability in a text format, emoticons/avatars corresponding to immediate counseling availability, etc.) in immediately available counseling items on one side of the expert search result screen displayed on the corresponding terminal 100.

In addition, when a preset "my profile" card menu is selected from the dashboard screen displayed on the expert terminal 300 according to the expert selection of the expert terminal 300, the server 200 is linked with the expert terminal 300 to provide a "my profile" card screen corresponding to the selected "my profile" card menu to the expert terminal 300.

In addition, when a preset calendar item is selected from the dashboard screen displayed on the expert terminal 300 according to the expert selection of the expert terminal 300, the server 200 is linked with the expert terminal 300 to provide a calendar screen corresponding to the selected calendar item to the expert terminal 300.

In addition, the server 200 is linked with the expert terminal 300 to perform an information modification function in the "my profile" card screen according to the expert input of the expert terminal 300, and update (or store/manage) the content of the modified "my profile" card.

In addition, when a preset member list item is selected from the dashboard screen displayed on the expert terminal 300 according to the expert selection of the expert terminal 300, the server 200 is linked with the expert terminal 300 to provide a member list screen corresponding to the selected member list item to the expert terminal 300.

In addition, when a preset calendar menu is selected from an initial screen displayed on the expert terminal 300, the server 200 is linked with the expert terminal 300 to provide a calendar screen corresponding to the selected calendar menu to the expert terminal 300.

When a specific menu is selected from the calendar screen displayed on the expert terminal 300 according g to the expert selection (or expert/counselor input/touch/control) of the expert terminal 300, the server 200 is linked with the expert terminal 300 to provide the screen corresponding to the selected specific menu to the expert terminal 300 or perform the function corresponding to the selected specific menu and provide the function performance results according to the performance of the corresponding function to the expert terminal 300.

In addition, when a preset counseling request approval item is selected from the calendar screen displayed on the expert terminal 300, to provide information on one or more counseling request cases (or unapproved counseling request cases) for which the expert has not yet processed the counseling request approval among the counseling request cases requested to the corresponding expert, the server 200 is linked with the expert terminal 300 to provide a counseling request approval screen corresponding to the selected counseling request approval item to the expert terminal 300.

In addition, when a specific unapproved counseling request case (or specific counseling request case) is selected from one or more counseling request cases (or unapproved counseling request cases) that have not yet been approved in the counseling request approval screen displayed on the expert terminal 300 according to the expert selection, the server 200 is linked with the expert terminal 300 to provide detailed information on the selected specific unapproved counseling request case to the expert terminal 300.

In addition, when a preset acceptance item is selected from the detailed information on the specific unapproved counseling request case displayed on the expert terminal 300 according to the corresponding expert selection, the server 200 is linked with the expert terminal 300 to confirm the counseling schedule for the corresponding specific unapproved counseling request case.

That is, when the preset acceptance item is selected from the detailed information on the specific unapproved counseling request case displayed on the expert terminal 300 according to the corresponding expert selection, to add a new counseling schedule, the server 200 is linked with the expert terminal 300 to provide a new counseling addition screen corresponding to date and time zone items related to the corresponding specific unapproved counseling request case to the expert terminal 300.

In addition, the server 200 is linked with the expert terminal 300 to map (or match/link), on a new counseling addition screen displayed on the expert terminal 300, the new counseling schedule received according to the expert input from the expert terminal 300 with user information (or expert information) of the expert terminal 300 and member information (or user information/personal information) of a user of the terminal 100 corresponding to a client related to the new counseling schedule and store (or register/manage) the mapped information.

That is, the server 200 receives the new counseling schedule, the counseling schedule storage request information, the identification information of the expert terminal 300, etc., that are transmitted from the expert terminal 300.

In addition, the server 200 confirms (or searches for) the user information corresponding to the received identification information of the expert terminal 300 among user information (or personal information/member information/expert information) for each piece of identification information of the expert terminal being managed by the server 200.

In addition, the server 200 confirms (or searches for) member information corresponding to the client (or counseling requester/user) included in the received new counseling schedule among the member information for each counseling requester being managed by the server 200.

In addition, the server 200 maps (or matches/links) the user information corresponding to the identification information of the confirmed (or searched) corresponding expert terminal 300 and the member information corresponding to the client who will perform the confirmed corresponding counseling function with the received new counseling schedule, the received identification information of the expert terminal 300, the received identification information of the terminal 100, etc., and stores (or registers/manages) the mapped information in the server 200.

In addition, the server 200 transmits (or provides) information indicating that the counseling schedule with the corresponding expert has been confirmed to the terminal 100 owned by the confirmed counseling requester.

In addition, the server 200 transmits (or provides) information indicating that the counseling schedule with the corresponding expert has been confirmed in relation to the specific counseling request case requested by the corresponding counseling requester (or user/client) to the terminal 100 related to the corresponding specific counseling request case according to the determination of the counseling schedule for the corresponding specific unapproved counseling request case.

In addition, the server 200 is linked with the expert terminal 300 and the terminal 100 to perform a final confirmation function (or final acceptance/confirmation function) so that the counseling schedule for the corresponding specific counseling request case is finally confirmed (or reserved).

In addition, when a preset available reservation time item is selected from the calendar screen displayed on the expert terminal 300, the server 200 is linked with the expert terminal 300 to provide an available reservation time setting screen corresponding to the selected available reservation time item to the expert terminal 300.

In addition, when a specific date is selected from the available reservation time setting screen displayed on the expert terminal 300, the server 200 is linked with the expert terminal 300 to provide a time zone setting screen corresponding to the selected specific date to the expert terminal 300.

In addition, when a specific time zone is selected from the time zone setting screen displayed on the expert terminal 300 according to the corresponding expert selection, the server 200 is linked with the expert terminal 300 to set the corresponding specific date and the specific time zone as the available counseling reservation date and time zone of the corresponding expert. Here, the time zone may be set in a preset standard time unit (e.g., 1 hour, 30 minutes, etc.).

In addition, when any one counseling schedule (or a specific reserved counseling schedule/a specific date and time zone corresponding to a counseling schedule) is selected from the detailed counseling schedule items in the calendar screen displayed on the expert terminal 300 including one or more reserved counseling schedules, the server 200 is linked with the expert terminal 300 to provide a personal counseling management screen corresponding to the user (or client/counseling requester) related to the selected counseling schedule (or counseling schedule of the selected specific date and time zone) to the expert terminal 300.

In addition, when a preset additional counseling item is selected from the calendar screen displayed on the expert terminal 300 or the available counseling reservation date and time zone item is selected from the detailed counseling schedule items in the calendar screen displayed on the expert terminal 300, the server 200 is linked with the expert terminal 300 to provide a new counseling addition screen corresponding to the selected additional counseling item or the selected available counseling reservation date and time zone item to the expert terminal 300.

In addition, the server 200 is linked with the expert terminal 300 to map (or match/link) the new counseling schedule received from the expert terminal 300 with the user information (or expert information) of the expert terminal 300 and the member information (or user information/personal information) of the user of the terminal 100 corresponding to the client related to the corresponding new counseling schedule and store (or register/manage) the mapped information in the server 200.

That is, the server 200 receives the new counseling schedule, the counseling schedule storage request information, the identification information of the expert terminal 300, etc., that are transmitted from the expert terminal 300.

In addition, the server 200 confirms (or searches for) the user information corresponding to the received identification information of the expert terminal 300 among user information (or personal information/member information/expert information) for each piece of identification information of the expert terminal being managed by the server 200.

In addition, the server 200 confirms (or searches for) member information corresponding to the client (or counseling requester/user) included in the received new counseling schedule among the member information for each counseling requester being managed by the server 200.

In addition, the server 200 maps (or matches/links) the user information corresponding to the identification information of the confirmed (or searched) corresponding expert terminal 300 and the member information corresponding to the client who will perform the confirmed corresponding counseling function with the received new counseling schedule, the received identification information of the expert terminal 300, the received identification information of the terminal 100, etc., and stores (or registers/manages) the mapped information in the server 200.

In addition, the server 200 transmits (or provides) information indicating that the counseling schedule with the corresponding expert has been confirmed to the terminal 100 owned by the confirmed counseling requester.

In addition, the server 200 is linked with the expert terminal 300 and the terminal 100 to perform a final confirmation function (or final acceptance/confirmation function) for the counseling schedule case newly registered in the expert terminal 300 so that the counseling schedule for the counseling schedule case newly registered in the expert terminal 300 is finally confirmed.

In addition, when a preset member list menu is selected from the initial screen displayed on the expert terminal 300, the server 200 is linked with the expert terminal 300 to provide a member list screen corresponding to the selected member list menu to the expert terminal 300.

When a specific menu is selected from the member list screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform the function corresponding to the selected specific menu and provide the function performance results according to the performance of the corresponding function to the expert terminal 300.

In addition, when a preset list item is selected from the member list type item in the member list screen displayed on the expert terminal 300, the server 200 is linked with the expert terminal 300 to provide the member list information in the form of the list corresponding to the selected list item to the expert terminal 300.

In addition, when a specific member list (or specific member list item) is selected from the member list information in the form of the list displayed on the expert terminal 300, the server 200 is linked with the expert terminal 300 to provide detailed specific member list information corresponding to the selected specific member list to the expert terminal 300.

In addition, when a preset thumbnail item is selected from the member list type item in the member list screen displayed on the expert terminal 300, the server 200 is linked with the expert terminal 300 to provide the member list information in the form of the thumbnail corresponding to the selected thumbnail item to the expert terminal 300.

In addition, when the specific member list (or specific member list item) is selected from the member list information in the form of the thumbnail displayed on the expert terminal 300, the server 200 is linked with the expert terminal 300 to provide detailed specific member list information corresponding to the selected specific member list to the expert terminal 300.

In addition, when a preset member report menu is selected from the initial screen displayed on the expert terminal 300, the server 200 is linked with the expert terminal 300 to provide a member report screen corresponding to the selected member report menu to the expert terminal 300.

When a specific menu is selected from the report screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform a function corresponding to the selected specific menu and provide function performance results according to the performance of the corresponding function to the expert terminal 300.

In addition, when a specific member report (or specific member) is selected from a detailed member report item in the member report screen displayed on the expert terminal 300, the server 200 is linked with the expert terminal 300 to provide detailed member report information corresponding to the selected specific member report to the expert terminal 300.

In addition, when the specific menu is selected from the detailed member report information according to the expert selection (or expert/counselor input/touch/control) of the expert terminal 300, the server 200 is linked with the expert terminal 300 to provide the screen corresponding to the selected specific menu to the expert terminal 300 or perform the function corresponding to the selected specific menu and provide the function performance results according to the performance of the corresponding function to the expert terminal 300.

In addition, when a preset counseling record sheet item is selected from the detailed member report information displayed on the expert terminal 300, the server 200 is linked with the expert terminal 300 to provide a counseling record sheet screen corresponding to the selected counseling record sheet item to the expert terminal 300.

In addition, when a detail view item displayed on one side of a specific counseling record sheet is selected from the counseling record sheet screen displayed on the expert terminal 300, the server 200 is linked with the expert terminal 300 to provide detailed counseling record sheet information on the specific counseling record sheet related to the selected detail view item to the expert terminal 300.

In addition, when a preset cognitive behavior therapy record sheet item is selected from the detailed member report information displayed on the expert terminal 300, the server 200 is linked with the expert terminal 300 to provide a cognitive behavior therapy record sheet screen corresponding to the selected cognitive behavior therapy record sheet item to the expert terminal 300.

In addition, when a specific cognitive behavior therapy record sheet is selected from the cognitive behavior therapy record sheet screen displayed on the expert terminal 300 (or when an item that is being or has been written before/after the training related to the specific cognitive behavior therapy record sheet is selected), the server 200 is linked with the expert terminal 300 to provide detailed cognitive behavior therapy record sheet information on a specific cognitive behavior therapy record sheet case related to the selected specific cognitive behavior therapy record sheet to the expert terminal 300.

In addition, when a preset questionnaire result item is selected from the detailed member report information displayed on the expert terminal 300, the server 200 is linked with the expert terminal 300 to provide a questionnaire result screen corresponding to the selected questionnaire result item to the expert terminal 300.

In addition, when a specific file name (or specific file name item) is selected from one or more file names (or file name items) in the questionnaire result screen displayed on the expert terminal 300 or when a detailed item related to a specific file name is selected from one or more file names displayed on the questionnaire result screen, the server 200 is linked with the expert terminal 300 to provide detailed questionnaire information related to the selected specific file name or a specific file name corresponding to the selected detailed item to the expert terminal 300.

In addition, when a preset people diary item is selected from the detailed member report information displayed on the expert terminal 300, the server 200 is linked with the expert terminal 300 to provide a people diary screen corresponding to the selected people diary item to the expert terminal 300.

In addition, when a specific date including an emotional record state in the people diary screen displayed on the expert terminal 300 is selected, the server 200 is linked with the expert terminal 300 to provide a detailed people diary screen related to the selected specific date to the expert terminal 300.

In addition, when a preset chart report item is selected from the detailed member report information displayed on the expert terminal 300, the server 200 is linked with the expert terminal 300 to provide a chart report screen corresponding to the selected chart report item to the expert terminal 300.

In addition, when a preset past counseling record item is selected from the detailed member report information displayed on the expert terminal 300, to provide a participation list and a cognitive behavior therapy record (or cognitive behavior therapy record sheet) related to the chat room in which the user of the terminal 100 participates along with the expert of the expert terminal 300, the server 200 is linked with the expert terminal 300 to provide a past counseling record screen corresponding to the selected past counseling record item to the expert terminal 300.

In addition, when a preset participation list menu (or other participation list menus) is selected from the past counseling record screen displayed on the expert terminal 300, to provide other participation lists in which the user of the terminal 100 performs a counseling function, a speech lesson function, a mentoring function, etc., along with the expert of the expert terminal 300, the server 200 is linked with the expert terminal 300 to provide other participation list screens corresponding to the selected participation list menu to the expert terminal 300.

In addition, when other specific participation lists (or detail view item displayed on one side of the corresponding other specific participation lists) are selected from one or more other participation lists being displayed in the information display items for each expert chat participation case in the past counseling record screen displayed on the expert terminal 300, the server 200 is linked with the expert terminal 300 to provide the detailed information related to the selected other specific participation lists to the expert terminal 300.

In addition, when a preset cognitive behavior therapy record menu is selected from the past counseling record screen displayed on the expert terminal 300, to provide information on the cognitive behavior therapy record sheet written by the user of the terminal 100 according to the user's performance of a training function for an appropriate chat style in relation to a specific topic or situation, the server 200 is linked with the expert terminal 300 to provide a cognitive behavior therapy record screen corresponding to the selected cognitive behavior therapy record menu to the expert terminal 300.

In addition, when a specific cognitive behavior therapy record is selected from one or more cognitive behavior therapy record cases being displayed in the cognitive behavior therapy record information display items for each chat participation in the cognitive behavior therapy record screen displayed on the expert terminal 300, other detailed information related to the selected specific cognitive behavior therapy record case is provided in the expert terminal 300.

In addition, when a preset message menu is selected from the initial screen displayed on the expert terminal 300, to provide a message (or post message) function with a user who is counseling with the corresponding expert or has a counseling history with the corresponding expert, the server 200 is linked with the expert terminal 300 to provide a message screen corresponding to the selected message menu to the expert terminal 300.

In addition, the server 200 is linked with the terminal 100 and the expert terminal 300 related to a specific counseling requester selected from one or more counseling requesters included in the message screen to perform a message function (or chat function) with the terminal 100 related to the corresponding specific counseling requester.

When a specific menu is selected from the message screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform the function corresponding to the selected specific menu and provide the function performance results according to the performance of the corresponding function to the expert terminal 300.

In addition, when a preset "my performance" menu is selected from the initial screen displayed on the expert terminal 300, to provide information such as counseling performance performed by the corresponding expert, the server 200 is linked with the expert terminal 300 to provide a "my performance" screen corresponding to the selected "my performance" menu to the expert terminal 300.

When a specific menu is selected from the "my performance" screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform a function corresponding to the selected specific menu and provide function performance results according to the performance of the corresponding function to the expert terminal 300.

In addition, when a detailed history menu related to counseling performance in the "my performance" screen displayed on the expert terminal 300 is selected, the server 200 is linked with the expert terminal 300 to provide a detailed history screen corresponding to the detailed history menu related to the selected counseling performance to the expert terminal 300.

In addition, when a preset data management menu is selected from the initial screen displayed on the expert terminal 300, to manage information on a questionnaire or data related to a user who is counseling with the corresponding expert or has a counseling history with the corresponding expert, the server 200 is linked with the expert terminal 300 to provide a data management screen corresponding to the selected data management menu to the expert terminal 300.

When a specific menu is selected from the data management screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform the function corresponding to the selected specific menu and provide the function performance results according to the performance of the corresponding function to the expert terminal 300.

In addition, when a preset XR room-creation menu is selected from the initial screen displayed on the expert terminal 300, to select a client to be invited to the XR counseling room, the server 200 is linked with the expert terminal 300 to provide an XR counseling room invitation client selection screen corresponding to the selected XR room-creation menu to the expert terminal 300.

In addition, when a specific menu is selected from the XR counseling room invitation client selection screen displayed on the expert terminal 300 according to the expert selection (or expert/counselor input/touch/control) of the expert terminal 300, the server 200 is linked with the expert terminal 300 to provide the screen corresponding to the selected specific menu to the expert terminal 300 or perform a function corresponding to the selected specific menu and provide function performance results according to the performance of the corresponding function to the expert terminal 300.

In addition, when a specific user is selected from the XR counseling room invitation client selection screen displayed on the expert terminal 300, to perform a counseling function with an expert in an XR environment or a metaverse environment, the server 200 is linked with the expert terminal 300 and the terminal 100 owned by the selected specific user (or specific content) to provide the XR counseling room screen to the expert 300 and the terminal 100.

In addition, when a preset questionnaire writing request item is selected from the XR counseling room screen displayed on the expert terminal 300, the server 200 is linked with the expert terminal 300 to provide a questionnaire list screen corresponding to the selected questionnaire writing request item to the expert terminal 300.

In addition, when a specific questionnaire is selected from one or more questionnaires included in the questionnaire list screen displayed on the expert terminal 300, the server 200 is linked with the expert terminal 300 to provide the detailed information on the selected specific questionnaire to the expert terminal 300.

In addition, when a preset transmission item displayed on one side of the detailed information on a specific questionnaire of the expert terminal 300 is selected, the server 200 is linked with the expert terminal 300 to transmit the selected specific questionnaire to the terminal 100 corresponding to the corresponding user.

That is, when a preset transmission item displayed on one side of the detailed information on the specific questionnaire of the expert terminal 300 is selected, the server 200 receives the specific questionnaire, the questionnaire writing request information, the identification information of the expert terminal 300, the unique information related to the user who participates in the XR counseling room (or identification information of the terminal 100 related to the corresponding user), etc., that are transmitted from the expert terminal 300.

In addition, the server 200 transmits the specific questionnaire, the questionnaire writing request information, the identification information of the expert terminal 300, etc., to the terminal 100 corresponding to the unique information related to the user participating in the XR counseling room.

In addition, the server 200 receives questionnaire response information transmitted from the terminal 100 and transmits the received questionnaire response information to the expert terminal 300.

In addition, the server 200 transmits a response result related to the corresponding questionnaire response information transmitted from the expert terminal 300 to the terminal 100.

In addition, while a counseling function with the corresponding expert and the corresponding specific user is performed through the XR counseling room screen displayed on the expert terminal 300, to participate in a metaverse chat room related to a specific theme and perform a monitoring (or training/counseling) function for the corresponding specific user through the chat function, when an entry item is selected along with the chat training room displayed on one side of the XR counseling room screen, the server 200 is linked with the expert terminal 300 to create a new metaverse chat room or select a specific metaverse chat room from the one or more pre-created metaverse chat rooms according to the corresponding expert selection, and then provide the expert's position selection screen for selecting whether the counselor (or expert) enters as a spectator or as a chatter to the expert terminal 300.

In addition, when a spectator item or a chatter item is selected from the expert's position selection screen displayed on the expert terminal 300 according to the expert selection (or expert input/touch/control) of the expert terminal 300, the server 200 is linked with the expert terminal 300 and the terminal 100 to process (or manage) the expert of the expert terminal 300 to enter (or participate in) the metaverse chat room as a spectator corresponding to the selected spectator item or as chatter corresponding to the selected chatter item and process the user of the terminal 100 in counseling to enter (or participate in) the corresponding metaverse chat room as the chatter.

In addition, when a room leader who opens the metaverse chat room selects the preset start menu while the number of people (or number of participants) set in the metaverse chat room is satisfied, the server 200 is linked with the expert terminal 30 to perform a chat function related to a specific topic of the metaverse chat room with the expert of the expert terminal 300 as the spectator or chatter, and the server is linked with the terminal 100 and one or more other terminals (not illustrated) owned by one or more other users who entered the metaverse chat room to perform the chat function related to the specific topic of the metaverse chat room.

In addition, when the chat function in the specific metaverse chat room in which the expert terminal 300 and the terminal 100 participate ends, the server 200 is linked with the expert terminal 300 to map (or match/link) feedback information generated from the expert terminal 300, information on the metaverse chat room, user information (or expert information) of the expert terminal 300, and member information (or user information/personal information) of the user of the terminal 100 and store (register/manage) the mapped information in the server 200.

In addition, the server 200 provides (or transmits) the feedback information transmitted from the expert terminal 300 to the terminal 100.

In addition, while the counseling function with the corresponding expert and the corresponding specific user is performed through the XR counseling room screen displayed on the expert terminal 300, when a personal information item included in the detailed member information display area in the corresponding XR counseling room screen is selected, the server 200 is linked with the expert terminal 300 to provide a personal information screen seen only by the expert corresponding to the selected personal information item to the expert terminal 300.

In addition, while the counseling function with the corresponding expert and the corresponding specific user is performed through the XR counseling room screen displayed on the expert terminal 300, when a counseling record sheet item included in the detailed member information display area in the corresponding XR counseling room screen is selected, the server 200 is linked with the expert terminal 300 to provide detailed information related to the selected counseling record sheet item to the expert terminal 300.

In addition, when the additional item is selected from the counseling record sheet screen seen by the expert displayed on the expert terminal 300, to store (or record) counseling content related to a specific user currently receiving counseling the server 200 is linked with the expert terminal 300 to provide a counseling record sheet input screen corresponding to the selected additional item to the expert terminal 300.

In addition, the server 200 is linked with the expert terminal 300 to map the counseling record information provided from the expert terminal 300 with the personal information corresponding to the corresponding specific user and the user information of the expert terminal 300 and store (or register) the mapped information in the server 200.

In addition, when a detail view item displayed on one side of a specific counseling record sheet case is selected from the counseling record sheet screen for the expert displayed on the expert terminal 300, the server 200 is linked with the expert terminal 300 to provide the detailed counseling record sheet information on the specific counseling record sheet case related to the selected detail view item to the expert terminal 300.

In addition, while the counseling function with the corresponding expert and the corresponding specific user is performed through the XR counseling room screen displayed on the expert terminal 300, when a cognitive behavior therapy record sheet item included in the detailed member information display area in the corresponding XR counseling room screen is selected, the server 200 is linked with the expert terminal 300 to provide detailed information related to the selected cognitive behavior therapy record sheet item to the expert terminal 300.

In addition, when a specific cognitive behavior therapy record sheet is selected from the cognitive behavior therapy record sheet screen for the expert displayed on the expert terminal 300 (or when an item that is being or has been written before/after the training related to the specific cognitive behavior therapy record sheet is selected), the server 200 is linked with the expert terminal 300 to provide detailed cognitive behavior therapy record sheet information on a specific cognitive behavior therapy record sheet case related to the selected specific cognitive behavior therapy record sheet to the expert terminal 300.

In addition, when a questionnaire result item included in the detailed member information display area in the corresponding XR counseling room screen is selected while the counseling function with the corresponding expert and the corresponding specific user is being performed through the XR counseling room screen displayed on the expert terminal 300, the server 200 is linked with the expert terminal 300 to provide detailed information related to the selected questionnaire result item to the expert terminal 300.

In addition, when a specific file name (or specific file name item) is selected from one or more file names (or file name items) in a questionnaire result screen for the expert displayed on the expert terminal 300 or when a detailed item related to a specific file name is selected from one or more file names displayed on the questionnaire result screen for the expert, the server 200 is linked with the expert terminal 300 to provide the detailed questionnaire information related to the selected specific file name or a specific file name corresponding to the selected detailed item to the expert terminal 300.

In addition, when a people diary item included in the detailed member information display area in the corresponding XR counseling room screen is selected while the counseling function with the corresponding expert and the corresponding specific user is being performed through the XR counseling room screen displayed on the expert terminal 300, the server 200 is linked with the expert terminal 300 to provide detailed information related to the selected people diary item to the expert terminal 300.

In addition, when a specific date including an emotional record state in a people diary screen for the expert displayed on the expert terminal 300 is selected, the server 200 is linked with the expert terminal 300 to provide a detailed people diary screen viewed by the expert related to the selected specific date to the expert terminal 300.

In addition, when a chart report item included in the detailed member information display area in the corresponding XR counseling room screen is selected while the counseling function with the corresponding expert and the corresponding specific user is being performed through the XR counseling room screen displayed on the expert terminal 300, the server 200 is linked with the expert terminal 300 to provide detailed information related to the selected chart report item to the expert terminal 300.

In addition, when a past counseling record item included in the detailed member information display area in the corresponding XR counseling room screen is selected while the counseling function with the corresponding expert and the corresponding specific user is being performed through the XR counseling room screen displayed on the expert terminal 300, the server 200 is linked with the expert terminal 300 to provide detailed information related to the selected past counseling record item to the expert terminal 300.

In addition, when a preset participation list menu (or other participation list menus) is selected from the past counseling record screen for the expert displayed on the expert terminal 300, to provide other participation lists in which the user of the terminal 100 performs a counseling function, a speech lesson function, a mentoring function, etc., with the expert of the expert terminal 300, the server 200 is linked with the expert terminal 300 to provide other participation list screens corresponding to the selected participation list menu to the expert terminal 300.

In addition, when other specific participation lists are selected from one or more other participation lists (or detail view items displayed on one side of the corresponding other specific participation lists) being displayed in the information display items for each expert chat participation case in other participation list screens displayed on the expert terminal 300, the server 200 is linked with the expert terminal 300 to provide the detailed information related to the selected other specific participation lists to the expert terminal 300.

In addition, when a preset cognitive behavior therapy record menu is selected from the past counseling record screen displayed on the expert terminal 300, to provide the information on the cognitive behavior therapy record sheet written by the user of the terminal 100 according to the user's performance of the training function for the appropriate chat style in relation to the specific topic or situation, the server 200 is linked with the expert terminal 300 to provide a cognitive behavior therapy record screen corresponding to the selected cognitive behavior therapy record menu to the expert terminal 300.

In addition, when a specific cognitive behavior therapy record is selected from one or more cognitive behavior therapy record cases being displayed in the cognitive behavior therapy record information display items for each chat participation in the cognitive behavior therapy record screen displayed on the expert terminal 300, the server 200 is linked with the expert terminal 300 to provide other detailed information related to the selected specific cognitive behavior therapy record case to the expert terminal 300.

In addition, when other specific users are performing a chat function (e.g., topic talk chatting, role-playing chatting, theme practice chatting, etc.) with another user while the corresponding other specific users are selected from the XR counseling room invitation client selection screen displayed on the expert terminal 300, the server 200 is linked with the expert terminal 300 to process the expert terminal 300 to enter a chat room in which the corresponding other specific users and another user who are performing a chat function in a spectator mode.

In addition, while the corresponding other specific users are performing the chat function with another user or after the chat function ends, the server 200 is linked with the expert terminal 300 to transmit customized advice information, analysis information, etc., related to the corresponding other specific users according to the expert input of the expert terminal 300 transmitted from the expert terminal 300 to the terminal 100 owned by the other specific users.

In addition, the server 200 calculates (or computes) the amount (or cost) to be paid to the corresponding expert on a preset date according to the counseling function performed by the expert terminal 300.

In addition, the server 200 deposits the calculated amount into a bank account related to the expert of the expert terminal 300 (or an account in the server 200 related to the expert of the expert terminal 300).

The expert terminal 300 communicates with the terminal 100, the server 200, etc. In this case, the expert terminal 300 may be a terminal owned by an expert (or counselor) who wishes to receive a counseling function for a user, a people diary/"my report" confirm function for a specific user while performing the counseling function, a counseling result generation and management function, a speech lesson function, a mentor function (or mentoring function), a psychological counseling function and an XR chat room (or metaverse chat room) creation and management function, etc.

In addition, the expert terminal 300 is linked with the server 200 to subscribe as the expert (or counselor) to receive the counseling function for the user through the dedicated app and/or website provided by the server 200, the people diary/"my report" confirmation function for a specific user while performing the counseling function, the counseling result writing and management function, the speech lesson function, the mentor function (or mentoring function), the XR chat room (or metaverse chat room) writing and management function, etc., and register the personal information, etc., to the server 200. In this case, the personal information includes an ID, an email address, a password (or passcode), a name, a gender, a date of birth, contact information, an address (or address information), an authorized certificate proving expertise etc.

In addition, the expert terminal 300 may subscribe a user as a member on the server 200 using SNS account information to which the user of the expert terminal 300 subscribes or other site account information. Here, the SNS account may be information related to Facebook, Twitter, Instagram, Kakao Story, Naver Blog, etc. In addition, other site accounts may be information related to YouTube, Kakao, Naver, etc. In this case, the dedicated websites (or app) may be configured as different user interfaces according to an expert (or counselor) who receives a counseling function for a user, a people diary/my report check function for a specific user while performing the counseling function, a counseling result writing and management function, a speech lesson function, a mentor function (or mentoring function), a psychological counseling function, an XR chat room (or metaverse chat room) creation and management function, etc., and a user (or counseling requester/client) who receives a chat room search function, a chat function/user-to-user chat function, a counseling with expert function/expert search function, a room creation function, a topic talk chat room function, a role-playing chat room function, a theme practice chat room function, a people diary writing and/or management function, a "my report" management function, etc.

In addition, when performing the member subscription process, the expert terminal 300 should complete an authentication function through an identity authentication method (e.g., including a mobile phone, a credit card, an i-PIN, etc.) to complete the member subscription process for the server 200 normally.

In addition, when subscribing as the expert, the expert terminal 300 may transmit a certificate (or a certificate in the form of a file such as PDF format) that can prove that the expert is the corresponding expert to the server 200, and when the expert verification procedure is completed normally in the corresponding server 200, complete the member subscription process for the server 200 normally.

In this case, the expert terminal 300 is linked with the server 200 to receive the results according to approval, rejection, request for additional supplementation, etc., through the review of the corresponding certificate, and displays (or outputs) the received results.

In addition, the expert terminal 300 accesses a website provided by the server 200 and displays an initial screen provided by the website to manage the counseling function related to the expert of the expert terminal 300. In this case, the initial screen includes an expert information display menu (or button/item/area) for displaying information related to the expert of the corresponding expert terminal 300, a dashboard menu for displaying general information related to an expert, a calendar menu for displaying a counseling schedule of the corresponding expert, a member list menu for displaying member information of a user receiving counseling from the corresponding expert, a member report menu for displaying activity details for a preset period of a user receiving counseling from the corresponding expert, a message menu for a message (or post message) function with a user who is receiving counseling from or has a counseling history with the corresponding expert, a "my performance" menu for providing information such as the counseling performance performed by the corresponding expert, a data management menu for managing information on a questionnaire or data related to a user that an expert is counseling or has a counseling history with, a setting menu (or my page menu) for setting user information, a website function, etc., an XR room creation menu for performing a counseling function with a user in an XR or metaverse environment, a detailed information display area (or detailed information display menu) for displaying detailed information (or additional information) according to the menu selection, etc. Here, the expert terminal 300 may perform a login procedure when accessing the website using the ID and password according to member subscription, a barcode or QR code including the ID, etc., while subscribed as a member in the server 200 that provides the dedicated app (or website) to perform one or more functions of the corresponding website (e.g., including a counseling function for a user, a function of confirming people diary/"my report" for a specific user while performing the counseling function, a function of generating and managing counseling results, a speech lesson function, a mentor function (or mentoring function), a psychological counseling function, an XR chat room (or metaverse chat room) creation and management function, etc.). In this case, the dedicated app (or the website) may be configured as different user interfaces according to an expert (or counselor) who receives the counseling function for a user, the function of confirming a people diary/"my report" for a specific user while performing the counseling function, the function of generating and managing counseling results, the speech lesson function, the mentor function (or mentoring function), a psychological counseling function, the XR chat room (or metaverse chat room) creation and management function, etc., and a user (or counseling requester/client) who receives the chat room search function, the chat function/user-to-user chat function, the counseling with expert function/expert search function, the room creation function, the topic talk chat room function, the role-playing chat room function, the theme practice chat room function, the people diary creation and/or management function, the "my report" management function, etc.

In addition, when a preset dashboard menu is selected from the initial screen displayed on the expert terminal 300, the expert terminal 300 displays the selected dashboard menu to display the information related to the expert of the expert terminal 300. In this case, the expert terminal 300 may display the dashboard screen corresponding to the selected dashboard menu in the detailed information display area. Here, the dashboard screen includes an immediate counseling menu for performing a counseling function with a user (or client) in real time while accessing a website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a calendar item (or calendar menu/area/screen) for displaying an expert's counseling schedule by day, week, month, etc., a "my profile card" menu for displaying an expert's profile card, a counseling request approval count menu for displaying the number of counseling request approvals in relation to counseling requests requested from the corresponding expert, the total number of reserved counseling sessions display menu for displaying the total number of counseling sessions requested from the corresponding expert, a number of new members this month display menu for displaying the number of users who requested new counseling sessions from the expert in that month, a total number of members display menu for displaying the total number of users who have requested counseling from the corresponding expert, a member list item (or member list menu/area/screen) for displaying member information of the user receiving counseling from the corresponding expert, etc. In this case, when accessing the dedicated website on the expert terminal 300 (when logged into the website), the expert terminal 300 may display a dashboard screen corresponding to the dashboard menu set by default in the detailed information display area.

In addition, according to the settings of the expert terminal 300, the expert terminal 300 may set the content displayed on the dashboard screen corresponding to the dashboard menu in the initial screen for each expert (or for each user) in consideration of an expert's preference, etc.

In addition, when a specific menu is selected from the dashboard screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

That is, when a preset immediate counseling menu is selected from the dashboard screens displayed on the expert terminal 300 according to the expert selection of the corresponding expert terminal 300, to confirm profile information of the corresponding expert and a usage fee per counseling session (or cost per counseling session), the expert terminal 300 is linked with the server 200 to display an immediate counseling screen corresponding to the selected immediate counseling menu. Here, the immediate counseling screen includes an expert name item, a counseling field (or specialty field) item (e.g., including psychological counseling, speech lessons, mentoring, etc.), a brief introduction item, a character (or photo/image) item, a usage fee per counseling item, a rating (or star rating) item, a review information item, a popularity (or number of likes) item, a modifying item, a completion item, a close item, etc., and may be displayed in the form of a pop-up or a new screen (e.g., including a new window, a new screen, etc.).

In addition, after the profile information, the usage fee per counseling session, etc., are set (or confirmed) according to the corresponding expert selection in the immediate counseling screen displayed on the expert terminal 300, when the completion item displayed on one side of the immediate counseling screen is selected, the expert terminal 300 is linked with the server 200 to register the expert of the expert terminal 300 as an expert available for real-time counseling based on one or more input values set in the corresponding immediate counseling screen. Here, the one or more input values include an expert name, a counseling field (or specialty field) (examples include psychological counseling, speech lessons, mentoring, etc.), a brief introduction, a character (or photo/image), a rating (or star rating), review information, popularity (or number of likes), etc., and the rating (or star rating), review information, popularity (or number of likes), etc., may be calculated (or processed) by the server 200 and entered automatically.

In this way, the expert terminal 300 may immediately conduct counseling with the user through the immediate counseling function when the expert has time to spare. In this case, the terminal 300 may register an immediate counseling ticket by applying the discount rate suggested by the expert for immediate counseling with a one-time counseling ticket.

In addition, when the expert search result screen is displayed on a random terminal 100 that accesses the server 200 to search and confirm the expert, to indicate that among the experts searched by the terminal 100, those who have set the immediate counseling function are in an immediately available counseling state, the server 200 is configured to display preset marks (e.g., including immediate counseling availability in a text format, emoticons/avatars corresponding to immediate counseling availability, etc.) in immediately available counseling items on one side of the expert search result screen displayed on the corresponding terminal 100.

In addition, when a preset "my profile" card menu is selected from the dashboard screen displayed on the expert terminal 300 according to the expert selection of the expert terminal 300, to confirm and modify the profile information of the corresponding expert, the expert terminal 300 is linked with the server 200 to display a "my profile" card screen corresponding to the selected "my profile" card menu. Here, the "my profile" card screen above includes an expert display item including content displayed on a "my profile" card, a default information item for setting an expert's default information, a service information item (or counseling information items) for setting the information necessary to perform the counseling function, an expert information item (or counselor information items) to provide additional information on an expert, a review information item for providing registered review information regarding an expert, a storing item for storing edited content, a previous item (or cancel item) for returning to a previous screen (e.g., including a dashboard screen, etc.) with previously written content maintained (or without modifications), etc. In addition, the expert display item (a "my profile" card item) includes an expert name, a counseling field (or specialty field) (e.g., including psychological counseling, speech lessons, mentoring, etc.), a brief introduction, a character (or photo/image), a usage fee per counseling session, a rating (or star rating), review information, whether immediate counseling is possible, popularity (or number of likes), etc. In addition, the default information item (or user information item) of the expert includes an expert name/name, a gender, a title (or brief introduction), a tag related to a main specialty field of the corresponding expert, an expert type (or counseling field), a topic for which counseling is available, a situation in which counseling is possible, etc. In this case, examples of the tag (or hashtag) related to the expert's major specialty field include #dream/career, #employment, #anxiety, #depression, a self-written item, etc. In addition, examples of the topic for which counseling is available include "my item," a social life item, an interpersonal relationship item, a dream/career item, an emotional/psychological item, an expert item, etc. In addition, examples of the situation in which counseling is possible include an item that express an individual, a work situation item, a presentation situation item, a difficult target item, a friendship item, a conflict situation item, an emotional expression item, a discussion/persuasion item, etc. In addition, examples of the service information item (or counseling information item) include a service description (e.g., detailed content, a key point, an image, a video link, etc.), a service option (e.g., a default option, a location, etc.), etc. Here, examples of the default option include a usage ticket, content, an additional configuration (e.g., including XR chat room training and a data analysis rate, etc.), a time, a number of times, a price, etc. In addition, the location includes a name, an address, etc. In addition, examples of the expert information item (or counselor information item) include expert (or counselor) introduction content, career information according to an affiliation, a position, a period depending on an employment status, certificate information by issuance institution, supporting materials, etc. In addition, examples of the review information item include an overall star rating, ratings for each category (e.g., including use of XR, friendliness, analytical skills, empathy and comfort, appropriate advice, etc.), the total number of reviews, detailed content of recent reviews, etc.

In addition, the expert terminal 300 is linked with the server 200 to perform an information modification function in the "my profile" card screen according to the expert input of the expert terminal 300, and update (or store/manage) the content of the modified "my profile" card.

In addition, when a preset calendar item is selected from the dashboard screen displayed on the expert terminal 300 according to the expert selection of the expert terminal 300, to display the corresponding expert's counseling schedule by day, week, month, etc., the expert terminal 300 is linked with the server 200 to display a calendar screen corresponding to the selected calendar item. Here, the expert terminal 300 may perform additional functions according to the expert selection for a specific menu on the calendar screen, which will be described later.

In addition, when the preset counseling request approval number display menu is selected from the dashboard screen displayed on the expert terminal 300 according to the expert selection of the expert terminal 300, to provide information on one or more counseling request cases for which the expert has not yet processed counseling request approval among the counseling request cases that have requested counseling from the corresponding expert, the expert terminal 300 is linked with the server 200 to display a counseling request approval screen corresponding to the selected counseling request approval number display menu. Here, the counseling request approval screen includes a monthly calendar item (or a daily calendar item for displaying the number of daily counseling cases for the corresponding month) for displaying the number of monthly counseling cases based on the month corresponding to the current date in the expert terminal 300, counseling request approval processing items by date (or by day of the week) to display one or more counseling request cases (or unapproved counseling request cases) that have not yet been approved among the counseling request cases, and a close item (or end item), etc., and may be displayed in a pop-up form or a new screen form (e.g., including a new window form, a new screen form, etc.). In addition, the counseling request approval processing items by date include the nickname item of a counseling requester corresponding to a counseling request case that has not yet been approved by date (or by day of the week), a request time information item (e.g., 10 minutes ago, 1 hour ago, etc.), counseling ticket type items (e.g., 5 basic counseling tickets, 10 basic counseling tickets, 5 in-depth counseling tickets, 10 in-depth counseling tickets, etc.), desired counseling time items (e.g., date, time information, etc.), an approval processing item, a deletion item, etc.

In addition, the expert terminal 300 is linked with the server 200 to confirm the date and time of the counseling request for one or more counseling request cases that have not yet been approved according to the corresponding expert input and then perform the counseling request approval processing function (e.g., counseling request approval, counseling request rejection, etc.).

In addition, when a preset total reservation counseling number display menu is selected from the dashboard screen displayed on the expert terminal 300 according to the expert selection of the expert terminal 300, to display the total number of counseling sessions requested from the corresponding expert, the expert terminal 300 is linked with the server 200 to display a total reservation counseling number screen corresponding to the selected total reservation counseling number display menu. Here, the total reservation counseling number screen includes information (e.g., a date, a counseling requester's nickname, a recent counseling date, a graph of reservation counseling cases by date, etc.) on reservation counseling cases by date, etc.

In addition, when a preset new member number display menu of the current month is selected from the dashboard screen displayed on the expert terminal 300 according to the expert selection of the expert terminal 300, to display the number of users who requested a new counseling session from the corresponding expert in the given month, the expert terminal 300 is linked with the server 200 to display a new member screen of the current month corresponding to the selected new member number display menu of the current month. Here, the new member screen of the current month includes new member information by date (e.g., a new member's nickname, a counseling ticket type (e.g., the time, the number of sessions, etc., for each), a graph of the number of new members by date, etc.).

In addition, when the preset total member number display menu is selected from the dashboard screen displayed on the expert terminal 300 according to the expert selection of the expert terminal 300, to display the total number of users who requested counseling from the corresponding expert, the expert terminal 300 is linked with the server 200 to display a total member number screen corresponding to the selected total member number display menu. Here, the total member number screen includes state information on the total number of members by date, a state graph of the total number of members by date, etc.

In addition, when a preset member list item is selected from the dashboard screen displayed on the expert terminal 300 according to the expert selection of the expert terminal 300, to display member information of a user who is counseling with the corresponding expert, the expert terminal 300 is linked with the server 200 to display the member list screen corresponding to the selected member list item. Here, the expert terminal 300 may perform additional functions according to the expert selection for a specific menu on the member list screen, which will be described later.

In addition, when the preset calendar menu is selected from the initial screen displayed on the expert terminal 300, the expert terminal 300 displays the calendar screen corresponding to the selected calendar menu to display the counseling schedule of the corresponding expert. In this case, the expert terminal 300 may display the calendar screen corresponding to the selected calendar menu in the detailed information display area. Here, the calendar screen includes a calendar type menu for selecting the type of calendar provided (e.g., including list, monthly, weekly, etc.), an immediate counseling menu for performing a counseling function with the user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a detailed counseling schedule menu for displaying the counseling schedule of the expert according to the calendar type and selected period selected in the calendar type item, a counseling request approval menu for providing information on one or more counseling requests for which the expert has not yet processed counseling request approval among the counseling requests requested from the corresponding expert, an available reservation time menu for setting the available counseling reservation date and time zone of the corresponding expert, an output menu for outputting the expert's counseling schedule displayed on the calendar screen, a filter menu for providing a filter function for the expert's counseling schedule, a counseling addition menu for adding a new counseling schedule, etc. In this case, the calendar type item may be in a state in which a weekly item is selected by default. In addition, the detailed counseling schedule item may display (or include) some of the counseling schedules reserved for a specific date and time zone (e.g., including a user/client's nickname, a reservation time zone, etc.) when the counseling schedule is reserved for the specific date and time zone, and separately display a date and time zone that are available for reservation and a date and time zone that are not available for reservation among all dates and time zones depending on the expert setting (e.g., including different background colors and/or background patterns, etc., for each date and time zone that are available for reservation and are not available for reservation). In addition, examples of the output item include a print item through a printer (not illustrated), a print (or store/output) item in a file format such as a PDF format or an HWP format, etc.

In addition, when the specific menu is selected from the calendar screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a preset counseling request approval item is selected from the calendar screen displayed on the expert terminal 300, to provide information on one or more counseling request cases (or unapproved counseling request cases) for which the expert has not yet processed counseling request approval among the counseling request cases in which counseling from the corresponding expert has been requested, the expert terminal 300 is linked with the server 200 to display a counseling request approval screen corresponding to the selected counseling request approval item. Here, the counseling request approval screen includes a monthly calendar item for displaying the number of monthly counseling cases (or a daily calendar item for displaying the number of daily counseling cases for the corresponding month) based on the month corresponding to the current date in the expert terminal 300, counseling request approval processing items by date (or by day of the week) to display one or more counseling request cases (or unapproved counseling request cases) that have not yet been approved among the counseling request cases, and a close item (or end item), etc., and may be displayed in a pop-up form or a new screen form (e.g., including a new window form, a new screen form, etc.). In addition, the counseling request approval processing items by date include the nickname item of a counseling requester corresponding to a counseling request case that has not yet been approved by date (or by day of the week), a request time information item (e.g., including 10 minutes ago, 1 hour ago, etc.), counseling ticket type items (e.g., including 5 basic counseling tickets, 10 basic counseling tickets, 5 in-depth counseling tickets, 10 in-depth counseling tickets, etc.), desired counseling time items (e.g., including date, time information, etc.), an approval processing item, a deletion item, etc.

In addition, when a specific unapproved counseling request (or specific counseling request case) is selected from one or more counseling request cases (or unapproved counseling request cases) that have not yet been approved in the counseling request approval screen displayed on the expert terminal 300 according to the expert selection, the expert terminal 300 displays detailed information on the selected specific unapproved counseling request case. Here, the detailed information (or detailed specific unapproved counseling request information) includes a counseling request approval processing item (or area) by date, a detailed counseling requester information display item for the counseling requester corresponding to the corresponding specific unapproved counseling request case, etc. In addition, examples of the detailed counseling requester information display item include a nickname item of a counseling requester, a character (or photo/image) item of a counseling requester, a gender item, a birth date item, an emergency contact network (or phone number) item, a counseling ticket type item (e.g., time, number of times, etc., for each type), a desired counseling time item (e.g., date, time, etc.), an item for displaying a topic on which the counseling requester would like to receive counseling, an additional inquiry item, an acceptance item, a reschedule item, a close item, etc.

In addition, when the preset acceptance item is selected from the detailed information on the specific unapproved counseling request case displayed on the expert terminal 300 according to the corresponding expert selection, the expert terminal 300 is linked with the terminal 100 and the server 200 corresponding to the corresponding specific unapproved counseling request case to confirm the counseling schedule for the corresponding specific unapproved counseling request case.

That is, when the preset acceptance item is selected from the detailed information on the specific unapproved counseling request case displayed on the expert terminal 300 according to the corresponding expert selection, to add a new counseling schedule, the expert terminal 300 is linked with the server 200 to provide a new counseling addition screen corresponding to date and time zone items related to the corresponding specific unapproved counseling request case. Here, the new counseling addition screen includes expert information items (e.g., including a character/photo/image, an expert name/name, a counseling field (or specialty field), etc.) for displaying the information related to the expert of the expert terminal 300, a counseling topic selection item for selecting a counseling topic (e.g., including anxiety, depression, interpersonal relationships, etc.), a counseling completion number display item for displaying the number of counseling cases completed by the corresponding expert, a current progress display item for displaying the number of counseling sessions the corresponding expert currently has in progress, an average counseling time display item for displaying an average counseling time of the corresponding expert, a counseling content writing item for writing counseling content, an additional client selection item for selecting information on a counseling requester, a date and time zone selection item for selecting an available counseling reservation date and time zone, a cancel item for canceling a process of adding new counseling content, a storing item for a storage function according to input values for each item, a close item for ending (or closing) the corresponding new counseling addition screen, etc.

In addition, the expert terminal 300 receives a new counseling schedule including a plurality of input values corresponding to a plurality of input items related to the new counseling schedule according to the expert input of the expert terminal 300 on the new counseling addition screen displayed on the expert terminal 300. Here, the new counseling schedule includes expert information (e.g., a counselor name/expert name, a counseling field, etc.), a counseling topic, counseling content, client (or counseling requester/user) information (e.g., a client's nickname, etc.), a counseling reservation date and time zone, etc. In this case, the expert information, the counseling topic, etc., may be preset in response to the expert terminal 300 (or the expert of the expert terminal 300).

In addition, the expert terminal 300 is linked with the server 200 to map (or match/link) the received new counseling schedule with the user information (or expert information) of the expert terminal 300 and the member information (or user information/personal information) of the user of the terminal 100 corresponding to the client related to the corresponding new counseling schedule and store (or register/manage) the mapped information in the server 200.

That is, the expert terminal 300 transmits the received new counseling schedule, counseling schedule storage request information, identification information of the expert terminal 300, identification information (or a nickname/member unique ID) of the terminal 100 corresponding to the client related to the new counseling schedule to the server 200. Here, the identification information of the expert terminal 300 includes a mobile directory number (MDN), a mobile Internet protocol (IP), mobile media access control (MAC), subscriber identification module (SIM) card unique information, a serial number, etc.

In addition, the expert terminal 300 is linked with the server 200 to display the calendar screen to which the newly registered counseling schedule is applied (or reflected).

In addition, the expert terminal 300 is linked with the server 200 to display the calendar screen to which the newly registered counseling schedule is applied (or reflected).

In addition, the terminal 100 receives the information indicating that the counseling schedule with the corresponding expert transmitted from the server 200 is confirmed for the specific counseling request case previously requested through the server 200, and displays (or outputs) the information indicating that the counseling schedule with the received corresponding expert has been confirmed.

In addition, the terminal 100 is linked with the server 200 to perform a final confirmation function (or final acceptance/confirmation function) so that the counseling schedule for the corresponding specific counseling request case is finally confirmed (or reserved).

In addition, when a preset reschedule item is selected from detailed information on a specific unapproved counseling request case displayed on the expert terminal 300 according to the corresponding expert selection, the expert terminal 300 may be linked with the server 200 and the terminal 100 related to the corresponding specific unapproved counseling request case to perform a readjustment function for a counseling schedule (e.g., including date, time, etc.) initially requested from the corresponding terminal 100.

In addition, when the preset available reservation time item is selected from the calendar screen displayed on the expert terminal 300, to set the available counseling reservation date and time zone of the corresponding expert, the expert terminal 300 is linked with the server 200 to display the available reservation time setting screen corresponding to the selected available reservation time item. Here, the available reservation time setting screen includes a calendar item corresponding to the current date in the expert terminal 300, a close item, etc., and may be displayed in the form of a pop-up or a new screen (e.g., including a new window, a new screen, etc.).

In addition, when a specific date is selected from the available reservation time setting screen displayed on the expert terminal 300, to set an available counseling reservation time zone, the expert terminal 300 is linked with the server 200 to display the time zone setting screen corresponding to the selected specific date. Here, the time zone setting screen includes an available reservation time zone item in relation to the corresponding specific date, a cancel item for canceling a time zone setting, a storing item for storing the information on the selected available reservation time zone, a close item for ending (or closing) the screen without storing content, etc., and may be displayed in the form of a pop-up or a new screen (e.g., including a new window, a new screen, etc.)

In addition, when a specific time zone is selected from the time zone setting screen displayed on the expert terminal 300 according to the corresponding expert selection, the expert terminal 300 is linked with the server 200 to set the corresponding specific date and the specific time zone as the available counseling reservation date and time zone of the corresponding expert. Here, the time zone may be set in a preset standard time unit (e.g., 1 hour, 30 minutes, etc.).

In addition, the expert terminal 300 displays a calendar screen in which a newly set available date and time zone of the corresponding expert is reflected (or applied). In this case, in the detailed counseling schedule item of the calendar screen, among all dates and time zones, the available reservation date and time zone to which the newly set available counseling reservation date and time zone are applied among all dates and time zones according to the expert setting and an unavailable reservation date and time zone may be displayed separately (e.g., including different background colors and/or background patterns, etc., for when reservations are and are not available in the time zone for each date, etc.).

In addition, when any one counseling schedule (or specific date and time zone corresponding to a specific reserved counseling schedule/counseling schedule) is selected from the detailed counseling schedule items in the calendar screen displayed on the expert terminal 300 including one or more reserved counseling schedules, the expert terminal 300 is linked with the server 200 to display the personal counseling management screen corresponding to the user (or client/counseling requester) related to the selected counseling schedule (or counseling schedule of the selected specific date and time zone). Here, the personal counseling management screen includes some of personal information display items for displaying some of the personal information (e.g., including a nickname, the remaining number of counseling sessions out of the total number of available counseling sessions, etc.) of the counseling requester, an XR room invitation item for inviting the corresponding counseling requester to the XR room to perform the counseling function in the XR chat room (or metaverse chat room) with the counseling requester, a reservation date change item for changing the counseling schedule with the counseling requester (e.g., a specific date and time zone related to the selected counseling schedule), a default information item for providing default information (or personal information) on the corresponding counseling requester, a reservation timeline item for providing a reservation situation for the corresponding counseling requester, a counseling record sheet item for providing a counseling record sheet for the corresponding counseling requester, a memo item for providing an unusual situation related to the corresponding counseling requester, and a close item for ending (or closing) the personal counseling management screen, etc., and may be displayed in the form of a pop-up or a new screen (e.g., including a new window, a new screen, etc.). In this case, the XR room invitation item may be activated when the corresponding counseling requester is accessing the website (or online/logged in), and may be deactivated by default. In addition, examples of the reservation timeline item include a counseling topic item, an item for displaying the number of counseling sessions completed, an item for displaying the remaining number of counseling sessions, an average counseling time display item, a counseling content item by date and time zone, a reservation change item, an expert (or person in charge/counselor) item, a counseling time item, a detail view item for a detail view for additional information, etc. In this case, the reservation change item may not change the counseling requester related to the counseling case, and may be configured to change only the expert of the expert terminal 300.

In addition, the expert terminal 300 may confirm (or display/modify) the default information, the reservation schedule (or reservation timeline), the counseling record sheet, notes, etc., in relation to the user related to the corresponding counseling schedule according to the default information item, the reservation timeline item, the counseling record sheet item, the memo items, etc., that are included in the personal counseling management screen displayed on the expert terminal 300.

In addition, when a preset additional counseling item is selected from the calendar screen displayed on the expert terminal 300 or the available counseling reservation date and time zone item is selected from the detailed counseling schedule time in the calendar screen displayed on the expert terminal 300, to add a new counseling schedule, the expert terminal 300 is linked with the server 300 to display a new counseling addition screen corresponding to the selected additional counseling item or the selected available counseling reservation date and time zone item. Here, the new counseling addition screen includes expert information items (e.g., including a character/photo/image, an expert name/name, a counseling field (or specialty field), etc.) for displaying the information related to the expert of the expert terminal 300, counseling topic selection items for selecting a counseling topic (e.g., including anxiety, depression, interpersonal relationships, etc.), a counseling completion number display item for displaying the number of counseling cases completed by the corresponding expert, a current progress display item for displaying the number of counseling sessions the corresponding expert currently has in progress, an average counseling time display item for displaying an average counseling time of the corresponding expert, a counseling content writing item for writing counseling content, an additional client selection item for selecting information on a counseling requester, a date and time zone selection item for selecting an available counseling reservation date and time zone, a cancel item for canceling a process of adding new counseling content, a storing item for a storage function according to input values for each item, a close item for ending (or closing) the corresponding new counseling addition screen, etc.

In addition, the expert terminal 300 receives a new counseling schedule including a plurality of input values corresponding to a plurality of input items related to the new counseling schedule according to the expert input of the expert terminal 300 on the new counseling addition screen displayed on the expert terminal 300. Here, the new counseling schedule includes expert information (e.g., a counselor name/expert name, a counseling field, etc.), a counseling topic, counseling content, client (or counseling requester/user) information (e.g., a client's nickname, etc.), a counseling reservation date and time zone, etc. In this case, the expert information, the counseling topic, etc., may be preset in response to the expert terminal 300 (or the expert of the expert terminal 300).

In addition, the expert terminal 300 is linked with the server 200 to map (or match/link) the received new counseling schedule with the user information (or expert information) of the expert terminal 300 and the member information (or user information/personal information) of the user of the terminal 100 corresponding to the client related to the corresponding new counseling schedule and store (or register/manage) the mapped information in the server 200.

That is, the expert terminal 300 transmits the received new counseling schedule, counseling schedule storage request information, identification information of the expert terminal 300, identification information (or nickname/member unique ID) of the terminal 100 corresponding to the client related to the new counseling schedule to the server 200. Here, the identification information of the expert terminal 300 includes a mobile directory number (MDN), a mobile Internet protocol (IP), mobile media access control (MAC), subscriber identification module (SIM) card unique information, a serial number, etc.

In addition, the terminal 100 receives the information indicating that the counseling schedule with the corresponding expert transmitted from the server 200 is confirmed for the specific counseling request case previously requested through the server 200, and displays (or outputs) the information indicating that the counseling schedule with the received corresponding expert has been confirmed.

In addition, the server 200 is linked with the expert terminal 300 and the terminal 100 to perform a final confirmation function (or final acceptance/confirmation function) for the counseling schedule case newly registered in the expert terminal 300 so that the counseling schedule for the counseling schedule case newly registered in the expert terminal 300 is finally confirmed.

In addition, the expert terminal 300 is linked with the server 200 to display the calendar screen to which the newly registered counseling schedule is applied (or reflected).

In addition, when a preset member list menu is selected from the initial screens displayed on the expert terminal 300, the expert terminal 300 displays a member list screen corresponding to the selected member list menu to display the member information of the user who is counseling with the corresponding expert. In this case, the expert terminal 300 may display the member list screen corresponding to the selected calendar menu in the detailed information display area. Here, the member list screen includes a member list type menu for selecting the member list type provided (e.g., including list, thumbnail, etc.), an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including expert character/picture, expert name/name, etc.), a number of current counseling members display menu for displaying the number of members receiving counseling from the corresponding expert, a sorting menu for providing a sorting function for the member list (e.g., including the order of the earliest next reservation date, the most recently completed counseling date, the order of the longest membership period remaining, the order of the shortest membership period remaining, the order of the first registration date, etc.), a member search menu for searching for members, a counseling request approval menu for providing information on one or more counseling requests for which the expert has not yet processed counseling request approval among the counseling requests requested from the corresponding expert, a filter menu for providing a filter function for the expert's counseling schedule, an output menu for outputting a member list displayed on the member list screen, a deletion menu for deleting information on a specific member displayed on the member list screen, a detailed member list display area (or detailed member list display menu) for displaying information on a user (or client) who has registered with (or is receiving counseling from) the expert according to the member list type selected in the member list type item, etc. In this case, the member list type menu may be in a state in which a list item is selected as default.

In addition, when the specific menu is selected from the member list screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a preset list item is selected from the member list type item in the member list screen displayed on the expert terminal 300, the expert terminal 300 is linked with the server 200 to display the member list information in the form of the list corresponding to the selected list item. In this case, the expert terminal 300 may display the member list information in the form of the list corresponding to the selected list item in the detailed member list display area. Here, the member list information in the list form includes color items for each user, a user's name display item (or user/member/counseling requester nickname display items), an item for displaying whether the user is currently online, an emergency contact network display item, an item for displaying a counseling membership type and the remaining number of sessions (e.g., 7/10 of the basic 10 counseling tickets, etc.), an initial registration date display item, a recently completed counseling date item, a next reservation date display item, etc., and may be displayed in the form of a pop-up or a new screen (e.g., including a new window, a new screen, etc.). In this case, the color items for each user may be set for each member (or for each counseling requester) by the corresponding expert for the purpose of helping the corresponding expert easily understand the characteristics of the counseling requester.

In addition, when a specific member list (or specific member list item/specific member) is selected from the member list information in the form of the list displayed on the expert terminal 300, the expert terminal 300 is linked with the server 300 to provide detailed specific member list information corresponding to the selected specific member list to the expert terminal 300. Here, the detailed specific member list information (or detailed specific member information) includes a message transmission item for performing a message function with the counseling requester corresponding to the corresponding specific member, an activity history view item for providing an activity history of the corresponding counseling requester, an XR room invitation item for inviting the corresponding counseling requester to the XR room to perform the counseling function in the XR chat room (or metaverse chat room) with the corresponding counseling requester, a detailed personal information item related to the counseling requester corresponding to the corresponding specific member list, a reservation timeline item for providing a reservation situation for the corresponding counseling requester, a close item for ending (or closing) the corresponding detailed specific member information, etc., and may be displayed in the form of a pop-up or new screen (e.g., including a new window, a new screen, etc.). Examples of the detailed personal information item include a character item for the counseling requester, a nickname item, an item for displaying the remaining number of uses out of the total number of uses, an output item for outputting the information included in the corresponding detailed specific member list information, a deletion item for deleting the information on the specific member included in the corresponding detailed specific member list information, a gender item, a birth date item, an emergency contact network (or phone number) item, a counseling ticket type item (e.g., time, the number of sessions, etc., for each type), an initial registration date item, an average counseling time display item, a recent counseling date display item, a next registration date display item, an item for displaying a topic on which a requester would like to receive counseling, an additional inquiry item, etc. In addition, examples of the reservation timeline item include a counseling content item by date and time zone, a reservation change item, an expert (or person in charge/counselor) item, a counseling time item, a detail view item for a detail view of additional information, etc.

In this case, when a specific member (or a specific member list item) is selected from the member list information in the form of the list displayed on the expert terminal 300, the expert terminal 300 may display the chat report related to the corresponding counseling requester to be described below.

In addition, when a preset list thumbnail item is selected from the member list type item in the member list screen displayed on the expert terminal 300, the expert terminal 300 is linked with the server 200 to display the member list information in the form of the thumbnail corresponding to the selected thumbnail item. In this case, the expert terminal 300 may display the member list information in the form of the thumbnail corresponding to the selected thumbnail item in the detailed member list display area. Here, the member list information in the form of the thumbnail is configured in the form of a profile card, and includes a fixed setting item for selecting whether to fix the profile card of the corresponding counseling requester, a character (or photo/image) item of a counseling requester, a nickname item (or name item), a recent counseling date item (or recently completed counseling date item), a counseling reservation date item (or next reservation date item), an item for displaying a counseling membership type and the remaining number of sessions (e.g., 7/10 of the basic 10 counseling tickets, etc.), a reservation change item, a message sending item (or message transmission item), an XR room invitation item (or XR room invitation item/metaverse chat room invitation item), etc.

In addition, when another specific member (or another specific member list item) is selected from the member list information in the form of the thumbnail displayed on the expert terminal 300, the expert terminal 300 is linked with the server 300 to display other detailed specific member information corresponding to the selected other specific member. Here, the other detailed specific member list information includes a message transmission item for performing a message function with the counseling requester corresponding to the corresponding other specific member, an activity history view item for providing an activity history of the corresponding counseling requester, an XR room invitation item for inviting the corresponding counseling requester to the XR room to perform the counseling function in the XR chat room (or metaverse chat room) with the corresponding counseling requester, a detailed personal information item related to the counseling requester corresponding to the corresponding other specific member, a reservation timeline item for providing a reservation situation for the corresponding counseling requester, a close item for ending (or closing) the corresponding other detailed specific member information, etc., and may be displayed in the form of a pop-up or a new screen (e.g., including a new window, a new screen, etc.). Examples of the detailed personal information item include a character item for the counseling requester, a nickname item, an item for displaying the remaining number of uses out of the total number of uses, an output item for outputting the information included in the corresponding other detailed specific member information, a deletion item for deleting the information on the other specific member included in the corresponding other detailed specific member information, a gender item, a birth date item, an emergency contact network (or phone number) item, a counseling ticket type item (e.g., time, the number of sessions, etc., for each type), an initial registration date item, an average counseling time display item, a recent counseling date display item, a next registration date display item, an item for displaying a topic on which a user would like to receive counseling, an additional inquiry item, etc. In addition, examples of the reservation timeline item include a counseling content item by date and time zone, a reservation change item, an expert (or person in charge/counselor) item, a counseling time item, a detail view item for a detail view of additional information, etc.

In this case, when other specific members (or other specific member list items) are selected from the member list information in the form of the thumbnail displayed on the expert terminal 300, the expert terminal 300 may display the chat report related to the corresponding counseling requester to be described below.

In addition, when a preset member report menu is selected from the initial screens displayed on the expert terminal 300, the expert terminal 300 displays a member report screen corresponding to the selected member report menu to display the activity history of the user who is counseling with the corresponding expert for a preset period. In this case, the expert terminal 300 may display the member report screen corresponding to the selected member report menu in the detailed information display area. Here, the member report screen includes an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a sorting menu for providing a sorting function (e.g. currently online, most recent activity, high "free expression" index, low "free expression" index, etc.) for the member report in order to provide a member report based on activity details for a preset period (e.g. 7 days), a member search menu for searching for members, a counseling request approval menu for providing information on one or more counseling requests for which the expert has not yet processed counseling request approval among the counseling requests requested from the corresponding expert, a filter menu for providing a filter function for the expert's counseling schedule, an output menu for outputting information displayed on the member report screen, a deletion menu for deleting information on a specific member displayed on the member report screen, a detailed member report display area for displaying information on one or more members that meet the sort item, etc. In addition, the detailed member report display area (or detailed member report detail menu) is configured in the form of a profile card, and includes a fixed setting item for selecting whether to fix the profile card of the corresponding counseling requester, a character (or photo/image) of a counseling requester, a nickname item (or name item), a total counseling time item (or total played time item), a "free expression" index item, etc. In addition, the "free expression" index item includes a total "free expression" index (or average "free expression" index) item, a topic talk "free expression" index item, a role-playing "free expression" index item, a theme practice "free expression" index item, etc. In addition, the "free expression" index represents an evaluation index for the user (or counseling requester) of the terminal 100 according to the performance of the chat function, and may be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates.

In addition, when the specific menu is selected from the member report screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a specific member report (or a specific member) is selected from the detailed member report display area in the member report screen displayed on the expert terminal 300, the expert terminal 300 is linked with the server 200 to display detailed member report information corresponding to the selected specific member report. Here, the detailed member report information (or detailed member report screen) includes a return-to-member-report item for returning to a previous screen (or a member report screen), a detailed personal information display item for displaying personal information on the counseling requester (or specific user) corresponding to the corresponding specific member report, a counseling record sheet item for displaying a counseling record sheet related to one or more counseling sessions performed by the corresponding counseling requester, a cognitive behavior therapy record sheet item (or cognitive behavior record sheet item) for displaying cognitive behavior therapy record sheet related to one or more counseling sessions performed by the corresponding counseling requester, a questionnaire result item for displaying questionnaire results related to the questionnaire performed by the corresponding counseling requester, a people diary item for displaying content of an emotional state by date written by the corresponding counseling requester (or the content of the emotional state by date written by the corresponding specific user), a chat report item for displaying a chat report (or "my report") related to the corresponding counseling requester, a past counseling record item for displaying past counseling record content performed by the corresponding counseling requester, a detailed information display area (or detailed information display item) for providing detailed information on a specific item selected among multiple items, etc. In addition, examples of the detailed personal information item above include an item for displaying whether one is currently online for displaying information on the real-time connection state of the corresponding counseling requester, a character (or image/photo) item of the corresponding counseling requester, a nickname item of the corresponding counseling requester, an item for displaying a type (e.g., topic talk, role-playing, theme practice, etc.) of a counseling case in progress when the corresponding counseling requester is currently in counseling, an item for displaying the remaining number of uses out of the total number of uses (or a counseling progress situation item), a gender item, a birth date item, an emergency contact network (or phone number) item, a counseling ticket type item (e.g., time, number of sessions, etc., for each type), an initial registration date item, an average counseling time item, a recent counseling date item (or recently completed counseling date item), a next reservation date item (or counseling reservation date item), etc.

In addition, when the specific menu is selected from the detailed member report information displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a preset counseling record sheet item is selected from the member report detailed information displayed on the expert terminal 300, the expert terminal 300 is linked with the server 200 to display a counseling record sheet screen corresponding to the selected counseling record sheet item. Here, the counseling record sheet screen includes a sorting item for providing the sorting function (e.g., including sorting by most recent, sorting by the expert/person in charge, etc.) in relation to one or more counseling cases performed by the corresponding counseling requester, an output item for outputting the information displayed on the relevant counseling record sheet screen, a deletion item for deleting the information on the specific counseling record case displayed on the corresponding counseling record sheet screen, a counseling content items by date and time, an expert item by date and time (or person in charge/counselor item by date and time), a counseling time item by date and time, a detail view item for the counseling record sheet by date and time, etc.

In this case, when a specific member report (or a specific member) is selected from the detailed member report display area in the member report screen displayed on the expert terminal 300, the expert terminal 300 may be linked with the server 200 to display a counseling record sheet screen corresponding to the selected specific member report preset by default in the detailed information display area.

In addition, when the detail view item displayed on one side of a specific counseling record sheet is selected from the counseling record sheet screen displayed on the expert terminal 300, the expert terminal 300 is linked with the server 200 to display the detailed counseling record sheet information on the specific counseling record sheet related to the selected detail view item. Here, the detailed counseling record sheet information includes a counseling record sheet writing date item related to the corresponding specific counseling record sheet case, a modification item for modifying the content of the corresponding specific counseling record sheet, an output item for outputting the content of the corresponding specific counseling record sheet, a deletion item for deleting the content of the corresponding specific counseling record sheet, a session number and counseling topic item, an expert name item, a last modified date display item, a user's subjective item, an expert's objective item, a future plan item, a feedback item to a user, etc. In this case, the expert's objective item may vary depending on whether the expert of the expert terminal 300 is a mentor expert, a psychological counseling expert, or a speech lesson expert. That is, when the expert of the expert terminal 300 is a mentor expert, examples of the expert's objective item include a common checklist item (e.g., including anxiety, assertiveness/confidence, mind control, communication skills, listening skills, sociability, situational judgment power, will to improve, strength/levels for each item, brief descriptions for each item, etc.), a mentoring checklist item (e.g., including professionalism, interest/degree of interest, propensity coincidence, counseling purpose, etc.), a problem situation item (e.g., including a chat situation, a presentation situation, an interview situation, etc.), an expert recommendation item (e.g., including "I think you need to go to the hospital," "I think you would benefit from psychological counseling," "I think you would benefit from speech training," "I think you would benefit more from help from a specific mentor expert," etc.), a difficult target item (e.g., including family, a romantic relationship, a friend, a workplace, others, etc.), a topic/situation item (e.g., including a daily topic, a professional topic, etc.) required for training, an expert's opinion item, etc. In addition, when the expert of the expert terminal 300 is a psychological counseling expert, examples of the expert's objective item include a common checklist item (e.g., anxiety, assertiveness/confidence, mind control, communication skills, listening skills, sociability, situational judgment power, will to improve, strength/levels for each item, brief descriptions for each item, etc.), a psychological state checklist item (e.g., social anxiety, depression/anxiety, panic disorder, sleep disorder, bipolar disorder, alcoholic dementia, addiction (e.g., including game addiction, drug addiction, gambling addiction, etc.), cognitive distortion, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation item (e.g., a daily topic, a professional topic, etc.) required for training, an expert's opinion item, etc. In addition, when the expert of the expert terminal 300 is a speech lesson expert, examples of the expert's objective item include a common checklist item (e.g., anxiety, assertiveness/confidence, mind control, communication skills, listening skills, sociability, situational judgment power, will to improve, strength/levels for each item, brief descriptions for each item, etc.), a speech checklist item (e.g., fluency, logic, speed/pace, vocalization/tone, leadership, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation item (e.g., a daily topic, a professional topic, etc.) required item for training, an expert's opinion item, etc.

In addition, the expert terminal 300 may additionally perform a modification function, an output function, a deletion function, etc., on the content of the detailed counseling record sheet information being displayed on the expert terminal 300.

In addition, when a preset cognitive behavior therapy record sheet item is selected from the detailed member report information displayed on the expert terminal 300, the expert terminal 300 is linked with the server 200 to display the cognitive behavior therapy record sheet screen corresponding to the selected cognitive behavior therapy record sheet item. Here, the cognitive behavior therapy record sheet screen (or cognitive behavior record sheet screen) includes an output item for outputting information displayed on the corresponding cognitive behavior therapy record sheet screen, a deletion item for deleting information on a specific cognitive behavior therapy record sheet displayed on that cognitive behavior therapy record sheet screen, a record sheet item written by the user together during the counseling to provide a list of cognitive behavior therapy record sheets written by the user together during the counseling, a record sheet item written by the user alone to provide a list of cognitive behavior therapy record sheets written by the user alone, etc. In addition, the record sheet item written together during the counseling includes a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), etc. In addition, the record sheet item written by the user alone includes a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), an item on whether to confirm the written cognitive behavior therapy record sheet (e.g., including confirmation needed, confirmation not needed, confirmed, etc.), etc.

In addition, when the specific cognitive behavior therapy record sheet is selected from the cognitive behavior therapy record sheet screen displayed on the expert terminal 300 (or when the item that is being or has been written before/after the training related to the specific cognitive behavior therapy record sheet is selected), the expert terminal 300 is linked with the server 200 to display the detailed cognitive behavior therapy record sheet information on the specific cognitive behavior therapy record sheet case related to the selected specific cognitive behavior therapy record sheet. Here, the detailed cognitive behavior therapy record sheet information (or detailed cognitive behavior therapy record sheet information related to the selected specific cognitive behavior therapy record sheet) includes a writing date item of the cognitive behavior therapy record sheet related to the corresponding specific cognitive behavior therapy record sheet case, a modification item for modifying the content of the corresponding specific cognitive behavior therapy record sheet, an output item for outputting the content of the corresponding specific cognitive behavior therapy record sheet, a deletion item for deleting the content of the corresponding specific cognitive behavior therapy record sheet, a session number and counseling topic display item, a writer ID and name display item, a writing state display item before/after training (e.g., not written, being written, written, etc.), a last modified date display item, a cognitive behavior information item for each item before training, a cognitive behavior information item for each item before training, etc. In addition, examples of the cognitive behavior information item for each item before training include: an item for displaying "What are situations that make you anxious?," an item for displaying "How are you feeling at this time?" (e.g., including anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.); an item for displaying "What are your thoughts in that situation?" (e.g., including a confidence level, a cognitive error, etc.); an item for displaying "Please correct my wrong thoughts!" (or a reasonable response finding item, a behavioral goal setting item, etc.). In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item (e.g., an improvement-related item, an anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/fury, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before training and/or the cognitive behavior information item for each item after training may be commonly preset or may be set differently for each expert.

In addition, the expert terminal 300 may additionally perform a modification function, an output function, a deletion function, etc., on the content of the detailed cognitive behavior therapy record sheet information being displayed on the expert terminal 300.

In addition, when the cognitive behavior therapy record sheet handwritten by the user of the corresponding terminal 100 is shared (or linked), the expert terminal 300 may display detailed cognitive behavior therapy record sheet information handwritten by the user of the terminal 100.

In addition, when a preset questionnaire result item is selected from the detailed member report information displayed on the expert terminal 300, the expert terminal 300 is linked with the server 200 to display a questionnaire result screen corresponding to the selected questionnaire result item. Here, the questionnaire result screen includes a sorting item for providing the sorting function (including, for example, sorting by most recent, by format, etc.) in relation to one or more questionnaire cases performed by the corresponding counseling requester, a deletion item for deleting the selected questionnaire results (or selected questionnaire items), a file name item for each questionnaire, a last modified time item for each questionnaire, a format item for each questionnaire (or questionnaire type item), a result item (or detail view item) for each questionnaire, etc.

In addition, when a specific file name (or specific file name item) is selected from one or more file names (or file name items) in the questionnaire result screen displayed on the expert terminal 300 or when a detailed item related to a specific file name is selected from one or more file names displayed on the questionnaire result screen, the expert terminal 300 is linked with the server 200 to display detailed questionnaire information related to the selected specific file name or a specific file name corresponding to the selected detailed item. Here, the detailed questionnaire information is configured variously depending on the purpose of the questionnaire, and may include content of one or more questions for each questionnaire, answers/responses to the question content, etc.

In addition, when a preset people diary item is selected from the detailed member report information displayed on the expert terminal 300, the expert terminal 300 is linked with the server 200 to display a people diary screen corresponding to the selected people diary item. In this case, the expert terminal 300 may display the people diary screen corresponding to the selected people diary item in the detailed information display area. Here, the people diary screen includes a calendar screen, etc., including the emotional record state by date in preset period units (e.g., including 3 months, 6 months, etc.). Here, when the calendar screen (or calendar item) is in a state where the emotional record information (e.g., including detailed emotional record information, simple emotional record information, etc.) is stored on a specific date, the calendar screen (or calendar item) includes an emotional record state (or mind state), such as images (or emoticon/avatar) representing feeling comfortable, normal, and uncomfortable, corresponding to mental state information, which is part of the information in the corresponding emotional record information on the corresponding specific date.

In addition, when a specific date including the emotional record state in the people diary screen displayed on the expert terminal 300 is selected, the expert terminal 300 is linked with the server 200 to display a detailed people diary screen related to the selected specific date. Here, the detailed people diary screen includes a calendar screen (or calendar item) related to the corresponding specific date, an emotional record information item related to the corresponding specific date, an emotional pattern graph item for the corresponding month related to the corresponding specific date, an information display item related to the corresponding counseling requester's emotional record state for the corresponding week related to the corresponding specific date, etc. In addition, examples of the emotional record information item include date information, situation information (e.g., including who else is there, a counterpart's actions, one's own actions, etc.), and emotional information (e.g., including one's emotional state, whether to express emotions, one's current emotions, etc.), review information (e.g., comfort level in chat, future resolutions, personal notes, etc.), etc. In addition, examples of the information display item (or weekly emotional record information item) about the counseling requester's emotional record state include mental state items by day of the week (or date), a situation information item (e.g., including who else is there, a counterpart's actions, one's own actions, etc.), an emotional information item (e.g., including one's emotional state, whether to express emotions, one's current emotions, etc.), a review information item (e.g., including comfort level in chat, future resolutions, personal notes, etc.), a detail view item, etc.

In addition, when a preset chat report item is selected from the detailed member report information displayed on the expert terminal 300, the expert terminal 300 is linked with the server 200 to display a chat report screen for the expert corresponding to the selected chart report item. In this case, the expert terminal 300 may display the chat report screen seen by the expert corresponding to the selected chat report item in the detailed information display area. Here, the chat report screen seen by the expert (or the "my report" screen seen by the expert) includes an analysis result item for providing the analysis results according to the performance of the functions such as topic talk, role-playing, and theme practice in relation to the corresponding counseling requester, a participation list item for providing the participation list related to the chat list in which the corresponding user participates, a content display item (or content display area) for displaying the detailed information according to the selection of the analysis result item or the participation list item, etc.

In addition, when a preset analysis result item is selected from the chat report screen for the expert (or a "my report" screen used by the expert) displayed on the expert terminal 300, to provide the analysis results according to the performance of chat functions such as topic talk, role-playing, and theme practice in relation to the user of the terminal 100, the expert terminal 300 displays the detailed information corresponding to the selected analysis result menu in the content display area. In this case, when the preset chat report item is selected from the app execution result screen displayed on the expert terminal 300, the expert terminal 300 may display the analysis result screen (or the detailed information) corresponding to the analysis result item set by default in response to the selected chat report item in the content display area by default. Here, the analysis result item (or the analysis result screen/detailed information) includes a sort item for sorting functions related to all, topic talk, role-playing, theme practice, etc., a "number of times you've participated in the chat room" display item for displaying the number of times the user has participated in the chat room within a preset period, a period display item for displaying the corresponding preset period, a "number of times you've participated in the chat room by category" display item for displaying the number of times the user has participated in the chat room by category, a "free expression" index display item for displaying the "free expression" index calculated in relation to the user, an anxiety index display item for displaying the anxiety index calculated in relation to the user, a detailed score view item for displaying additional detailed information in relation to the "free expression" index or the anxiety index, a relative evaluation display item for displaying information on oneself as evaluated by other users who performed the chat function together, a "my 'free expression' score aspect" display item for displaying the "free expression" score aspect, a "my anxiety score pattern" display item for displaying the user's anxiety score pattern, a "my confidence/assertiveness, mind control, communication skills/logic/persuasive power, immersion, empathy/listening skills score aspect" display item for displaying the user's confidence/assertiveness, mind control, communication skills/logic/persuasive power, immersion, empathy/listening skills score aspect, a "topic I have practiced a lot" display item for displaying a topic that the user has practiced a lot in relation to the topic talk, a "keyword that I have practiced a lot" display item for displaying keywords that the user has practiced a lot in relation to the topic talk, a "target I've practiced a lot" display item for displaying what the user has practiced a lot in relation to role-playing, a "situation I've practiced a lot" display item for displaying situations in which the user has practiced a lot in relation to role-playing, a "What emotions am I sensitive to?" display item for displaying what emotions the user is sensitive to in relation to role-playing, a "Which experts I have practiced with a lot?" display item for a displaying indicating with which experts the user has practiced a lot in relation to the theme, a "theme I practiced a lot" display item for displaying a theme that the user has practiced a lot in relation to theme practice, etc. Here, the "free expression" index display item includes an overall rating display item, a "free expression" index overall average display item, a satisfaction graph display item for overall average, a "free expression" index change graph display item by day of the week, a score display item for each item (e.g., including confidence/assertiveness, mind control, communication skills/logic/persuasive power, immersion, empathy/listening skills, etc.), a graph display item of a score change for each item by day of the week, an exponential distribution display item for each topic and situation, a detailed score view item, etc. In addition, the anxiety index display item includes a total rating display item, an anxiety index overall average display item, an anxiety graph display item for the overall average, a graph display item of an anxiety index change by day of the week, etc. In this case, the "free expression" index can be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates. In addition, the anxiety index represents the average value of the anxiety self-evaluated by the user after performing the chat function in the chat room (e.g., including the topic talk chat room, the role-playing chat room, the theme practice chat room, etc.) in which the user participates in relation to one or more chat rooms in which the user of the corresponding terminal 100 participates for a preset period or all chat rooms in which the user of the corresponding terminal 100 participates. In addition, examples of the relative evaluation display item include the reason for receiving a good evaluation, the reason for receiving a bad evaluation, and the satisfaction of chat evaluated by others. In addition, examples of the "my 'free expression' score aspect" display item include a "How many people am I with when my free expression score gets high?" item, a "What age group of people am I talking with when I have a high score in 'free expression'?" item, a "What MBTI type am I talking with when I have a high score in 'free expression'?" item, a "What gender is the person I'm talking with when I have a high score in 'free expression'?" item, a "When I talk in a certain place, do I have a high score in free expression?" item, etc. In addition, the "my anxiety score aspect" display item includes a "How many people am I with when my anxiety score gets high?" item, a "What age group of people am I talking with when I have a high score in anxiety?" item, a "What MBTI type am I talking with when I have a high score in anxiety?" item, a "What gender is the person I'm talking with when I have a high score in anxiety?" item, a "When I talk in a certain place, do I have a high score in anxiety?" item, etc. In addition, examples of the "topic that I have practiced a lot" display item include an interpersonal relationship item, a daily life item, an employment/workplace item, a knowledge sharing item, a well-being item, other items, etc. In addition, examples of the "keyword that I have practiced a lot" display item include a boss item, a soccer item, a job preparation item, a presentation preparation item, a health item, other items, etc. In addition, examples of the "target that I have practiced a lot" display item include a husband item, a boss item, a coworker item, a chairman item, a stranger item, other items, etc. In addition, examples of the "situation that I have practiced a lot" display item include a rejection expression item, an affection expression item, an opinion expression item, a gratitude/sorry expression item, a conflict item, other items, etc. In addition, examples of the "What emotions am I sensitive to?" display item include a joy/pleasure item, an empathy item, an appreciation item, a sorry item, a grief/hurt item, an anger/annoyance/rage item, etc. In addition, examples of the "Which experts I have practiced with a lot?" display item include a psychological counselor item, a speech trainer item, a mentor item, etc. In addition, examples of the "theme that I practiced a lot" display item include a blind date item, a phone item, an interview item, a business report item, a small-scale presentation item, a large-scale presentation item, a professional discussion item, a pros and cons discussion item, etc.

In addition, when a preset detailed score view item is selected from the detailed information included in the content display area displayed on the expert terminal 300, the expert terminal 300 is linked with the server 200 to display detailed score information corresponding to the selected detailed score view item. Here, the detailed score information (or detailed score screen) includes the sort items for sorting functions related to all, topic talk, role-playing, theme practice, etc., the "number of times you've participated in the chat room" display item, the period display item for displaying the corresponding preset period, the "number of times you've participated in the chat room for each category" display item, the "free expression" index display item, the anxiety index display item, the relative evaluation display item, the "my 'free expression' score aspect" display item, the "my anxiety score aspect" display item, the "my confidence/assertiveness, mind control, communication skills/logic/persuasive power, immersion, empathy/listening skills score pattern" display item, the "topic I have practiced a lot" display item, the "keyword that I have practiced a lot" display item, the "target that I have practiced a lot" display item, the "situation that I have practiced a lot" display item, the "Which emotions I am sensitive to?" display item, the "Which experts have I practiced with a lot?" display item, the "theme which I have practiced a lot" display item, etc. In this case, when the detailed score view item related to the "free expression" index is selected, the terminal 100 may display one or more pieces of information related to the "free expression" index among the information included in the detailed score information, and when the detailed score view item related to the anxiety index is selected, the terminal 100 may mainly display one or more other pieces of information related to the anxiety index among the information included in the detailed score information.

That is, when a preset detailed score view item is selected from the detailed information included in the content display area displayed on the expert terminal 300, the expert terminal 300 is linked with the server 200 to display the detailed score information corresponding to the selected detailed score view item instead of the "free expression" index display item or anxiety index display item displayed previously.

In addition, when a preset period display item (or date selection item/calendar item) is selected from the chat report screen viewed by the expert (or the "my report" screen used by the expert) displayed on the expert terminal 300, the expert terminal 300 displays a calendar screen corresponding to the selected period. Here, the calendar screen includes information on the presence or absence of chat records by date recorded by the user of the terminal 100 within the corresponding period (or corresponding month).

In addition, when a specific date within the calendar screen is selected, if a chat record exists on the corresponding specific date, the expert terminal 300 displays detailed score information related to the chat record, and if no chat record exists on the corresponding specific date, the expert terminal 300 displays information indicating that no chat record exists.

In addition, when the preset participation list item is selected from the chat report screen seen by the expert (or the "my report" screen used by the expert) displayed on the expert terminal 300, to provide the participation list related to the conversation list in which the user of the terminal 100 participates, the expert terminal 300 displays the participation list screen corresponding to the selected participation list item. Here, the participation list screen includes a sort item for sorting functions related to all, topic talk, role-playing, theme practice, etc., a change information display item for providing information on changes in self-evaluation results or other's evaluation results compared to a preset period (or last week), a "number of times you've participated in the chat room" display item for displaying the number of times the user has participated in the chat room within a preset period, an information display item for each chat participation case for providing information related to topic talk, role-playing, theme practice, etc., in which the user participates, etc. In this case, the information display item for each chat participation includes a date information display item of participation in the chat room, a detail view item for displaying the detailed information, a chat room type (or chat room category) display item (e.g., including topic talk, role-playing, theme practice, etc.) for displaying the type of chat room in which the user participates, a chat room topic display item for displaying the topic of the chat room, a chat room name display item for displaying the room title (or chat room name) of the chat room, a keyword display item for displaying the main keywords/hashtags related to the corresponding chat room, a self-evaluation information display item for displaying the self-evaluation results, a received evaluation information display item for displaying the evaluation information received from other users participating in the corresponding chat room, a chat recording display item for the re-listening function of chat content from the chat room, etc.

In addition, when a specific participation list (or a detail view item displayed on one side of the corresponding specific participation list) is selected from one or more participation lists displayed in the information display items for each chat participation in the participation list screen displayed on the expert terminal 300, the expert terminal 300 is linked with the server 200 to display the detailed item information related to the selected specific participation list. Here, the detailed view information includes a date information display item of participation in the chat room corresponding to the selected specific participation list, a chat room type (or chat room category) display item for displaying the type of chat room in which the user participates (e.g., including a topic talk chat room, a role-playing chat room, a theme practice chat room, etc.), a chat room topic display item for displaying the topic of the chat room, a chat room name display item for displaying the room title of the chat room, a keyword display item for displaying main keywords/hashtags related to the chat room, a chat participant information display item for displaying information (e.g., including nicknames) of other users participating in the corresponding chat room, a self-evaluation result display item (or self-evaluation information display item) for displaying self-evaluation results, a received evaluation result display item (or a received evaluation information display item) for displaying evaluation results received from other users participating in the chat room, a chat recording display item for re-listening to chat content from the chat room, etc.

In addition, when a preset past counseling record item is selected from the detailed member report information displayed on the expert terminal 300, to provide a participation list and a cognitive behavior therapy record (or cognitive behavior therapy record sheet) related to the chat room in which the user of the terminal 100 participates with the expert of the expert terminal 300, the expert terminal 300 is linked with the server 200 to display a past counseling record screen corresponding to the selected past counseling record item. In this case, the expert terminal 300 may display the past counseling record screen seen by the expert corresponding to the selected past counseling record item in the detailed information display area. Here, the past counseling record screen seen by the expert (or past counseling record screen) includes a participation list menu for providing the list of who has performed the psychological counseling, the speech lesson function, or the mentoring function with the expert in relation to the specific topic or situation, a cognitive behavior therapy record menu for providing the cognitive behavior therapy record (or cognitive behavior therapy record sheet) written by the user according to the performance of the training function for the appropriate chat style in relation to the specific topic or situation, a content display area (or content display menu) for displaying the detailed information according to the selection of the participation list menu or the cognitive behavior therapy record menu, etc.

In addition, when a preset participation list menu (or another participation list menu) is selected from the past counseling record screen seen by the expert displayed on the expert terminal 300, to provide other participation lists in which the user of the terminal 100 performs a counseling function, a speech lesson function, a mentoring function, etc., with the expert of the expert terminal 300, the expert terminal 300 displays other participation list screens corresponding to the selected participation list menu in the content display area. Here, all the other participation list screens include another sorting item for sorting functions related to psychological counseling, speech, mentoring, etc., another sorting item for sorting functions related to most recent, highest score, lowest score, etc., other change information display items for providing information on changes in the number of counseling sessions, the number of chat training sessions with an expert, or a cognitive behavior therapy record compared to a preset period (or last week), an item for displaying the number of times the user participates in other chat rooms for displaying the number of times the user participates in the chat room within a preset period, an information display item for each expert chat participation case for providing information related to psychological counseling, speech, mentoring, etc., in which a user participates, etc. In this case, examples of the item for displaying the number of times the user participates in other chat rooms include an item for displaying the number of counseling sessions, an item for displaying the number of chat training sessions with an expert, a cognitive behavior therapy record item, etc. In addition, examples of the information display item for each expert chat participation case include other chat room type (or chat room category) display items for displaying the type of chat room (e.g., including psychological counseling, speech, mentoring, etc.) in which they participate, another chat room topic display item for displaying the topic of the chat room, a detail view item for displaying detailed information, an expert information display item for displaying an expert's photo and name, a counseling date display item for displaying a counseling date, other keyword display items for displaying main keywords/hashtags related to the corresponding chat room, an expert feedback item for providing expert feedback, a cognitive behavior therapy record sheet item for providing a cognitive behavior therapy record sheet, a written questionnaire item for providing questionnaire content written by a user, a chat room training display item for displaying chat room training content, etc. Here, when a past counseling record item is selected from the detailed member report information displayed on the expert terminal 300, the expert terminal 300 may display other participation list screens corresponding to the participation list menu preset by default in response to the selected past counseling record item in the content display area by default.

In addition, when other specific participation lists (or detail view items displayed on one side of the corresponding other specific participation lists) are selected from one or more other participation lists being displayed in the information display items for each expert chat participation case in the past counseling record screen seen by the expert displayed on the expert terminal 300, the expert terminal 300 is linked with the server 200 to display the detailed information related to the selected other specific participation lists. Here, the detailed information (or detailed counseling result item screen) includes other chat room type (or chat room category) display items for displaying the types of chat rooms (e.g., including psychological counseling, speech, mentoring, etc.) in relation to the other specific participation lists, other chat room topic display items for displaying the topic of the chat room, an expert information display item for displaying the expert's photo and name, a counseling date display item for displaying the counseling date, other keyword display items for displaying the main keywords/hashtags related to the corresponding chat room, an expert feedback display item for displaying the expert feedback, a cognitive behavior therapy record sheet item for providing the cognitive behavior therapy record sheet before and after training, a questionnaire item written during counseling for providing the type and results of the questionnaire written by the user, a chat room participation record display item for providing the chat room participation record, etc. In this case, examples of the questionnaire item written during counseling may include information on various types of tests (or questionnaires) such as a self-esteem self-diagnosis test, a communication type test, an anxiety test, etc. In addition, examples of the chat room participation record display item include a date information display item on participation in the chat room, an expert state item for displaying whether the expert is participating in training or observing the expert, a chat room type (or chat room category) display item for displaying the type of chat room (including, for example, a topic talk chat room, a role-playing chat room, a theme practice chat room, etc.) in which the user participates, a chat room topic display item for displaying the topic of the chat room, a chat room name display item for displaying the room title of the chat room, a chat participant information display item for displaying information (including, for example, nicknames) of other users participating in the corresponding chat room, a self-evaluation result display item (or self-evaluation information display item) for displaying the self-evaluation results, a received evaluation result display item (or received evaluation information display item) for displaying the evaluation results received from other users participating in the corresponding chat room, a chat recording display item for re-listening to the chat content from the chat room, etc.

In addition, when a preset cognitive behavior therapy record menu (or cognitive behavior record menu) is selected from the past counseling record screen for the expert displayed on the expert terminal 300, to provide the information on the cognitive behavior therapy record sheet written by the user of the terminal 100 according to the user's performance of the training function for the appropriate chat style in relation to the specific topic or situation, the terminal 300 displays a cognitive behavior therapy record screen corresponding to the selected cognitive behavior therapy record menu. Here, the cognitive behavior therapy record screen (or cognitive behavior therapy record sheet screen) includes the cognitive behavior therapy record information display item for each chat participation case, etc., to provide the cognitive behavior therapy record (or cognitive behavior therapy record sheet) written before and after training in relation to the specific topic or situation in which the user of the corresponding terminal 100 participates. In addition, examples of the cognitive behavior therapy record information display item for each chat participation case include a cognitive behavior therapy record sheet title display item for displaying the title, a result view item for displaying the written cognitive behavior therapy record result, a record date display item for displaying the date when the cognitive behavior therapy record (or cognitive behavior therapy record sheet) is written, a record sheet progress situation display item for displaying the record sheet progress situation before/after training, a confirmed expert display item for displaying the expert who has confirmed the cognitive behavior therapy record sheet written by the user, etc.

In addition, when the specific cognitive behavior therapy record is selected from one or more cognitive behavior therapy record cases being displayed in the cognitive behavior therapy record information display item for each chat participation in the cognitive behavior therapy record screen displayed on the expert terminal 300, the expert terminal 300 is linked with the server 200 to display other detailed information related to the selected specific cognitive behavior therapy record case. Here, the other detailed information (or cognitive behavior therapy record sheet/cognitive behavior therapy record sheet screen) includes a cognitive behavior therapy record sheet title display item to display the title, a last modified date display item, a writer ID and name display item, a writing state display item before and after training (e.g., including not written, being written, written, etc.), a cognitive behavior information item for each item before training, a cognitive behavior information item for each item after training, etc. In addition, examples of the cognitive behavior information item for each item before training include an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for displaying "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item (e.g., an improvement-related item, an anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/fury, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before training and/or the cognitive behavior information item for each item after training may be commonly preset or may be set differently for each expert.

In addition, when a preset psychological test result item (not illustrated) is selected from the detailed member report information displayed on the expert terminal 300, the expert terminal 300 is linked with the server 200 to display a psychological test result screen corresponding to the selected psychological test result. Here, the psychological test result screen includes a sorting item for providing a sorting function (e.g., including latest order, psychological test type order, etc.) in relation to one or more psychological test cases performed by the corresponding counseling requester, a psychological test name item, a psychological test performance date item, a result item (or detail view item), etc.

In addition, when a specific psychological test name (or specific psychological test name/type) is selected from one or more psychological test names (or psychological test names/types) in the psychological test result screen displayed on the expert terminal 300, the expert terminal 300 is linked with the server 200 to display psychological test results of the corresponding counseling requester in relation to the selected specific psychological test name. Here, the psychological test results include a test performance counseling requester name, a psychological test name, a psychological test performance date, a psychological test type, detailed psychological test results, etc.

In addition, when a preset message menu is selected from the initial screen displayed on the expert terminal 300, to provide a message (or post message) function with a user who is counseling with the corresponding expert or has a counseling history with the corresponding expert, the expert terminal 300 is linked with the server 200 to display a message screen corresponding to the selected message menu. In this case, the expert terminal 300 may display the message screen corresponding to the selected message menu in the detailed information display area. Here, the message screen includes an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g. including an expert character/picture, an expert name/name, etc.), a member search menu for searching for members, a message list menu for providing a list of one or more counseling requesters who have exchanged messages with the expert, when a specific counseling requester (or the nickname of the counseling requester) is selected from the list of counseling requestors included in the message list, a message content display menu for displaying the content of the message exchanged with the specific counseling requester, a detailed personal information display menu for displaying personal information on the specific counseling requester, etc. In addition, the detailed personal information display menu includes a current online state display item for displaying information on the real-time connection state of the person requesting counseling, a character (or image/photo) item of a person requesting counseling, a nickname, a gender, a date of birth, an emergency contact network (or phone number) of the person requesting counseling, a counseling ticket type item (e.g., time, number of sessions, etc. for each type), a first registration date item, an average counseling time display item, the most recent counseling date display item (or the most recently completed counseling date display item), a next reservation date display item (or counseling reservation date display item), a deletion item for deleting content of messages with the person requesting counseling, a report item for reporting content of messages with the person requesting counseling, etc.

In addition, the expert terminal 300 is linked with the terminal 100 and the server 300 related to the specific counseling requester selected from one or more counseling requesters included in the message screen to perform the message function (or chat function) with the terminal 100 related to the corresponding specific counseling requester.

In addition, when the specific menu is selected from the message screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a preset "my performance" menu is selected from the initial screen displayed on the expert terminal 300, to provide information such as counseling performance performed by the corresponding expert, the expert terminal 300 is linked with the server 200 to display a "my performance" screen corresponding to the selected "my performance" menu. In this case, the expert terminal 300 may display the "my performance" screen corresponding to the selected "my performance" menu in the detailed information display area. Here, the "my performance" screen is an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a "my performance" period menu for selecting the type of "my performance" provided (e.g., including, weekly, monthly, yearly, etc.), a total number of counseling ticket purchase case display menu according to "my performance" type selected in the "my performance" period menu, a counseling ticket repurchase rate display menu, a total revenue display menu, a total number of members consulted display menu, a monthly new counseling member information display menu, a recently registered member display menu for displaying information on a preset number of (e.g., 6) recently registered members, a monthly counseling performance display menu, a detail menu for displaying counseling performance details, a menu for displaying an expert's average rating (or rating/star rating), a menu for displaying the total number of reviews, a menu for displaying the number of new reviews for a preset period (e.g., the last 7 days), etc.

In addition, when the specific menu is selected from the "my performance" screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when the detailed history menu related to counseling performance in the "my performance" screen displayed on the expert terminal 300 is selected, the expert terminal 300 is linked with the server 200 to display a detailed history screen corresponding to the detailed history menu related to the selected counseling performance. Here, the detailed history screen includes an immediate counseling item for performing the counseling function with the user (or client) in real time while accessing the website on the expert terminal 300, a search item for searching for functions or menus corresponding to the search term, a notification item for confirming notices or notification messages, etc., a user information display item for displaying the user information (e.g., including an expert character/picture, an expert name/name, etc.), a "return to my performance" item for returning to the previous screen (or the "my performance" screen), a period setting item for setting a period (for example, the last 7 days) for providing the counseling performance, a current date display item for displaying the current date, a counseling performance detail history item for providing the counseling performance of the corresponding expert within the period set in the period setting item, a storage item for storing the detailed history of the counseling performance displayed on the detailed history screen, an output item for outputting the detailed history of the counseling performance displayed on the detailed history screen, etc. In addition, examples of the detailed history item of the counseling performance include an item for displaying the number of counseling cases/immediate counseling cases by date, a total counseling time item, an item for displaying the number of new member registrations, an item for displaying the number of review registrations, an item for displaying the number of expert cases chosen, and a profit (unit: won) time, etc.

In addition, the expert terminal 300 may additionally perform a storage function, an output function, etc., on the content of the detailed history screen being displayed on the expert terminal 300.

In addition, when a preset data management menu is selected from the initial screen displayed on the expert terminal 300, to manage information on a questionnaire or data related to a user who is counseling with the corresponding expert or has a counseling history with the corresponding expert, the expert terminal 300 is linked with the server 200 to display a data management screen corresponding to the selected data management menu. In this case, the expert terminal 300 may display the data management screen corresponding to the selected data management menu in the detailed information display area. Here, the data management screen includes an immediate counseling menu for performing a counseling function with the user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a number of questionnaires held display menu for displaying the number of questionnaires held by the expert in relation to the counseling requester in counseling, an amount of data held display menu for displaying the amount of data held by the expert in relation to the person requesting counseling, a member search menu for searching for members, an additional menu for adding questionnaires or data held by the expert, an output menu for outputting the information displayed on the data management screen, a deletion menu for deleting specific information displayed on the data management screen, a data information display menu related to the counseling requester being managed by the corresponding expert, etc. In addition, the data information display menu includes a file name item, a format item (e.g., including a questionnaire, data, etc.), a writer item (or expert item), a last modified date item, a file size item, etc., according to the data type.

In addition, the expert terminal 300 may additionally perform the output function, the deletion function, and the additional function of new data, etc., on the content of the data management screen being displayed on the expert terminal 300.

In addition, when the specific menu is selected from the data management screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a preset setting menu is selected from the initial screen displayed on the expert terminal 300, to set a user information (or account information) setting function, a push notification setting function, a member withdrawal function, etc., the expert terminal 300 is linked with the server 200 to display a setting screen corresponding to the selected setting menu.

In addition, the expert terminal 300 performs an email address change function, a password change function, a phone number change function, etc., according to the corresponding expert input on the settings screen displayed on the expert terminal 300.

In addition, the expert terminal 300 performs a push notification setting function for a new counseling request notification or message reception notification according to the corresponding expert input on the setting screen displayed on the expert terminal 300.

In addition, the expert terminal 300 performs the member withdrawal function according to the corresponding expert input on the setting screen displayed on the expert terminal 300.

In addition, when a preset XR room-creation menu is selected from the initial screen displayed on the expert terminal 300, to select a client to be invited to the XR counseling room, the expert terminal 300 is linked with the server 200 to display an XR counseling room invitation client selection screen corresponding to the selected XR room-creation menu. In this case, the expert terminal 300 may display the XR counseling room invitation client selection screen corresponding to the selected XR room-creation menu in the detailed information display area. Here, the XR counseling room invitation client selection screen (or the metaverse counseling room invitation client selection screen) includes an additional client menu for adding a client, a menu (e.g., including a list of one or more users/clients who have currently applied/chosen an expert as a counselor, etc.) for selecting a client invited to the XR counseling room (or metaverse counseling room), a close menu, etc., and may be displayed in the form of a pop-up or a new screen (e.g., including a new window, a new screen, etc.).

In addition, when the specific menu is selected from the XR counseling room invitation client selection screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

In addition, when a specific user is selected from the XR counseling room invitation client selection screen displayed on the expert terminal 300, to perform a counseling function with an expert in an XR environment or a metaverse environment, the expert terminal 300 is linked with the server 200 and the terminal 100 owned by the selected specific user (or specific content) to display the XR counseling room screen. Here, the XR counseling room screen (or metaverse counseling room screen) includes a counseling screen area for displaying the counseling function performance state with the specific user of the terminal 100, a detailed member information display area for displaying the detailed information on the specific user of the terminal 100. In addition, the counseling screen area includes a video information display area for displaying video information related to the expert and the specific user, a counseling time display item for displaying a counseling time, a current time display item for displaying a current time, a microphone item for setting whether to output voice, a video item for setting whether to output the video information, an entry item with the chat training room for a counselor and the specific user to enter a new metaverse chat room related to a specific theme to perform a chat function, a questionnaire writing request item for requesting the specific user in counseling to write a questionnaire, a file item (shared item) for sharing (or transmitting) a file during the counseling, and a counseling end item for ending the counseling function, etc. In addition, the detailed member information display area includes a personal information item (personal information tab) for displaying personal information on the specific user in counseling, a counseling record sheet item for displaying a counseling record sheet related to one or more counseling sessions performed by the specific user in counseling, a cognitive behavior therapy record sheet item (or cognitive behavior record sheet item) for displaying a cognitive behavior therapy record sheet related to one or more counseling sessions performed by the specific user in counseling, a questionnaire result item for displaying a questionnaire result related to the questionnaire performed by the specific user in counseling, a people diary item for displaying the content (or the content of the emotional state by date written by the corresponding specific user) of the emotional state by date written by the corresponding counseling requester, a chat report item for displaying a chat report (or my report) related to the corresponding counseling requester, a past counseling record item for displaying a past counseling record performed by the corresponding counseling requester, an additional detailed information display area (or additional detailed information display item) for providing detailed information on a specific item selected among multiple items, etc. In addition, the personal information items (or personal information screen) include an item for displaying whether one is currently online for displaying the information on the real-time connection state of the corresponding counseling requester, a character (or image/photo) item of the corresponding counseling requester, a nickname item of the corresponding counseling requester, an item for displaying a type (e.g., topic talk, role-playing, theme practice, etc.) of a counseling case in progress when the corresponding counseling requester is currently counseling, an item (or counseling progress situation item) for displaying the remaining number of uses out of the total number of uses, a basic questionnaire view item for confirming the basic questionnaire content written by the corresponding counseling requester, a schedule reservation item for reserving the counseling schedule with the expert of the expert terminal 300, a gender item, a birth date item, an emergency contact network (or phone number) item, a use ticket/counseling ticket type item (e.g., time, the number of sessions, etc., for each type), an initial registration date item, an average counseling time display item, a most recent use date/counseling date display item (or recently completed counseling date), a next reservation date display item (or counseling reservation date item), an item for displaying the service/topic on which a user would like to receive counseling, an item (or additional inquiry content item) for displaying service/content on which a user would like to receive counseling, a counseling recording item for recording the counseling content, a memo item, etc.

In addition, when a basic questionnaire view item included in the XR counseling room screen (or detailed personal information item) of the expert terminal 300 is selected, the expert terminal 300 displays a pre-stored questionnaire (or questionnaire content/information) related to the user of the terminal 100 corresponding to the selected basic questionnaire view item.

In addition, when a preset questionnaire writing request item is selected from the XR counseling room screen displayed on the expert terminal 300, the expert terminal 300 is linked with the server 200 to display a questionnaire list screen corresponding to the selected questionnaire writing request item. Here, the questionnaire list screen includes one or more pre-registered questionnaire lists, and includes a questionnaire name item, a questionnaire question number item, a questionnaire preview item, a date item last written by the user, an additional item, a sending item, etc.

In addition, when a specific questionnaire is selected from one or more questionnaires included in the questionnaire list screen displayed on the expert terminal 300, the expert terminal 300 displays detailed information on the selected specific questionnaire. Here, the detailed information on the specific questionnaire includes a preview item, a question content item for each question, a view item for each question, a modification item, a confirmation item, a sending item, etc. In this case, the expert terminal 300 may modify content of at least one question and view an item among one or more question content items and view items included in the selected specific questionnaire, and then transmit a specific questionnaire, in which the modified content is reflected (or applied/updated), to the terminal 100 corresponding to the corresponding user via the server 200.

In addition, when a preset transmission item displayed on one side of the detailed information on a specific questionnaire of the expert terminal 300 is selected, the expert terminal 300 transmits the selected specific questionnaire to the terminal 100 corresponding to the corresponding user via the server 200.

That is, when a preset sending item displayed on one side of the detailed information on the specific questionnaire of the expert terminal 300 is selected, the expert terminal 300 transmits the selected specific questionnaire, the questionnaire writing request information, the identification information of the expert terminal 300, the unique information (or identification information of the terminal 100 related to the user) related to the user who participates in the XR counseling room, etc., to the server 200. In this case, after the specific questionnaire (or at least one specific questionnaire) is selected from one or more questionnaires included in the questionnaire list screen displayed on the expert terminal 300, when the preset sending item displayed on one side of the questionnaire list screen is selected, the expert terminal 300 may transmit the selected specific questionnaire, the questionnaire writing request information, the identification information of the expert terminal 300, the unique information related to the user (or identification information of the terminal 100 related to the user) who participates in the XR counseling room, etc., to the server 200.

In addition, the expert terminal 300 displays information indicating that a response is waiting for a request to fill out the questionnaire (or information indicating that the corresponding user is filling out the questionnaire) on one side of the counseling screen area.

The embodiment of the present invention mainly describes that the expert terminal 300 selects one item of questionnaire content from a list of one or more previously written (or registered) questionnaires and requests a response to the questionnaire from the user of the terminal 100 invited to the corresponding XR counseling room through the selected questionnaire content, but is not limited thereto. The expert terminal 300 may receive (or configure/generate) new questionnaire content according to the expert input (or expert selection/touch/control) of the corresponding expert terminal 300 and may request a response to the questionnaire from the user of the terminal 100 invited to the corresponding XR counseling room through the received new questionnaire content.

In addition, the expert terminal 300 receives questionnaire response information transmitted from the corresponding terminal 100 in response to a specific previously transmitted questionnaire. In this case, after transmitting the specific questionnaire, the questionnaire writing request information, etc., from the expert terminal 300 to the terminal 100, when the questionnaire response information is not received from the terminal 100 within a preset time (e.g., 10 minutes), the expert terminal 300 may retransmit the corresponding specific questionnaire, etc., to the terminal 100 or end the counseling function in the corresponding XR counseling room (or metaverse chat room).

In addition, the expert terminal 300 generates a response result by adding up preset scores for the view items for each question corresponding to the question content for each question included in the corresponding specific questionnaire. Here, when a respondent (or user) responds to view items for each question on a 1 to 5 point scale (e.g., very much, yes, neutral, no, not at all), a 1 to 4 point scale (e.g., very much, yes, no, not at all), etc., the response result includes a score obtained by adding up the corresponding response scores (or scores corresponding to answers to each question included in the questionnaire response information).

In addition, the expert terminal 300 transmits (or provides) the generated response results, etc., to the terminal 100 through the server 200.

In addition, the expert terminal 300 displays (or outputs) the generated response results.

The embodiment of the present invention mainly describes that the expert terminal 300 performs a scoring function, but it is not limited thereto, and the scoring function may be performed by the server 200.

That is, the server 200 may receive questionnaire response information transmitted from the terminal 100 in response to a specific questionnaire, etc., transmitted to the terminal 100, identification information of the terminal 100, etc., generate the response results by adding up scores according to the received questionnaire response information, and transmit (or provide) the generated response results, the specific questionnaire, etc., to the expert terminal 300 and the terminal 100.

In addition, the expert terminal 300 is linked with the terminal 100 and the server 200 through the generated XR counseling room screen and performs the counseling function with the counseling requester of the corresponding terminal 100.

In this way, the expert terminal 300 may invite the counseling requester corresponding to the counseling schedule to the XR counseling room screen generated through the XR room-creation menu according to the reservation time on the reservation day to perform the counseling function.

In addition, while a counseling function with the corresponding expert and the corresponding specific user is performed through the XR counseling room screen displayed on the expert terminal 300, to participate in a metaverse chat room related to a specific theme and perform a monitoring (or training/counseling) function for the corresponding specific user through the chat function, when an entry item is selected along with the chat training room displayed on one side of the XR counseling room screen, the expert terminal 300 creates a new metaverse chat room or selects a specific metaverse chat room from the one or more pre-created metaverse chat rooms according to the corresponding expert selection, and then displays the expert's position selection screen for selecting whether the counselor (or expert) enters as a spectator or as a chatter to the expert terminal 300. Here, the expert's position selection screen includes a spectator item, a participant item, a go-back item, an entry item, etc. In this case, the expert's position selection screen may be displayed in the form of a pop-up window on one side of the counseling screen area.

In addition, when a spectator item or a chatter item is selected from the expert's position selection screen displayed on the expert terminal 300 according to the expert selection (or expert input/touch/control) of the expert terminal 300, the expert terminal 300 is linked with the server 200 and the terminal 100 and enters (or participates in) the metaverse chat room as the spectator corresponding to the selected spectator item or as the chatter corresponding to the selected chatter item, and the terminal 100 related to the specific user in counseling is linked with the server 200 and enters (or participates in) the corresponding metaverse chat room as the chatter along with the corresponding expert. Here, the metaverse chat room includes the metaverse chat room newly created in the expert terminal 300, the specific metaverse chat room selected from the one or more pre-created metaverse chat rooms, etc. In this case, the expert terminal 300 displays a waiting screen according to the entry into the metaverse chat room. Here, the waiting screen includes the type of the corresponding chat room, the topic, the chat room name, the keyword (or hashtag), the nickname (or screen name) of the user who enters the corresponding chat room, the chat temperature, and the number of chats (or the number of times someone has participated in the chat room), etc. In this case, the chat temperature may be calculated based on the number of chats, the received evaluation results, etc. In addition, when the expert terminal 300 participates in the metaverse chat room as the spectator, the expert terminal 300 and one side of the screen of the terminal 100 may display an image, an emoticon, etc., indicating that the expert terminal 300 (or the expert of the expert terminal 300) is participating as the spectator.

In addition, when the room leader who opens the corresponding metaverse chat room selects the preset start menu while the number of people (or the number of participants) set in the corresponding metaverse chat room is met, the expert terminal 300 is a spectator or chatter, and is linked with the corresponding terminal 100, one or more other terminals 100 (not illustrated) owned by one or more other users who entered the corresponding metaverse chat room, and the server 200 to perform the chat function related to the specific topic of the metaverse chat room. In this case, the terminal 100 is linked with the server 200 and uses the avatar (or character) preset in the terminal 100 to change (or apply/reflect) and display the expression (e.g., including happiness, joy, excitement, passion, pleasure, frustration, outrage, sadness, surprise, pain, rage, etc.) of the corresponding avatar according to the analysis (e.g., including a change in the user's gaze, a change in facial expression, a voice tremor, a change in heart rate, etc.) of the psychological state of the corresponding user's voice and/or facial expression while the user of the terminal 100 is chatting.

In this way, the expert terminal 300 is a spectator or chatter, and may freely perform (or monitor) the chat function with other users, including the user of the terminal 100.

In addition, when the chat function in the specific metaverse chat room in which the expert terminal 300 and the terminal 100 participate ends, the expert terminal 300 generates the feedback information related to the user of the terminal 100. Here, the feedback information includes information such as an expert's view (or opinion) regarding the psychological counseling function, the speech lesson function, the mentor function, etc., performed in the chat room.

In addition, the expert terminal 300 is linked with the server 200 to map (or match/link) the generated feedback information, the information on the metaverse chat room, the user information (or expert information) of the expert terminal 300, and the member information (or user information/personal information) of the user of the terminal 100 and store (or register/manage) the mapped generated feedback information in the server 200.

In addition, the expert terminal 300 provides (or transmits) the generated feedback information to the terminal 100 through the server 200.

In addition, when the personal information item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the personal information screen seen by the expert corresponding to the selected personal information item in the corresponding additional detailed information display area. Here, the personal information screen seen by the expert (or detailed personal information display screen) includes an item for displaying whether a user is currently online for displaying the information on the corresponding specific user's real-time connection state, a character (or image/photo) item of the corresponding specific user, a nickname item of the corresponding specific user, an item (e.g., including topic talk, role-playing, theme practice, etc.) for displaying the type of counseling cases in progress when the corresponding specific user is currently counseling, an item (or counseling progress situation item) for displaying the remaining number of uses out of the total number of use, a basic questionnaire view item for confirming the basic questionnaire content written by the corresponding specific user, a schedule reservation item for reserving the counseling schedule with the expert of the corresponding expert terminal 300, a gender item, a birth date item, an emergency contact network (or phone number) item, a use ticket/counseling ticket type item (e.g., time, the number of sessions, etc., for each type), an initial registration date item, an average counseling time display item, a most recent use date/counseling date display item (or recently completed counseling date), a next reservation date display item (or counseling reservation date display item), an item for displaying the service/topic on which a user would like to receive counseling, an item (or additional inquiry content item) for displaying service/content on which a user would like to receive counseling, a counseling recording item for recording the counseling content, a memo item, etc. In this case, when the expert terminal 300 displays the XR counseling room screen, the expert terminal 300 may display a personal information screen corresponding to the personal information item set by default in the additional detailed information display area.

In addition, while the counseling function with the corresponding expert and the corresponding specific user is performed through the XR counseling room screen displayed on the expert terminal 300, when a counseling record sheet item included in the detailed member information display area in the corresponding XR counseling room screen is selected, the expert terminal 300 is linked with the server 200 to display the detailed information related to the selected counseling record sheet item in the corresponding additional detailed information display area.

That is, when a counseling record sheet item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the counseling record sheet screen seen by the expert corresponding to the selected counseling record sheet item in the corresponding additional detailed information display area. Here, the counseling record sheet screen foreseen by the expert includes an additional item for adding the counseling record sheet related to the corresponding specific user, a deletion item for deleting the information on the specific counseling record case displayed on the corresponding counseling record sheet screen seen by the expert, a counseling content item by date and time, an expert item by date and time (or person in charge/counselor item by date and time), a counseling time item by date and time, a detail view item for the counseling record sheet by date and time, a memo item for recording simple memo content, etc.

In addition, when the additional item is selected from the counseling record sheet screen seen by the expert displayed on the expert terminal 300, to store (or record) counseling content related to a specific user currently in counseling, the expert terminal 300 is linked with the server 200 to display the counseling record sheet input screen corresponding to the selected additional item. Here, the counseling record sheet input screen includes a session number and counseling topic item, a specific user's nickname item (or name item), an expert name item (or person in charge name/counseling name item), a current recording time item, a user's subjective item, an expert's objective item, a future plan item, a feedback item to a user, a temporary storage item for temporarily storing written content, a writing completion item for storing written content, etc. In this case, the expert's objective item may vary depending on whether the expert of the expert terminal 300 is a mentor expert, a psychological counseling expert, or a speech lesson expert. That is, when the expert of the expert terminal 300 is a mentor expert, examples of the expert's objective item include a common checklist item (e.g., including anxiety, assertiveness/confidence, mind control, communication skills, listening skills, sociability, situational judgment power, will to improve, strength/information for each item, brief description for each item, etc.), a mentoring checklist item (e.g., professionalism, interest/degree of interest, propensity coincidence, counseling purpose, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc. In addition, when the expert of the expert terminal 300 is a psychological counseling expert, examples of the expert's objective item include a common checklist item (e.g., anxiety, assertiveness/confidence, mind control, communication skills, listening skills, sociability, situational judgment power, will to improve, strength/information for each item, brief description for each item, etc.), a psychological state checklist item (e.g., social anxiety, depression/anxiety, panic disorder, sleep disorder, bipolar disorder, alcoholic dementia, addiction (e.g., game addiction, drug addiction, gambling addiction, etc.), cognitive distortion, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc. In addition, when the expert of the expert terminal 300 is a speech lesson expert, examples of the expert's objective item include a common checklist item (e.g., anxiety, assertiveness/confidence, mind control, communication skills, listening skills, sociability, situational judgment power, will to improve, strength/information for each item, brief description for each item, etc.), a speech checklist item (e.g., including fluency, logic, speed/pace, vocalization/tone, leadership, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc.

In addition, the expert terminal 300 receives counseling record information including a plurality of different input values corresponding to a plurality of different input items included in the counseling record sheet input screen displayed on the expert terminal 300. Here, the counseling record information includes session number and counseling topic information, nickname information (or name information) of a specific user, expert name information (or person in charge name/counselor name information), current record time information, a user's subjective information, an expert's objective information, future plan information, feedback information to a user, etc. In this case, the specific user's nickname information, the expert name information, the current recording time information, etc., may be automatically input under the control of the server 200.

In addition, the expert terminal 300 is linked with the server 200 to map the received counseling record information with the personal information corresponding to the corresponding specific user and the user information of the expert terminal 300 and store (or register) the mapped information in the server 200.

In addition, when the detail view item displayed on one side of a specific counseling record sheet case is selected from the counseling record sheet screen for the expert displayed on the expert terminal 300, the expert terminal 300 is linked with the server 200 to display the detailed counseling record sheet information on the specific counseling record sheet case related to the selected detail view item. Here, the detailed counseling record sheet information includes a counseling record sheet writing date item related to the corresponding specific counseling record sheet case, a modification item for modifying the content of the corresponding specific counseling record sheet, an output item for outputting the content of the corresponding specific counseling record sheet, a deletion item for deleting the content of the corresponding specific counseling record sheet, a session number and counseling topic item, an expert name item, a last modified date display item, a user's subjective item, an expert's objective item, a future plan item, a feedback item to a user, etc. In this case, as described above, the expert's objective item may vary depending on whether the expert of the expert terminal 300 is a mentor expert, a psychological counseling expert, or a speech lesson expert.

In addition, the expert terminal 300 may additionally perform a modification function, an output function, a deletion function, etc., on the content of the detailed counseling record sheet information being displayed on the expert terminal 300.

In addition, when a cognitive behavior therapy record sheet item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected cognitive behavior therapy record sheet item in the corresponding additional detailed information display area.

That is, when the cognitive behavior therapy record sheet included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the cognitive behavior therapy record sheet screen seen by the expert corresponding to the selected cognitive behavior therapy record sheet in the corresponding additional detailed information display area. Here, the cognitive behavior therapy record sheet screen seen by the expert includes an additional item (or an adding item) for adding the cognitive behavior therapy record sheet related to the corresponding specific user, a deletion item for deleting the information on the specific cognitive behavior therapy record sheet displayed on the cognitive behavior therapy record sheet screen for the corresponding expert, a record sheet item written together during counseling for providing the list of the corresponding cognitive behavior therapy record sheets generated by the user in counseling, a record sheet item generated by the user alone for providing the list of the cognitive behavior therapy record sheets generated by the corresponding specific user, etc. In addition, examples of the record sheet item written together during the counseling include a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), etc. In addition, examples of the record sheet item written by the user alone include a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), an item on whether to confirm the written cognitive behavior therapy record sheet (e.g., confirmation needed, confirmation not needed, confirmed, etc.), etc.

In addition, when the specific cognitive behavior therapy record sheet is selected from the cognitive behavior therapy record sheet screen for the expert displayed on the expert terminal 300 (or when an item being written or an item written before/after the training related to the specific cognitive behavior therapy record sheet is selected), the expert terminal 300 is linked with the server 200 to display the detailed cognitive behavior therapy record sheet information on the specific cognitive behavior therapy record sheet case related to the selected specific cognitive behavior therapy record sheet. Here, the detailed cognitive behavior therapy record sheet information (or detailed cognitive behavior therapy record sheet information related to the selected specific cognitive behavior therapy record sheet) includes a displayed session number and counseling topics, a writer ID and name display item, a writing state display item before/after training (e.g., including not written, being written, written, etc.), a last modified date display item, a cognitive behavior information item for each item before training, a cognitive behavior information item for each item after training, etc. In addition, the cognitive behavior information item for each item before training includes an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for displaying "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, the cognitive behavior information item for each item after training includes an item (e.g., improvement-related item, anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/rage, irritation, disbelief, displeasure, disappointment, sadness/depression, anxiety, tiredness, fatigue, frustration, etc.) for selecting how one feels now, and an item for displaying "What did you learn?" etc.

In addition, the expert terminal 300 may additionally perform a modification function, an output function, a deletion function, etc., on the content of the detailed cognitive behavior therapy record sheet information being displayed on the expert terminal 300.

In addition, when a questionnaire result item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected questionnaire result item in the corresponding additional detailed information display area.

That is, when the questionnaire result item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the questionnaire result screen viewed by the expert corresponding to the selected questionnaire result item in the corresponding additional detailed information display area. Here, the questionnaire result screen viewed by the expert includes the sorting item for providing the sorting function (including, for example, sorting by most recent, by format, etc.) in relation to one or more questionnaire cases performed by the corresponding specific user, the deletion item for deleting the selected questionnaire results (or selected questionnaire items), the file name item for each questionnaire, the last modified time item for each questionnaire, the format item for each questionnaire (or questionnaire type item), the result item (or detail view item) for each questionnaire, the memo item for recording simple memo content, etc.

In addition, when a specific file name (or specific file name item) is selected from one or more file names (or file name items) in the questionnaire result screen for the expert displayed on the expert terminal 300 or when a detailed item related to a specific file name is selected from one or more file names displayed on the questionnaire result screen viewed by the expert, the expert terminal 300 is linked with the server 200 to display detailed questionnaire information related to the selected specific file name or a specific file name corresponding to the selected detail view item. Here, the detailed questionnaire information is configured variously depending on the purpose of the questionnaire, and may include content of one or more questions for each questionnaire, answers/responses to the question content, etc.

In addition, when the people diary item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected people diary item in the corresponding additional detailed information display area.

That is, when the people diary item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the people diary item viewed by the expert corresponding to the selected people diary item in the corresponding additional detailed information display area. Here, the people diary screen viewed by the expert includes a calendar screen, etc., including the emotional record state by date in preset period units (e.g., including 3 months, 6 months, etc.). In addition, when the calendar screen (or calendar item) is in a state where the emotional record information (e.g., including detailed emotional record information, simple emotional record information, etc.) is stored on a specific date, the calendar screen (or calendar item) includes an emotional record state (or mind state), such as images (or emoticon/avatar) representing feeling comfortable, normal, and uncomfortable, corresponding to mental state information, which is part of the information in the corresponding emotional record information on the corresponding specific date.

In addition, when a specific date including the emotional record state in the people diary screen viewed by the expert displayed on the expert terminal 300 is selected, the expert terminal 300 is linked with the server 200 to display the detailed people diary screen viewed by the expert related to the selected specific date. Here, the detailed people diary screen viewed by the expert includes a calendar screen (or calendar item) related to the corresponding specific date, an emotional record information item related to the corresponding specific date, an emotional pattern graph item for the corresponding month related to the corresponding specific date, an information display item related to the corresponding specific user's emotional record state for the corresponding week related to the corresponding specific date, etc. In addition, examples of the emotional record information item include date information, situation information (e.g., including who else is there, a counterpart's actions, one's own actions, etc.), and emotional information (e.g., including one's emotional state, whether to express emotions, one's current emotions, etc.), review information (e.g., a comfort level in chat, future resolutions, personal notes, etc.), etc. In addition, examples of the information display item (or weekly emotional record information item) about the counseling requester's emotional record state include mental state items by day of the week (or date), a situation information item (e.g., who else is there, a counterpart's actions, one's own actions, etc.), an emotional information item (e.g., one's emotional state, whether to express emotions, one's current emotions, etc.), a review information item (e.g., a comfort level in chat, future resolutions, personal notes, etc.), a detail view item, etc.

In addition, when a chart report item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected chart report item in the corresponding additional detailed information display area.

That is, when the chart report item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the chart report screen viewed by the expert corresponding to the selected chart report item in the corresponding additional detailed information display area. Here, the chat report screen viewed by the expert (or a "my report" screen used by the expert) includes an analysis result item for providing the analysis results according to the performance of the functions such as topic talk, role-playing, and theme practice in relation to the corresponding counseling requester, a participation list item for providing the participation list related to the chat list in which the corresponding user participates, a content display item (or a content display area) for displaying the detailed information according to the selection of the analysis result item or the participation list item, etc.

In addition, when a preset analysis result item is selected from the chat report screen viewed by the expert (or a "my report" screen used by the expert) displayed on the expert terminal 300, to provide the analysis results according to the performance of chat functions such as topic talk, role-playing, and theme practice in relation to the user of the terminal 100, the expert terminal 300 displays the detailed information corresponding to the selected analysis result menu in the content display area. In this case, when the preset chat report item is selected from the app execution result screen displayed on the expert terminal 300, the expert terminal 300 may display the analysis result screen (or the detailed information) corresponding to the analysis result item set by default in response to the selected chat report item in the content display area by default. Here, the analysis result item (or the analysis result screen/detailed information) includes a sort item for sorting functions related to all, topic talk, role-playing, theme practice, etc., a "number of times you've participated in the chat room" display item for displaying the number of times the user has participated in the chat room within a preset period, a period display item for displaying the corresponding preset period, a "number of times you've participated in the chat room by category" display item for displaying the number of times the user has participated in the chat room by category, a "free expression" index display item for displaying the "free expression" index calculated in relation to the user, an anxiety index display item for displaying the anxiety index calculated in relation to the user, a detailed score view item for displaying additional detailed information in relation to the "free expression" index or the anxiety index, a relative evaluation display item for displaying information on oneself as evaluated by other users who performed the chat function together, a "my 'free expression' score aspect" display item for displaying the "free expression" score aspect, a "my anxiety score pattern" display item for displaying the user's anxiety score pattern, a "my confidence/assertiveness, mind control, communication skills/logic/persuasive power, immersion, empathy/listening skills score aspect" display item for displaying the user's confidence/assertiveness, mind control, communication skills/logic/persuasive power, immersion, empathy/listening skills score aspect, a "topic I have practiced a lot" display item for displaying a topic that the user has practiced a lot in relation to the topic talk, a "keyword that I have practiced a lot" display item for displaying keywords that the user has practiced a lot in relation to the topic talk, a "target I've practiced a lot" display item for displaying what the user has practiced a lot in relation to role-playing, a "situation I've practiced a lot" display item for displaying situations in which the user has practiced a lot in relation to role-playing, a "What emotions am I sensitive to?" display item for displaying what emotions the user is sensitive to in relation to role-playing, a "Which experts I have practiced with a lot?" display item for a displaying indicating with which experts the user has practiced a lot in relation to the theme, a "theme I practiced a lot" display item for displaying a theme that the user has practiced a lot in relation to theme practice, etc. Here, the "free expression" index display item includes an overall rating display item, a "free expression" index overall average display item, a satisfaction graph display item for overall average, a "free expression" index change graph display item by day of the week, a score display item for each item (e.g., including confidence/assertiveness, mind control, communication skills/logic/persuasive power, immersion, empathy/listening skills, etc.), a graph display item of a score change for each item by day of the week, an exponential distribution display item for each topic and situation, a detailed score view item, etc. In addition, the anxiety index display item includes a total rating display item, an anxiety index overall average display item, an anxiety graph display item for the overall average, a graph display item of an anxiety index change by day of the week, etc. In this case, the "free expression" index can be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates. In addition, the anxiety index represents the average value of the anxiety self-evaluated by the user after performing the chat function in the chat room (e.g., including the topic talk chat room, the role-playing chat room, the theme practice chat room, etc.) in which the user participates in relation to one or more chat rooms in which the user of the corresponding terminal 100 participates for a preset period or all chat rooms in which the user of the corresponding terminal 100 participates. In addition, examples of the relative evaluation display item include the reason for receiving a good evaluation, the reason for receiving a bad evaluation, and the satisfaction of chat evaluated by others. In addition, examples of the "my 'free expression' score aspect" display item include a "How many people am I with when my free expression score gets high?" item, a "What age group of people am I talking with when I have a high score in 'free expression'?" item, a "What MBTI type am I talking with when I have a high score in 'free expression'?" item, a "What gender is the person I'm talking with when I have a high score in 'free expression'?" item, a "When I talk in a certain place, do I have a high score in free expression?" item, etc. In addition, the "my anxiety score aspect" display item includes a "How many people am I with when my anxiety score gets high?" item, a "What age group of people am I talking with when I have a high score in anxiety?" item, a "What MBTI type am I talking with when I have a high score in anxiety?" item, a "What gender is the person I'm talking with when I have a high score in anxiety?" item, a "When I talk in a certain place, do I have a high score in anxiety?" item, etc. In addition, examples of the "topic that I have practiced a lot" display item include an interpersonal relationship item, a daily life item, an employment/workplace item, a knowledge sharing item, a well-being item, other items, etc. In addition, examples of the "keyword that I have practiced a lot" display item include a boss item, a soccer item, a job preparation item, a presentation preparation item, a health item, other items, etc. In addition, examples of the "target that I have practiced a lot" display item include a husband item, a boss item, a coworker item, a chairman item, a stranger item, other items, etc. In addition, examples of the "situation that I have practiced a lot" display item include a rejection expression item, an affection expression item, an opinion expression item, a gratitude/sorry expression item, a conflict item, other items, etc. In addition, examples of the "What emotions am I sensitive to?" display item include a joy/pleasure item, an empathy item, an appreciation item, a sorry item, a grief/hurt item, an anger/annoyance/rage item, etc. In addition, examples of the "Which experts I have practiced with a lot?" display item include a psychological counselor item, a speech trainer item, a mentor item, etc. In addition, examples of the "theme that I practiced a lot" display item include a blind date item, a phone item, an interview item, a business report item, a small-scale presentation item, a large-scale presentation item, a professional discussion item, a pros and cons discussion item, etc.

In addition, when a preset detailed score view item is selected from the detailed information included in the content display area displayed on the expert terminal 300, the expert terminal 300 is linked with the server 200 to display detailed score information corresponding to the selected detailed score view item. Here, the detailed score information (or detailed score screen) includes the sort items for sorting functions related to all, topic talk, role-playing, theme practice, etc., the "number of times you've participated in the chat room" display item, the period display item for displaying the corresponding preset period, the "number of times you've participated in the chat room for each category" display item, the "free expression" index display item, the anxiety index display item, the relative evaluation display item, the "my 'free expression' score aspect" display item, the "my anxiety score aspect" display item, the "my confidence/assertiveness, mind control, communication skills/logic/persuasive power, immersion, empathy/listening skills score pattern" display item, the "topic I have practiced a lot" display item, the "keyword that I have practiced a lot" display item, the "target that I have practiced a lot" display item, the "situation that I have practiced a lot" display item, the "Which emotions I am sensitive to?" display item, the "Which experts have I practiced with a lot?" display item, the "theme which I have practiced a lot" display item, etc. In this case, when the detailed score view item related to the "free expression" index is selected, the expert terminal 300 may display one or more pieces of information related to the "free expression" index among the information included in the detailed score information, and when the detailed score view item related to the anxiety index is selected, the expert terminal 300 may mainly display one or more other pieces of information related to the anxiety index among the information included in the detailed score information.

That is, when a preset detailed score view item is selected from the detailed information included in the content display area displayed on the expert terminal 300, the expert terminal 300 is linked with the server 200 to display the detailed score information corresponding to the selected detailed score view item instead of the "free expression" index display item or anxiety index display item displayed previously.

In addition, when a preset period display item (or date selection item/calendar item) is selected from the chat report screen viewed by the expert (or the "my report" screen used by the expert) displayed on the expert terminal 300, the expert terminal 300 displays a calendar screen corresponding to the selected period. Here, the calendar screen includes the information on the presence or absence of chat records by date recorded by the user of the terminal 100 within the corresponding period (or corresponding month).

In addition, when the specific date within the calendar screen is selected, if a chat record exists on the corresponding specific date, the expert terminal 300 displays the detailed score information related to the chat record and if no chat record exists on the corresponding specific date, the expert terminal 300 displays the information indicating that no chat record exists.

In addition, when a preset participation list item is selected from the chat report screen for the expert (or a "my report" screen used by the expert) displayed on the expert terminal 300, to provide the participation list related to the conversation list in which the user of the terminal 100 participates, the expert terminal 300 displays the participation list screen corresponding to the selected participation list item. Here, the participation list screen includes a sort item for sorting functions related to all, topic talk, role-playing, theme practice, etc., a change information display item for providing information on changes in self-evaluation results or other's evaluation results compared to a preset period (or last week), a "number of times you've participated in the chat room" display item for displaying the number of times the user has participated in the chat room within a preset period, an information display item for each chat participation case for providing information related to topic talk, role-playing, theme practice, etc., in which the user participates, etc. In this case, the information display item for each chat participation includes a date information display item of participation in the chat room, a detail view item for displaying the detailed information, a chat room type (or chat room category) display item (e.g., including topic talk, role-playing, theme practice, etc.) for displaying the type of chat room in which the user participates, a chat room topic display item for displaying the topic of the chat room, a chat room name display item for displaying the room title (or chat room name) of the chat room, a keyword display item for displaying the main keywords/hashtags related to the corresponding chat room, a self-evaluation information display item for displaying the self-evaluation results, a received evaluation information display item for displaying the evaluation information received from other users participating in the corresponding chat room, a chat recording display item for the re-listening function of chat content from the chat room, etc.

In addition, when a specific participation list (or a detail view item displayed on one side of the corresponding specific participation list) is selected from one or more participation lists displayed in the information display items for each chat participation in the participation list screen displayed on the expert terminal 300, the expert terminal 300 is linked with the server 200 to display the detail view item information related to the selected specific participation list. Here, the detail view item information includes a date information display item of participation in the chat room corresponding to the selected specific participation list, a chat room type (or chat room category) display item for displaying the type of chat room (e.g., including a topic talk chat room, a role-playing chat room, a theme practice chat room, etc.) in which someone is participating, a chat room topic display item for displaying the topic of the chat room, a chat room name display item for displaying the room title of the chat room, a keyword display item for displaying main keywords/hashtags related to the chat room, a chat participant information display item for displaying information (e.g., including a nickname) of other users participating in the corresponding chat room, a self-evaluation result display item (or self-evaluation information display item) for displaying self-evaluation results, a received evaluation result display item (or a received evaluation information display item) for displaying evaluation results received from other users participating in the chat room, a chat recording display item for re-listening to chat content from the chat room.

In addition, when a past counseling record item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected past counseling record item in the corresponding additional detailed information display area.

That is, when a past counseling record item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the past counseling record screen viewed by the expert corresponding to the selected past counseling record item in the corresponding additional detailed information display area. Here, the past counseling record screen viewed by the expert includes a participation list menu for providing the list of who has performed the psychological counseling function, the speech lesson function, or the mentoring function with the expert in relation to the specific topic or situation, a cognitive behavior therapy record menu for providing the cognitive behavior therapy record (or cognitive behavior therapy record sheet) written by the user according to the performance of the training function for the appropriate chat style in relation to the specific topic or situation, a content display area (or content display menu) for displaying the detailed information according to the selection of the participation list menu or the cognitive behavior therapy record menu, etc.

In addition, when a preset participation list menu (or other participation list menu) is selected from the past counseling record screen for the expert displayed on the expert terminal 300, to provide other participation lists in which the user of the terminal 100 performs a counseling function, a speech lesson function, a mentoring function, etc., with the expert of the expert terminal 300, the expert terminal 300 displays other participation list screens corresponding to the selected participation list menu in the content display area. Here, all the other participation list screens include another sorting item for sorting functions related to psychological counseling, speech, mentoring, etc., another sorting item for sorting functions related to most recent, highest score, lowest score, etc., other change information display items for providing information on changes in the number of counseling sessions, the number of times one has performed chat training with an expert, or a cognitive behavior therapy record compared to a preset period (or the last week), an item for displaying the number of times one has participated in other chat rooms for displaying the number of chat room participations within a preset period, an information display item for each expert chat participation case for providing information related to psychological counseling, speech, mentoring, etc., in which a user participates, etc. In this case, examples of the item for displaying the number of times one has participated in other chat rooms include an item for displaying the number of counseling sessions, an item for displaying the number of times one has performed chat training sessions with an expert, a cognitive behavior therapy record item, etc. In addition, examples of the information display item for each expert chat participation case include other chat room type (or chat room category) display items for displaying the type of chat room (e.g., including psychological counseling, speech, mentoring, etc.) in which one is participating, another chat room topic display item for displaying the topic of the chat room, a detail view item for displaying detailed information, an expert information display item for displaying an expert's photo and name, a counseling date display item for displaying a counseling date, other keyword display items for displaying main keywords/hashtags related to the corresponding chat room, an expert feedback item for providing expert feedback, a cognitive behavior therapy record sheet item for providing a cognitive behavior therapy record sheet, a written questionnaire item for providing questionnaire content written by a user, a chat room training display item for displaying chat room training content, etc. Here, when the psychological test result item included in the detailed member information display area in the corresponding XR counseling room screen is selected while the counseling function with the corresponding expert and the corresponding specific user is being performed through the XR counseling room screen displayed on the expert terminal 300, the expert terminal 300 may display other participation list screens corresponding to the participation list item preset by default in response to the selected past counseling record item in the additional detailed information display area by default.

In addition, when other specific participation lists (or detail view items displayed on one side of the corresponding other specific participation lists) are selected from one or more other participation lists being displayed in the information display items for each expert chat participation case in other participation list screens displayed on the expert terminal 300, the expert terminal 300 is linked with the server 200 to display the detailed information related to the selected other specific participation lists. Here, the detailed information (or detailed counseling result item screen) includes other chat room type (or chat room categories) display items for displaying the types of chat rooms (e.g., including psychological counseling, speech, mentoring, etc.) in relation to the other specific participation lists, other chat room topic display items for displaying the topic of the chat room, an expert information display item for displaying the expert's photo and name, a counseling date display item for displaying the counseling date, other keyword display items for displaying the main keywords/hashtags related to the corresponding chat room, an expert feedback display item for displaying the expert feedback, a cognitive behavior therapy record sheet item for providing the cognitive behavior therapy record sheet before and after training, a questionnaire item written during counseling for providing the type and results of the questionnaire written by the user, a chat room participation record display item for providing the chat room participation record, etc. In this case, examples of the questionnaire item written during counseling may include information on various types of tests (or questionnaires) such as a self-esteem self-diagnosis test, a communication type test, an anxiety test, etc. In addition, examples of the chat room participation record display item include a date information display item participating in the chat room, an expert state item for displaying whether the expert is participating in training or observing the expert, a chat room type (or chat room category) display item for displaying the type of a chat room (including, for example, a topic talk chat room, a role-playing chat room, a theme practice chat room, etc.) in which the user participates, a chat room topic display item for displaying the topic of the chat room, a chat room name display item for displaying the room title of the chat room, a chat participant information display item for displaying information (including, for example, nicknames) of other users participating in the corresponding chat room, a self-evaluation result display item (or self-evaluation information display item) for displaying the self-evaluation results, a received evaluation result display item (or received evaluation information display item) for displaying the evaluation results received from other users participating in the corresponding chat room, a chat recording display item for re-listening to the chat content from the chat room, etc.

In addition, when a preset cognitive behavior therapy record menu is selected from the past counseling record screen displayed on the expert terminal 300, to provide the information on the cognitive behavior therapy record sheet written by the user of the terminal 100 according to the user's performance of the training function for the appropriate chat style in relation to the specific topic or situation, the terminal 300 displays a cognitive behavior therapy record screen corresponding to the selected cognitive behavior therapy record menu. Here, the cognitive behavior therapy record screen (or cognitive behavior therapy record sheet screen) includes the cognitive behavior therapy record information display item for each chat participation case, etc., to provide the cognitive behavior therapy record (or cognitive behavior therapy record sheet) written before and after training in relation to the specific topic or situation in which the user of the terminal 100 participates. In addition, examples of the cognitive behavior therapy record information display item for each chat participation case include a cognitive behavior therapy record sheet title display item for displaying the title, a result view item for displaying the written cognitive behavior therapy record result, a record date display item for displaying the date when the cognitive behavior therapy record (or cognitive behavior therapy record sheet) was written, a record sheet progress situation display item for displaying the record sheet progress situation before/after training, a confirmed expert display item for displaying the expert who confirmed that the cognitive behavior therapy record sheet had been written by the user, etc.

In addition, when the specific cognitive behavior therapy record is selected from one or more cognitive behavior therapy record cases being displayed in the cognitive behavior therapy record information display item for each chat participation in the cognitive behavior therapy record screen displayed on the expert terminal 300, the expert terminal 300 is linked with the server 200 to display other detailed information related to the selected specific cognitive behavior therapy record case. Here, the other detailed information (or cognitive behavior therapy record sheet/cognitive behavior therapy record sheet screen) includes a cognitive behavior therapy record sheet title display item to display the title, a last modified date display item, a writer ID and name display item, a writing state display item before and after training (e.g., not written, being written, written, etc.), a cognitive behavior information item for each item before training, a cognitive behavior information item for each item after training, etc. In addition, examples of the cognitive behavior information item for each item before training include an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item for displaying (e.g., improvement-related item, anxiety-related item, etc.) "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/rage, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before the training and/or the cognitive behavior information item for each item after the training may be commonly preset or may be set differently for each expert.

In addition, while the counseling function with the corresponding expert and the corresponding specific user is performed through the XR counseling room screen displayed on the expert terminal 300, when a psychological test result item (not illustrated) included in the detailed member information display area in the corresponding XR counseling room screen is selected, the expert terminal 300 is linked with the server 200 to display a psychological test screen corresponding to the selected psychological test result item in the corresponding additional detailed information display area. Here, the psychological test result screen includes a sorting item for providing a sorting function (e.g., including latest order, psychological test type order, etc.) in relation to one or more psychological test cases performed by the corresponding specific user, a psychological test name item, a psychological test performance date item, a result item (or detail view item), etc.

In addition, when the specific psychological test name (or specific psychological test name/type) is selected from one or more psychological test names (or psychological test names/types) in the psychological test result screen displayed on the expert terminal 300, the expert terminal 300 is linked with the server 200 to display the psychological test results of the corresponding specific user in relation to the selected specific psychological test name. Here, the psychological test results include a test performance user name, a psychological test name, a psychological test performance date, a psychological test type, detailed psychological test results, etc.

In addition, while other specific users are selected from the XR counseling room invitation client selection screen displayed on the expert terminal 300, when the corresponding other specific users are performing a chat function (e.g., including topic talk chatting, role-playing chatting, theme practice chatting, etc.) with another user, the expert terminal 300 is linked with the server 200 to enter (or participate in) the chat room in which the corresponding other specific users and another user who are performing the chat function in the spectator mode.

In addition, the expert terminal 300 (or an expert possessing the expert terminal 300) is linked with the server 200 to confirm (or monitor) the chat content shared between the corresponding other specific users and another user in the chat room who has entered in the spectator mode state. In this case, the expert terminal 300 may use artificial intelligence to check (or monitor/analyze) the chat content shared between the corresponding other specific users and another user in the chat room in the spectator mode state in which it has entered. Here, the spectator mode may perform only the function of confirming chat content between users participating in the corresponding chat room, and may not perform the chat function with the users participating in the corresponding chat room.

In this case, the expert terminal 300 displays the chat room in the spectator mode state related to the user of the terminal 100 on one side of the screen of the corresponding expert terminal 300, and to perform the counseling function with the expert in the XR, the expert terminal 300 is linked with the server 200 and the terminal 100 owned by the corresponding other selected specific users on the other side of the screen of the expert terminal 300 to display the XR counseling room screen.

That is, the expert terminal 300 uses a screen split function to display the chat room in the spectator mode state on one side and display the XR counseling room screen for performing the counseling function with the terminal 100 on the other side.

In this way, the expert terminal 300 can not only perform counseling within the XR counseling room through the exposure training during the cognitive behavior therapy performed on users with social anxiety, but also perform 1:1 training in a specific situation (e.g., role-playing, theme practice, etc.) with an expert, and also provides group therapy in which an expert may conduct counseling while simultaneously confirming the user's state, actions, and activities in a situation where the user is talking to other users.

In addition, in this way, when the expert terminal 300 performs the counseling function, the speech lesson function, the mentor function, etc., with the terminal 100 that has previously written (or registered) a personal information use agreement in the form of an electronic document, the expert terminal 300 confirms personal information related to the user of the terminal 100 during the counseling/lesson/mentoring, a counseling record sheet (or counseling record information), a cognitive behavior therapy record sheet (or cognitive behavior therapy record information), questionnaire results, a people diary (or people diary information), a chat report (or "my report" information), a past counseling record (or past counseling record information), etc., in real time, confirms (or analyzes) the exact state of the user of the terminal 100 and provides an appropriate response plan accordingly. In this case, the personal information related to the user provided to the expert terminal 300, the counseling record sheet (or counseling record information), the cognitive behavior therapy record sheet (or cognitive behavior therapy record information), the questionnaire results, the people diary (or people diary information), the chat report (or my report information), the past counseling record (or past counseling record information), etc., may have a digital rights management (DRM) function set so that the storage function may not be performed and only the viewing function is possible.

In addition, while the corresponding other specific users are performing the chat function with another user or after the chat function ends, the expert terminal 300 is linked with the server 200 to transmit the customized advice information, the analysis information, etc., related to the corresponding other specific users according to the expert input of the corresponding expert terminal 300 to the terminal 100 owned by the other specific users.

In addition, the terminal 100 receives the customized advice information, the analysis information, etc., related to the corresponding other specific users transmitted from the expert terminal 300 via the server 200, and displays (or outputs) the received customized advice information, analysis information, etc., related to the corresponding other specific users. In this case, when the other specific users are performing the chat function with another user, the expert terminal 300 may be linked with the server 200 and the terminal 100 to display the customized advice information, the analysis information, etc., related to the corresponding other specific users in real time through the created XR counseling room screen.

In addition, by performing the counseling function, the expert terminal 300 deposits (or is provided) the remaining amount excluding a preset fee (e.g., including 0.5%, free, etc.) from a payment amount paid by the terminal 100 to a bank account related to the expert of the expert terminal 300 (or account on the server 200 related to the user of the expert terminal 300) according to a preset settlement date (or settlement conditions) by linking between the server 200 and/or a bank server (not illustrated).

An embodiment of the present invention describes performing a people diary/"my report" confirmation function for a specific user, a counseling result writing and management function, a speech lesson function, a mentor function (or mentoring function), an XR chat room (or metaverse chat room) creation and management function, etc., while the expert terminal 300 is performing a counseling function for the user in the form of a website, but is not limited thereto. In addition to the website, a dedicated app provided by the server 200 is installed on the expert terminal 300, and the counseling function for the user, the people diary/"my report" confirmation function for the specific user while the counseling function is performed, the counseling result writing and management function, the speech lesson function, the mentor function (or mentoring function), the XR chat room (or metaverse chat room) creation and management function, etc., may be performed through the installed dedicated app, etc.

In this way, when a preset XR room-creation menu is selected from a website screen, the expert of the expert terminal may perform the psychological counseling function in the metaverse chat room with the specific user under management, and the user of the terminal and the expert of the expert terminal may participate in another metaverse chat room together while the counseling function is performed to perform the chat function.

In addition, in this way, the user of the terminal and the expert of the expert terminal may provide the questionnaire or the counseling record sheet related to the user while the counseling function is performed through the metaverse chat room.

In addition, in this way, the user of the terminal and the expert of the expert terminal may provide the cognitive behavior therapy record sheet related to the user while the counseling function is performed through the metaverse chat room.

In addition, in this way, the user of the terminal and the expert of the expert terminal may provide the information on the chat report or the people diary related to the user while the counseling function is performed through the metaverse chat room.

In addition, in this way, the user of the terminal and the expert of the expert terminal may provide the past counseling record related to the user while the counseling function is performed through the metaverse chat room.

In addition, when a preset people diary menu is selected from the website screen, the expert of the expert terminal may confirm the information on the emotional state by date recorded by the corresponding specific user in the diary format in relation to the specific user under management.

In addition, in this way, when a preset chat report menu is selected from the website screen, the expert of the expert terminal can provide the free expression index, the anxiety index, etc., that correspond to the comprehensive psychological state of the corresponding specific user in relation to the specific user under management.

In addition, in this way, when a preset XR room-creation menu is selected from the website screen, the expert of the expert terminal may perform the psychological counseling function in the XR room with the specific user under management.

Hereinafter, the method of providing psychological counseling according to the present invention will be described in detail with reference to FIGS. 1 to 72.

FIGS. 2 to 8 are flowcharts illustrating a method of providing psychological counseling according to an embodiment of the present invention.

First, the expert terminal 300 accesses a website provided by the server 200 and displays an initial screen provided by the website to manage the counseling function related to the expert of the expert terminal 300. In this case, the initial screen includes an expert information display menu (or button/item/area) for displaying information related to the expert of the corresponding expert terminal 300, a dashboard menu for displaying general information related to an expert, a calendar menu for displaying a counseling schedule of the corresponding expert, a member list menu for displaying member information of a user receiving counseling from the corresponding expert, a member report menu for displaying activity details for a preset period of a user receiving counseling from the corresponding expert, a message menu for a message (or post message) function with a user who is receiving counseling from or has a counseling history with the corresponding expert, a "my performance" menu for providing information such as the counseling performance performed by the corresponding expert, a data management menu for managing information on a questionnaire or data related to a user that an expert is counseling or has a counseling history with, a setting menu (or my page menu) for setting user information, a website function, etc., an XR room creation menu for performing a counseling function with a user in an XR or metaverse environment, a detailed information display area (or detailed information display menu) for displaying detailed information (or additional information) according to the menu selection, etc. Here, the expert terminal 300 may perform a login procedure when accessing the website using the ID and password according to member subscription, a barcode or QR code including the ID, etc., while subscribed as a member in the server 200 that provides the dedicated app (or website) to perform one or more functions of the corresponding website (e.g., including a counseling function for a user, a function of confirming people diary/"my report" for a specific user while performing the counseling function, a function of generating and managing counseling results, a speech lesson function, a mentor function (or mentoring function), a psychological counseling function, an XR chat room (or metaverse chat room) creation and management function, etc.). In this case, the dedicated app (or the website) may be configured as different user interfaces according to an expert (or counselor) who receives the counseling function for a user, the function of confirming a people diary/"my report" for a specific user while performing the counseling function, the function of generating and managing counseling results, the speech lesson function, the mentor function (or mentoring function), a psychological counseling function, the XR chat room (or metaverse chat room) creation and management function, etc., and a user (or counseling requester/client) who receives the chat room search function, the chat function/user-to-user chat function, the counseling with expert function/expert search function, the room creation function, the topic talk chat room function, the role-playing chat room function, the theme practice chat room function, the people diary creation and/or management function, the "my report" management function, etc.

In addition, when a preset dashboard menu is selected from the initial screen displayed on the expert terminal 300, the expert terminal 300 displays the selected dashboard menu to display the information related to the expert of the expert terminal 300. In this case, the expert terminal 300 may display the dashboard screen corresponding to the selected dashboard menu in the detailed information display area. Here, the dashboard screen includes an immediate counseling menu for performing a counseling function with a user (or client) in real time while accessing a website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a calendar item (or calendar menu/area/screen) for displaying an expert's counseling schedule by day, week, month, etc., a "my profile card" menu for displaying an expert's profile card, a counseling request approval count menu for displaying the number of counseling request approvals in relation to counseling requests requested from the corresponding expert, the total number of reserved counseling sessions display menu for displaying the total number of counseling sessions requested from the corresponding expert, a number of new members this month display menu for displaying the number of users who requested new counseling sessions from the expert in that month, a total number of members display menu for displaying the total number of users who have requested counseling from the corresponding expert, a member list item (or member list menu/area/screen) for displaying member information of the user receiving counseling from the corresponding expert, etc. In this case, when accessing the dedicated website on the expert terminal 300 (when logged into the website), the expert terminal 300 may display a dashboard screen corresponding to the dashboard menu set by default in the detailed information display area.

Figure 9:
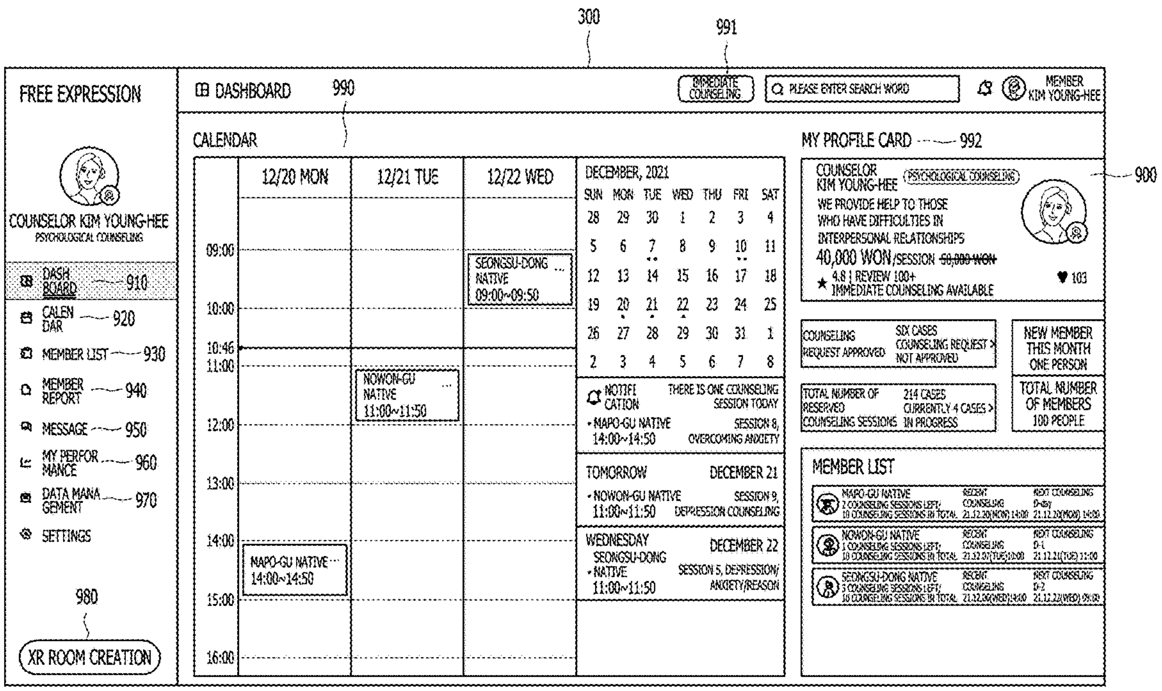
FIGS. 9 to 72 are diagrams illustrating examples of screen configurations of a terminal according to an embodiment of the present invention.

As an example, the first expert terminal 300 accesses a first website (e.g., https://pro.dahae.io/main, which is a free expression website) that provides the counseling function with the user, and as illustrated in FIG. 9, displays an initial screen 900. In this case, the first expert terminal may have performed a login procedure after accessing the corresponding first website using the account information (e.g., first ID and first password) of the first expert of the corresponding first expert terminal.

In addition, as illustrated in FIG. 9, the first expert terminal displays a dashboard screen 990 corresponding to a dashboard menu 910 set by default in the detailed information display area (S210).

Thereafter, when a specific menu is selected from the dashboard screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

That is, when a preset immediate counseling menu is selected from the dashboard screens displayed on the expert terminal 300 according to the expert selection of the corresponding expert terminal 300, to confirm profile information of the corresponding expert and a usage fee per counseling session (or cost per counseling session), the expert terminal 300 is linked with the server 200 to display an immediate counseling screen corresponding to the selected immediate counseling menu. Here, the immediate counseling screen includes an expert name item, a counseling field (or specialty field) item (e.g., including psychological counseling, speech lessons, mentoring, etc.), a brief introduction item, a character (or photo/image) item, a usage fee per counseling item, a rating (or star rating) item, a review information item, a popularity (or number of likes) item, a modifying item, a completion item, a close item, etc., and may be displayed in the form of a pop-up or a new screen (e.g., including a new window, a new screen, etc.).

In addition, after the profile information, the usage fee per counseling session, etc., are set (or confirmed) according to the corresponding expert selection in the immediate counseling screen displayed on the expert terminal 300, when the completion item displayed on one side of the immediate counseling screen is selected, the expert terminal 300 is linked with the server 200 to register the expert of the expert terminal 300 as an expert available for real-time counseling based on one or more input values set in the corresponding immediate counseling screen. Here, the one or more input values include an expert name, a counseling field (or specialty field) (examples include psychological counseling, speech lessons, mentoring, etc.), a brief introduction, a character (or photo/image), a rating (or star rating), review information, popularity (or number of likes), etc., and the rating (or star rating), review information, popularity (or number of likes), etc., may be calculated (or processed) by the server 200 and entered automatically.

In this way, the expert terminal 300 may immediately conduct counseling with the user through the immediate counseling function when the expert has time to spare. In this case, the terminal 300 may register an immediate counseling ticket by applying the discount rate suggested by the expert for immediate counseling with a one-time counseling ticket.

In addition, when the expert search result screen is displayed on a random terminal 100 that accesses the server 200 to search and confirm the expert, to indicate that among the experts searched by the terminal 100, those who have set the immediate counseling function are in an immediately available counseling state, the server 200 is configured to display preset marks (e.g., including immediate counseling availability in a text format, emoticons/avatars corresponding to immediate counseling availability, etc.) in immediately available counseling items on one side of the expert search result screen displayed on the corresponding terminal 100.

In addition, when a preset "my profile" card menu is selected from the dashboard screen displayed on the expert terminal 300 according to the expert selection of the expert terminal 300, to confirm and modify the profile information of the corresponding expert, the expert terminal 300 is linked with the server 200 to display a "my profile" card screen corresponding to the selected "my profile" card menu. Here, the "my profile" card screen above includes an expert display item including content displayed on a "my profile" card, a default information item for setting an expert's default information, a service information item (or counseling information items) for setting the information necessary to perform the counseling function, an expert information item (or counselor information items) to provide additional information on an expert, a review information item for providing registered review information regarding an expert, a storing item for storing edited content, a previous item (or cancel item) for returning to a previous screen (e.g., including a dashboard screen, etc.) with previously written content maintained (or without modifications), etc. In addition, the expert display item (a "my profile" card item) includes an expert name, a counseling field (or specialty field) (e.g., including psychological counseling, speech lessons, mentoring, etc.), a brief introduction, a character (or photo/image), a usage fee per counseling session, a rating (or star rating), review information, whether immediate counseling is possible, popularity (or number of likes), etc. In addition, the default information item (or user information item) of the expert includes an expert name/name, a gender, a title (or brief introduction), a tag related to a main specialty field of the corresponding expert, an expert type (or counseling field), a topic for which counseling is available, a situation in which counseling is possible, etc. In this case, examples of the tag (or hashtag) related to the expert's major specialty field include #dream/career, #employment, #anxiety, #depression, a self-written item, etc. In addition, examples of the topic for which counseling is available include "my item," a social life item, an interpersonal relationship item, a dream/career item, an emotional/psychological item, an expert item, etc. In addition, examples of the situation in which counseling is possible include an item that express an individual, a work situation item, a presentation situation item, a difficult target item, a friendship item, a conflict situation item, an emotional expression item, a discussion/persuasion item, etc. In addition, examples of the service information item (or counseling information item) include a service description (e.g., detailed content, a key point, an image, a video link, etc.), a service option (e.g., a default option, a location, etc.), etc. Here, examples of the default option include a usage ticket, content, an additional configuration (e.g., including XR chat room training and a data analysis rate, etc.), a time, a number of times, a price, etc. In addition, the location includes a name, an address, etc. In addition, examples of the expert information item (or counselor information item) include expert (or counselor) introduction content, career information according to an affiliation, a position, a period depending on an employment status, certificate information by issuance institution, supporting materials, etc. In addition, examples of the review information item include an overall star rating, ratings for each category (e.g., including use of XR, friendliness, analytical skills, empathy and comfort, appropriate advice, etc.), the total number of reviews, detailed content of recent reviews, etc.

In addition, the expert terminal 300 is linked with the server 200 to perform an information modification function in the "my profile" card screen according to the expert input of the expert terminal 300, and update (or store/manage) the content of the modified "my profile" card.

In addition, when a preset calendar item is selected from the dashboard screen displayed on the expert terminal 300 according to the expert selection of the expert terminal 300, to display the corresponding expert's counseling schedule by day, week, month, etc., the expert terminal 300 is linked with the server 200 to display a calendar screen corresponding to the selected calendar item. Here, the expert terminal 300 may perform additional functions according to the expert selection for a specific menu on the calendar screen, which will be described later.

In addition, when a preset member list item is selected from the dashboard screen displayed on the expert terminal 300 according to the expert selection of the expert terminal 300, to display member information of a user who is counseling with the corresponding expert, the expert terminal 300 is linked with the server 200 to display the member list screen corresponding to the selected member list item. Here, the expert terminal 300 may perform additional functions according to the expert selection for a specific menu on the member list screen, which will be described later.

Figure 10:
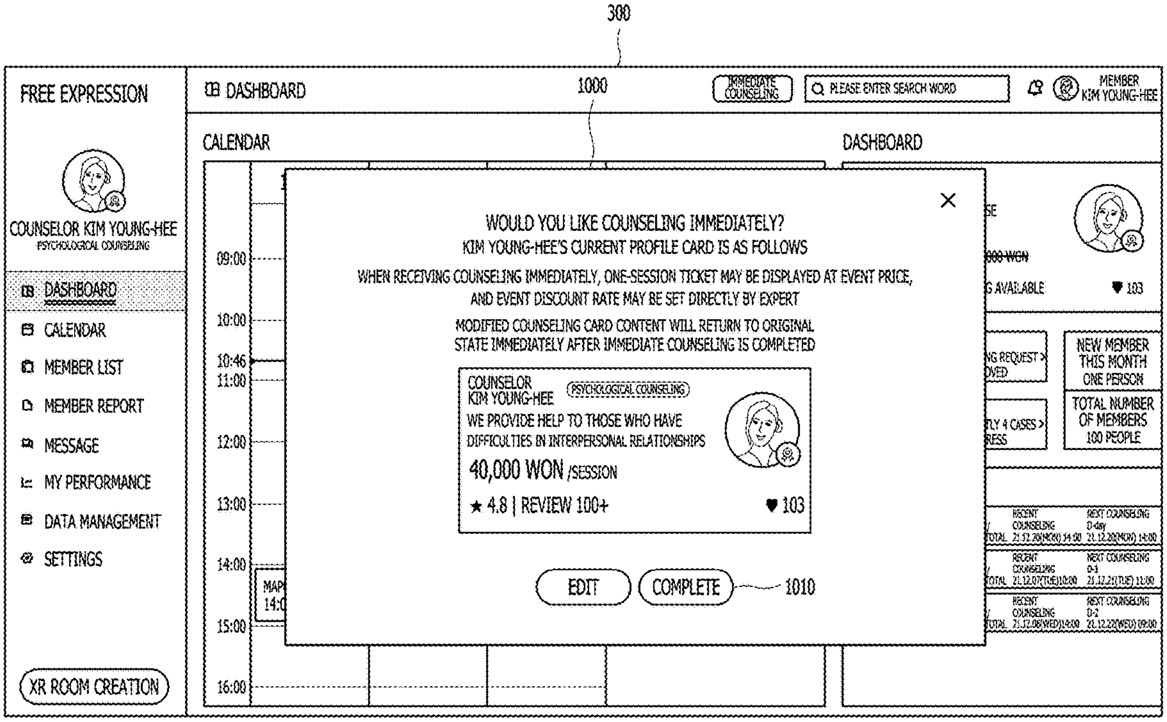

As an example, when a preset immediate counseling menu 991 is selected from the dashboard screen 990 displayed on the first expert terminal according to the first expert selection of the corresponding first expert terminal, as illustrated in FIG. 10, the first expert terminal displays an immediate counseling screen 1000 corresponding to the selected immediate counseling menu 991 in a pop-up form.

In addition, after first profile information (e.g., Counselor Kim Young-Hee, psychological counseling, provides help to those who have difficulties with interpersonal relationships~!), a first usage fee per counseling session (e.g., 40,000 won per counseling session), a first star rating (e.g., 4.8 points out of 5 points), a first number of reviews of 100 or more, etc., are set in the immediate counseling screen 1000 displayed on the first expert terminal according to the corresponding first expert selection, when the completion item 1010 displayed on one side of the immediate counseling screen (1000) is selected, the first expert terminal is linked with the server 200 to register the corresponding first expert as an expert available for real-time counseling using the set input values.

Figure 11:
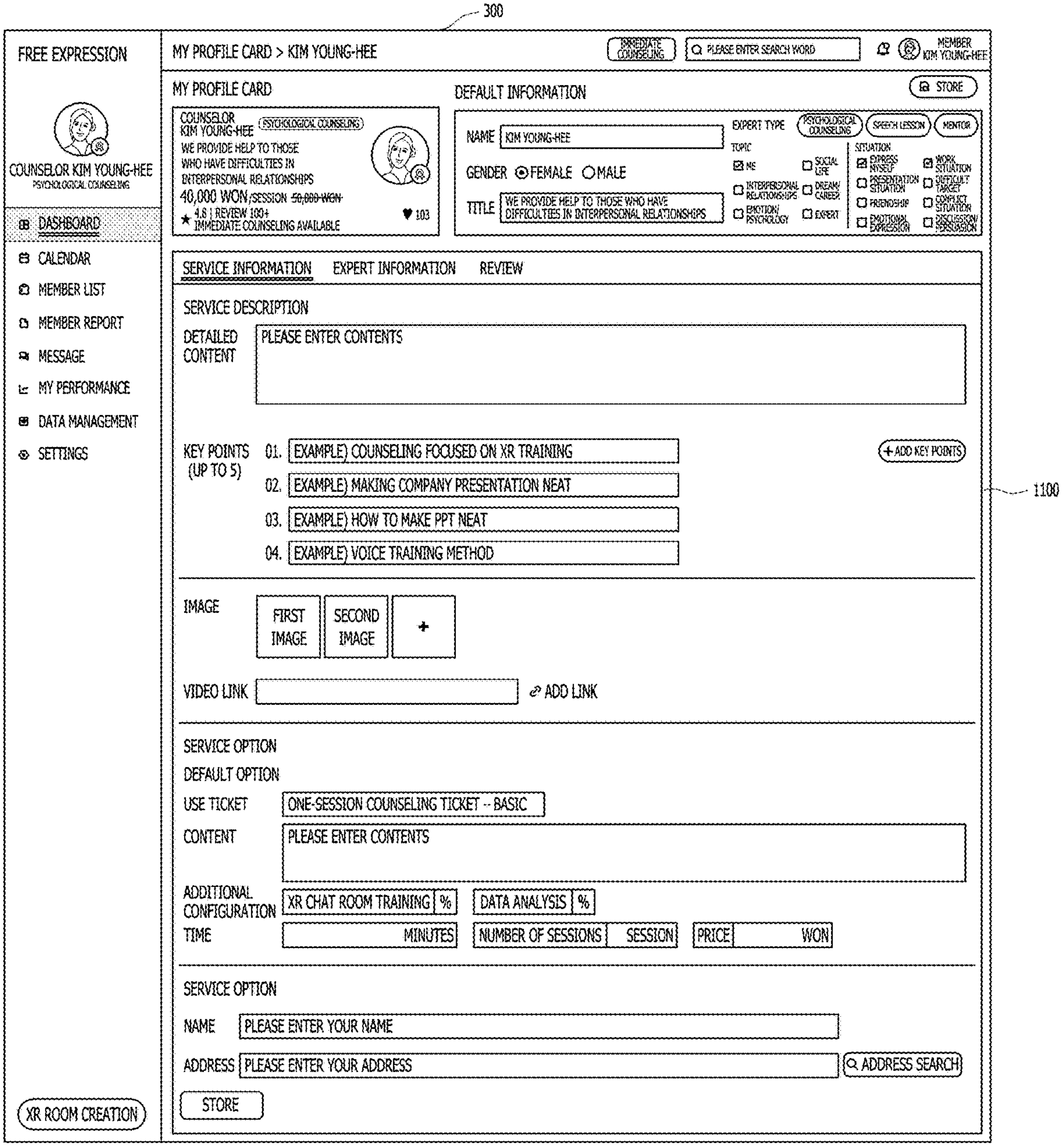

As another example, when a preset "my profile" card menu 992 is selected from the dashboard screen 990 displayed on the first expert terminal according to the first expert selection of the corresponding first expert terminal, as illustrated in FIG. 11, the first expert terminal is linked with the server 200 to display a "my profile" card screen 1100 corresponding to the selected "my profile" card menu 992.

In addition, the first expert terminal is linked with the server 200 to reflect the content set according to the expert input in the "my profile" card screen 1100 and update the first "my profile" card related to the first expert (e.g., Kim Young-Hee) of the corresponding first expert terminal (S220).

In addition, when the preset calendar menu is selected from the initial screen displayed on the expert terminal 300, the expert terminal 300 displays the calendar screen corresponding to the selected calendar menu to display the counseling schedule of the corresponding expert. In this case, the expert terminal 300 may display the calendar screen corresponding to the selected calendar menu in the detailed information display area. Here, the calendar screen includes a calendar type menu for selecting the type of calendar provided (e.g., including list, monthly, weekly, etc.), an immediate counseling menu for performing a counseling function with the user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a detailed counseling schedule menu for displaying the counseling schedule of the expert according to the calendar type and selected period selected in the calendar type item, a counseling request approval menu for providing information on one or more counseling requests for which the expert has not yet processed counseling request approval among the counseling requests requested from the corresponding expert, an available reservation time menu for setting the available counseling reservation date and time zone of the corresponding expert, an output menu for outputting the expert's counseling schedule displayed on the calendar screen, a filter menu for providing a filter function for the expert's counseling schedule, a counseling addition menu for adding a new counseling schedule, etc. In this case, the calendar type item may be in a state in which a weekly item is selected by default. In addition, the detailed counseling schedule item may display (or include) some of the counseling schedules reserved for a specific date and time zone (e.g., including a user/client's nickname, a reservation time zone, etc.) when the counseling schedule is reserved for the specific date and time zone, and separately display a date and time zone that are available for reservation and a date and time zone that are not available for reservation among all dates and time zones depending on the expert setting (e.g., including different background colors and/or background patterns, etc., for each date and time zone that are available for reservation and are not available for reservation). In addition, examples of the output item include a print item through a printer (not illustrated), a print (or store/output) item in a file format such as a PDF format or an HWP format, etc.

In addition, when the specific menu is selected from the calendar screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 12:
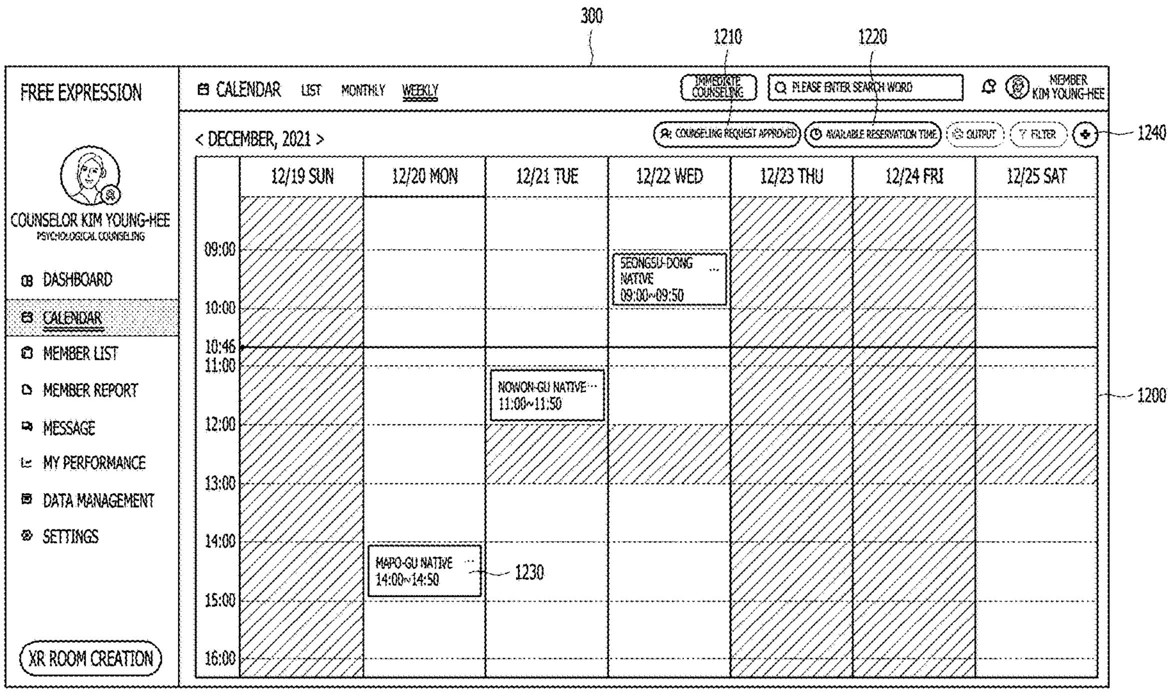

As an example, when a preset calendar menu 920 is selected from the initial screen 900 displayed on the first expert terminal according to the first expert selection of the corresponding first expert terminal, as illustrated in FIG. 12, the first expert terminal displays a calendar screen 1200 corresponding to the selected calendar menu 920 (S230).

Thereafter, when a preset counseling request approval item is selected from the calendar screen displayed on the expert terminal 300, to provide information on one or more counseling request cases (or unapproved counseling request cases) for which the expert has not yet processed counseling request approval among the counseling request cases in which counseling from the corresponding expert has been requested, the expert terminal 300 is linked with the server 200 to display a counseling request approval screen corresponding to the selected counseling request approval item. Here, the counseling request approval screen includes a monthly calendar item for displaying the number of monthly counseling cases (or a daily calendar item for displaying the number of daily counseling cases for the corresponding month) based on the month corresponding to the current date in the expert terminal 300, counseling request approval processing items by date (or by day of the week) to display one or more counseling request cases (or unapproved counseling request cases) that have not yet been approved among the counseling request cases, and a close item (or end item), etc., and may be displayed in a pop-up form or a new screen form (e.g., including a new window form, a new screen form, etc.). In addition, the counseling request approval processing items by date include the nickname item of a counseling requester corresponding to a counseling request case that has not yet been approved by date (or by day of the week), a request time information item (e.g., including 10 minutes ago, 1 hour ago, etc.), counseling ticket type items (e.g., including 5 basic counseling tickets, 10 basic counseling tickets, 5 in-depth counseling tickets, 10 in-depth counseling tickets, etc.), desired counseling time items (e.g., including date, time information, etc.), an approval processing item, a deletion item, etc.

In addition, when a specific unapproved counseling request (or specific counseling request case) is selected from one or more counseling request cases (or unapproved counseling request cases) that have not yet been approved in the counseling request approval screen displayed on the expert terminal 300 according to the expert selection, the expert terminal 300 displays detailed information on the selected specific unapproved counseling request case. Here, the detailed information (or detailed specific unapproved counseling request information) includes a counseling request approval processing item (or area) by date, a detailed counseling requester information display item for the counseling requester corresponding to the corresponding specific unapproved counseling request case, etc. In addition, examples of the detailed counseling requester information display item include a nickname item of a counseling requester, a character (or photo/image) item of a counseling requester, a gender item, a birth date item, an emergency contact network (or phone number) item, a counseling ticket type item (e.g., time, number of times, etc., for each type), a desired counseling time item (e.g., date, time, etc.), an item for displaying a topic on which the counseling requester would like to receive counseling, an additional inquiry item, an acceptance item, a reschedule item, a close item, etc.

Figure 13:
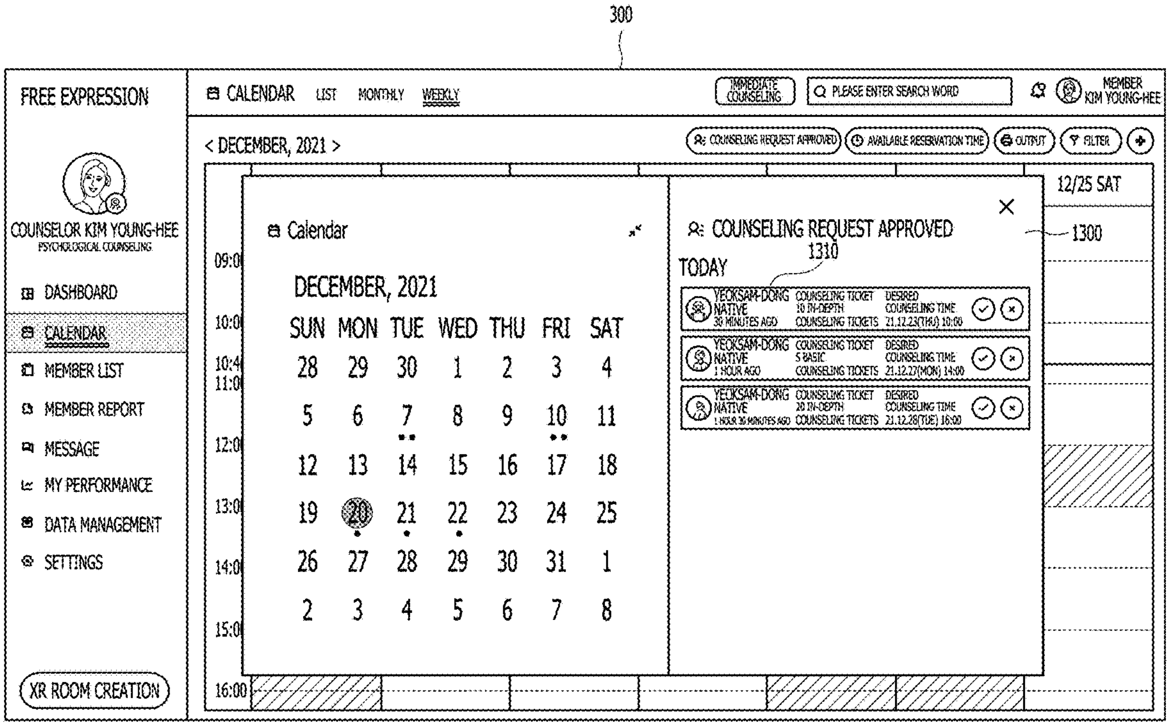

For example, when a counseling request approval item 1210 is selected from a calendar screen 1200 displayed on the first expert terminal, as illustrated in FIG. 13, the first expert terminal displays the counseling request approval screen 1300 corresponding to the selected counseling request approval item 1210.

Figure 14:
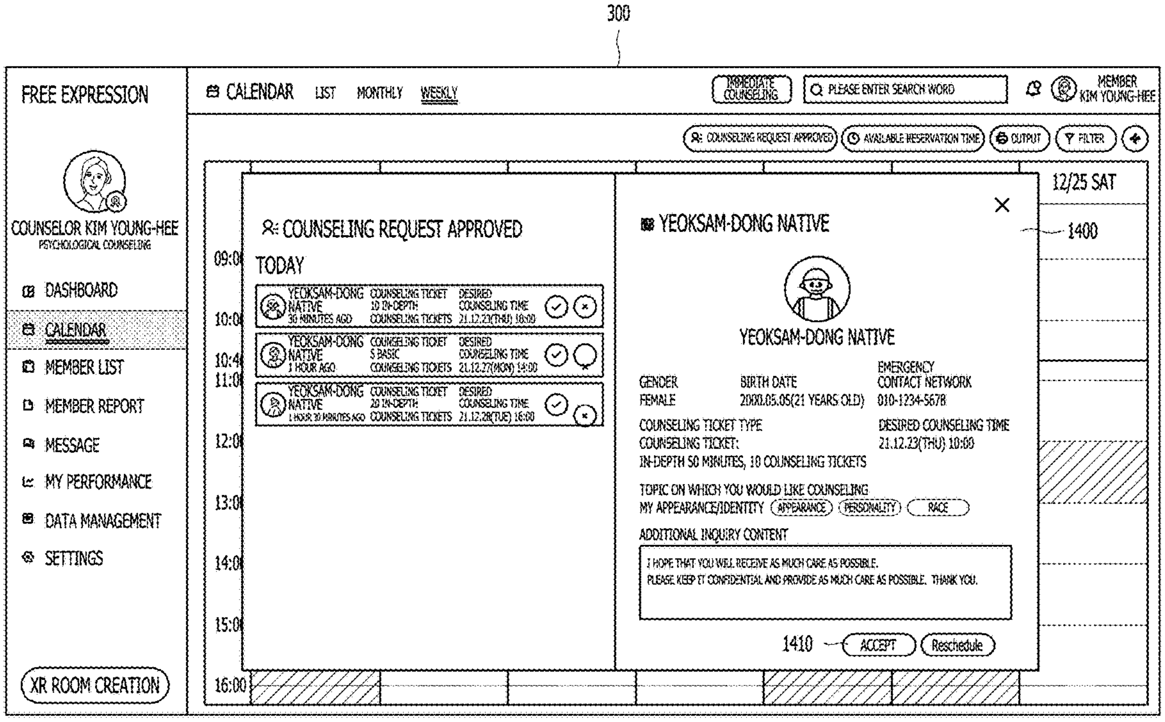

In addition, when a first unapproved counseling request case (or first counseling request case) 1310 is selected from one or more unapproved counseling request cases in the counseling request approval screen 1300 displayed on the first expert terminal, as illustrated in FIG. 14, the first expert terminal displays first detailed unapproved counseling request information 1400 corresponding to the selected first unapproved counseling request case 1310 related to a Yeoksam-dong native who requested counseling with the corresponding first expert, Kim Young-Hee (S240).

Thereafter, when the preset acceptance item is selected from the detailed information on the specific unapproved counseling request case displayed on the expert terminal 300 according to the corresponding expert selection, the expert terminal 300 is linked with the terminal 100 and the server 200 corresponding to the corresponding specific unapproved counseling request case to confirm the counseling schedule for the corresponding specific unapproved counseling request case.

That is, when the preset acceptance item is selected from the detailed information on the specific unapproved counseling request case displayed on the expert terminal 300 according to the corresponding expert selection, to add a new counseling schedule, the expert terminal 300 is linked with the server 200 to provide a new counseling addition screen corresponding to date and time zone items related to the corresponding specific unapproved counseling request case. Here, the new counseling addition screen includes expert information items (e.g., including a character/photo/image, an expert name/name, a counseling field (or specialty field), etc.) for displaying the information related to the expert of the expert terminal 300, a counseling topic selection item for selecting a counseling topic (e.g., including anxiety, depression, interpersonal relationships, etc.), a counseling completion number display item for displaying the number of counseling cases completed by the corresponding expert, a current progress display item for displaying the number of counseling sessions the corresponding expert currently has in progress, an average counseling time display item for displaying an average counseling time of the corresponding expert, a counseling content writing item for writing counseling content, an additional client selection item for selecting information on a counseling requester, a date and time zone selection item for selecting an available counseling reservation date and time zone, a cancel item for canceling a process of adding new counseling content, a storing item for a storage function according to input values for each item, a close item for ending (or closing) the corresponding new counseling addition screen, etc.

In addition, the expert terminal 300 receives a new counseling schedule including a plurality of input values corresponding to a plurality of input items related to the new counseling schedule according to the expert input of the expert terminal 300 on the new counseling addition screen displayed on the expert terminal 300. Here, the new counseling schedule includes expert information (e.g., a counselor name/expert name, a counseling field, etc.), a counseling topic, counseling content, client (or counseling requester/user) information (e.g., a client's nickname, etc.), a counseling reservation date and time zone, etc. In this case, the expert information, the counseling topic, etc., may be preset in response to the expert terminal 300 (or the expert of the expert terminal 300).

In addition, the expert terminal 300 is linked with the server 200 to map (or match/link) the received new counseling schedule with the user information (or expert information) of the expert terminal 300 and the member information (or user information/personal information) of the user of the terminal 100 corresponding to the client related to the corresponding new counseling schedule and store (or register/manage) the mapped information in the server 200.

That is, the expert terminal 300 transmits the received new counseling schedule, counseling schedule storage request information, identification information of the expert terminal 300, identification information (or a nickname/member unique ID) of the terminal 100 corresponding to the client related to the new counseling schedule to the server 200. Here, the identification information of the expert terminal 300 includes a mobile directory number (MDN), a mobile Internet protocol (IP), mobile media access control (MAC), subscriber identification module (SIM) card unique information, a serial number, etc.

In addition, the server 200 receives the new counseling schedule, the counseling schedule storage request information, the identification information of the expert terminal 300, the identification information (or nickname/member unique ID) of the terminal 100 corresponding to the client related to the new counseling schedule, etc., that are transmitted from the expert terminal 300.

In addition, the server 200 confirms (or searches for) the user information corresponding to the received identification information of the expert terminal 300 among user information (or personal information/member information/expert information) for each piece of identification information of the expert terminal being managed by the server 200.

In addition, the server 200 confirms (or searches for) member information corresponding to the client (or counseling requester/user) (or client related to the identification information of the terminal 100) included in the received new counseling schedule among the member information for each counseling requester being managed by the server 200.

In addition, the server 200 maps (or matches/links) the user information corresponding to the identification information of the confirmed (or searched) corresponding expert terminal 300 and the member information corresponding to the client who will perform the confirmed corresponding counseling function with the received new counseling schedule, the received identification information of the expert terminal 300, the received identification information of the terminal 100, etc., and stores (or registers/manages) the mapped information in the server 200.

In addition, the server 200 transmits (or provides) information indicating that the counseling schedule with the corresponding expert has been confirmed to the terminal 100 owned by the confirmed counseling requester.

In addition, the terminal 100 receives the information indicating that the counseling schedule with the corresponding expert transmitted from the server 200 is confirmed, and displays (or outputs) the information indicating that the counseling schedule with the received corresponding expert has been confirmed.

In addition, the terminal 100 is linked with the server 200 to perform a final confirmation function (or final acceptance/confirmation function) for the counseling schedule case newly registered in the expert terminal 300 so that the counseling schedule for the counseling schedule case newly registered in the expert terminal 300 is finally confirmed.

In addition, the expert terminal 300 is linked with the server 200 to display the calendar screen to which the newly registered counseling schedule is applied (or reflected).

In addition, the server 200 transmits (or provides) information indicating that the counseling schedule with the corresponding expert has been confirmed in relation to the specific counseling request case requested by the corresponding counseling requester (or user/client) to the terminal 100 related to the corresponding specific counseling request case according to the confirmation of the counseling schedule for the corresponding specific unapproved counseling request case.

In addition, the terminal 100 receives the information indicating that the counseling schedule with the corresponding expert transmitted from the server 200 is confirmed for the specific counseling request case previously requested through the server 200, and displays (or outputs) the information indicating that the counseling schedule with the received corresponding expert has been confirmed.

In addition, the terminal 100 is linked with the server 200 to perform a final confirmation function (or final acceptance/confirmation function) so that the counseling schedule for the corresponding specific counseling request case is finally confirmed (or reserved).

Figure 15:
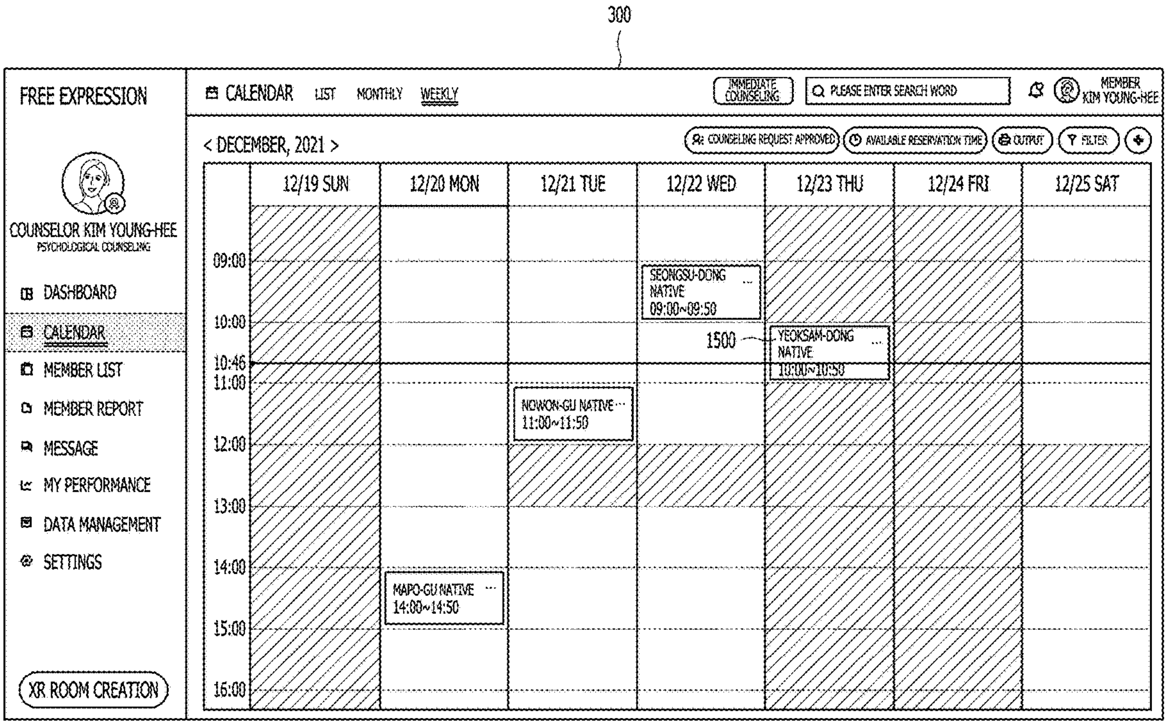

As an example, when an acceptance item 1410 is selected from first detailed counseling request approval information 1400 displayed on the first expert terminal, the first expert terminal is linked with the server 200 to confirm the first counseling schedule according to the corresponding first detailed counseling request approval information 1400, and as illustrated in FIG. 15, display a calendar screen 1500 in which the corresponding first counseling schedule is reflected.

In addition, the server 200 transmits the information indicating that the counseling schedule with the corresponding first expert has been confirmed for the selected first counseling request case related to a Yeoksam-dong native who requests counseling with the corresponding first expert, Kim Young-Hee, to the first terminal 100 possessed by the Yeoksam-dong native.

In addition, the first terminal receives the information indicating that the counseling schedule with the corresponding first expert has been confirmed for the corresponding first counseling request case transmitted from the server 200, and displays the information indicating that the counseling schedule with the corresponding first expert has been confirmed for the received corresponding first counseling request case (S250).

In addition, when the preset available reservation time item is selected from the calendar screen displayed on the expert terminal 300, to set the available counseling reservation date and time zone of the corresponding expert, the expert terminal 300 is linked with the server 200 to display the available reservation time setting screen corresponding to the selected available reservation time item. Here, the available reservation time setting screen includes a calendar item corresponding to the current date in the expert terminal 300, a close item, etc., and may be displayed in the form of a pop-up or a new screen (e.g., including a new window, a new screen, etc.).

Figure 16:
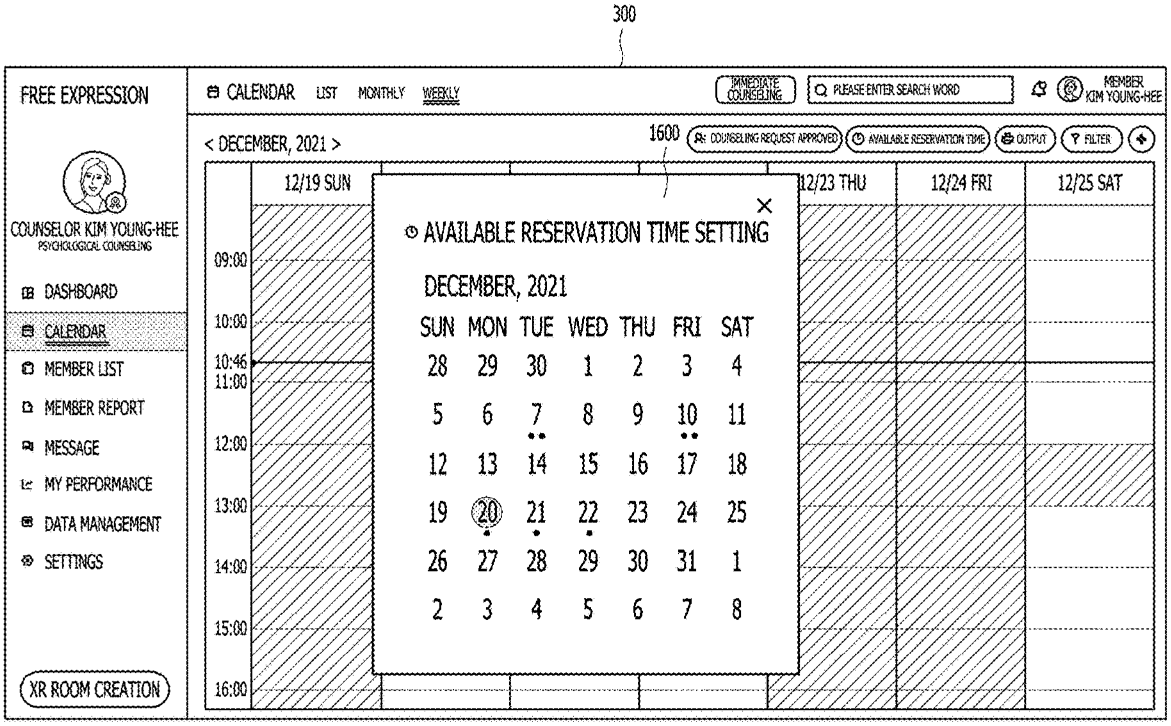

For example, when the available reservation time item 1220 is selected from the calendar screen 1200 displayed on the first expert terminal, as illustrated in FIG. 16, the first expert terminal display an available reservation time setting screen 1600 corresponding to the selected available reservation time item 1220 (S260).

Thereafter, when a specific date is selected from the available reservation time setting screen displayed on the expert terminal 300, to set an available counseling reservation time zone, the expert terminal 300 is linked with the server 200 to display the time zone setting screen corresponding to the selected specific date. Here, the time zone setting screen includes an available reservation time zone item in relation to the corresponding specific date, a cancel item for canceling a time zone setting, a storing item for storing the information on the selected available reservation time zone, a close item for ending (or closing) the screen without storing content, etc., and may be displayed in the form of a pop-up or a new screen (e.g., including a new window, a new screen, etc.)

In addition, when a specific time zone is selected from the time zone setting screen displayed on the expert terminal 300 according to the corresponding expert selection, the expert terminal 300 is linked with the server 200 to set the corresponding specific date and the specific time zone as the available counseling reservation date and time zone of the corresponding expert. Here, the time zone may be set in a preset standard time unit (e.g., 1 hour, 30 minutes, etc.).

In addition, the expert terminal 300 displays a calendar screen in which a newly set available date and time zone of the corresponding expert is reflected (or applied). In this case, in the detailed counseling schedule item of the calendar screen, among all dates and time zones, the available reservation date and time zone to which the newly set available counseling reservation date and time zone are applied among all dates and time zones according to the expert setting and an unavailable reservation date and time zone may be displayed separately (e.g., including different background colors and/or background patterns, etc., for when reservations are and are not available in the time zone for each date, etc.).

Figure 17:
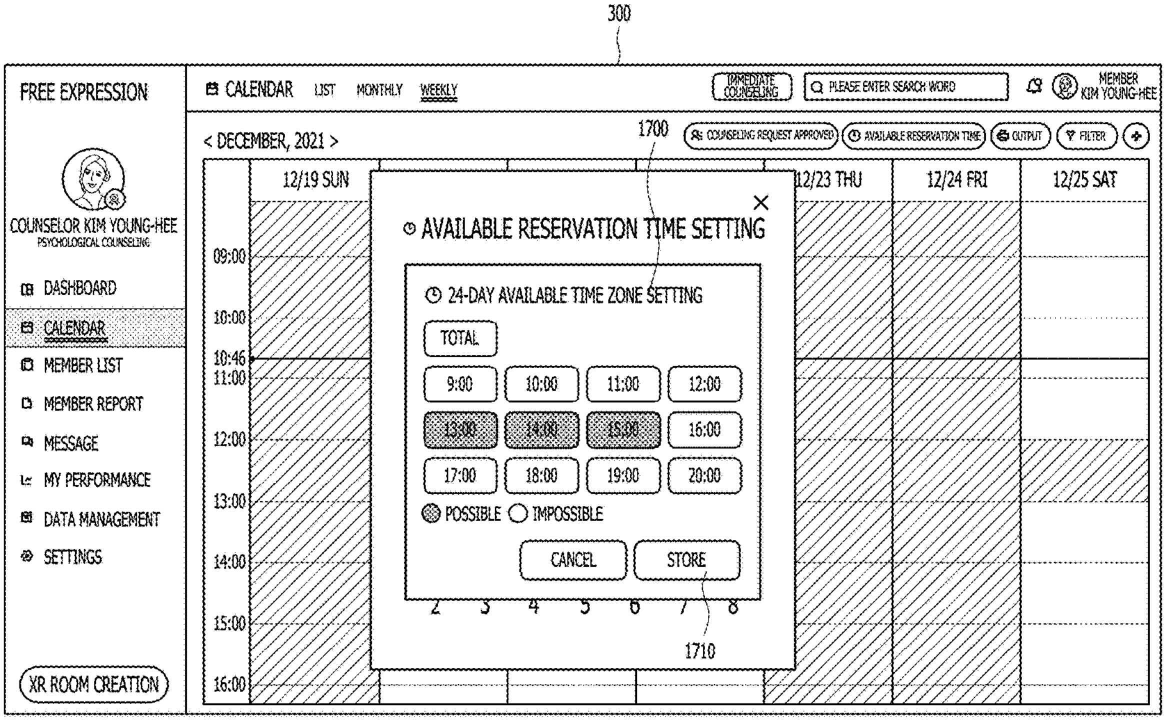

For example, when Dec. 24, 2021, is selected from the available reservation time setting screen 1600 displayed on the first expert terminal according to the first expert selection, as illustrated in FIG. 17, the first expert terminal displays a time zone setting screen 1700 corresponding to the selected Dec. 24, 2021.

In addition, in the time zone setting screen 1700 displayed on the first expert terminal, the first time zone (e.g., in 1 hour units, including start times 13:00, 14:00, 15:00, etc.) is selected according to the first expert selection, and then, when a preset storing item 1710 is selected, the first expert terminal is linked with the server 200 to set the available counseling reservation date and time zone from 1:00 PM to 4:00 PM on Friday, Dec. 24, 2021, in relation to the corresponding first expert.

Figure 18:
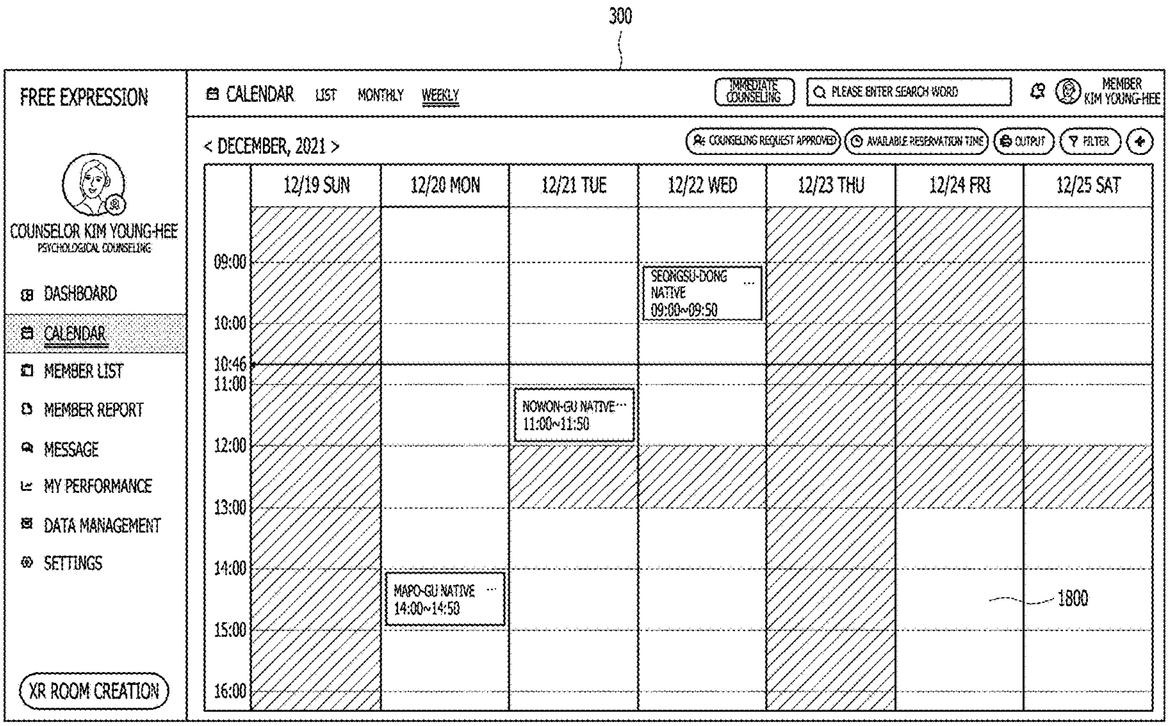

In addition, as illustrated in FIG. 18, the first expert terminal displays a calendar screen 1800 in which the new available counseling reservation date and time zone (e.g., 1:00 PM to 4:00 PM on Friday, Dec. 24, 2021) is reflected (S270).

In addition, when any one counseling schedule (or specific date and time zone corresponding to a specific reserved counseling schedule/counseling schedule) is selected from the detailed counseling schedule items in the calendar screen displayed on the expert terminal 300 including one or more reserved counseling schedules, the expert terminal 300 is linked with the server 200 to display the personal counseling management screen corresponding to the user (or client/counseling requester) related to the selected counseling schedule (or counseling schedule of the selected specific date and time zone). Here, the personal counseling management screen includes some of personal information display items for displaying some of the personal information (e.g., including a nickname, the remaining number of counseling sessions out of the total number of available counseling sessions, etc.) of the counseling requester, an XR room invitation item for inviting the corresponding counseling requester to the XR room to perform the counseling function in the XR chat room (or metaverse chat room) with the counseling requester, a reservation date change item for changing the counseling schedule with the counseling requester (e.g., a specific date and time zone related to the selected counseling schedule), a default information item for providing default information (or personal information) on the corresponding counseling requester, a reservation timeline item for providing a reservation situation for the corresponding counseling requester, a counseling record sheet item for providing a counseling record sheet for the corresponding counseling requester, a memo item for providing an unusual situation related to the corresponding counseling requester, and a close item for ending (or closing) the personal counseling management screen, etc., and may be displayed in the form of a pop-up or a new screen (e.g., including a new window, a new screen, etc.). In this case, the XR room invitation item may be activated when the corresponding counseling requester is accessing the website (or online/logged in), and may be deactivated by default. In addition, examples of the reservation timeline item include a counseling topic item, an item for displaying the number of counseling sessions completed, an item for displaying the remaining number of counseling sessions, an average counseling time display item, a counseling content item by date and time zone, a reservation change item, an expert (or person in charge/counselor) item, a counseling time item, a detail view item for a detail view for additional information, etc. In this case, the reservation change item may not change the counseling requester related to the counseling case, and may be configured to change only the expert of the expert terminal 300.

In addition, the expert terminal 300 may confirm (or display/modify) the default information, the reservation schedule (or reservation timeline), the counseling record sheet, notes, etc., in relation to the user related to the corresponding counseling schedule according to the default information item, the reservation timeline item, the counseling record sheet item, the memo items, etc., that are included in the personal counseling management screen displayed on the expert terminal 300.

Figure 19:
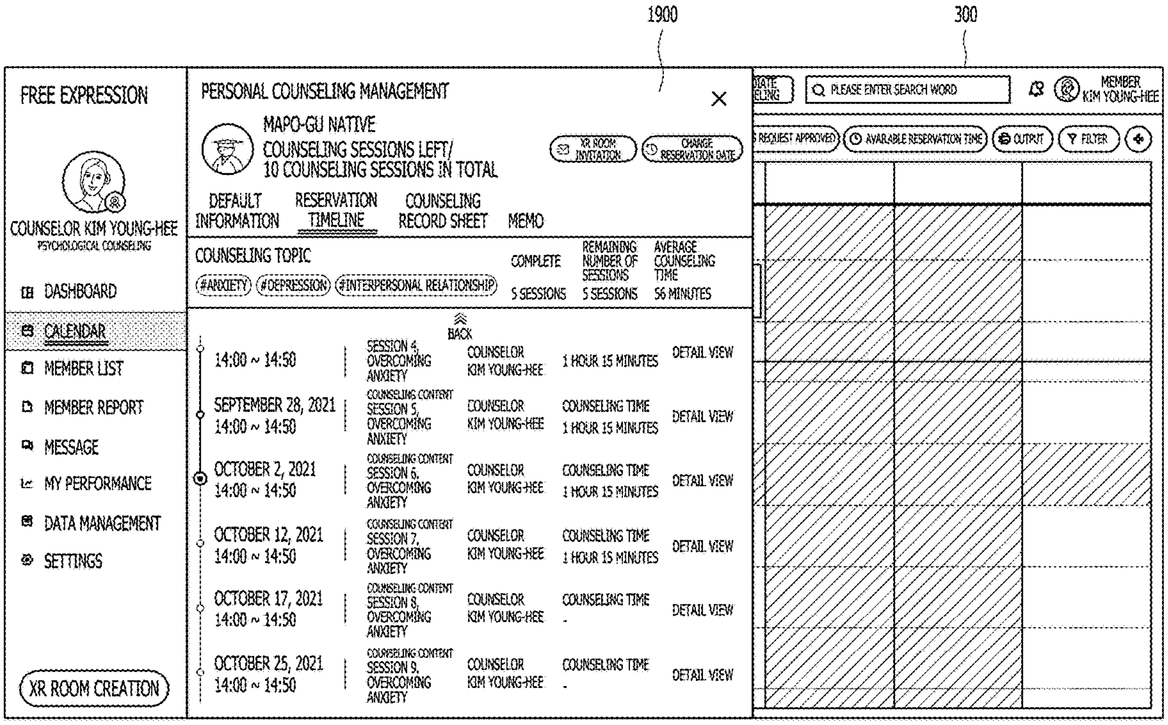

As an example, when a second counseling schedule 1230 with a Mapo-gu native from 2:00 to 3:00 PM on Monday, December 20 is selected from the calendar screen 1200 displayed on the first expert terminal, as illustrated in FIG. 19, the first expert terminal displays a personal counseling management screen 1900 corresponding to the Mapo-gu native related to the selected second counseling schedule 1230 (S280)

In addition, when a preset additional counseling item is selected from the calendar screen displayed on the expert terminal 300 or the available counseling reservation date and time zone item is selected from the detailed counseling schedule time in the calendar screen displayed on the expert terminal 300, to add a new counseling schedule, the expert terminal 300 is linked with the server 300 to display a new counseling addition screen corresponding to the selected additional counseling item or the selected available counseling reservation date and time zone item. Here, the new counseling addition screen includes expert information items (e.g., including a character/photo/image, an expert name/name, a counseling field (or specialty field), etc.) for displaying the information related to the expert of the expert terminal 300, counseling topic selection items for selecting a counseling topic (e.g., including anxiety, depression, interpersonal relationships, etc.), a counseling completion number display item for displaying the number of counseling cases completed by the corresponding expert, a current progress display item for displaying the number of counseling sessions the corresponding expert currently has in progress, an average counseling time display item for displaying an average counseling time of the corresponding expert, a counseling content writing item for writing counseling content, an additional client selection item for selecting information on a counseling requester, a date and time zone selection item for selecting an available counseling reservation date and time zone, a cancel item for canceling a process of adding new counseling content, a storing item for a storage function according to input values for each item, a close item for ending (or closing) the corresponding new counseling addition screen, etc.

In addition, the expert terminal 300 receives a new counseling schedule including a plurality of input values corresponding to a plurality of input items related to the new counseling schedule according to the expert input of the expert terminal 300 on the new counseling addition screen displayed on the expert terminal 300. Here, the new counseling schedule includes expert information (e.g., a counselor name/expert name, a counseling field, etc.), a counseling topic, counseling content, client (or counseling requester/user) information (e.g., a client's nickname, etc.), a counseling reservation date and time zone, etc. In this case, the expert information, the counseling topic, etc., may be preset in response to the expert terminal 300 (or the expert of the expert terminal 300).

In addition, the expert terminal 300 is linked with the server 200 to map (or match/link) the received new counseling schedule with the user information (or expert information) of the expert terminal 300 and the member information (or user information/personal information) of the user of the terminal 100 corresponding to the client related to the corresponding new counseling schedule and store (or register/manage) the mapped information in the server 200.

That is, the expert terminal 300 transmits the received new counseling schedule, counseling schedule storage request information, identification information of the expert terminal 300, identification information (or nickname/member unique ID) of the terminal 100 corresponding to the client related to the new counseling schedule to the server 200. Here, the identification information of the expert terminal 300 includes a mobile directory number (MDN), a mobile Internet protocol (IP), mobile media access control (MAC), subscriber identification module (SIM) card unique information, a serial number, etc.

In addition, the server 200 receives the new counseling schedule, the counseling schedule storage request information, the identification information of the expert terminal 300, the identification information (or nickname/member unique ID) of the terminal 100 corresponding to the client related to the new counseling schedule, etc., that are transmitted from the expert terminal 300.

In addition, the server 200 confirms (or searches for) the user information corresponding to the received identification information of the expert terminal 300 among user information (or personal information/member information/expert information) for each piece of identification information of the expert terminal being managed by the server 200.

In addition, the server 200 confirms (or searches for) member information corresponding to the client (or counseling requester/user) (or client related to the identification information of the terminal 100) included in the received new counseling schedule among the member information for each counseling requester being managed by the server 200.

In addition, the server 200 maps (or matches/links) the user information corresponding to the identification information of the confirmed (or searched) corresponding expert terminal 300 and the member information corresponding to the client who will perform the confirmed corresponding counseling function with the received new counseling schedule, the received identification information of the expert terminal 300, the received identification information of the terminal 100, etc., and stores (or registers/manages) the mapped information in the server 200.

In addition, the server 200 transmits (or provides) information indicating that the counseling schedule with the corresponding expert has been confirmed to the terminal 100 owned by the confirmed counseling requester.

In addition, the terminal 100 receives the information indicating that the counseling schedule with the corresponding expert transmitted from the server 200 is confirmed for the specific counseling request case previously requested through the server 200, and displays (or outputs) the information indicating that the counseling schedule with the received corresponding expert has been confirmed.

In addition, the server 200 is linked with the expert terminal 300 and the terminal 100 to perform a final confirmation function (or final acceptance/confirmation function) for the counseling schedule case newly registered in the expert terminal 300 so that the counseling schedule for the counseling schedule case newly registered in the expert terminal 300 is finally confirmed.

In addition, the expert terminal 300 is linked with the server 200 to display the calendar screen to which the newly registered counseling schedule is applied (or reflected).

Figure 20:
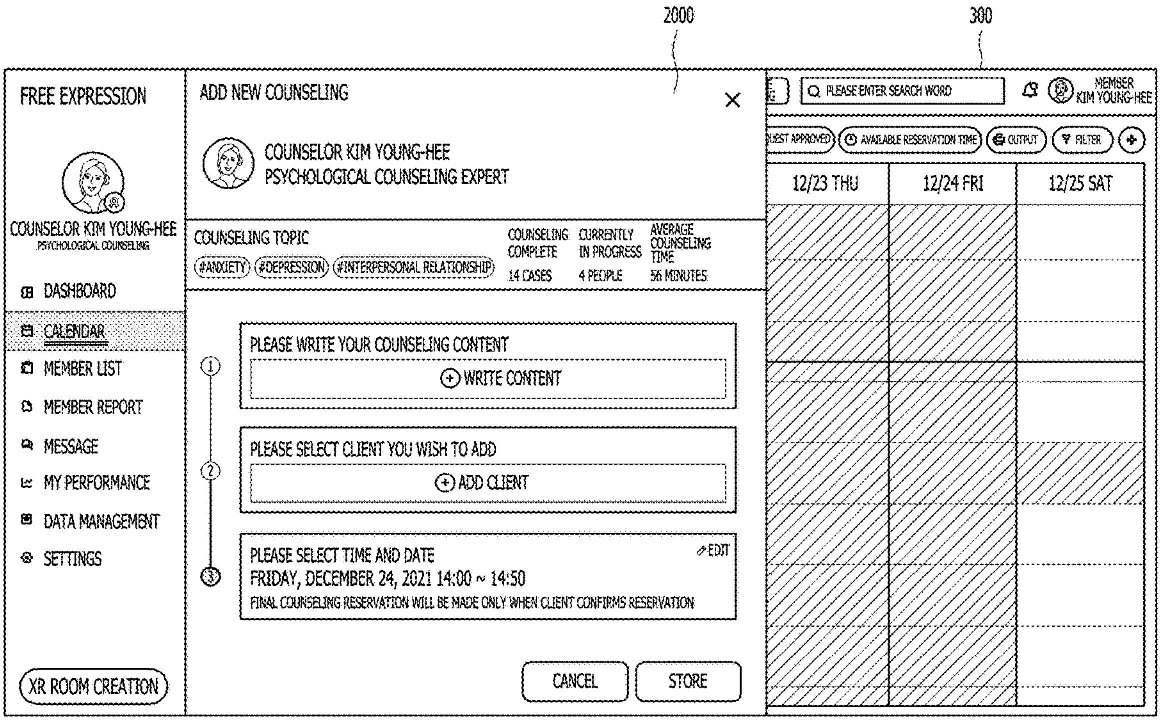

For example, when a reservation available time item 1240 an additional counseling menu is selected from the calendar screen 1200 displayed on the first expert terminal, as illustrated in FIG. 20, the first expert terminal displays a new counseling addition screen 2000 corresponding to the selected additional counseling menu 1240.

In addition, the first expert terminal receives a third new counseling schedule that includes the first expert information (e.g., including Counselor Kim Young-Hee, psychological counseling, etc.) and a third counseling topic (e.g., psychological counseling, etc.) set as a default in the new counseling addition screen 2000 displayed on the first expert terminal, third counseling content (e.g., including session 8, overcoming anxiety), a third client (e.g., a Songpa-gu native), a third counseling reservation date and time zone (e.g., 14:00 to 14:50 on Friday, Dec. 24, 2021, etc.).

In addition, the first expert terminal transmits the received third new counseling schedule, third counseling schedule storage request information, identification information of the first expert terminal, etc., to the server 200.

In addition, the server 200 receives the third new counseling schedule, third counseling schedule storage request information, and identification information of the first expert terminal, etc., that are transmitted from the first expert terminal.

In addition, the server 200 confirms the first user information corresponding to the received identification information of the first expert terminal among the user information for each piece of identification information of the expert terminal being managed by the server 200.

In addition, the server 200 confirms the third member information corresponding to the third client, the Songpa-gu native, included in the received third new counseling schedule among the member information for each counseling requester being managed by the server 200.

In addition, the server 200 maps and stores the confirmed first user information, the confirmed third personal information, the third new counseling schedule, and the identification information of the first expert terminal, etc.

In addition, the server 200 transmits information indicating that the counseling schedule with the corresponding first expert, Kim Young-Hee, has been confirmed, the third counseling reservation date and time zone (e.g., 14:00 to 14:50 on Friday, Dec. 24, 2021, etc.), etc., to the third terminal 100 owned by the Songpa-gu native related to the third new counseling schedule case for which the corresponding first expert, Kim Young-Hee, has newly registered.

In addition, the third terminal receives the information indicating that the counseling schedule with the corresponding first expert, Kim Young-Hee transmitted from the server 200, has been confirmed, the third counseling reservation date and time zone (e.g., including 14:00 to 14:50 on Friday, Dec. 24, 2021, etc.), and displays the information indicating that the counseling schedule with the received corresponding first expert, Kim Young-Hee, has been confirmed, the third counseling reservation date and time zone (e.g., 14:00 to 14:50 on Friday, Dec. 24, 2021, etc.), etc.

In addition, the third terminal is linked with the server 200 to process final approval for the third new counseling schedule case and finally establish the corresponding third counseling schedule.

Figure 21:
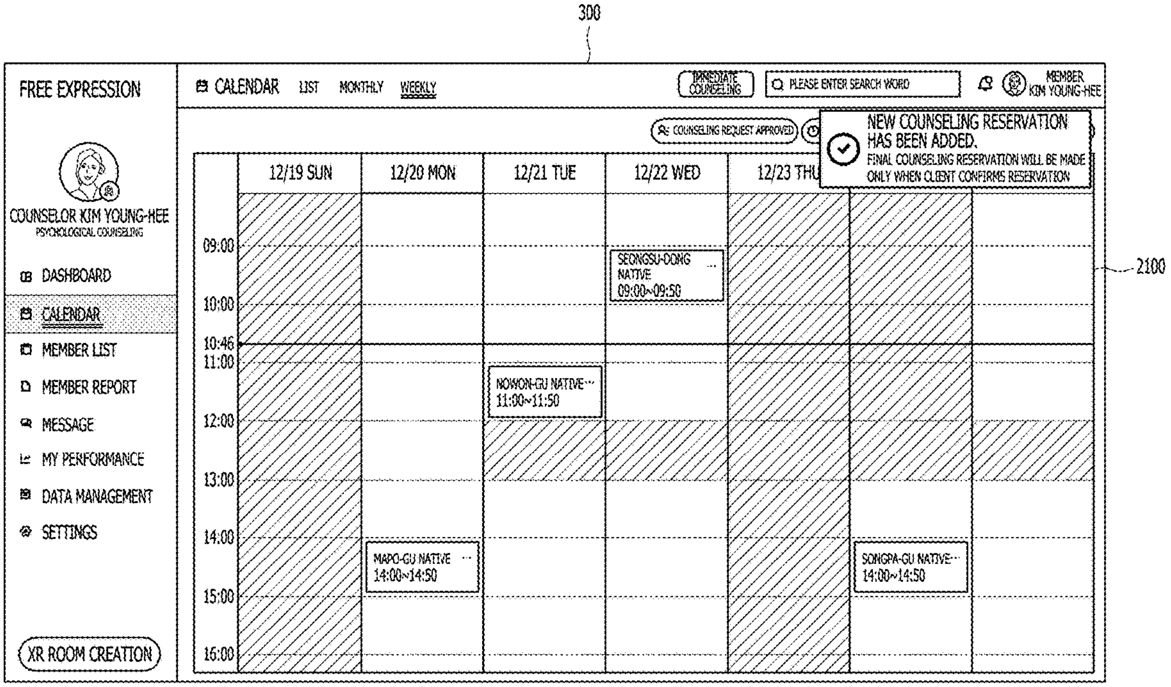

In addition, the first expert terminal is linked with the server 200 to display a calendar screen 2100 reflecting the third new counseling schedule according to the registration of the corresponding third new counseling schedule as illustrated in FIG. 21 (S290).

In addition, when a preset member list menu is selected from the initial screens displayed on the expert terminal 300, the expert terminal 300 displays a member list screen corresponding to the selected member list menu to display the member information of the user who is counseling with the corresponding expert. In this case, the expert terminal 300 may display the member list screen corresponding to the selected calendar menu in the detailed information display area. Here, the member list screen includes a member list type menu for selecting the member list type provided (e.g., including list, thumbnail, etc.), an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including expert character/picture, expert name/name, etc.), a number of current counseling members display menu for displaying the number of members receiving counseling from the corresponding expert, a sorting menu for providing a sorting function for the member list (e.g., including the order of the earliest next reservation date, the most recently completed counseling date, the order of the longest membership period remaining, the order of the shortest membership period remaining, the order of the first registration date, etc.), a member search menu for searching for members, a counseling request approval menu for providing information on one or more counseling requests for which the expert has not yet processed counseling request approval among the counseling requests requested from the corresponding expert, a filter menu for providing a filter function for the expert's counseling schedule, an output menu for outputting a member list displayed on the member list screen, a deletion menu for deleting information on a specific member displayed on the member list screen, a detailed member list display area (or detailed member list display menu) for displaying information on a user (or client) who has registered with (or is receiving counseling from) the expert according to the member list type selected in the member list type item, etc. In this case, the member list type menu may be in a state in which a list item is selected as default.

In addition, when the specific menu is selected from the member list screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 22:
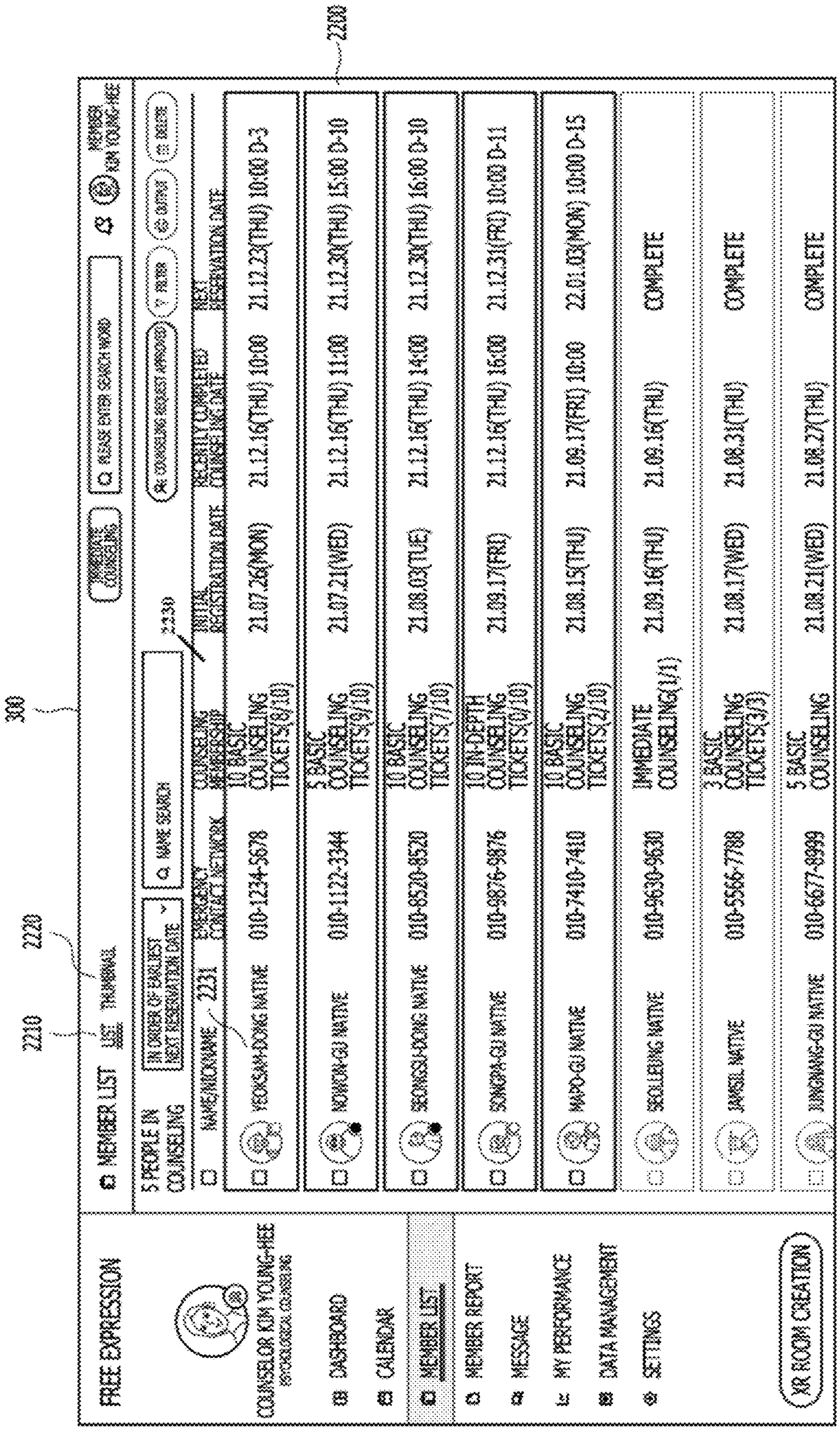

As an example, when a preset member list menu 930 is selected from the initial screen 900 displayed on the first expert terminal according to the first expert selection of the corresponding first expert terminal, as illustrated in FIG. 22, the first expert terminal displays a member list screen 2200 corresponding to the selected member list menu 930 (S300).

In addition, when a preset list item is selected from the member list type item in the member list screen displayed on the expert terminal 300, the expert terminal 300 is linked with the server 200 to display the member list information in the form of the list corresponding to the selected list item. In this case, the expert terminal 300 may display the member list information in the form of the list corresponding to the selected list item in the detailed member list display area. Here, the member list information in the list form includes color items for each user, a user's name display item (or user/member/counseling requester nickname display items), an item for displaying whether the user is currently online, an emergency contact network display item, an item for displaying a counseling membership type and the remaining number of sessions (e.g., 7/10 of the basic 10 counseling tickets, etc.), an initial registration date display item, a recently completed counseling date item, a next reservation date display item, etc., and may be displayed in the form of a pop-up or a new screen (e.g., including a new window, a new screen, etc.). In this case, the color items for each user may be set for each member (or for each counseling requester) by the corresponding expert for the purpose of helping the corresponding expert easily understand the characteristics of the counseling requester.

For example, as illustrated in FIG. 22, the first expert terminal displays member list information 2230 in the form of the list corresponding to the list item 2210 set by default in the detailed member list display area (S310).

Thereafter, when a specific member list (or specific member list item/specific member) is selected from the member list information in the form of the list displayed on the expert terminal 300, the expert terminal 300 is linked with the server 300 to provide detailed specific member list information corresponding to the selected specific member list to the expert terminal 300. Here, the detailed specific member list information (or detailed specific member information) includes a message transmission item for performing a message function with the counseling requester corresponding to the corresponding specific member, an activity history view item for providing an activity history of the corresponding counseling requester, an XR room invitation item for inviting the corresponding counseling requester to the XR room to perform the counseling function in the XR chat room (or metaverse chat room) with the corresponding counseling requester, a detailed personal information item related to the counseling requester corresponding to the corresponding specific member list, a reservation timeline item for providing a reservation situation for the corresponding counseling requester, a close item for ending (or closing) the corresponding detailed specific member information, etc., and may be displayed in the form of a pop-up or new screen (e.g., including a new window, a new screen, etc.). Examples of the detailed personal information item include a character item for the counseling requester, a nickname item, an item for displaying the remaining number of uses out of the total number of uses, an output item for outputting the information included in the corresponding detailed specific member list information, a deletion item for deleting the information on the specific member included in the corresponding detailed specific member list information, a gender item, a birth date item, an emergency contact network (or phone number) item, a counseling ticket type item (e.g., time, the number of sessions, etc., for each type), an initial registration date item, an average counseling time display item, a recent counseling date display item, a next registration date display item, an item for displaying a topic on which a requester would like to receive counseling, an additional inquiry item, etc. In addition, examples of the reservation timeline item include a counseling content item by date and time zone, a reservation change item, an expert (or person in charge/counselor) item, a counseling time item, a detail view item for a detail view of additional information, etc.

In this case, when a specific member (or a specific member list item) is selected from the member list information in the form of the list displayed on the expert terminal 300, the expert terminal 300 may display the chat report related to the corresponding counseling requester to be described below.

Figure 23:
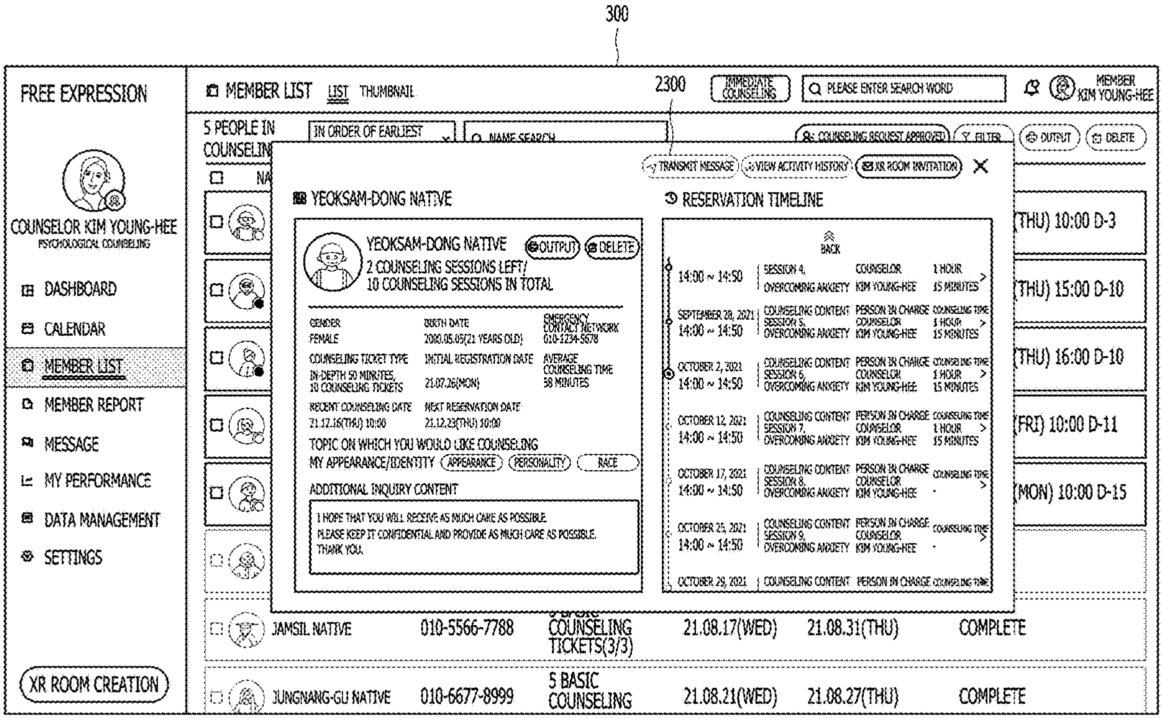

For example, when a Yeoksam-dong native 2231 is selected from the member list information 2230 in the form of the list displayed on the first expert terminal, as illustrated in FIG. 23, the first expert terminal displays the Yeoksam-dong native's detailed information 2300 corresponding to the selected Yeoksam-dong native 2231 (S320)

In addition, when a preset list thumbnail item is selected from the member list type item in the member list screen displayed on the expert terminal 300, the expert terminal 300 is linked with the server 200 to display the member list information in the form of the thumbnail corresponding to the selected thumbnail item. In this case, the expert terminal 300 may display the member list information in the form of the thumbnail corresponding to the selected thumbnail item in the detailed member list display area. Here, the member list information in the form of the thumbnail is configured in the form of a profile card, and includes a fixed setting item for selecting whether to fix the profile card of the corresponding counseling requester, a character (or photo/image) item of a counseling requester, a nickname item (or name item), a recent counseling date item (or recently completed counseling date item), a counseling reservation date item (or next reservation date item), an item for displaying a counseling membership type and the remaining number of sessions (e.g., 7/10 of the basic 10 counseling tickets, etc.), a reservation change item, a message sending item (or message transmission item), an XR room invitation item (or XR room invitation item/metaverse chat room invitation item), etc.

In addition, when another specific member (or another specific member list item) is selected from the member list information in the form of the thumbnail displayed on the expert terminal 300, the expert terminal 300 is linked with the server 300 to display other detailed specific member information corresponding to the selected other specific member. Here, the other detailed specific member list information includes a message transmission item for performing a message function with the counseling requester corresponding to the corresponding other specific member, an activity history view item for providing an activity history of the corresponding counseling requester, an XR room invitation item for inviting the corresponding counseling requester to the XR room to perform the counseling function in the XR chat room (or metaverse chat room) with the corresponding counseling requester, a detailed personal information item related to the counseling requester corresponding to the corresponding other specific member, a reservation timeline item for providing a reservation situation for the corresponding counseling requester, a close item for ending (or closing) the corresponding other detailed specific member information, etc., and may be displayed in the form of a pop-up or a new screen (e.g., including a new window, a new screen, etc.). Examples of the detailed personal information item include a character item for the counseling requester, a nickname item, an item for displaying the remaining number of uses out of the total number of uses, an output item for outputting the information included in the corresponding other detailed specific member information, a deletion item for deleting the information on the other specific member included in the corresponding other detailed specific member information, a gender item, a birth date item, an emergency contact network (or phone number) item, a counseling ticket type item (e.g., time, the number of sessions, etc., for each type), an initial registration date item, an average counseling time display item, a recent counseling date display item, a next registration date display item, an item for displaying a topic on which a user would like to receive counseling, an additional inquiry item, etc. In addition, examples of the reservation timeline item include a counseling content item by date and time zone, a reservation change item, an expert (or person in charge/counselor) item, a counseling time item, a detail view item for a detail view of additional information, etc.

In this case, when other specific members (or other specific member list items) are selected from the member list information in the form of the thumbnail displayed on the expert terminal 300, the expert terminal 300 may display the chat report related to the corresponding counseling requester to be described below.

Figure 24:
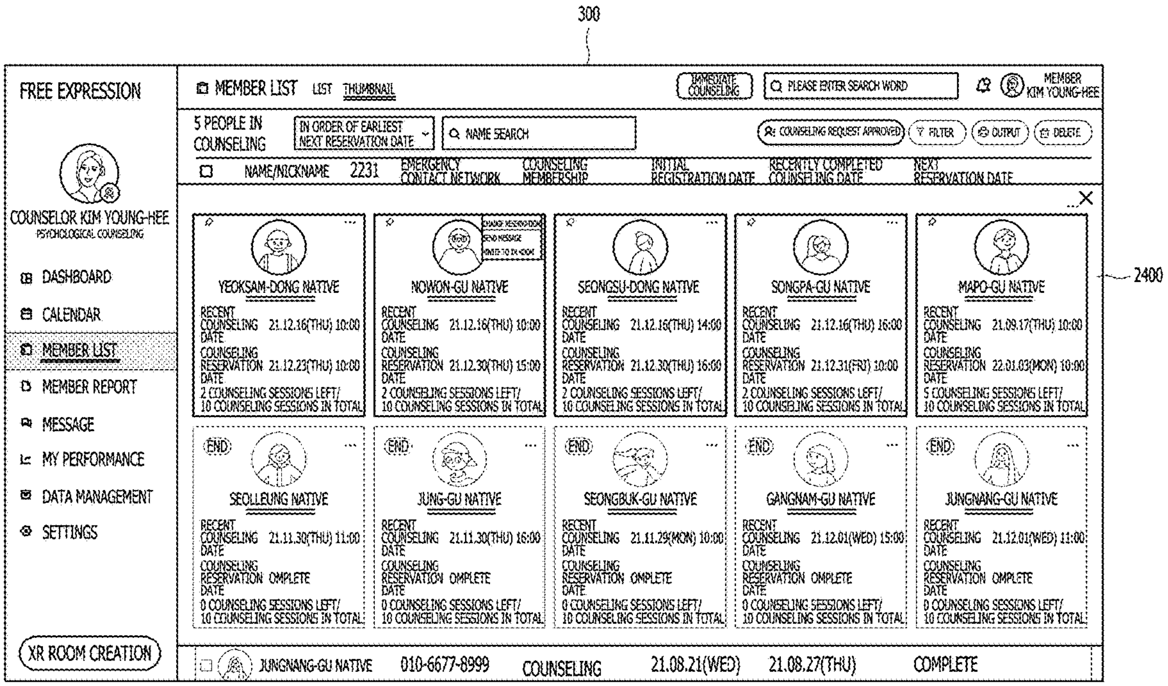

As an example, when a thumbnail item 2220 is selected from the member list type item in the member list screen 2200 displayed on the first expert terminal, as illustrated in FIG. 24, the first expert terminal displays member list information 2400 in the form of the thumbnail corresponding to the selected thumbnail item 2220 (S330).

In addition, when a preset member report menu is selected from the initial screens displayed on the expert terminal 300, the expert terminal 300 displays a member report screen corresponding to the selected member report menu to display the activity history of the user who is counseling with the corresponding expert for a preset period. In this case, the expert terminal 300 may display the member report screen corresponding to the selected member report menu in the detailed information display area. Here, the member report screen includes an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a sorting menu for providing a sorting function (e.g. currently online, most recent activity, high "free expression" index, low "free expression" index, etc.) for the member report in order to provide a member report based on activity details for a preset period (e.g. 7 days), a member search menu for searching for members, a counseling request approval menu for providing information on one or more counseling requests for which the expert has not yet processed counseling request approval among the counseling requests requested from the corresponding expert, a filter menu for providing a filter function for the expert's counseling schedule, an output menu for outputting information displayed on the member report screen, a deletion menu for deleting information on a specific member displayed on the member report screen, a detailed member report display area for displaying information on one or more members that meet the sort item, etc. In addition, the detailed member report display area (or detailed member report detail menu) is configured in the form of a profile card, and includes a fixed setting item for selecting whether to fix the profile card of the corresponding counseling requester, a character (or photo/image) of a counseling requester, a nickname item (or name item), a total counseling time item (or total played time item), a "free expression" index item, etc. In addition, the "free expression" index item includes a total "free expression" index (or average "free expression" index) item, a topic talk "free expression" index item, a role-playing "free expression" index item, a theme practice "free expression" index item, etc. In addition, the "free expression" index represents an evaluation index for the user (or counseling requester) of the terminal 100 according to the performance of the chat function, and may be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates.

In addition, when the specific menu is selected from the member report screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 25:
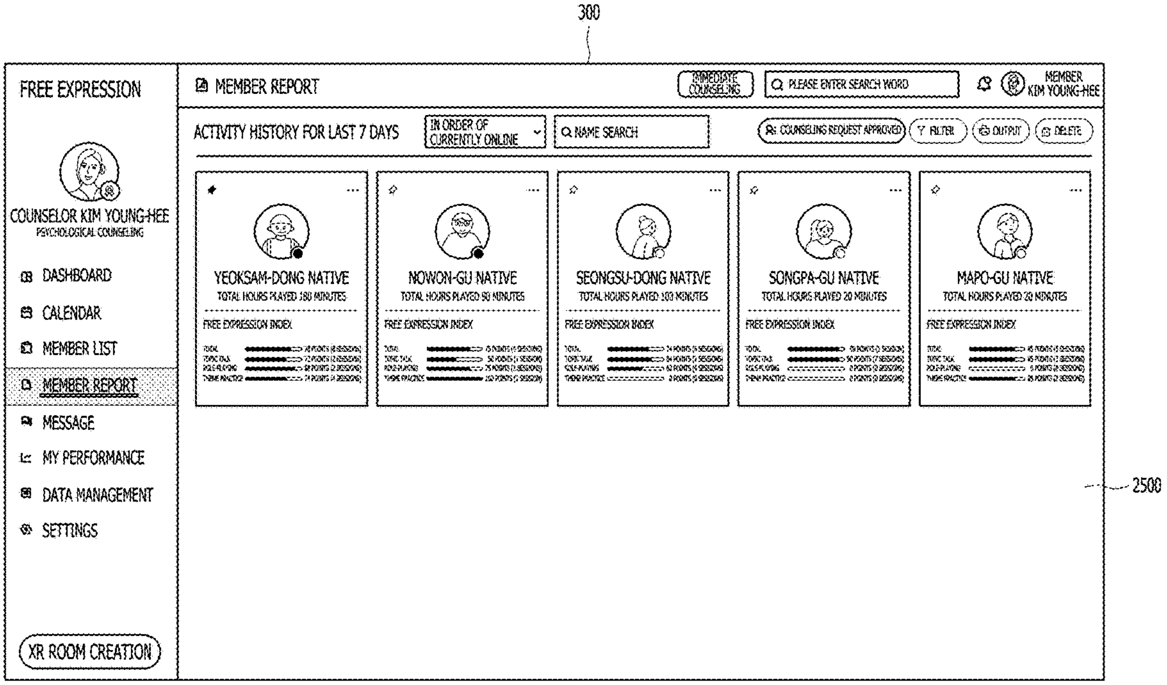

As an example, when a preset member report menu 940 is selected from the initial screen 900 displayed on the first expert terminal according to the first expert selection of the corresponding first expert terminal, as illustrated in FIG. 25, the first expert terminal displays a member report screen 2500 corresponding to the selected member report menu 940 (S340).

Thereafter, when a specific member report (or a specific member) is selected from the detailed member report display area in the member report screen displayed on the expert terminal 300, the expert terminal 300 is linked with the server 200 to display detailed member report information corresponding to the selected specific member report. Here, the detailed member report information (or detailed member report screen) includes a return-to-member-report item for returning to a previous screen (or a member report screen), a detailed personal information display item for displaying personal information on the counseling requester (or specific user) corresponding to the corresponding specific member report, a counseling record sheet item for displaying a counseling record sheet related to one or more counseling sessions performed by the corresponding counseling requester, a cognitive behavior therapy record sheet item (or cognitive behavior record sheet item) for displaying cognitive behavior therapy record sheet related to one or more counseling sessions performed by the corresponding counseling requester (or specific user), a questionnaire result item for displaying questionnaire results related to the questionnaire performed by the corresponding counseling requester, a people diary item for displaying content of an emotional state by date written by the corresponding counseling requester (or the content of the emotional state by date written by the corresponding specific user), a chat report item for displaying a chat report (or "my report") related to the corresponding counseling requester, a past counseling record item for displaying past counseling record content performed by the corresponding counseling requester, a detailed information display area (or detailed information display item) for providing detailed information on a specific item selected among multiple items, etc. In addition, examples of the detailed personal information item above include an item for displaying whether one is currently online for displaying information on the real-time connection state of the corresponding counseling requester, a character (or image/photo) item of the corresponding counseling requester, a nickname item of the corresponding counseling requester, an item for displaying a type (e.g., topic talk, role-playing, theme practice, etc.) of a counseling case in progress when the corresponding counseling requester is currently in counseling, an item for displaying the remaining number of uses out of the total number of uses (or a counseling progress situation item), a gender item, a birth date item, an emergency contact network (or phone number) item, a counseling ticket type item (e.g., time, number of sessions, etc., for each type), an initial registration date item, an average counseling time item, a recent counseling date item (or recently completed counseling date item), a next reservation date item (or counseling reservation date item), etc.

In addition, when the specific menu is selected from the detailed member report information displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 26:
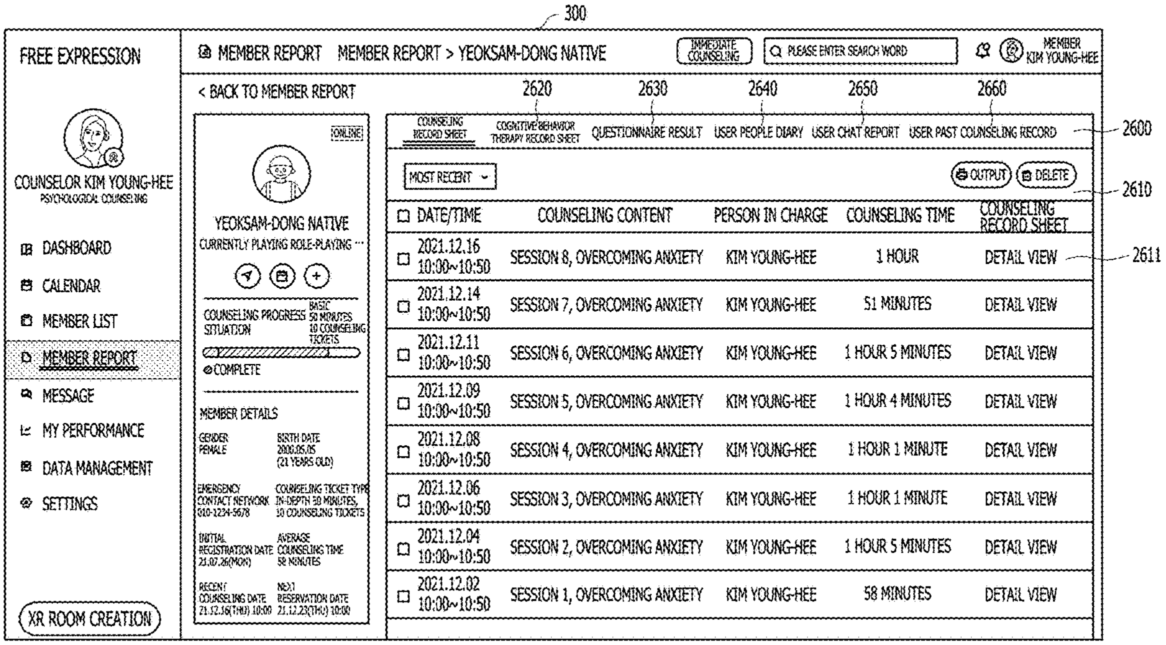

As an example, when a Yeoksam-dong native 2510 is selected from the member report screen 2500 displayed on the first expert terminal according to the first expert selection of the corresponding first expert terminal, as illustrated in FIG. 26, the first expert terminal displays the Yeoksam-dong native's detailed report information 2600 corresponding to the selected Yeoksam-dong native 2510 (S350).

In addition, when a preset counseling record sheet item is selected from the member report detailed information displayed on the expert terminal 300, the expert terminal 300 is linked with the server 200 to display a counseling record sheet screen corresponding to the selected counseling record sheet item. Here, the counseling record sheet screen includes a sorting item for providing the sorting function (e.g., including sorting by most recent, sorting by the expert/erson in charge, etc.) in relation to one or more counseling cases performed by the corresponding counseling requester, an output item for outputting the information displayed on the relevant counseling record sheet screen, a deletion item for deleting the information on the specific counseling record case displayed on the corresponding counseling record sheet screen, a counseling content items by date and time, an expert item by date and time (or person in charge/counselor item by date and time), a counseling time item by date and time, a detail view item for the counseling record sheet by date and time, etc.

In this case, when a specific member report (or a specific member) is selected from the detailed member report display area in the member report screen displayed on the expert terminal 300, the expert terminal 300 may be linked with the server 200 to display a counseling record sheet screen corresponding to the selected specific member report preset by default in the detailed information display area.

As an example, as illustrated in FIG. 26, the first expert terminal displays a counseling record sheet screen 2610 corresponding to the counseling record sheet item set by default according to the display of the Yeoksam-dong native's detailed report information 2600 (S360).

Thereafter, when the detail view item displayed on one side of a specific counseling record sheet is selected from the counseling record sheet screen displayed on the expert terminal 300, the expert terminal 300 is linked with the server 200 to display the detailed counseling record sheet information on the specific counseling record sheet related to the selected detail view item. Here, the detailed counseling record sheet information includes a counseling record sheet writing date item related to the corresponding specific counseling record sheet case, a modification item for modifying the content of the corresponding specific counseling record sheet, an output item for outputting the content of the corresponding specific counseling record sheet, a deletion item for deleting the content of the corresponding specific counseling record sheet, a session number and counseling topic item, an expert name item, a last modified date display item, a user's subjective item, an expert's objective item, a future plan item, a feedback item to a user, etc. In this case, the expert's objective item may vary depending on whether the expert of the expert terminal 300 is a mentor expert, a psychological counseling expert, or a speech lesson expert. That is, when the expert of the expert terminal 300 is a mentor expert, examples of the expert's objective item include a common checklist item (e.g., including anxiety, assertiveness/confidence, mind control, communication skills, listening skills, sociability, situational judgment power, will to improve, strength/levels for each item, brief descriptions for each item, etc.), a mentoring checklist item (e.g., including professionalism, interest/degree of interest, propensity coincidence, counseling purpose, etc.), a problem situation item (e.g., including a chat situation, a presentation situation, an interview situation, etc.), an expert recommendation item (e.g., including "I think you need to go to the hospital," "I think you would benefit from psychological counseling," "I think you would benefit from speech training," "I think you would benefit more from help from a specific mentor expert," etc.), a difficult target item (e.g., including family, a romantic relationship, a friend, a workplace, others, etc.), a topic/situation item (e.g., including a daily topic, a professional topic, etc.) required for training, an expert's opinion item, etc. In addition, when the expert of the expert terminal 300 is a psychological counseling expert, examples of the expert's objective item include a common checklist item (e.g., anxiety, assertiveness/confidence, mind control, communication skills, listening skills, sociability, situational judgment power, will to improve, strength/levels for each item, brief descriptions for each item, etc.), a psychological state checklist item (e.g., social anxiety, depression/anxiety, panic disorder, sleep disorder, bipolar disorder, alcoholic dementia, addiction (e.g., including game addiction, drug addiction, gambling addiction, etc.), cognitive distortion, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation item (e.g., a daily topic, a professional topic, etc.) required for training, an expert's opinion item, etc. In addition, when the expert of the expert terminal 300 is a speech lesson expert, examples of the expert's objective item include a common checklist item (e.g., anxiety, assertiveness/confidence, mind control, communication skills, listening skills, sociability, situational judgment power, will to improve, strength/levels for each item, brief descriptions for each item, etc.), a speech checklist item (e.g., fluency, logic, speed/pace, vocalization/tone, leadership, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation item (e.g., a daily topic, a professional topic, etc.) required item for training, an expert's opinion item, etc.

In addition, the expert terminal 300 may additionally perform a modification function, an output function, a deletion function, etc., on the content of the detailed counseling record sheet information being displayed on the expert terminal 300.

Figure 27:
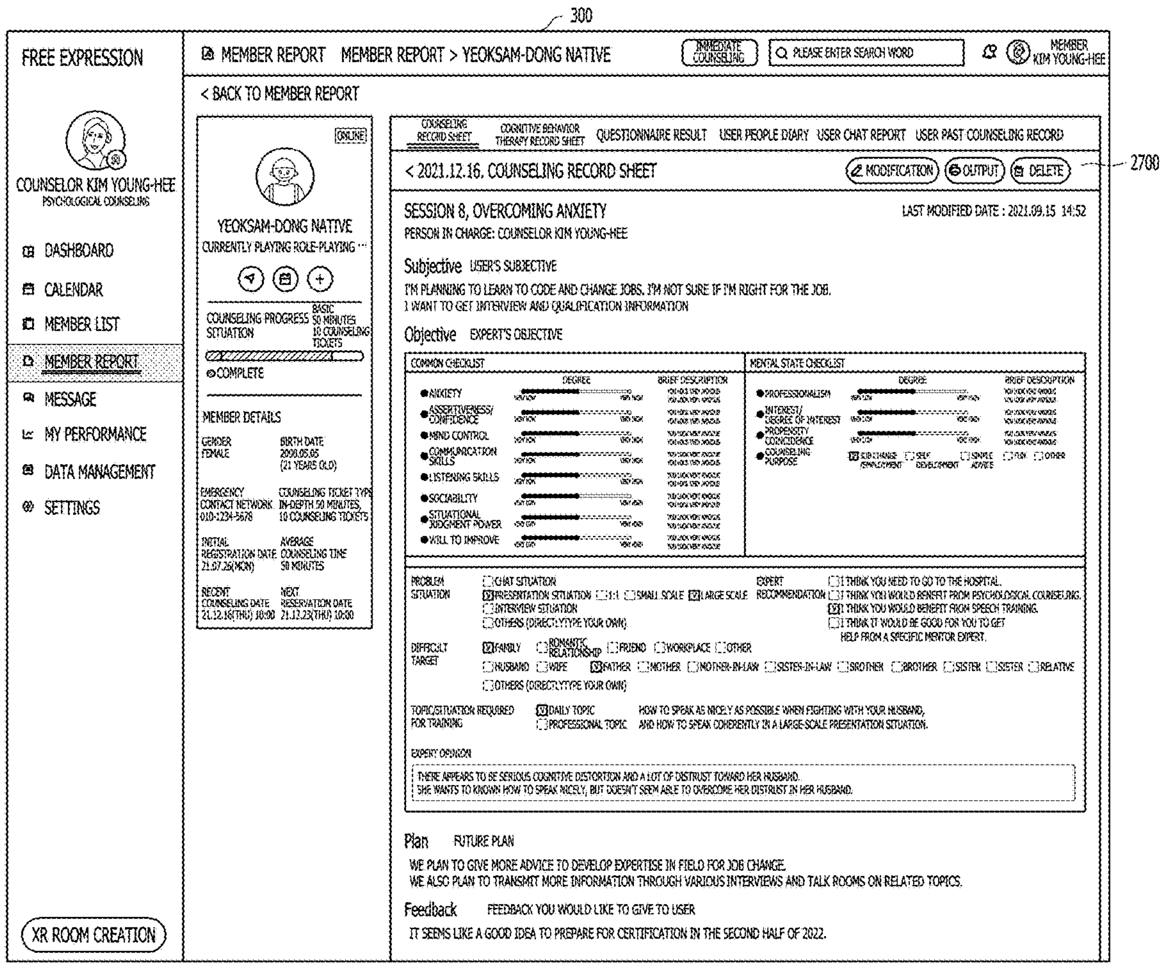

As an example, when the first expert is a mentor expert and a detail view item 2611 displayed on one side of the counseling record sheet case dated Dec. 16, 2021, is selected from the counseling record sheet screen 2610 displayed on the first expert terminal, as illustrated in FIG. 27, the first expert terminal displays the Yeoksam-dong native's detailed counseling record sheet information 2700 dated Dec. 16, 2021, corresponding to the selected detail view item 2611.

Figure 28:
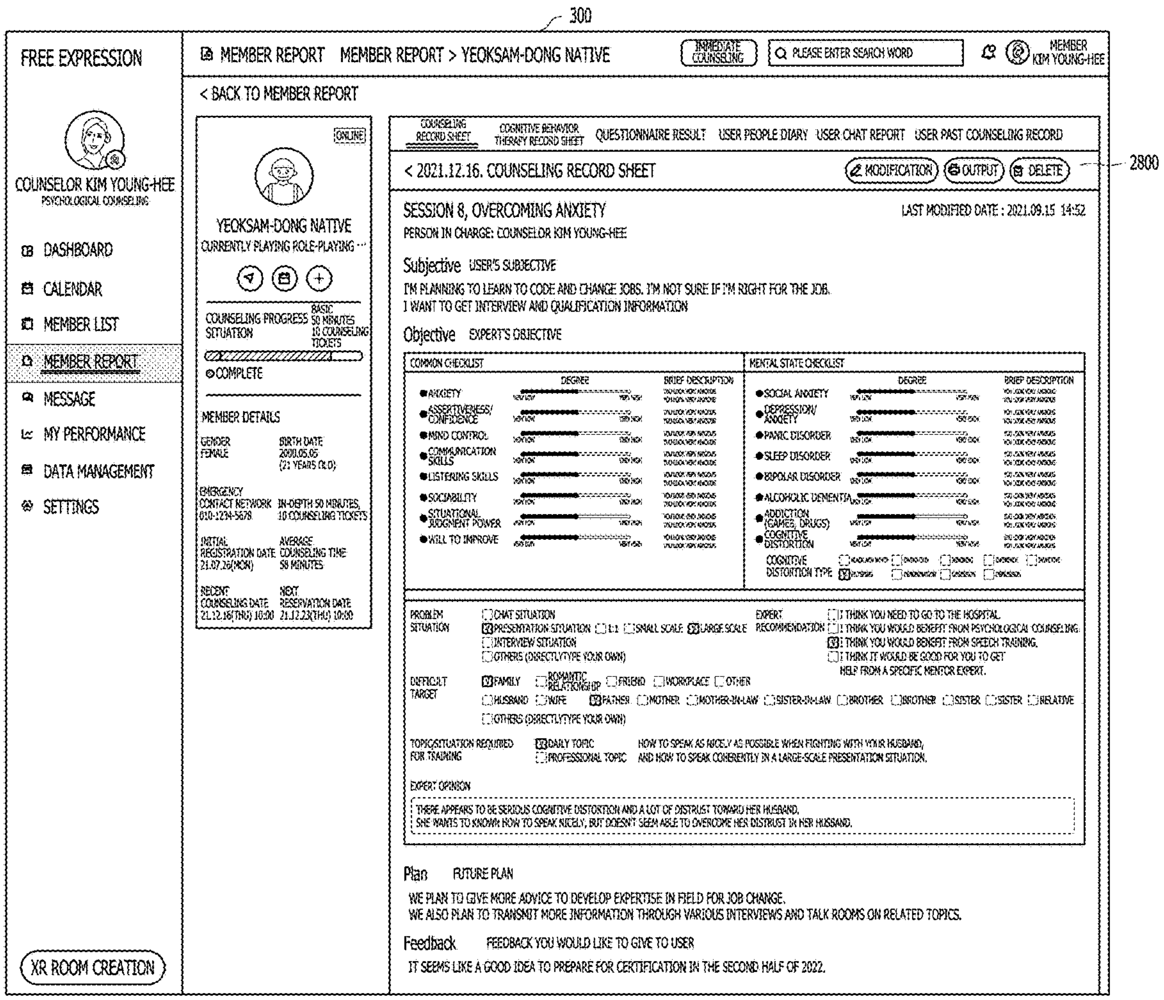

As another example, when the first expert is a psychological counseling expert and a detail view item 2611 displayed on one side of the counseling record sheet case dated Dec. 16, 2021, is selected from the counseling record sheet screen 2610 displayed on the first expert terminal, as illustrated in FIG. 28, the first expert terminal displays the Yeoksam-dong native's detailed counseling record sheet information 2800 dated Dec. 16, 2021, corresponding to the selected detail view item 2611.

Figure 29:
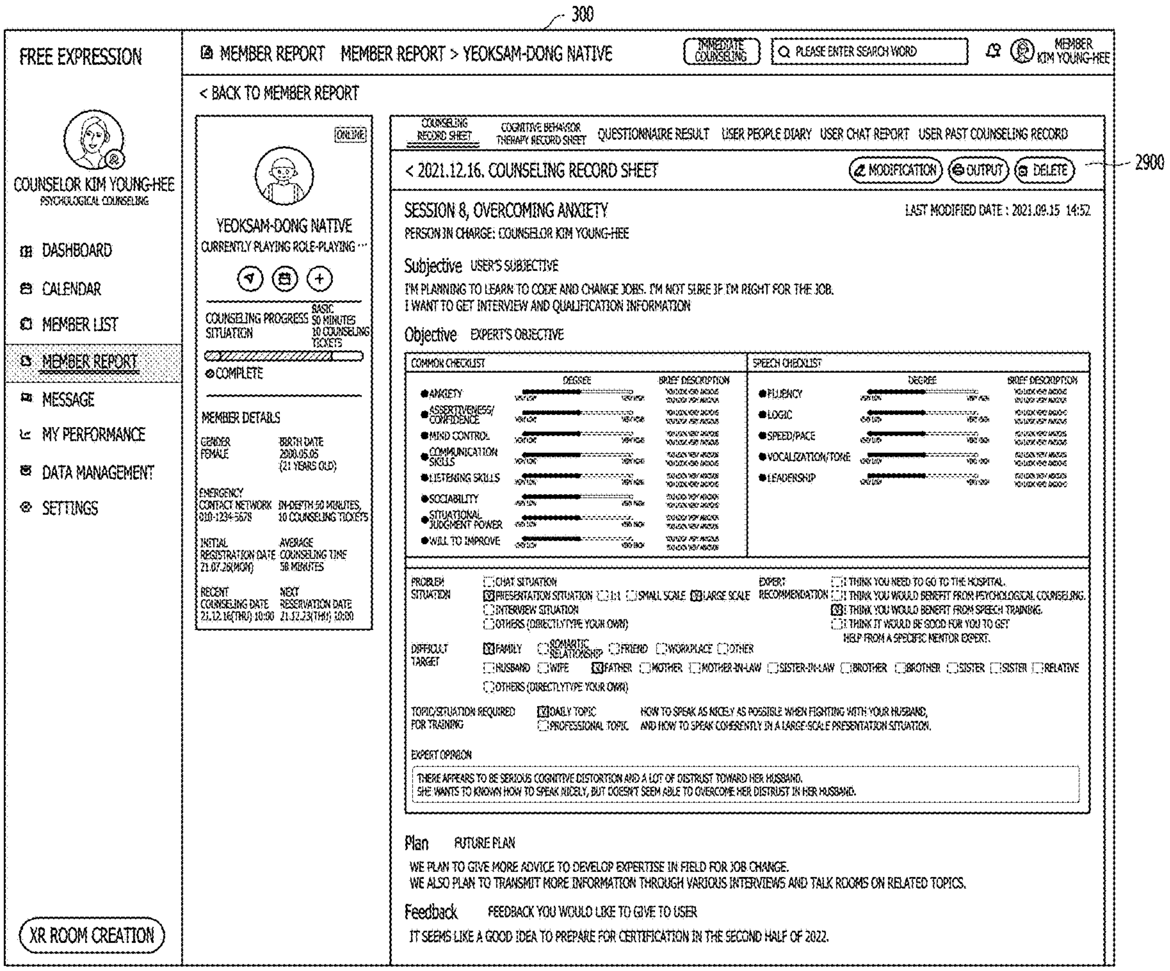

As another example, when the first expert is a speech lesson expert and the detail view item 2611 displayed on one side of the counseling record sheet case dated Dec. 16, 2021, is selected from the counseling record sheet screen 2610 displayed on the first expert terminal, as illustrated in FIG. 29, the first expert terminal displays the Yeoksam-dong native's detailed counseling record sheet information 2900 dated Dec. 16, 2021, corresponding to the selected detail view item 2611 (S370).

In addition, when a preset cognitive behavior therapy record sheet item is selected from the detailed member report information displayed on the expert terminal 300, the expert terminal 300 is linked with the server 200 to display the cognitive behavior therapy record sheet screen corresponding to the selected cognitive behavior therapy record sheet item. Here, the cognitive behavior therapy record sheet screen (or cognitive behavior record sheet screen) includes an output item for outputting information displayed on the corresponding cognitive behavior therapy record sheet screen, a deletion item for deleting information on a specific cognitive behavior therapy record sheet displayed on that cognitive behavior therapy record sheet screen, a record sheet item written by the user together during the counseling to provide a list of cognitive behavior therapy record sheets written by the user together during the counseling, a record sheet item written by the user alone to provide a list of cognitive behavior therapy record sheets written by the user alone, etc. In addition, the record sheet item written together during the counseling includes a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), etc. In addition, the record sheet item written by the user alone includes a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), an item on whether to confirm the written cognitive behavior therapy record sheet (e.g., including confirmation needed, confirmation not needed, confirmed, etc.), etc.

Figure 30:
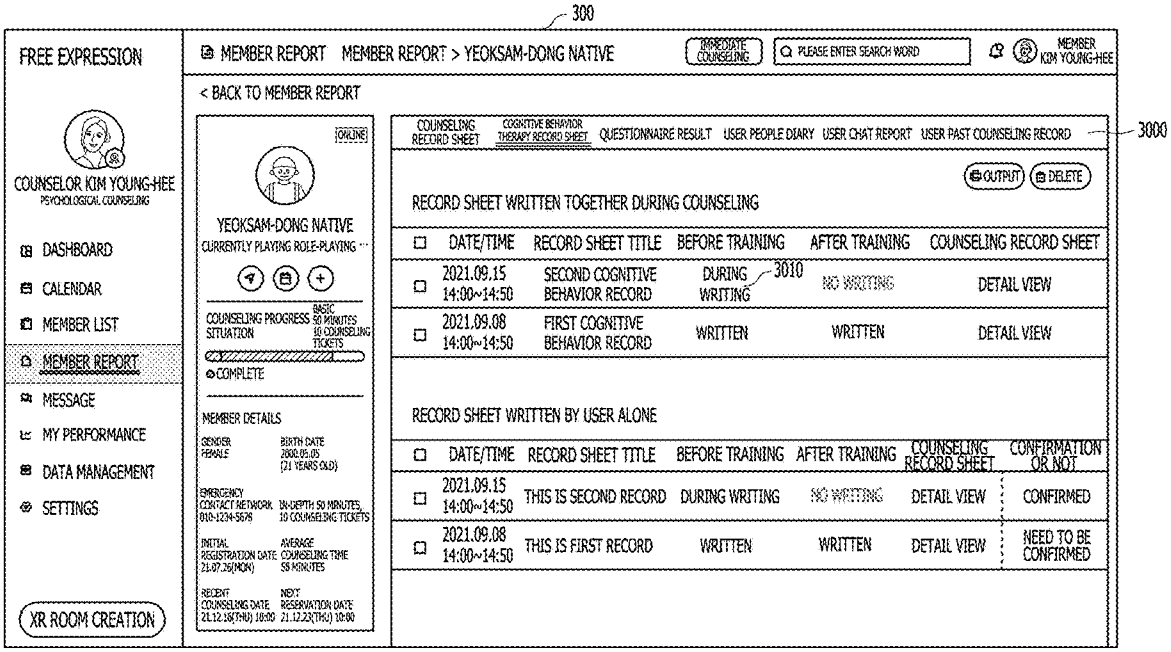

As an example, when the cognitive behavior therapy record sheet item 2620 is selected from the Yeoksam-dong native's detailed report information 2600 displayed on the first expert terminal, as illustrated in FIG. 30, the first expert terminal displays a cognitive behavior therapy record sheet screen 3000 corresponding to the selected cognitive behavior therapy record sheet item 2620 (S380).

Thereafter, when the specific cognitive behavior therapy record sheet is selected from the cognitive behavior therapy record sheet screen displayed on the expert terminal 300 (or when the item that is being or has been written before/after the training related to the specific cognitive behavior therapy record sheet is selected), the expert terminal 300 is linked with the server 200 to display the detailed cognitive behavior therapy record sheet information on the specific cognitive behavior therapy record sheet case related to the selected specific cognitive behavior therapy record sheet. Here, the detailed cognitive behavior therapy record sheet information (or detailed cognitive behavior therapy record sheet information related to the selected specific cognitive behavior therapy record sheet) includes a writing date item of the cognitive behavior therapy record sheet related to the corresponding specific cognitive behavior therapy record sheet case, a modification item for modifying the content of the corresponding specific cognitive behavior therapy record sheet, an output item for outputting the content of the corresponding specific cognitive behavior therapy record sheet, a deletion item for deleting the content of the corresponding specific cognitive behavior therapy record sheet, a session number and counseling topic display item, a writer ID and name display item, a writing state display item before/after training (e.g., not written, being written, written, etc.), a last modified date display item, a cognitive behavior information item for each item before training, a cognitive behavior information item for each item before training, etc. In addition, examples of the cognitive behavior information item for each item before training include: an item for displaying "What are situations that make you anxious?," an item for displaying "How are you feeling at this time?" (e.g., including anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.); an item for displaying "What are your thoughts in that situation?" (e.g., including a confidence level, a cognitive error, etc.); an item for displaying "Please correct my wrong thoughts!" (or a reasonable response finding item, a behavioral goal setting item, etc.). In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item (e.g., an improvement-related item, an anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/fury, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before training and/or the cognitive behavior information item for each item after training may be commonly preset or may be set differently for each expert.

In addition, the expert terminal 300 may additionally perform a modification function, an output function, a deletion function, etc., on the content of the detailed cognitive behavior therapy record sheet information being displayed on the expert terminal 300.

In addition, when the cognitive behavior therapy record sheet handwritten by the user of the corresponding terminal 100 is shared (or linked), the expert terminal 300 may display detailed cognitive behavior therapy record sheet information handwritten by the user of the terminal 100.

Figure 31:
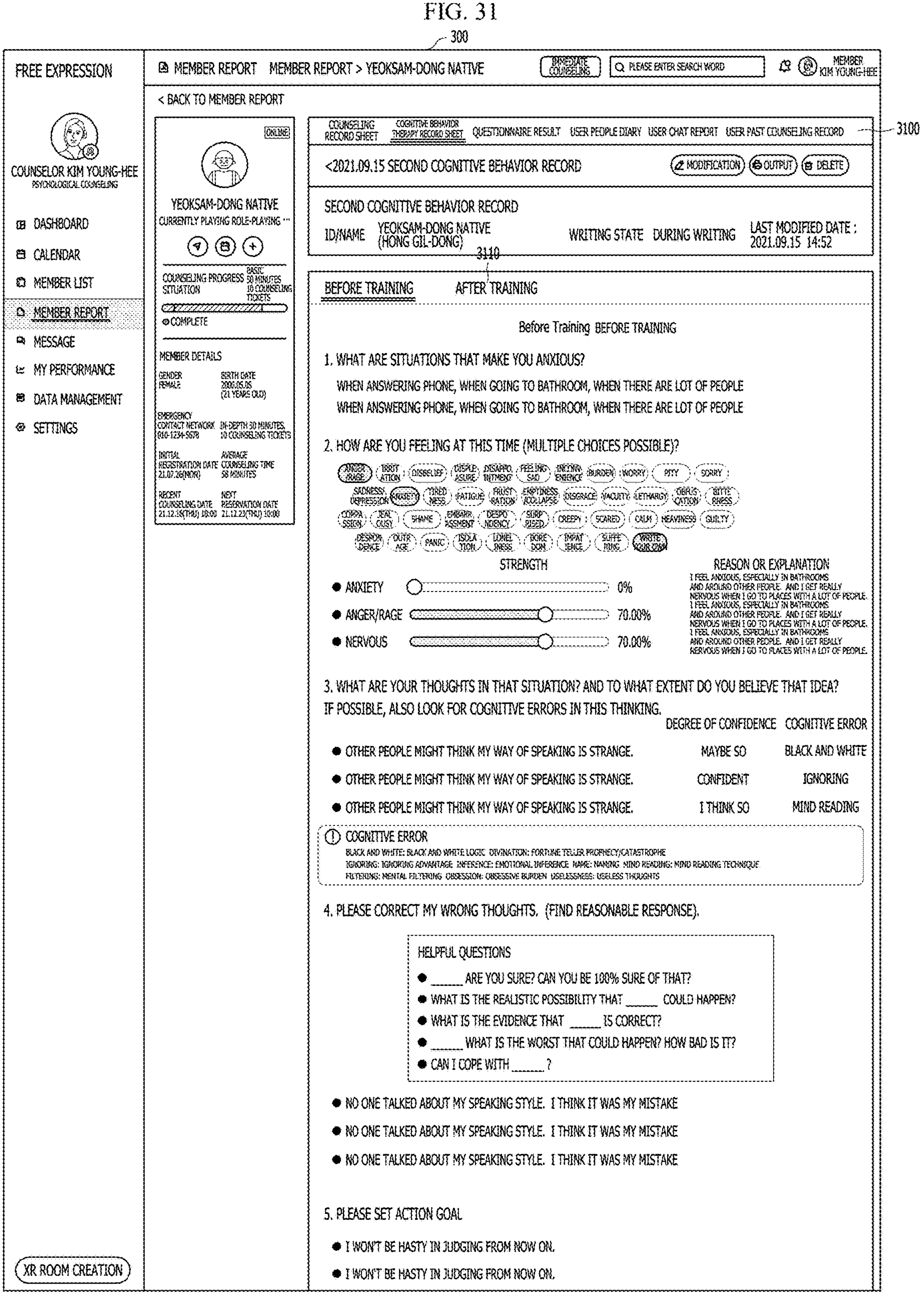

As an example, when a second cognitive behavior record case 3010 dated Sep. 15, 2021, is selected from the cognitive behavior therapy record sheet screen 3000 displayed on the first expert terminal, as illustrated in FIG. 31, the first expert terminal displays second detailed cognitive behavior therapy record sheet information 3100 of the corresponding Yeoksam-dong native dated Sep. 15, 2021, that is related to the selected second cognitive behavior record case 3010.

Figure 32:
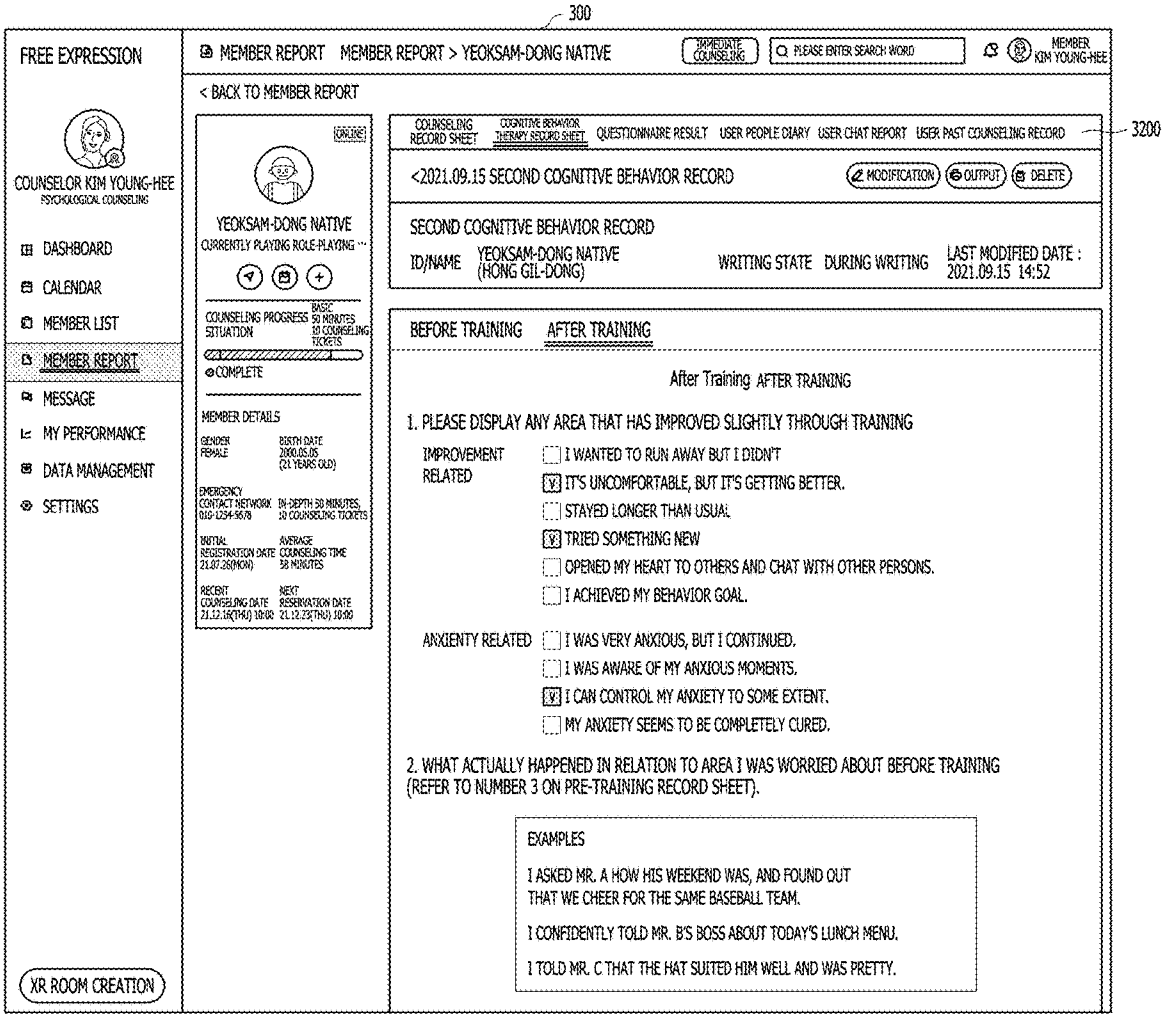

In addition, when a post-training tab 3110 is selected from the second detailed cognitive behavior therapy record sheet information 3100 of the corresponding Yeoksam-dong native dated Sep. 15, 2021, displayed on the first expert terminal, as illustrated in FIG. 32, the first expert terminal displays second detailed cognitive behavior therapy record sheet information 3200 of the corresponding Yeoksam-dong native dated Sep. 15, 2021, that includes the cognitive behavior information for each post-training item related to the selected post-training tab 3110.

As another example, when a second cognitive behavior record case 3010 dated Sep. 15, 2021, is selected from the cognitive behavior therapy record sheet screen 3000 displayed on the first expert terminal, the first expert terminal displays detailed cognitive behavior therapy record sheet information handwritten by the corresponding Yeoksam-dong native (S390).

In addition, when a preset questionnaire result item is selected from the detailed member report information displayed on the expert terminal 300, the expert terminal 300 is linked with the server 200 to display a questionnaire result screen corresponding to the selected questionnaire result item. Here, the questionnaire result screen includes a sorting item for providing the sorting function (including, for example, sorting by most recent, by format, etc.) in relation to one or more questionnaire cases performed by the corresponding counseling requester, a deletion item for deleting the selected questionnaire results (or selected questionnaire items), a file name item for each questionnaire, a last modified time item for each questionnaire, a format item for each questionnaire (or questionnaire type item), a result item (or detail view item) for each questionnaire, etc.

Figure 33:
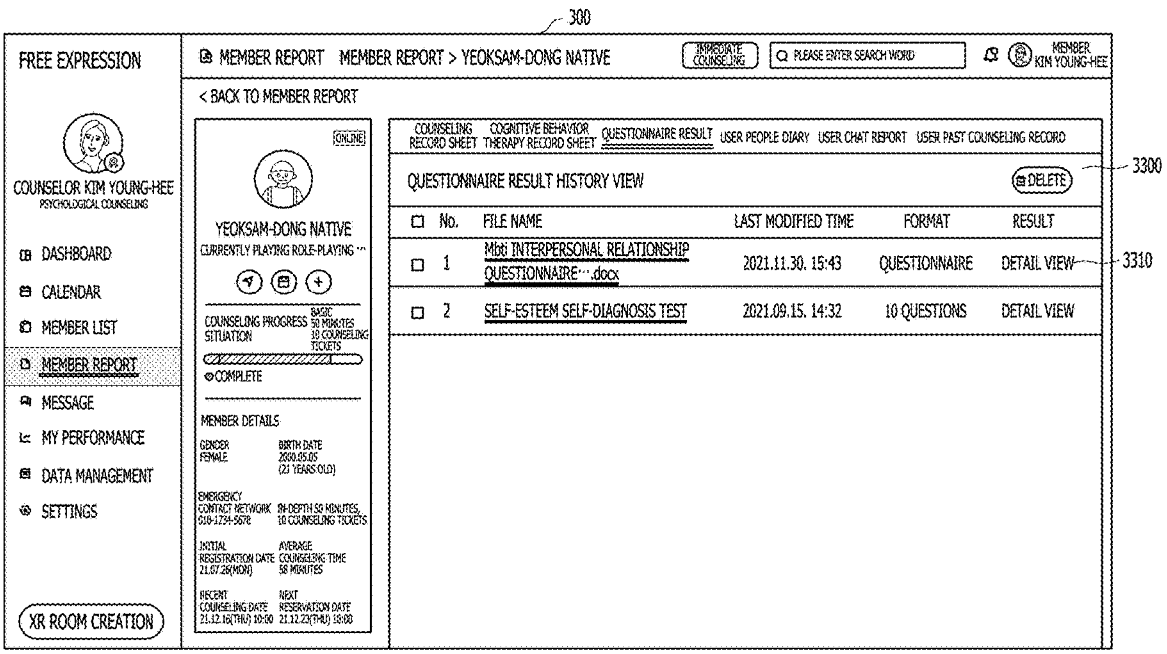

As an example, when the questionnaire result item 2630 is selected from the Yeoksam-dong native's detailed report information 2600 displayed on the first expert terminal, as illustrated in FIG. 33, the first expert terminal displays a questionnaire result screen 3300 corresponding to the selected questionnaire result item 2630 (S400).

Thereafter, when a specific file name (or specific file name item) is selected from one or more file names (or file name items) in the questionnaire result screen displayed on the expert terminal 300 or when a detailed item related to a specific file name is selected from one or more file names displayed on the questionnaire result screen, the expert terminal 300 is linked with the server 200 to display detailed questionnaire information related to the selected specific file name or a specific file name corresponding to the selected detailed item. Here, the detailed questionnaire information is configured variously depending on the purpose of the questionnaire, and may include content of one or more questions for each questionnaire, answers/responses to the question content, etc.

As an example, when the first MBTI interpersonal relationship questionnaire item 3310 is selected from the questionnaire result screen 3300 displayed on the first expert terminal, the first expert terminal displays detailed MBTI interpersonal relationship questionnaire information corresponding to the selected first MBTI interpersonal relationship questionnaire item 3310 (S410).

In addition, when a preset people diary item is selected from the detailed member report information displayed on the expert terminal 300, the expert terminal 300 is linked with the server 200 to display a people diary screen corresponding to the selected people diary item. In this case, the expert terminal 300 may display the people diary screen corresponding to the selected people diary item in the detailed information display area. Here, the people diary screen includes a calendar screen, etc., including the emotional record state by date in preset period units (e.g., including 3 months, 6 months, etc.). Here, when the calendar screen (or calendar item) is in a state where the emotional record information (e.g., including detailed emotional record information, simple emotional record information, etc.) is stored on a specific date, the calendar screen (or calendar item) includes an emotional record state (or mind state), such as images (or emoticon/avatar) representing feeling comfortable, normal, and uncomfortable, corresponding to mental state information, which is part of the information in the corresponding emotional record information on the corresponding specific date.

Figure 34:
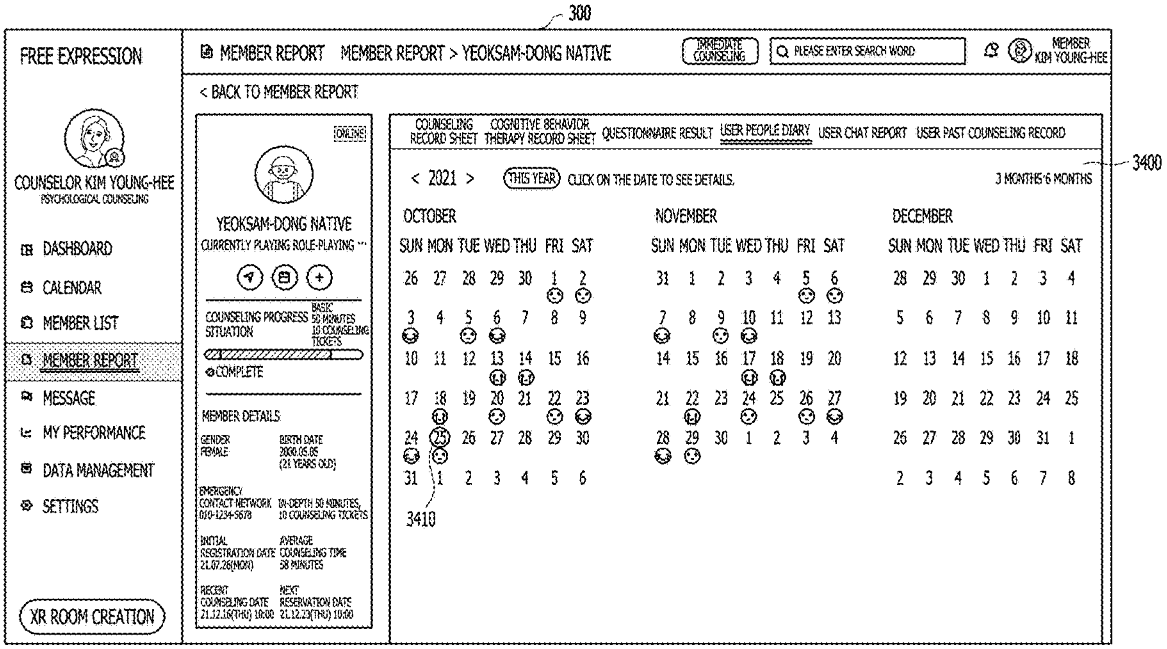

As an example, when the people diary item 2640 is selected from the Yeoksam-dong native's detailed report information 2640 displayed on the first expert terminal, as illustrated in FIG. 34, the first expert terminal displays a people diary screen 3400 corresponding to the selected people diary item 2640 (S420).

Thereafter, when a specific date including the emotional record state in the people diary screen displayed on the expert terminal 300 is selected, the expert terminal 300 is linked with the server 200 to display a detailed people diary screen related to the selected specific date. Here, the detailed people diary screen includes a calendar screen (or calendar item) related to the corresponding specific date, an emotional record information item related to the corresponding specific date, an emotional pattern graph item for the corresponding month related to the corresponding specific date, an information display item related to the corresponding counseling requester's emotional record state for the corresponding week related to the corresponding specific date, etc.

In addition, examples of the emotional record information item include date information, situation information (e.g., including who else is there, a counterpart's actions, one's own actions, etc.), and emotional information (e.g., including one's emotional state, whether to express emotions, one's current emotions, etc.), review information (e.g., comfort level in chat, future resolutions, personal notes, etc.), etc. In addition, examples of the information display item (or weekly emotional record information item) about the counseling requester's emotional record state include mental state items by day of the week (or date), a situation information item (e.g., including who else is there, a counterpart's actions, one's own actions, etc.), an emotional information item (e.g., including one's emotional state, whether to express emotions, one's current emotions, etc.), a review information item (e.g., including comfort level in chat, future resolutions, personal notes, etc.), a detail view item, etc.

Figure 35:
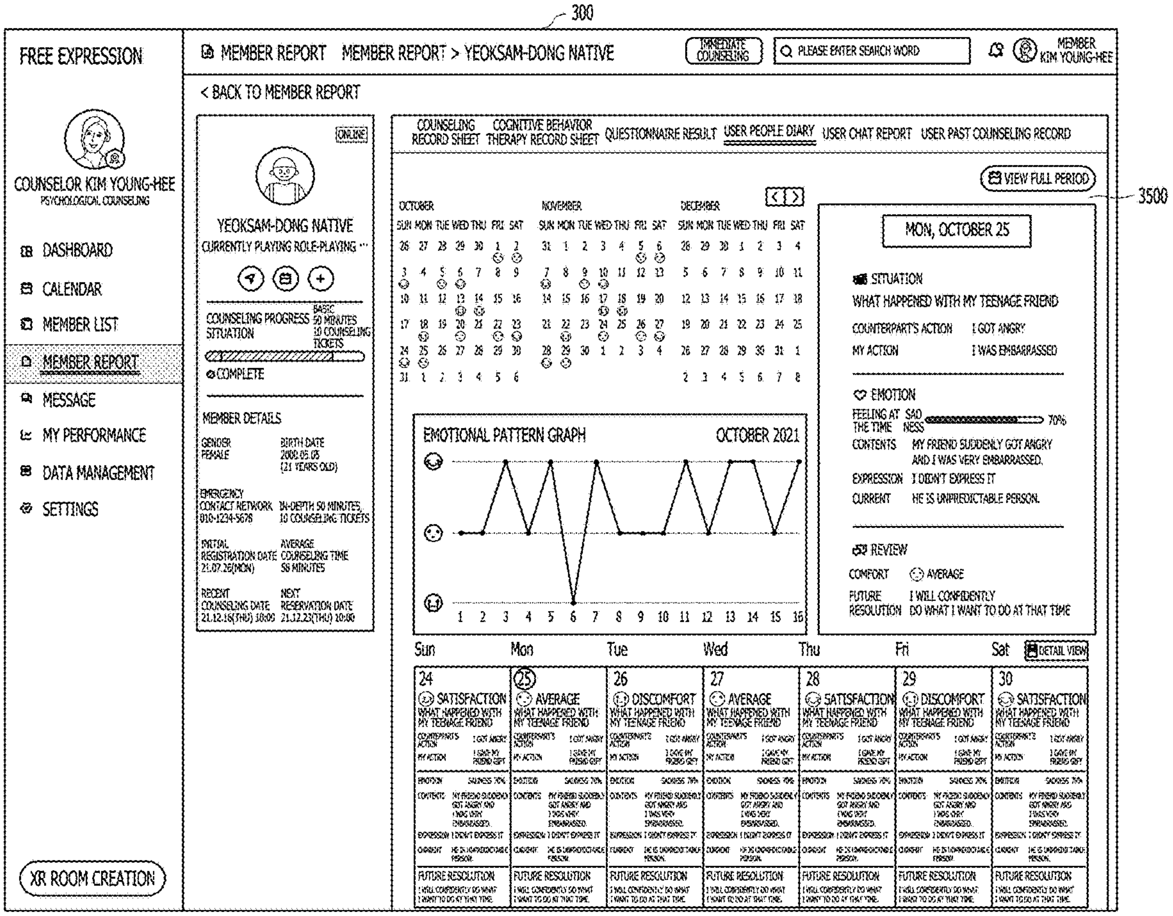

As an example, when Oct. 25, 2021, 3410 including the emotional record state in the people diary screen 3400 displayed on the first expert terminal is selected, as illustrated in FIG. 35, the first expert terminal displays a detailed people diary screen 3500 corresponding to the selected date (e.g., Oct. 25, 2021) 3410 (S430).

In addition, when a preset chat report item is selected from the detailed member report information displayed on the expert terminal 300, to provide the analysis results and participation list related to the chat room in which the user of the corresponding terminal 100 participates in relation to the corresponding counseling requester, the expert terminal 300 is linked with the server 200 to display a chat report screen for the expert corresponding to the selected chart report item. In this case, the expert terminal 300 may display the chat report screen seen by the expert corresponding to the selected chat report item in the detailed information display area. Here, the chat report screen seen by the expert (or the "my report" screen seen by the expert) includes an analysis result item for providing the analysis results according to the performance of the functions such as topic talk, role-playing, and theme practice in relation to the corresponding counseling requester, a participation list item for providing the participation list related to the chat list in which the corresponding user participates, a content display item (or content display area) for displaying the detailed information according to the selection of the analysis result item or the participation list item, etc.

In addition, when a preset analysis result item is selected from the chat report screen for the expert (or a "my report" screen used by the expert) displayed on the expert terminal 300, to provide the analysis results according to the performance of chat functions such as topic talk, role-playing, and theme practice in relation to the user of the terminal 100, the expert terminal 300 displays the detailed information corresponding to the selected analysis result menu in the content display area. In this case, when the preset chat report item is selected from the app execution result screen displayed on the expert terminal 300, the expert terminal 300 may display the analysis result screen (or the detailed information) corresponding to the analysis result item set by default in response to the selected chat report item in the content display area by default. display item for displaying the corresponding preset period, a "number of times you've participated in the chat room by category" display item for displaying the number of times the user has participated in the chat room by category, a "free expression" index display item for displaying the "free expression" index calculated in relation to the user, an anxiety index display item for displaying the anxiety index calculated in relation to the user, a detailed score view item for displaying additional detailed information in relation to the "free expression" index or the anxiety index, a relative evaluation display item for displaying information on oneself as evaluated by other users who performed the chat function together, a "my 'free expression' score aspect" display item for displaying the "free expression" score aspect, a "my anxiety score pattern" display item for displaying the user's anxiety score pattern, a "my confidence/assertiveness, mind control, communication skills/logic/persuasive power, immersion, empathy/listening skills score aspect" display item for displaying the user's confidence/assertiveness, mind control, communication skills/logic/persuasive power, immersion, empathy/listening skills score aspect, a "topic I have practiced a lot" display item for displaying a topic that the user has practiced a lot in relation to the topic talk, a "keyword that I have practiced a lot" display item for displaying keywords that the user has practiced a lot in relation to the topic talk, a "target I've practiced a lot" display item for displaying what the user has practiced a lot in relation to role-playing, a "situation I've practiced a lot" display item for displaying situations in which the user has practiced a lot in relation to role-playing, a "What emotions am I sensitive to?" display item for displaying what emotions the user is sensitive to in relation to role-playing, a "Which experts I have practiced with a lot?" display item for a displaying indicating with which experts the user has practiced a lot in relation to the theme, a "theme I practiced a lot" display item for displaying a theme that the user has practiced a lot in relation to theme practice, etc. Here, the "free expression" index display item includes an overall rating display item, a "free expression" index overall average display item, a satisfaction graph display item for overall average, a "free expression" index change graph display item by day of the week, a score display item for each item (e.g., including confidence/assertiveness, mind control, communication skills/logic/persuasive power, immersion, empathy/listening skills, etc.), a graph display item of a score change for each item by day of the week, an exponential distribution display item for each topic and situation, a detailed score view item, etc. In addition, the anxiety index display item includes a total rating display item, an anxiety index overall average display item, an anxiety graph display item for the overall average, a graph display item of an anxiety index change by day of the week, etc. In this case, the "free expression" index can be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates. In addition, the anxiety index represents the average value of the anxiety self-evaluated by the user after performing the chat function in the chat room (e.g., including the topic talk chat room, the role-playing chat room, the theme practice chat room, etc.) in which the user participates in relation to one or more chat rooms in which the user of the corresponding terminal 100 participates for a preset period or all chat rooms in which the user of the corresponding terminal 100 participates. In addition, examples of the relative evaluation display item include the reason for receiving a good evaluation, the reason for receiving a bad evaluation, and the satisfaction of chat evaluated by others. In addition, examples of the "my 'free expression' score aspect" display item include a "How many people am I with when my free expression score gets high?"

item, a "What age group of people am I talking with when I have a high score in 'free expression'?" item, a "What MBTI type am I talking with when I have a high score in 'free expression'?" item, a "What gender is the person I'm talking with when I have a high score in 'free expression'?" item, a "When I talk in a certain place, do I have a high score in free expression?" item, etc. In addition, the "my anxiety score aspect" display item includes a "How many people am I with when my anxiety score gets high?" item, a "What age group of people am I talking with when I have a high score in anxiety?" item, a "What MBTI type am I talking with when I have a high score in anxiety?" item, a "What gender is the person I'm talking with when I have a high score in anxiety?" item, a "When I talk in a certain place, do I have a high score in anxiety?" item, etc. In addition, examples of the "topic that I have practiced a lot" display item include an interpersonal relationship item, a daily life item, an employment/workplace item, a knowledge sharing item, a well-being item, other items, etc. In addition, examples of the "keyword that I have practiced a lot" display item include a boss item, a soccer item, a job preparation item, a presentation preparation item, a health item, other items, etc. In addition, examples of the "target that I have practiced a lot" display item include a husband item, a boss item, a coworker item, a chairman item, a stranger item, other items, etc. In addition, examples of the "situation that I have practiced a lot" display item include a rejection expression item, an affection expression item, an opinion expression item, a gratitude/sorry expression item, a conflict item, other items, etc. In addition, examples of the "What emotions am I sensitive to?" display item include a joy/pleasure item, an empathy item, an appreciation item, a sorry item, a grief/hurt item, an anger/annoyance/rage item, etc. In addition, examples of the "Which experts I have practiced with a lot?" display item include a psychological counselor item, a speech trainer item, a mentor item, etc. In addition, examples of the "theme that I practiced a lot" display item include a blind date item, a phone item, an interview item, a business report item, a small-scale presentation item, a large-scale presentation item, a professional discussion item, a pros and cons discussion item, etc.

In addition, when a preset detailed score view item is selected from the detailed information included in the content display area displayed on the expert terminal 300, the expert terminal 300 is linked with the server 200 to display detailed score information corresponding to the selected detailed score view item. Here, the detailed score information (or detailed score screen) includes the sort items for sorting functions related to all, topic talk, role-playing, theme practice, etc., the "number of times you've participated in the chat room" display item, the period display item for displaying the corresponding preset period, the "number of times you've participated in the chat room for each category" display item, the "free expression" index display item, the anxiety index display item, the relative evaluation display item, the "my 'free expression' score aspect" display item, the "my anxiety score aspect" display item, the "my confidence/assertiveness, mind control, communication skills/logic/persuasive power, immersion, empathy/listening skills score pattern" display item, the "topic I have practiced a lot" display item, the "keyword that I have practiced a lot" display item, the "target that I have practiced a lot" display item, the "situation that I have practiced a lot" display item, the "Which emotions I am sensitive to?" display item, the "Which experts have I practiced with a lot?" display item, the "theme which I have practiced a lot" display item, etc. In this case, when the detailed score view item related to the "free expression" index is selected, the expert terminal 300 may display one or more pieces of information related to the "free expression" index among the information included in the detailed score information, and when the detailed score view item related to the anxiety index is selected, the expert terminal 300 may mainly display one or more other pieces of information related to the anxiety index among the information included in the detailed score information.

That is, when a preset detailed score view item is selected from the detailed information included in the content display area displayed on the expert terminal 300, the expert terminal 300 is linked with the server 200 to display the detailed score information corresponding to the selected detailed score view item instead of the "free expression" index display item or anxiety index display item displayed previously.

In addition, when a preset period display item (or date selection item/calendar item) is selected from the chat report screen viewed by the expert (or the "my report" screen used by the expert) displayed on the expert terminal 300, the expert terminal 300 displays a calendar screen corresponding to the selected period. Here, the calendar screen includes information on the presence or absence of chat records by date recorded by the user of the terminal 100 within the corresponding period (or corresponding month).

In addition, when a specific date within the calendar screen is selected, if a chat record exists on the corresponding specific date, the expert terminal 300 displays detailed score information related to the chat record, and if no chat record exists on the corresponding specific date, the expert terminal 300 displays information indicating that no chat record exists.

In addition, when the preset participation list item is selected from the chat report screen seen by the expert (or the "my report" screen used by the expert) displayed on the expert terminal 300, to provide the participation list related to the conversation list in which the user of the terminal 100 participates, the expert terminal 300 displays the participation list screen corresponding to the selected participation list item. Here, the participation list screen includes a sort item for sorting functions related to all, topic talk, role-playing, theme practice, etc., a change information display item for providing information on changes in self-evaluation results or other's evaluation results compared to a preset period (or last week), a "number of times you've participated in the chat room" display item for displaying the number of times the user has participated in the chat room within a preset period, an information display item for each chat participation case for providing information related to topic talk, role-playing, theme practice, etc., in which the user participates, etc. In this case, the information display item for each chat participation includes a date information display item of participation in the chat room, a detail view item for displaying the detailed information, a chat room type (or chat room category) display item (e.g., including topic talk, role-playing, theme practice, etc.) for displaying the type of chat room in which the user participates, a chat room topic display item for displaying the topic of the chat room, a chat room name display item for displaying the room title (or chat room name) of the chat room, a keyword display item for displaying the main keywords/hashtags related to the corresponding chat room, a self-evaluation information display item for displaying the self-evaluation results, a received evaluation information display item for displaying the evaluation information received from other users participating in the corresponding chat room, a chat recording display item for the re-listening function of chat content from the chat room, etc.

In addition, when a specific participation list (or a detail view item displayed on one side of the corresponding specific participation list) is selected from one or more participation lists displayed in the information display items for each chat participation in the participation list screen displayed on the expert terminal 300, the expert terminal 300 is linked with the server 200 to display the detailed item information related to the selected specific participation list. Here, the detailed view information includes a date information display item of participation in the chat room corresponding to the selected specific participation list, a chat room type (or chat room category) display item for displaying the type of chat room in which the user participates (e.g., including a topic talk chat room, a role-playing chat room, a theme practice chat room, etc.), a chat room topic display item for displaying the topic of the chat room, a chat room name display item for displaying the room title of the chat room, a keyword display item for displaying main keywords/hashtags related to the chat room, a chat participant information display item for displaying information (e.g., including nicknames) of other users participating in the corresponding chat room, a self-evaluation result display item (or self-evaluation information display item) for displaying self-evaluation results, a received evaluation result display item (or a received evaluation information display item) for displaying evaluation results received from other users participating in the chat room, a chat recording display item for re-listening to chat content from the chat room, etc.

Figure 36:
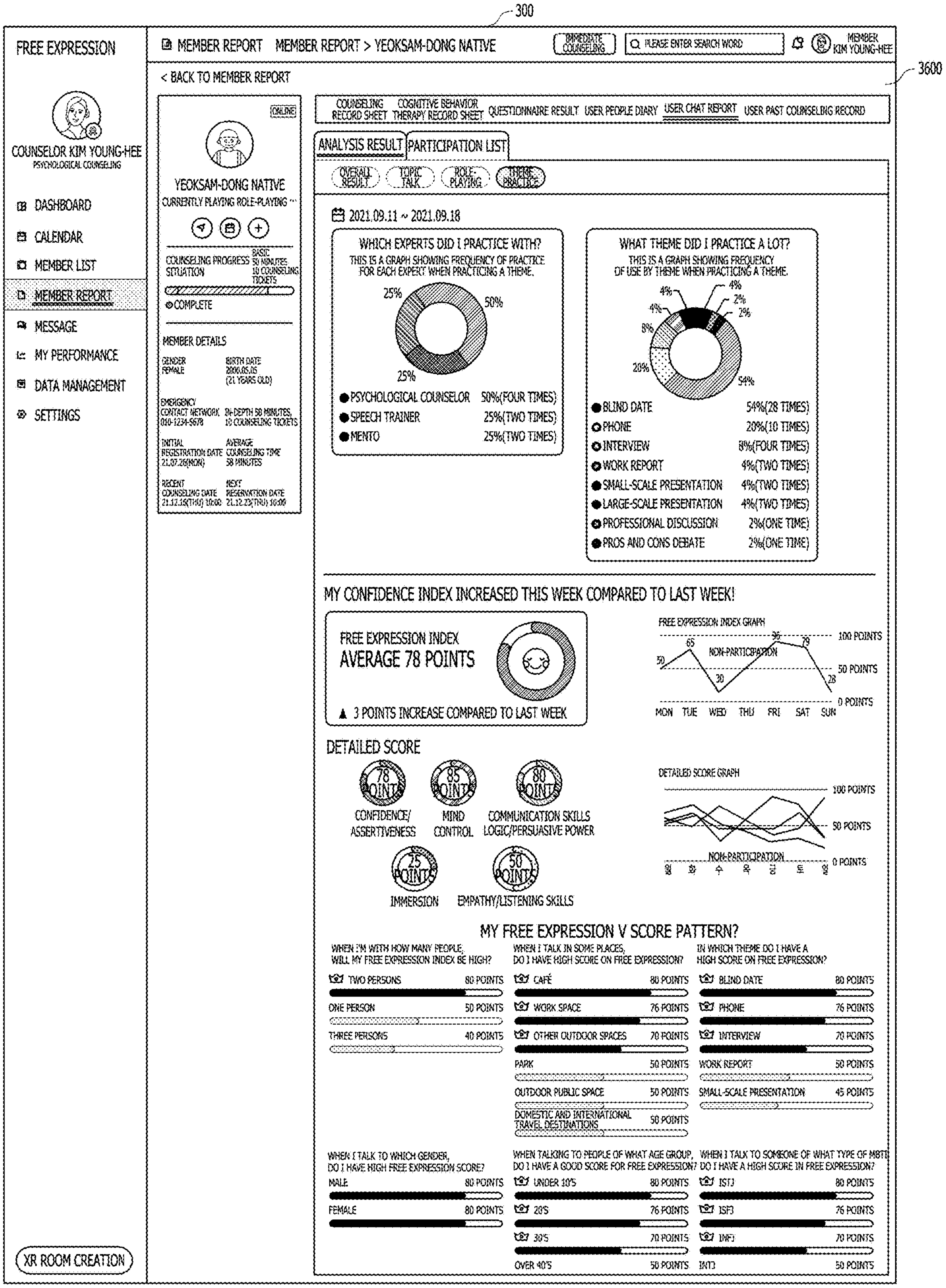

As an example, when the chart report item 2650 is selected from the Yeoksam-dong native's detailed report information 2650 displayed on the first expert terminal, as illustrated in FIG. 36, the first expert terminal displays a chat report screen seen by the expert 3600 corresponding to the selected chart report item 2650 (S440).

In addition, when a preset past counseling record item is selected from the detailed member report information displayed on the expert terminal 300, to provide a participation list and a cognitive behavior therapy record (or cognitive behavior therapy record sheet) related to the chat room in which the user of the terminal 100 participates with the expert of the expert terminal 300, the expert terminal 300 is linked with the server 200 to display a past counseling record screen corresponding to the selected past counseling record item. In this case, the expert terminal 300 may display the past counseling record screen seen by the expert corresponding to the selected past counseling record item in the detailed information display area. Here, the past counseling record screen seen by the expert (or past counseling record screen) includes a participation list menu for providing the list of who has performed the psychological counseling, the speech lesson function, or the mentoring function with the expert in relation to the specific topic or situation, a cognitive behavior therapy record menu for providing the cognitive behavior therapy record (or cognitive behavior therapy record sheet) written by the user according to the performance of the training function for the appropriate chat style in relation to the specific topic or situation, a content display area (or content display menu) for displaying the detailed information according to the selection of the participation list menu or the cognitive behavior therapy record menu, etc.

In addition, when a preset participation list menu (or another participation list menu) is selected from the past counseling record screen seen by the expert displayed on the expert terminal 300, to provide other participation lists in which the user of the terminal 100 performs a counseling function, a speech lesson function, a mentoring function, etc., with the expert of the expert terminal 300, the expert terminal 300 displays other participation list screens corresponding to the selected participation list menu in the content display area. Here, all the other participation list screens include another sorting item for sorting functions related to psychological counseling, speech, mentoring, etc., another sorting item for sorting functions related to most recent, highest score, lowest score, etc., other change information display items for providing information on changes in the number of counseling sessions, the number of chat training sessions with an expert, or a cognitive behavior therapy record compared to a preset period (or last week), an item for displaying the number of times the user participates in other chat rooms for displaying the number of times the user participates in the chat room within a preset period, an information display item for each expert chat participation case for providing information related to psychological counseling, speech, mentoring, etc., in which a user participates, etc. In this case, examples of the item for displaying the number of times the user participates in other chat rooms include an item for displaying the number of counseling sessions, an item for displaying the number of chat training sessions with an expert, a cognitive behavior therapy record item, etc. In addition, examples of the information display item for each expert chat participation case include other chat room type (or chat room category) display items for displaying the type of chat room (e.g., including psychological counseling, speech, mentoring, etc.) in which they participate, another chat room topic display item for displaying the topic of the chat room, a detail view item for displaying detailed information, an expert information display item for displaying an expert's photo and name, a counseling date display item for displaying a counseling date, other keyword display items for displaying main keywords/hashtags related to the corresponding chat room, an expert feedback item for providing expert feedback, a cognitive behavior therapy record sheet item for providing a cognitive behavior therapy record sheet, a written questionnaire item for providing questionnaire content written by a user, a chat room training display item for displaying chat room training content, etc. Here, when a past counseling record item is selected from the detailed member report information displayed on the expert terminal 300, the expert terminal 300 may display other participation list screens corresponding to the participation list menu preset by default in response to the selected past counseling record item in the content display area by default.

Figure 37:
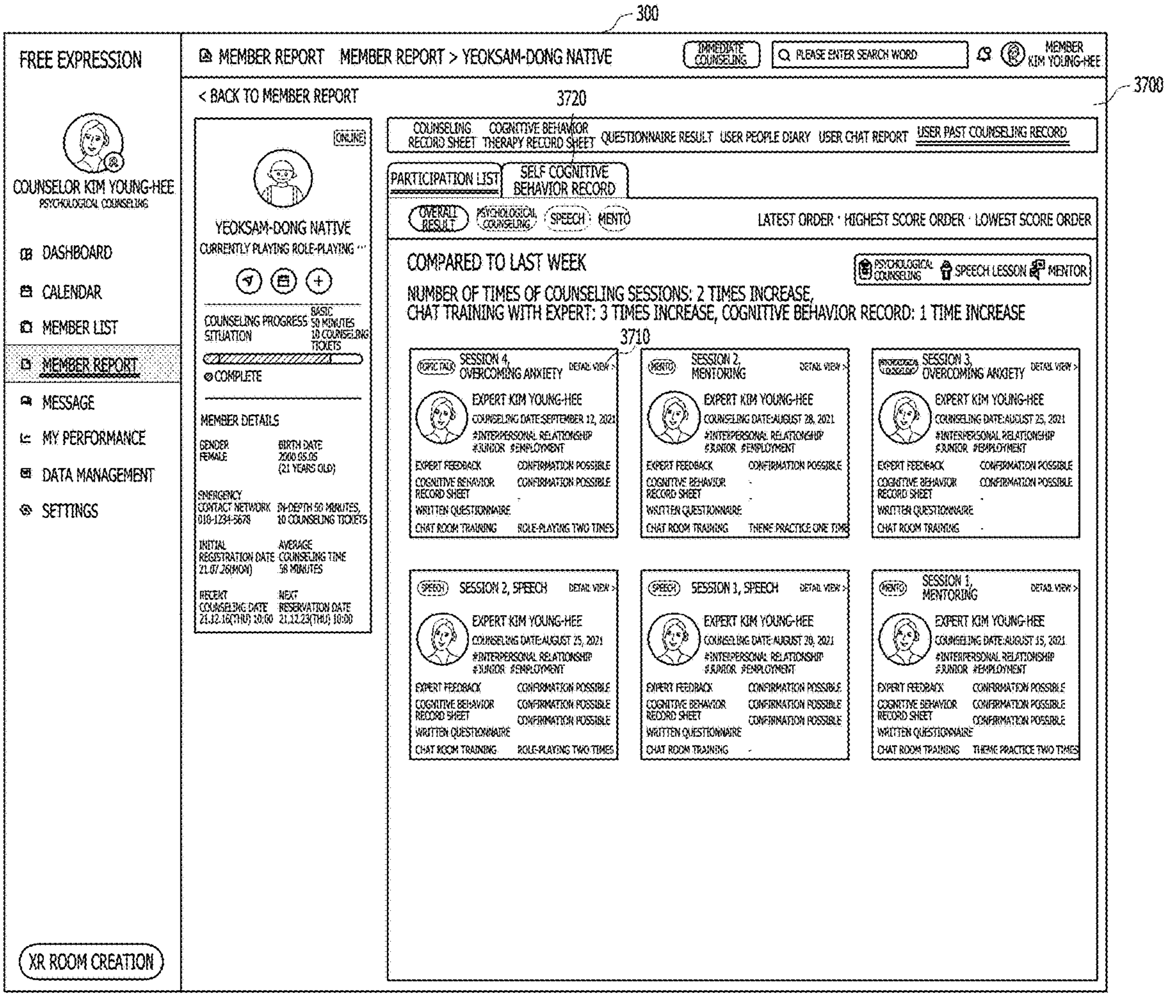

As an example, when a past counseling record item 2660 is selected from the Yeoksam-dong native's detailed report information 2600 displayed on the first expert terminal, as illustrated in FIG. 37, the first expert terminal displays other participation list screens 3700 corresponding to the participation list menu set by default in response to the selected past counseling record item 2660 (S450).

Thereafter, when other specific participation lists (or detail view items displayed on one side of the corresponding other specific participation lists) are selected from one or more other participation lists being displayed in the information display items for each expert chat participation case in the past counseling record screen seen by the expert displayed on the expert terminal 300, the expert terminal 300 is linked with the server 200 to display the detailed information related to the selected other specific participation lists. Here, the detailed information (or detailed counseling result item screen) includes other chat room type (or chat room category) display items for displaying the types of chat rooms (e.g., including psychological counseling, speech, mentoring, etc.) in relation to the other specific participation lists, other chat room topic display items for displaying the topic of the chat room, an expert information display item for displaying the expert's photo and name, a counseling date display item for displaying the counseling date, other keyword display items for displaying the main keywords/hashtags related to the corresponding chat room, an expert feedback display item for displaying the expert feedback, a cognitive behavior therapy record sheet item for providing the cognitive behavior therapy record sheet before and after training, a questionnaire item written during counseling for providing the type and results of the questionnaire written by the user, a chat room participation record display item for providing the chat room participation record, etc. In this case, examples of the questionnaire item written during counseling may include information on various types of tests (or questionnaires) such as a self-esteem self-diagnosis test, a communication type test, an anxiety test, etc. In addition, examples of the chat room participation record display item include a date information display item on participation in the chat room, an expert state item for displaying whether the expert is participating in training or observing the expert, a chat room type (or chat room category) display item for displaying the type of chat room (including, for example, a topic talk chat room, a role-playing chat room, a theme practice chat room, etc.) in which the user participates, a chat room topic display item for displaying the topic of the chat room, a chat room name display item for displaying the room title of the chat room, a chat participant information display item for displaying information (including, for example, nicknames) of other users participating in the corresponding chat room, a self-evaluation result display item (or self-evaluation information display item) for displaying the self-evaluation results, a received evaluation result display item (or received evaluation information display item) for displaying the evaluation results received from other users participating in the corresponding chat room, a chat recording display item for re-listening to the chat content from the chat room, etc.

Figure 38:
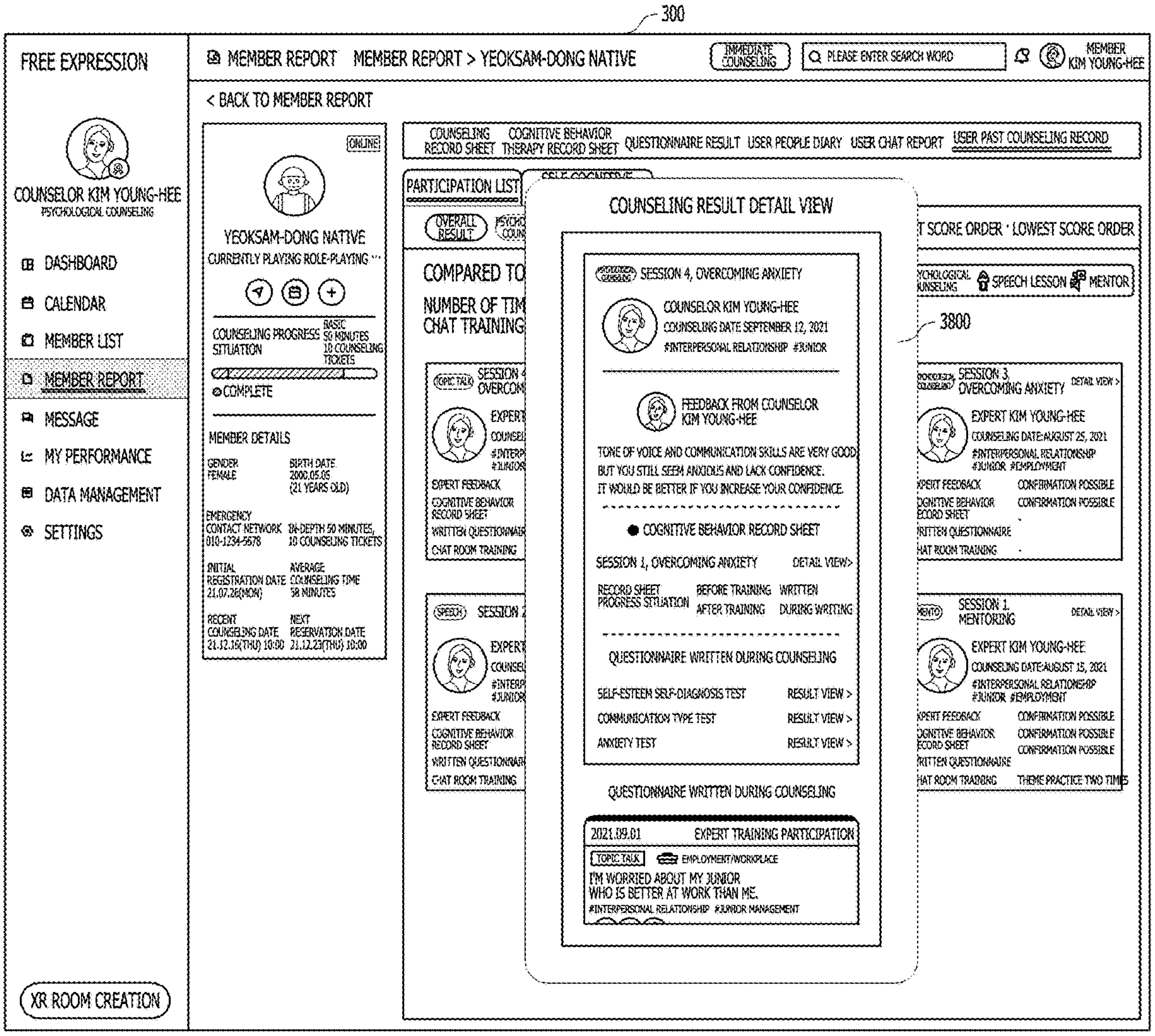

As an example, when a detail view item 3710 related to "session 4, overcoming anxiety" performed on Sep. 12, 2021, in the participation of other participation list screens 3700 displayed on the first expert terminal is selected, as illustrated in FIG. 38, the first expert terminal displays detailed item information 3800 corresponding to the selected detail view item 3710 provided from the server 200 (S460).

In addition, when a preset cognitive behavior therapy record menu (or cognitive behavior record menu) is selected from the past counseling record screen for the expert displayed on the expert terminal 300, to provide the information on the cognitive behavior therapy record sheet written by the user of the terminal 100 according to the user's performance of the training function for the appropriate chat style in relation to the specific topic or situation, the terminal 300 displays a cognitive behavior therapy record screen corresponding to the selected cognitive behavior therapy record menu. Here, the cognitive behavior therapy record screen (or cognitive behavior therapy record sheet screen) includes the cognitive behavior therapy record information display item for each chat participation case, etc., to provide the cognitive behavior therapy record (or cognitive behavior therapy record sheet) written before and after training in relation to the specific topic or situation in which the user of the corresponding terminal 100 participates. In addition, examples of the cognitive behavior therapy record information display item for each chat participation case include a cognitive behavior therapy record sheet title display item for displaying the title, a result view item for displaying the written cognitive behavior therapy record result, a record date display item for displaying the date when the cognitive behavior therapy record (or cognitive behavior therapy record sheet) is written, a record sheet progress situation display item for displaying the record sheet progress situation before/after training, a confirmed expert display item for displaying the expert who has confirmed the cognitive behavior therapy record sheet written by the user, etc.

Figure 39:
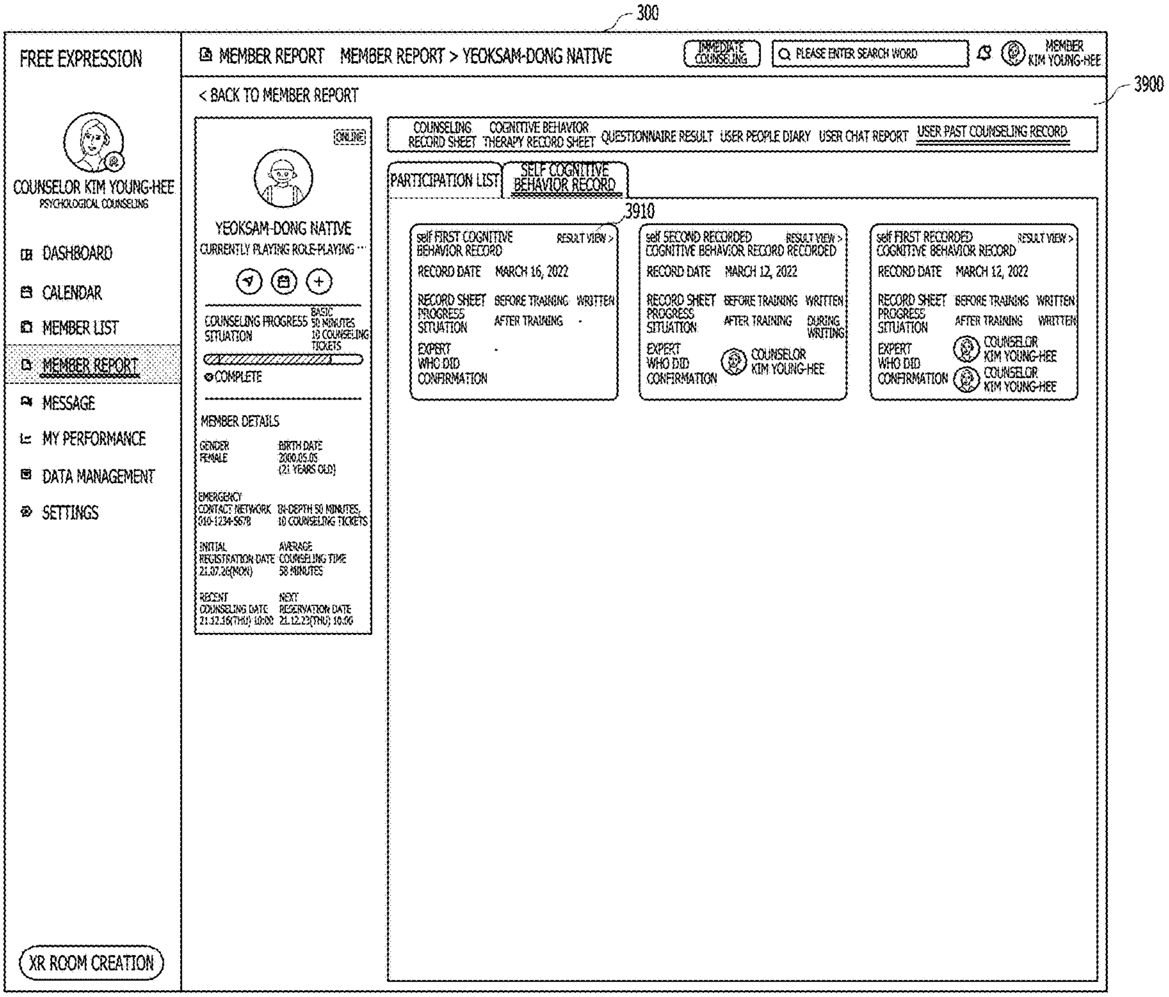

As an example, when a cognitive behavior therapy record menu 3720 is selected from the other participation list screens 3700 displayed on the first expert terminal, as illustrated in FIG. 39, the first expert terminal displays a cognitive behavior therapy record screen 3900 corresponding to the selected cognitive behavior therapy record menu 3720 (S470).

Thereafter, when the specific cognitive behavior therapy record is selected from one or more cognitive behavior therapy record cases being displayed in the cognitive behavior therapy record information display item for each chat participation in the cognitive behavior therapy record screen displayed on the expert terminal 300, the expert terminal 300 is linked with the server 200 to display other detailed information related to the selected specific cognitive behavior therapy record case. Here, the other detailed information (or cognitive behavior therapy record sheet/cognitive behavior therapy record sheet screen) includes a cognitive behavior therapy record sheet title display item to display the title, a last modified date display item, a writer ID and name display item, a writing state display item before and after training (e.g., including not written, being written, written, etc.), a cognitive behavior information item for each item before training, a cognitive behavior information item for each item after training, etc. In addition, examples of the cognitive behavior information item for each item before training include an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for displaying "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item (e.g., an improvement-related item, an anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/fury, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before training and/or the cognitive behavior information item for each item after training may be commonly preset or may be set differently for each expert.

Figure 40:
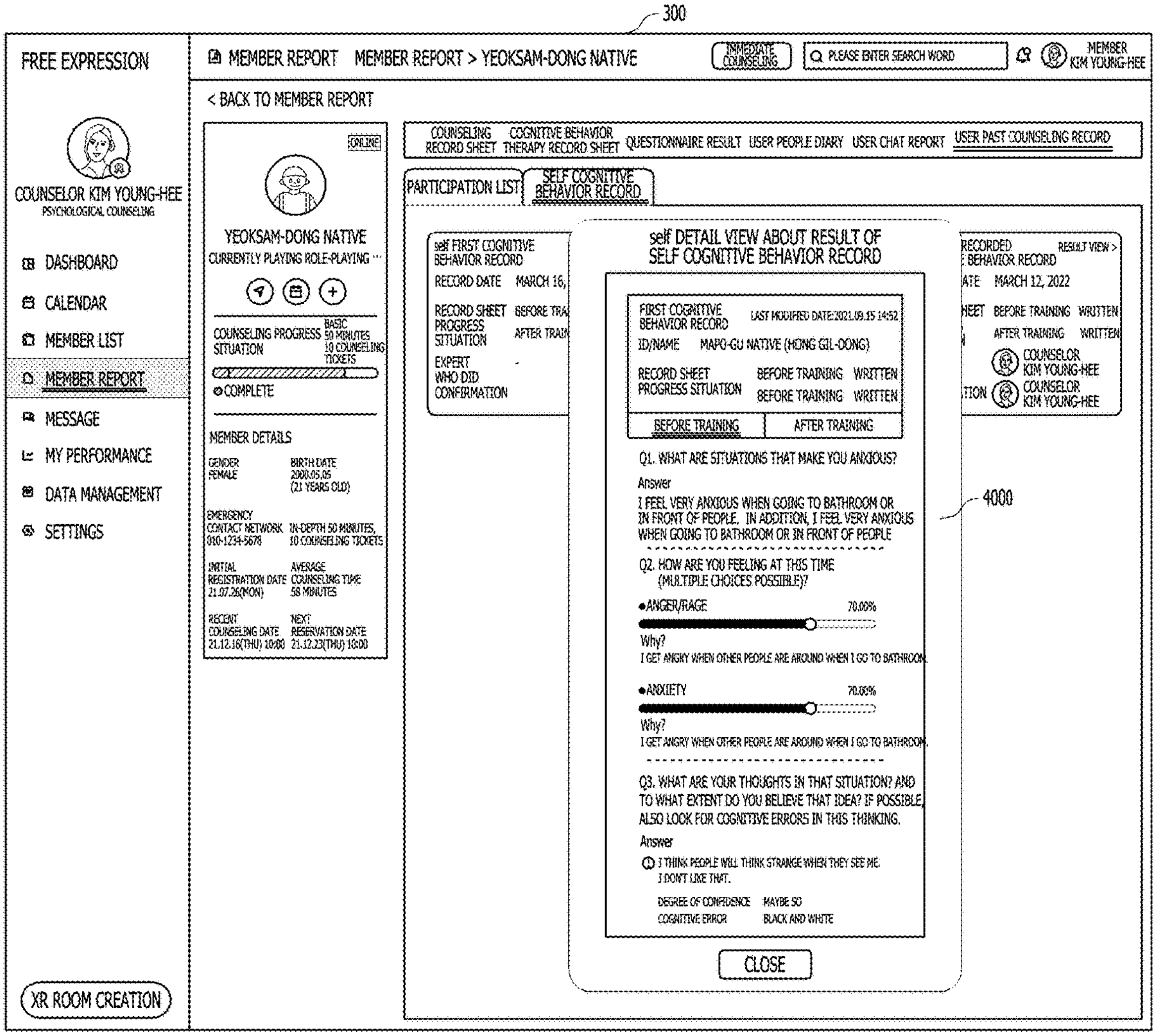

As an example, when a first cognitive behavior therapy record item 3910 is selected from the cognitive behavior therapy record screen 3900 displayed on the first expert terminal, as illustrated in FIG. 40, the first expert terminal displays a first cognitive behavior therapy record screen 4000 corresponding to the selected first cognitive behavior therapy record item 3910 (S480).

In addition, when a preset message menu is selected from the initial screen displayed on the expert terminal 300, to provide a message (or post message) function with a user who is counseling with the corresponding expert or has a counseling history with the corresponding expert, the expert terminal 300 is linked with the server 200 to display a message screen corresponding to the selected message menu. In this case, the expert terminal 300 may display the message screen corresponding to the selected message menu in the detailed information display area. Here, the message screen includes an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g. including an expert character/picture, an expert name/name, etc.), a member search menu for searching for members, a message list menu for providing a list of one or more counseling requesters who have exchanged messages with the expert, when a specific counseling requester (or the nickname of the counseling requester) is selected from the list of counseling requestors included in the message list, a message content display menu for displaying the content of the message exchanged with the specific counseling requester, a detailed personal information display menu for displaying personal information on the specific counseling requester, etc. In addition, the detailed personal information display menu includes a current online state display item for displaying information on the real-time connection state of the person requesting counseling, a character (or image/photo) item of a person requesting counseling, a nickname, a gender, a date of birth, an emergency contact network (or phone number) of the person requesting counseling, a counseling ticket type item (e.g., time, number of sessions, etc. for each type), a first registration date item, an average counseling time display item, the most recent counseling date display item (or the most recently completed counseling date display item), a next reservation date display item (or counseling reservation date display item), a deletion item for deleting content of messages with the person requesting counseling, a report item for reporting content of messages with the person requesting counseling, etc.

In addition, the expert terminal 300 is linked with the terminal 100 and the server 300 related to the specific counseling requester selected from one or more counseling requesters included in the message screen to perform the message function (or chat function) with the terminal 100 related to the corresponding specific counseling requester.

In addition, when the specific menu is selected from the message screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 41:
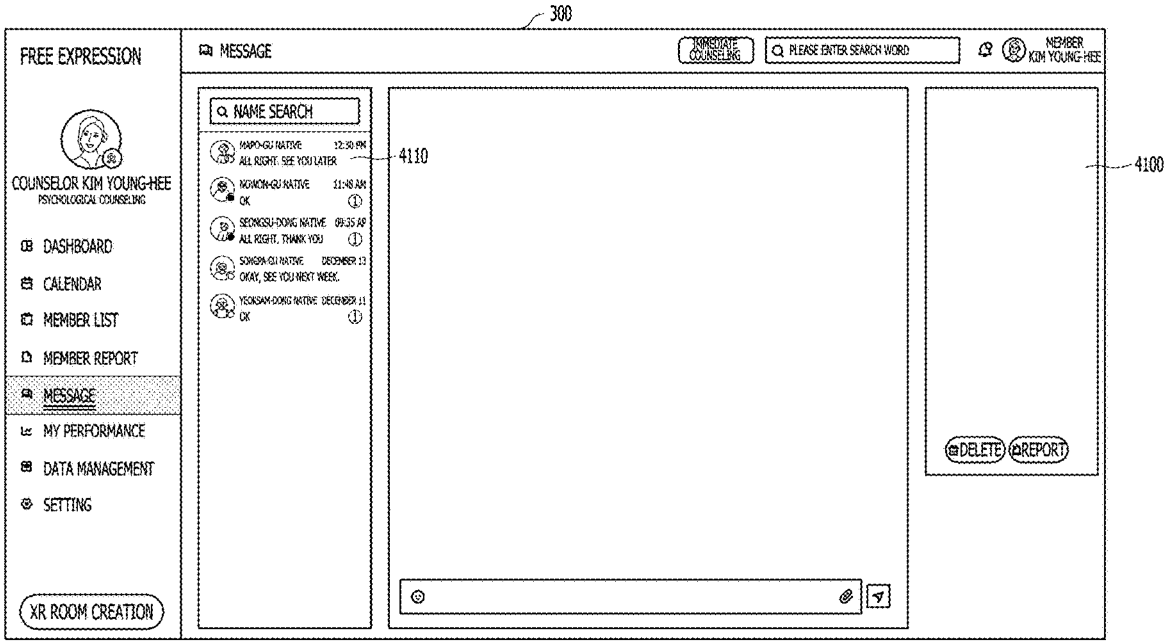

As an example, when a preset message menu 950 is selected from the initial screen 900 displayed on the first expert terminal according to the first expert selection of the corresponding first expert terminal, as illustrated in FIG. 41, the first expert terminal displays a message screen 4100 corresponding to the selected message menu 950.

Figure 42:
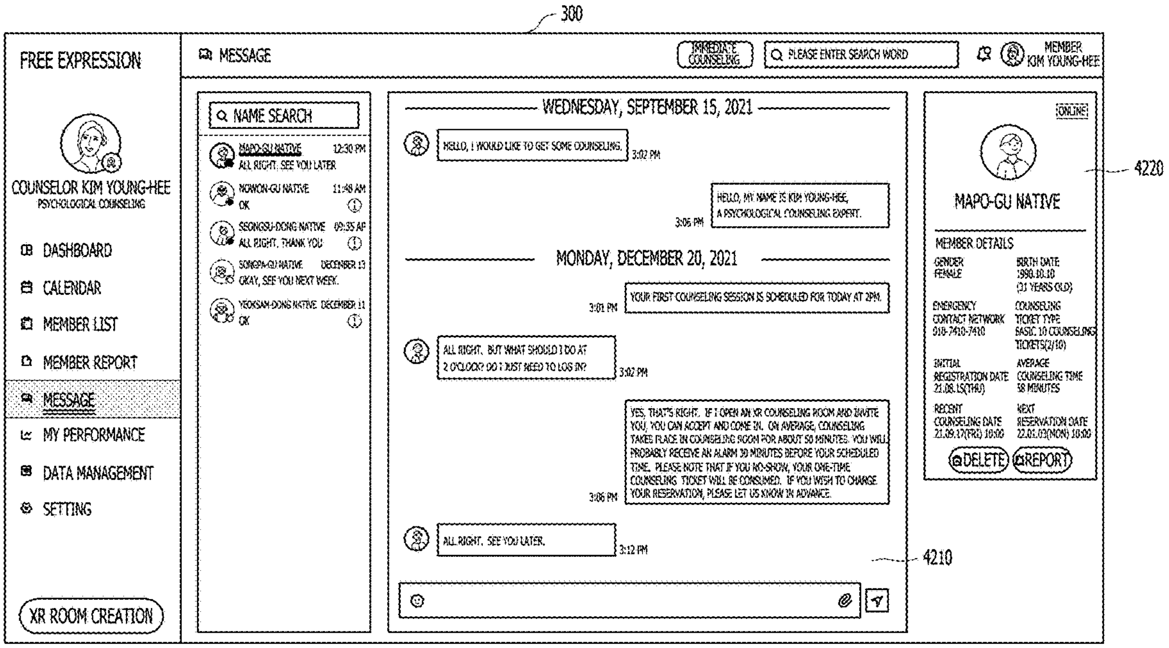

In addition, when a Mapo-gu native 4110 is selected from the list of one or more counseling requesters included in the message list item in the message screen 4100 displayed on the first expert terminal, as illustrated in FIG. 42, the first expert terminal displays the message content exchanged with the selected Mapo-gu native 4110 in the message content display item 4210, and displays the personal information related to the corresponding Mapo-gu native in the detailed personal information display item 4220 (S490).

In addition, when a preset "my performance" menu is selected from the initial screen displayed on the expert terminal 300, to provide information such as counseling performance performed by the corresponding expert, the expert terminal 300 is linked with the server 200 to display a "my performance" screen corresponding to the selected "my performance" menu. In this case, the expert terminal 300 may display the "my performance" screen corresponding to the selected "my performance" menu in the detailed information display area. Here, the "my performance" screen is an immediate counseling menu for performing a counseling function with a user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a "my performance" period menu for selecting the type of "my performance" provided (e.g., including, weekly, monthly, yearly, etc.), a total number of counseling ticket purchase case display menu according to "my performance" type selected in the "my performance" period menu, a counseling ticket repurchase rate display menu, a total revenue display menu, a total number of members consulted display menu, a monthly new counseling member information display menu, a recently registered member display menu for displaying information on a preset number of (e.g., 6) recently registered members, a monthly counseling performance display menu, a detail menu for displaying counseling performance details, a menu for displaying an expert's average rating (or rating/star rating), a menu for displaying the total number of reviews, a menu for displaying the number of new reviews for a preset period (e.g., the last 7 days), etc.

In addition, when the specific menu is selected from the "my performance" screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 43:
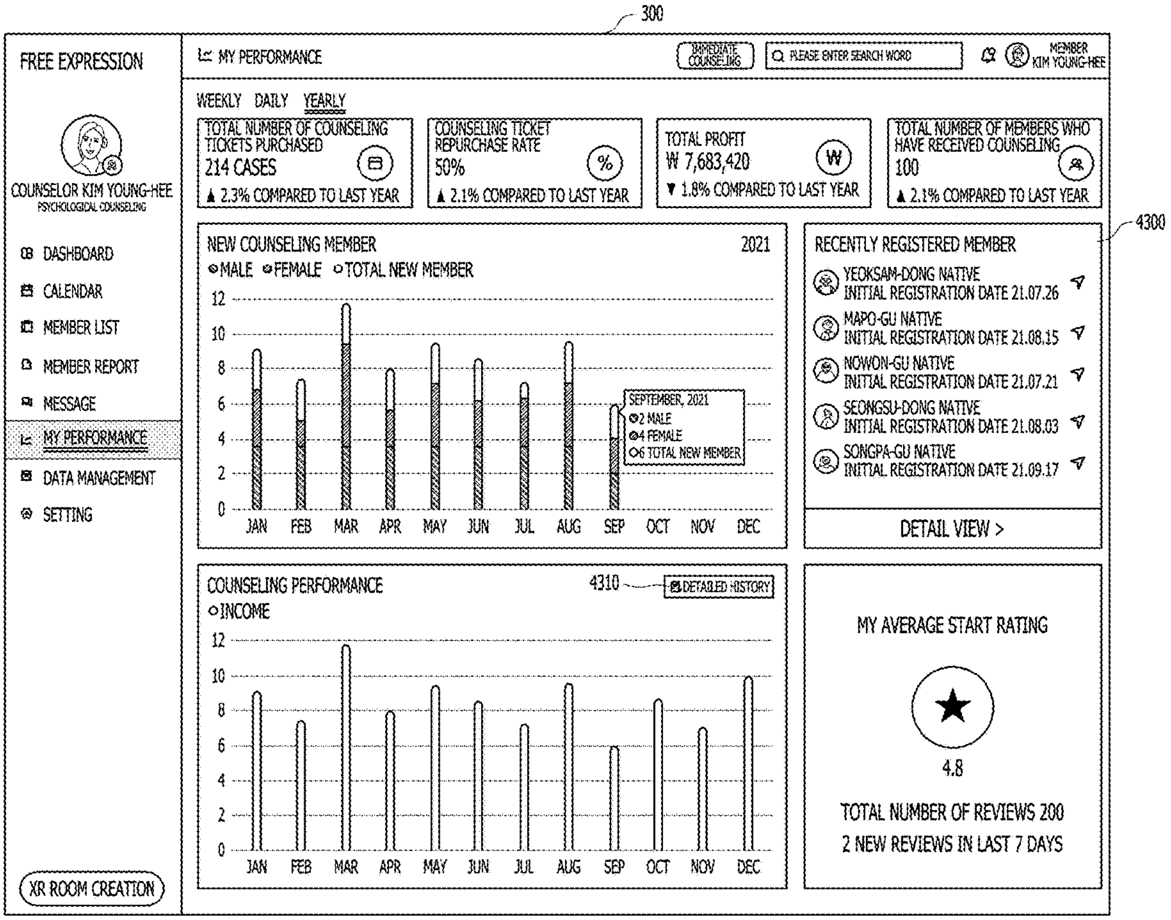

As an example, when a preset "my performance" menu 960 is selected from the initial screen 900 displayed on the first expert terminal according to the first expert selection of the corresponding first expert terminal, as illustrated in FIG. 43, the first expert terminal displays a "my performance" screen 4300 corresponding to the selected "my performance" menu 960 (S500).

Thereafter, when the detailed history menu related to counseling performance in the "my performance" screen displayed on the expert terminal 300 is selected, the expert terminal 300 is linked with the server 200 to display a detailed history screen corresponding to the detailed history menu related to the selected counseling performance. Here, the detailed history screen includes an immediate counseling item for performing the counseling function with the user (or client) in real time while accessing the website on the expert terminal 300, a search item for searching for functions or menus corresponding to the search term, a notification item for confirming notices or notification messages, etc., a user information display item for displaying the user information (e.g., including an expert character/picture, an expert name/name, etc.), a "return to my performance" item for returning to the previous screen (or the "my performance" screen), a period setting item for setting a period (for example, the last 7 days) for providing the counseling performance, a current date display item for displaying the current date, a counseling performance detail history item for providing the counseling performance of the corresponding expert within the period set in the period setting item, a storage item for storing the detailed history of the counseling performance displayed on the detailed history screen, an output item for outputting the detailed history of the counseling performance displayed on the detailed history screen, etc. In addition, examples of the detailed history item of the counseling performance include an item for displaying the number of counseling cases/immediate counseling cases by date, a total counseling time item, an item for displaying the number of new member registrations, an item for displaying the number of review registrations, an item for displaying the number of expert cases chosen, and a profit (unit: won) time, etc.

In addition, the expert terminal 300 may additionally perform a storage function, an output function, etc., on the content of the detailed history screen being displayed on the expert terminal 300.

Figure 44:
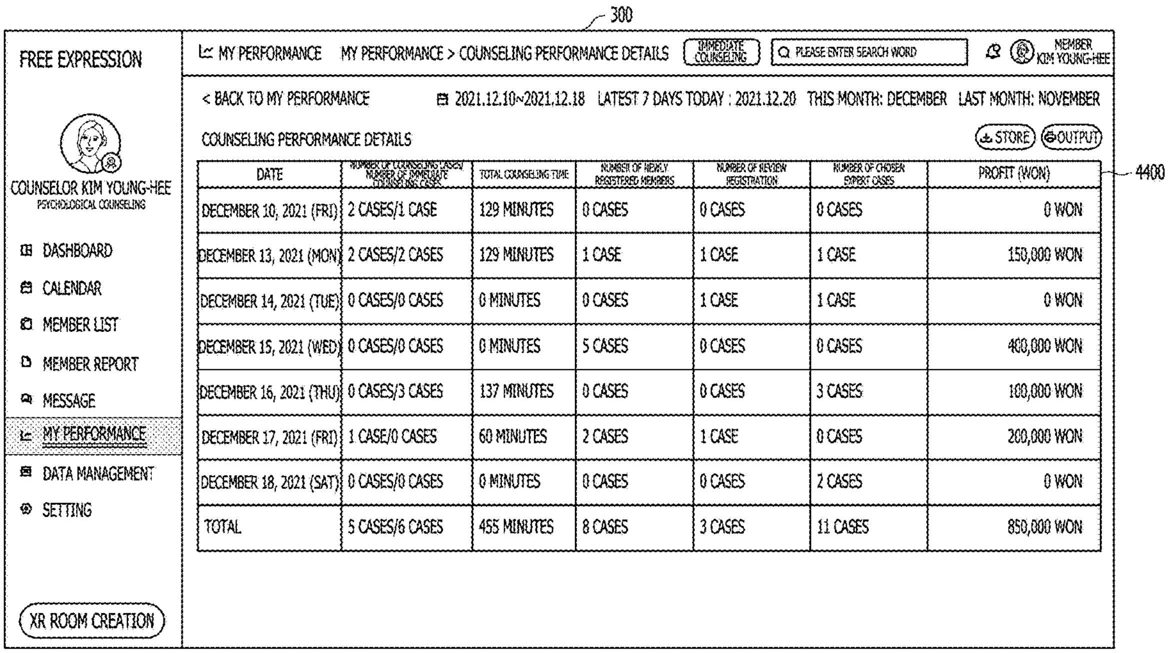

For example, when the detailed information item 4310 related to the counseling performance in the "my performance" screen 4300 displayed on the first expert terminal is selected, as illustrated in FIG. 44, the first expert terminal displays a detailed history screen 4400 corresponding to the selected detailed history item 4310 (S510).

In addition, when a preset data management menu is selected from the initial screen displayed on the expert terminal 300, to manage information on a questionnaire or data related to a user who is counseling with the corresponding expert or has a counseling history with the corresponding expert, the expert terminal 300 is linked with the server 200 to display a data management screen corresponding to the selected data management menu. In this case, the expert terminal 300 may display the data management screen corresponding to the selected data management menu in the detailed information display area. Here, the data management screen includes an immediate counseling menu for performing a counseling function with the user (or client) in real time while accessing the website on the expert terminal 300, a search menu for searching for functions or menus corresponding to the search word, a notification menu for confirming notices or notification messages, etc., a user information display menu for displaying user information (e.g., including an expert character/picture, an expert name/name, etc.), a number of questionnaires held display menu for displaying the number of questionnaires held by the expert in relation to the counseling requester in counseling, an amount of data held display menu for displaying the amount of data held by the expert in relation to the person requesting counseling, a member search menu for searching for members, an additional menu for adding questionnaires or data held by the expert, an output menu for outputting the information displayed on the data management screen, a deletion menu for deleting specific information displayed on the data management screen, a data information display menu related to the counseling requester being managed by the corresponding expert, etc. In addition, the data information display menu includes a file name item, a format item (e.g., including a questionnaire, data, etc.), a writer item (or expert item), a last modified date item, a file size item, etc., according to the data type.

In addition, the expert terminal 300 may additionally perform the output function, the deletion function, and the additional function of new data, etc., on the content of the data management screen being displayed on the expert terminal 300.

In addition, when the specific menu is selected from the data management screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 45:
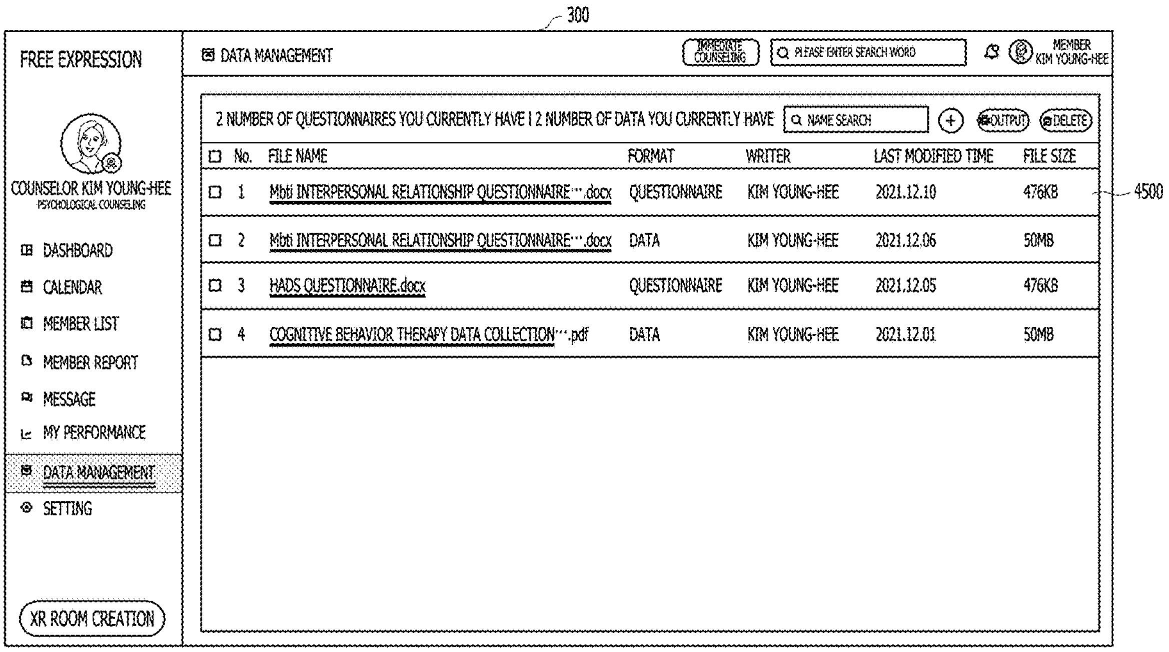

As an example, when a preset data management menu 970 is selected from the initial screen 900 displayed on the first expert terminal according to the first expert selection of the corresponding first expert terminal, as illustrated in FIG. 45, the first expert terminal displays a data management screen 4500 corresponding to the selected data management menu 970 (S520).

In addition, when a preset XR room-creation menu is selected from the initial screen displayed on the expert terminal 300, to select a client to be invited to the XR counseling room, the expert terminal 300 is linked with the server 200 to display an XR counseling room invitation client selection screen corresponding to the selected XR room-creation menu. In this case, the expert terminal 300 may display the XR counseling room invitation client selection screen corresponding to the selected XR room-creation menu in the detailed information display area. Here, the XR counseling room invitation client selection screen (or the metaverse counseling room invitation client selection screen) includes an additional client menu for adding a client, a menu (e.g., including a list of one or more users/clients who have currently applied/chosen an expert as a counselor, etc.) for selecting a client invited to the XR counseling room (or metaverse counseling room), a close menu, etc., and may be displayed in the form of a pop-up or a new screen (e.g., including a new window, a new screen, etc.).

In addition, when the specific menu is selected from the XR counseling room invitation client selection screen displayed on the expert terminal 300 according to the expert selection (or expert/counselor input/touch/control) of the expert terminal 300, the expert terminal 300 is linked with the server 200 to provide the screen corresponding to the selected specific menu to the expert terminal 300 or perform the function corresponding to the selected specific menu and display (or output) the function performance results according to the corresponding function performance.

Figure 46:
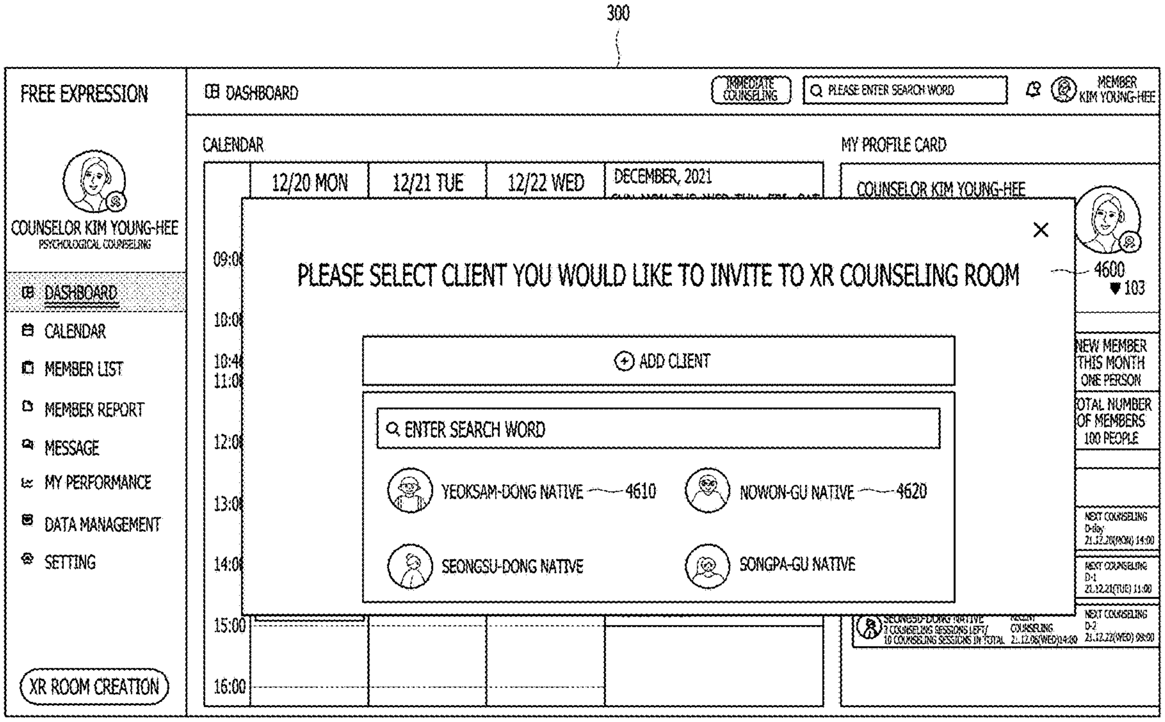

As an example, when a preset XR room-creation menu 980 is selected from the initial screen 900 displayed on the first expert terminal according to the first expert selection of the corresponding first expert terminal, as illustrated in FIG. 46, the corresponding first expert terminal displays an XR counseling room invitation client selection screen 4600 corresponding to the selected XR room-creation menu 980 (S530).

Thereafter, when a specific user is selected from the XR counseling room invitation client selection screen displayed on the expert terminal 300, to perform a counseling function with an expert in an XR environment or a metaverse environment, the expert terminal 300 is linked with the server 200 and the terminal 100 owned by the selected specific user (or specific content) to display the XR counseling room screen. Here, the XR counseling room screen (or metaverse counseling room screen) includes a counseling screen area for displaying the counseling function performance state with the specific user of the terminal 100, a detailed member information display area for displaying the detailed information on the specific user of the terminal 100. In addition, the counseling screen area includes a video information display area for displaying video information related to the expert and the specific user, a counseling time display item for displaying a counseling time, a current time display item for displaying a current time, a microphone item for setting whether to output voice, a video item for setting whether to output the video information, an entry item with the chat training room for a counselor and the specific user to enter a new metaverse chat room related to a specific theme to perform a chat function, a questionnaire writing request item for requesting the specific user in counseling to write a questionnaire, a file item (shared item) for sharing (or transmitting) a file during the counseling, and a counseling end item for ending the counseling function, etc. In addition, the detailed member information display area includes a personal information item (personal information tab) for displaying personal information on the specific user in counseling, a counseling record sheet item for displaying a counseling record sheet related to one or more counseling sessions performed by the specific user in counseling, a cognitive behavior therapy record sheet item (or cognitive behavior record sheet item) for displaying a cognitive behavior therapy record sheet related to one or more counseling sessions performed by the specific user in counseling, a questionnaire result item for displaying a questionnaire result related to the questionnaire performed by the specific user in counseling, a people diary item for displaying the content (or the content of the emotional state by date written by the corresponding specific user) of the emotional state by date written by the corresponding counseling requester, a chat report item for displaying a chat report (or my report) related to the corresponding counseling requester, a past counseling record item for displaying a past counseling record performed by the corresponding counseling requester, an additional detailed information display area (or additional detailed information display item) for providing detailed information on a specific item selected among multiple items, etc. In addition, the personal information items (or personal information screen) include an item for displaying whether one is currently online for displaying the information on the real-time connection state of the corresponding counseling requester, a character (or image/photo) item of the corresponding counseling requester, a nickname item of the corresponding counseling requester, an item for displaying a type (e.g., topic talk, role-playing, theme practice, etc.) of a counseling case in progress when the corresponding counseling requester is currently counseling, an item (or counseling progress situation item) for displaying the remaining number of uses out of the total number of uses, a basic questionnaire view item for confirming the basic questionnaire content written by the corresponding counseling requester, a schedule reservation item for reserving the counseling schedule with the expert of the expert terminal 300, a gender item, a birth date item, an emergency contact network (or phone number) item, a use ticket/counseling ticket type item (e.g., time, the number of sessions, etc., for each type), an initial registration date item, an average counseling time display item, a most recent use date/counseling date display item (or recently completed counseling date), a next reservation date display item (or counseling reservation date item), an item for displaying the service/topic on which a user would like to receive counseling, an item (or additional inquiry content item) for displaying service/content on which a user would like to receive counseling, a counseling recording item for recording the counseling content, a memo item, etc.

Figure 47:
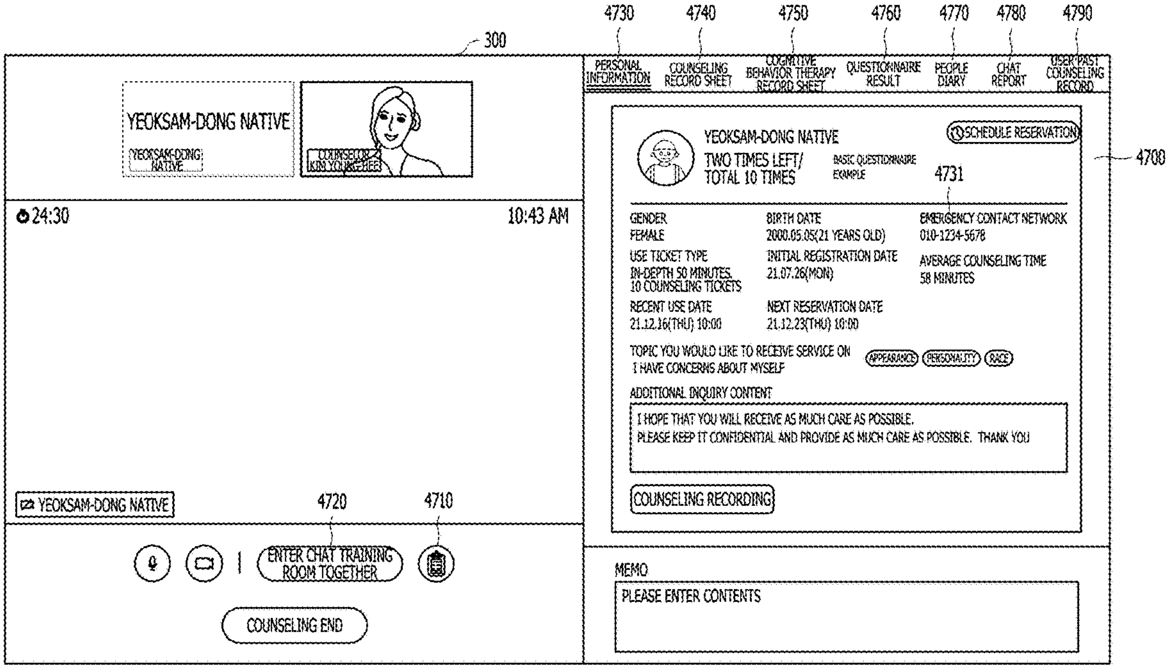

As an example, when a Yeoksam-dong native 4610 is selected from the XR counseling room invitation client selection screen 4600 displayed on the first expert terminal, as illustrated in FIG. 47, to perform the counseling function with the expert in the XR, the first expert terminal is linked with the server 200 and the first terminal owned by the Yeoksam-dong native to display an XR counseling room screen 4700 (S540).

Thereafter, when a preset questionnaire writing request item is selected from the XR counseling room screen displayed on the expert terminal 300, the expert terminal 300 is linked with the server 200 to display a questionnaire list screen corresponding to the selected questionnaire writing request item. Here, the questionnaire list screen includes one or more pre-registered questionnaire lists, and includes a questionnaire name item, a questionnaire question number item, a questionnaire preview item, a date item last written by the user, an additional item, a sending item, etc.

As an example, when the questionnaire writing request item 4710 is selected from the XR counseling room screen 4700 displayed on the first expert terminal, as illustrated in FIG. 48, the first expert terminal displays a questionnaire list screen 4800 corresponding to the selected questionnaire writing request item 4710.

Thereafter, when a specific questionnaire is selected from one or more questionnaires included in the questionnaire list screen displayed on the expert terminal 300, the expert terminal 300 displays detailed information on the selected specific questionnaire. Here, the detailed information on the specific questionnaire includes a preview item, a question content item for each question, a view item for each question, a modification item, a confirmation item, a sending item, etc. In this case, the expert terminal 300 may modify content of at least one question and view an item among one or more question content items and view items included in the selected specific questionnaire, and then transmit a specific questionnaire, in which the modified content is reflected (or applied/updated), to the terminal 100 corresponding to the corresponding user via the server 200.

In addition, when a preset transmission item displayed on one side of the detailed information on a specific questionnaire of the expert terminal 300 is selected, the expert terminal 300 transmits the selected specific questionnaire to the terminal 100 corresponding to the corresponding user via the server 200.

That is, when a preset sending item displayed on one side of the detailed information on the specific questionnaire of the expert terminal 300 is selected, the expert terminal 300 transmits the selected specific questionnaire, the questionnaire writing request information, the identification information of the expert terminal 300, the unique information (or identification information of the terminal 100 related to the user) related to the user who participates in the XR counseling room, etc., to the server 200. In this case, after the specific questionnaire (or at least one specific questionnaire) is selected from one or more questionnaires included in the questionnaire list screen displayed on the expert terminal 300, when the preset sending item displayed on one side of the questionnaire list screen is selected, the expert terminal 300 may transmit the selected specific questionnaire, the questionnaire writing request information, the identification information of the expert terminal 300, the unique information related to the user (or identification information of the terminal 100 related to the user) who participates in the XR counseling room, etc., to the server 200.

In addition, the server 200 receives the specific questionnaire, the questionnaire writing request information, the identification information of the expert terminal 300, the unique information related to the user who participates in the XR counseling room (or identification information of the terminal 100 related to the corresponding user), etc., that are transmitted from the expert terminal 300.

In addition, the server 200 transmits the specific questionnaire, the questionnaire writing request information, the identification information of the expert terminal 300, etc., to the terminal 100 corresponding to the unique information related to the user participating in the XR counseling room.

In addition, the expert terminal 300 displays information indicating that a response is waiting for a request to fill out the questionnaire (or information indicating that the corresponding user is filling out the questionnaire) on one side of the counseling screen area.

Figure 49:
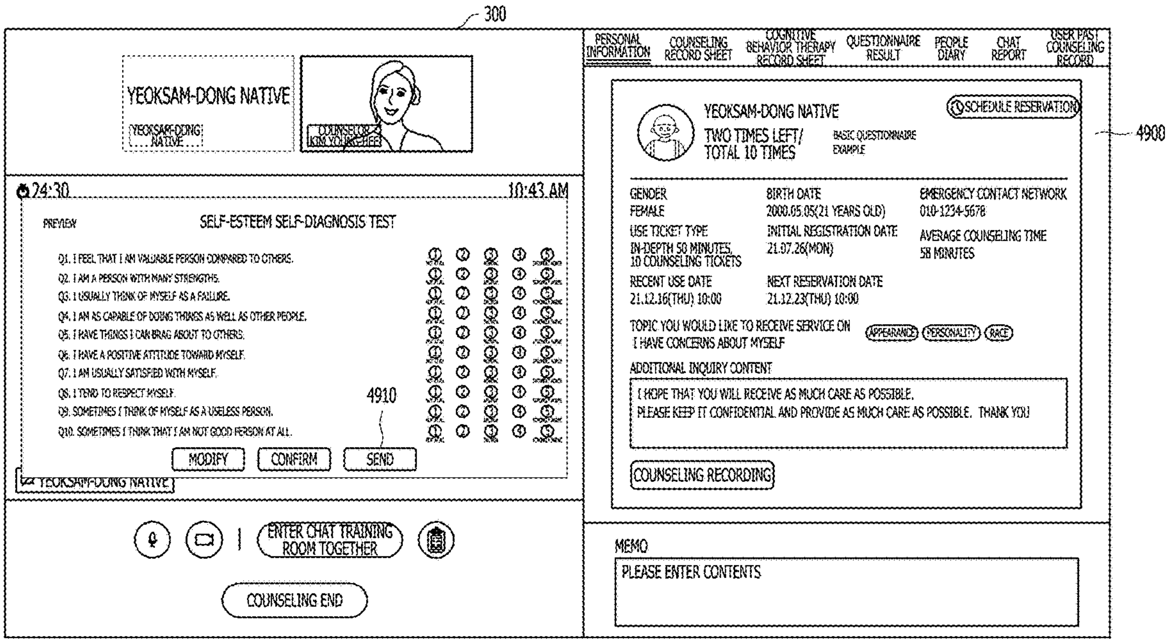

For example, when a self-esteem self-diagnosis test 4810 is selected from the questionnaire list screen 4800 displayed on the first expert terminal, as illustrated in FIG. 49, the first expert terminal displays the detailed information 4900 on the selected self-esteem self-diagnosis test 4810.

In addition, when a sending item 4910 displayed on one side of the detailed information 4900 on the self-esteem self-diagnosis test is selected, the first expert terminal transmits the self-esteem self-diagnosis test, the first questionnaire writing request information, the identification information of the first expert terminal, the identification information of the first terminal related to the first user who participates in the corresponding XR counseling room, etc., to the server 200.

Figure 50:
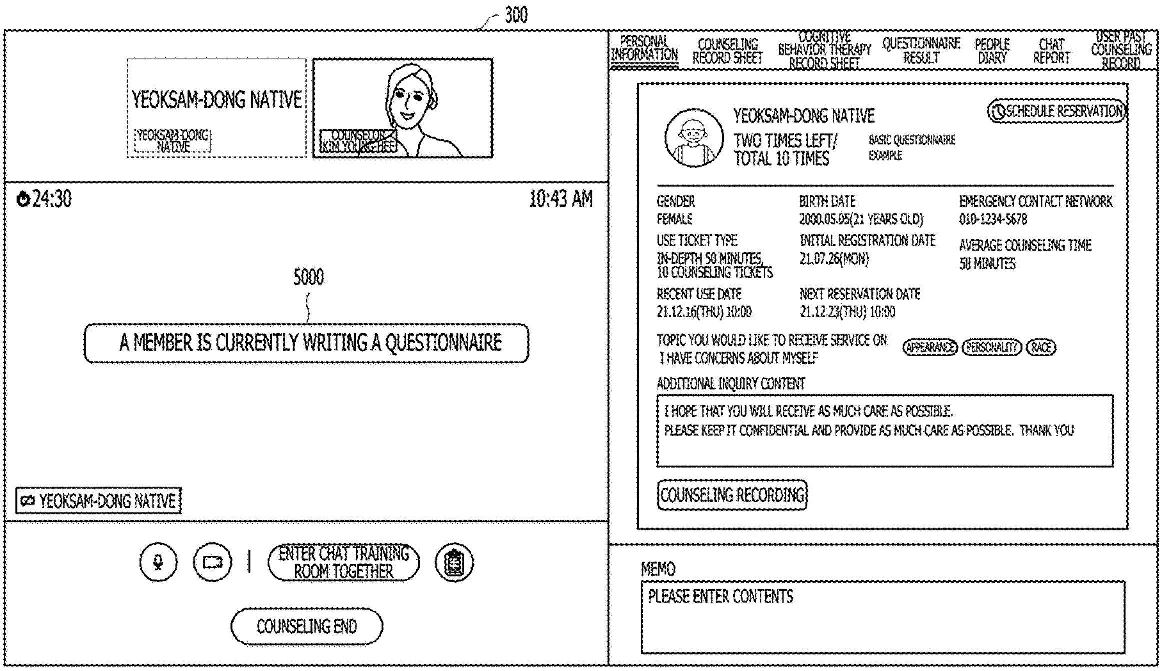

In addition, as illustrated in FIG. 50, the first expert terminal displays information 5000 indicating that the corresponding first user of the terminal is filling out the questionnaire.

In addition, the server 200 receives the self-esteem self-diagnosis test, the first questionnaire writing request information, the identification information of the first expert terminal, the identification information of the first terminal related to the first user who participates in the corresponding XR counseling room, etc., that are transmitted from the first expert terminal.

In addition, the server 200 transmits the received self-esteem self-diagnosis test, the first questionnaire writing request information, the identification information of the first expert terminal, etc., to the first terminal corresponding to the identification information of the first terminal (S560).

Thereafter, the expert terminal 300 receives questionnaire response information transmitted from the corresponding terminal 100 in response to a specific previously transmitted questionnaire. In this case, after transmitting the specific questionnaire, the questionnaire writing request information, etc., from the expert terminal 300 to the terminal 100, when the questionnaire response information is not received from the terminal 100 within a preset time (e.g., 10 minutes), the expert terminal 300 may retransmit the corresponding specific questionnaire, etc., to the terminal 100 or end the counseling function in the corresponding XR counseling room (or metaverse chat room).

In addition, the expert terminal 300 generates a response result by adding up preset scores for the view items for each question corresponding to the question content for each question included in the corresponding specific questionnaire. Here, when a respondent (or user) responds to view items for each question on a 1 to 5 point scale (e.g., very much, yes, neutral, no, not at all), a 1 to 4 point scale (e.g., very much, yes, no, not at all), etc., the response result includes a score obtained by adding up the corresponding response scores (or scores corresponding to answers to each question included in the questionnaire response information).

In addition, the expert terminal 300 transmits (or provides) the generated response results, etc., to the terminal 100 through the server 200.

In addition, the expert terminal 300 displays (or outputs) the generated response results.

In addition, the expert terminal 300 is linked with the terminal 100 and the server 200 through the generated XR counseling room screen and performs the counseling function with the counseling requester of the corresponding terminal 100.

In this way, the expert terminal 300 may invite the counseling requester corresponding to the counseling schedule to the XR counseling room screen generated through the XR room-creation menu according to the reservation time on the reservation day to perform the counseling function.

As an example, the first expert terminal receives the self-esteem self-diagnosis response information transmitted from the first terminal in response to the previously transmitted self-esteem self-diagnosis test.

In addition, the first expert terminal generates a first response result by adding up the scores corresponding to the viewing items selected by each of the users included in the received self-esteem self-diagnosis response information.

In addition, the first expert terminal transmits the generated first response result, etc., to the first terminal via the server 200.

Figure 51:
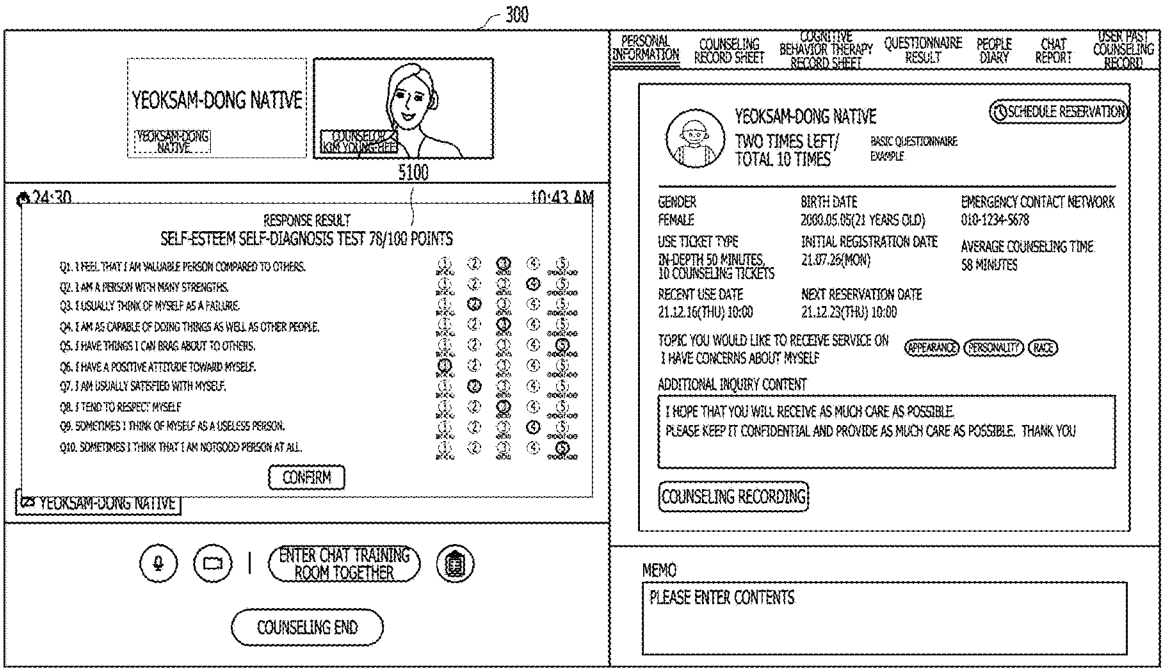

In addition, as illustrated in FIG. 51, the first expert terminal displays the generated first response result 5100 (S570).

In addition, while a counseling function with the corresponding expert and the corresponding specific user is performed through the XR counseling room screen displayed on the expert terminal 300, to participate in a metaverse chat room related to a specific theme and perform a monitoring (or training/counseling) function for the corresponding specific user through the chat function, when an entry item is selected along with the chat training room displayed on one side of the XR counseling room screen, the expert terminal 300 creates a new metaverse chat room or selects a specific metaverse chat room from the one or more pre-created metaverse chat rooms according to the corresponding expert selection, and then displays the expert's position selection screen for selecting whether the counselor (or expert) enters as a spectator or as a chatter to the expert terminal 300. Here, the expert's position selection screen includes a spectator item, a participant item, a go-back item, an entry item, etc. In this case, the expert's position selection screen may be displayed in the form of a pop-up window on one side of the counseling screen area.

Figure 52:
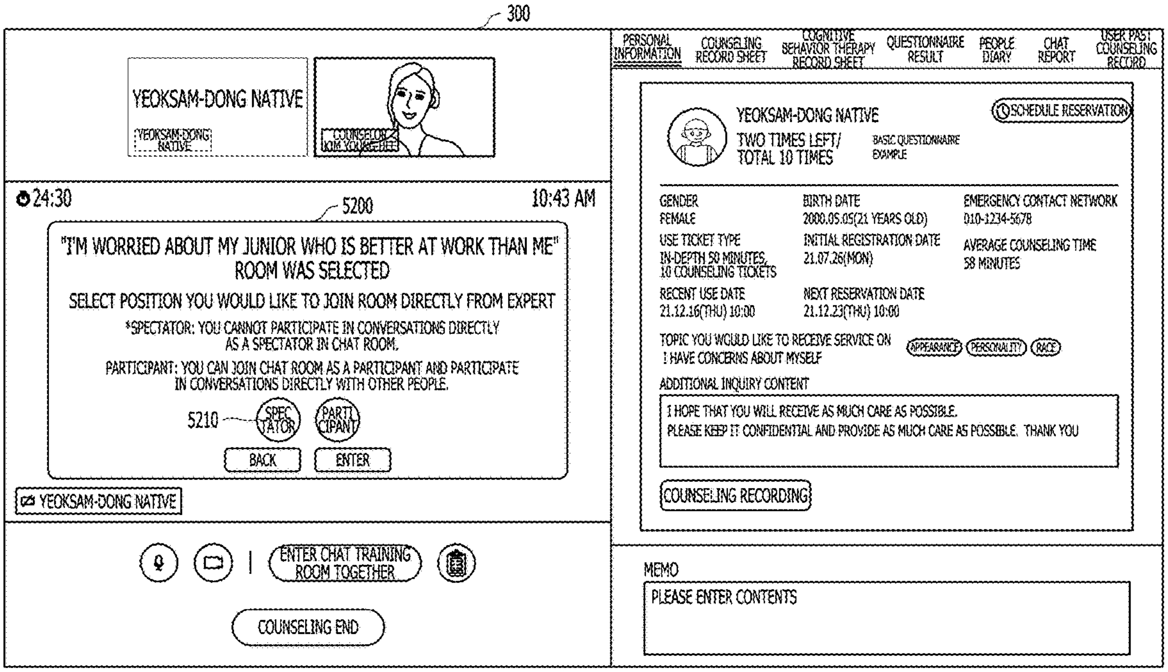

As an example, when a chat training room entry item 4720 is selected from the XR counseling room screen 4700 displayed on the first expert terminal, as illustrated in FIG. 52, the first expert terminal displays an expert's position selection screen 5200 corresponding to the entry item 4720 along with the selected chat training room. In this case, the first expert terminal may select the eleventh topic talk metaverse chat room S580

Thereafter, when a spectator item or a chatter item is selected from the expert's position selection screen displayed on the expert terminal 300 according to the expert selection (or expert input/touch/control) of the expert terminal 300, the expert terminal 300 is linked with the server 200 and the terminal 100 and enters (or participates in) the metaverse chat room as the spectator corresponding to the selected spectator item or as the chatter corresponding to the selected chatter item, and the terminal 100 related to the specific user in counseling is linked with the server 200 and enters (or participates in) the corresponding metaverse chat room as the chatter along with the corresponding expert. Here, the metaverse chat room includes the metaverse chat room newly created in the expert terminal 300, the specific metaverse chat room selected from the one or more pre-created metaverse chat rooms, etc. In this case, the expert terminal 300 displays a waiting screen according to the entry into the metaverse chat room. Here, the waiting screen includes the type of the corresponding chat room, the topic, the chat room name, the keyword (or hashtag), the nickname (or screen name) of the user who enters the corresponding chat room, the chat temperature, and the number of chats (or the number of times someone has participated in the chat room), etc. In this case, the chat temperature may be calculated based on the number of chats, the received evaluation results, etc. In addition, when the expert terminal 300 participates in the metaverse chat room as the spectator, the expert terminal 300 and one side of the screen of the terminal 100 may display an image, an emoticon, etc., indicating that the expert terminal 300 (or the expert of the expert terminal 300) is participating as the spectator.

In addition, when the room leader who opens the corresponding metaverse chat room selects the preset start menu while the number of people (or the number of participants) set in the corresponding metaverse chat room is met, the expert terminal 300 is a spectator or chatter, and is linked with the corresponding terminal 100, one or more other terminals 100 (not illustrated) owned by one or more other users who entered the corresponding metaverse chat room, and the server 200 to perform the chat function related to the specific topic of the metaverse chat room. In this case, the terminal 100 is linked with the server 200 and uses the avatar (or character) preset in the terminal 100 to change (or apply/reflect) and display the expression (e.g., including happiness, joy, excitement, passion, pleasure, frustration, outrage, sadness, surprise, pain, rage, etc.) of the corresponding avatar according to the analysis (e.g., including a change in the user's gaze, a change in facial expression, a voice tremor, a change in heart rate, etc.) of the psychological state of the corresponding user's voice and/or facial expression while the user of the terminal 100 is chatting.

In this way, the expert terminal 300 is a spectator or chatter, and may freely perform (or monitor) the chat function with other users, including the user of the terminal 100.

Figure 53:
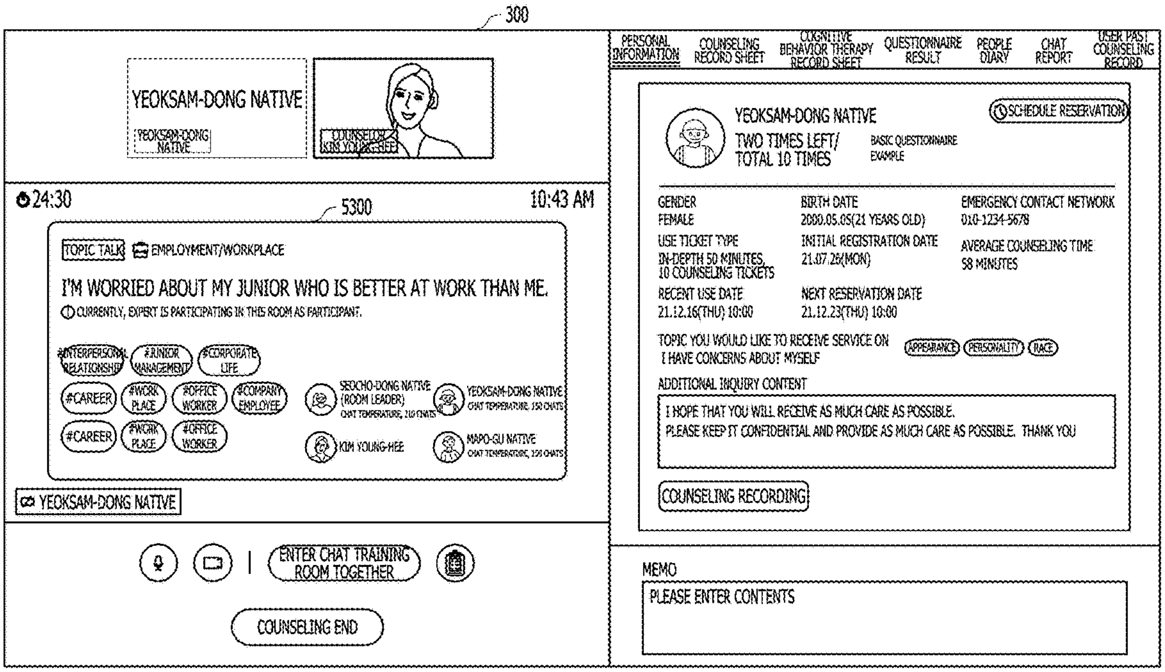

For example, when a spectator item 5210 is selected from the expert's position selection screen 5200 displayed on the first expert terminal according to the first expert selection, as illustrated in FIG. 53, the first expert terminal is linked with the server 200 and the first terminal to display the selected eleventh topic talk metaverse chat room screen (or eleventh topic talk metaverse chat room waiting screen) 5300.

In addition, while a room leader, a Seongsu-dong native (or a terminal owned by the Seongsu-dong native), who opens the corresponding chat room selects a preset start menu while the preset number of people (e.g., 4 people) in relation to the eleventh topic talk metaverse chat room is met, the first expert terminal confirms the performance of the chat function between a plurality of users including the first user as the spectator (S590).

Thereafter, when the chat function in the specific metaverse chat room in which the expert terminal 300 and the terminal 100 participate ends, the expert terminal 300 generates the feedback information related to the user of the terminal 100. Here, the feedback information includes information such as an expert's view (or opinion) regarding the psychological counseling function, the speech lesson function, the mentor function, etc., performed in the chat room.

In addition, the expert terminal 300 is linked with the server 200 to map (or match/link) the generated feedback information, the information on the metaverse chat room, the user information (or expert information) of the expert terminal 300, and the member information (or user information/personal information) of the user of the terminal 100 and store (or register/manage) the mapped generated feedback information in the server 200.

In addition, the expert terminal 300 provides (or transmits) the generated feedback information to the terminal 100 through the server 200.

For example, when the chat function in the eleventh topic talk metaverse chat room ends, the first expert terminal generates the eleventh feedback information according to the performance of the chat function in the corresponding eleventh topic talk metaverse chat room, and transmits the generated eleventh feedback information, the information on the corresponding eleventh topic talk metaverse chat room, the identification information of the first expert terminal, etc., to the server 200.

In addition, the server 200 receives the eleventh feedback information, the information on the corresponding eleventh topic talk metaverse chat room, the identification information of the first expert terminal, etc., that are transmitted from the first expert terminal.

In addition, the server 200 transmits the eleventh feedback information to the first terminal.

In addition, the first terminal receives the eleventh feedback information transmitted from the server 200 and displays the received eleventh feedback information (S600).

In addition, when the personal information item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the personal information screen seen by the expert corresponding to the selected personal information item in the corresponding additional detailed information display area. Here, the personal information screen seen by the expert (or detailed personal information display screen) includes an item for displaying whether a user is currently online for displaying the information on the corresponding specific user's real-time connection state, a character (or image/photo) item of the corresponding specific user, a nickname item of the corresponding specific user, an item (e.g., including topic talk, role-playing, theme practice, etc.) for displaying the type of counseling cases in progress when the corresponding specific user is currently counseling, an item (or counseling progress situation item) for displaying the remaining number of uses out of the total number of use, a basic questionnaire view item for confirming the basic questionnaire content written by the corresponding specific user, a schedule reservation item for reserving the counseling schedule with the expert of the corresponding expert terminal 300, a gender item, a birth date item, an emergency contact network (or phone number) item, a use ticket/counseling ticket type item (e.g., time, the number of sessions, etc., for each type), an initial registration date item, an average counseling time display item, a most recent use date/counseling date display item (or recently completed counseling date), a next reservation date display item (or counseling reservation date display item), an item for displaying the service/topic on which a user would like to receive counseling, an item (or additional inquiry content item) for displaying service/content on which a user would like to receive counseling, a counseling recording item for recording the counseling content, a memo item, etc. In this case, when the expert terminal 300 displays the XR counseling room screen, the expert terminal 300 may display a personal information screen corresponding to the personal information item set by default in the additional detailed information display area.

As an example, when a personal information item 4730 included in the detailed member information display area in the XR counseling room screen 4700 is selected according to the first expert selection while the counseling function between the first expert, Kim Young-Hee, and the user, a Yeoksam-dong native, is being performed through the generated XR counseling room screen 4700, as illustrated in FIG. 47, the first expert terminal displays a personal information screen seen by the expert 4731 related to the corresponding Yeoksam-dong native corresponding to the selected personal information item 4730 in the additional detailed information display area. In this case, when the first expert terminal displays the XR counseling room screen, the personal information screen seen by the expert 4731 corresponding to the personal information item 4730 may be displayed as a default (S610).

In addition, while the counseling function with the corresponding expert and the corresponding specific user is performed through the XR counseling room screen displayed on the expert terminal 300, when a counseling record sheet item included in the detailed member information display area in the corresponding XR counseling room screen is selected, the expert terminal 300 is linked with the server 200 to display the detailed information related to the selected counseling record sheet item in the corresponding additional detailed information display area.

That is, when a counseling record sheet item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the counseling record sheet screen seen by the expert corresponding to the selected counseling record sheet item in the corresponding additional detailed information display area. Here, the counseling record sheet screen foreseen by the expert includes an additional item for adding the counseling record sheet related to the corresponding specific user, a deletion item for deleting the information on the specific counseling record case displayed on the corresponding counseling record sheet screen seen by the expert, a counseling content item by date and time, an expert item by date and time (or person in charge/counselor item by date and time), a counseling time item by date and time, a detail view item for the counseling record sheet by date and time, a memo item for recording simple memo content, etc.

Figure 54:
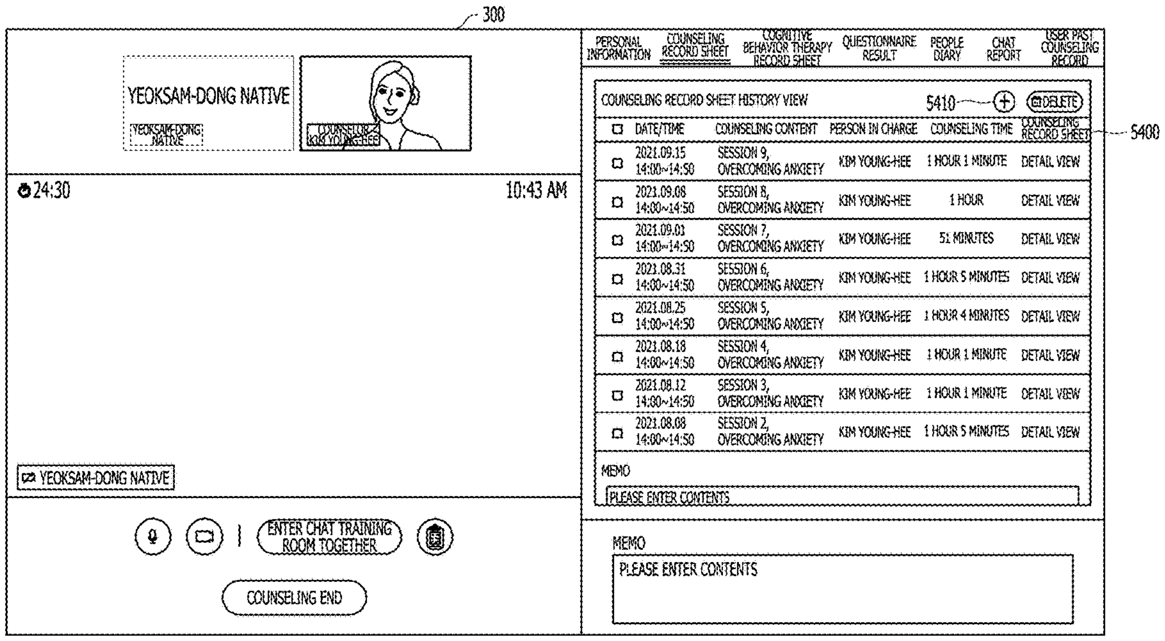

As an example, when a counseling record sheet item 4740 included in the detailed member information display area in the XR counseling room screen 4700 is selected according to the first expert selection while the counseling function between the first expert, Kim Young-Hee, and the user, the Yeoksam-dong native, is being performed through the generated XR counseling room screen 4700, as illustrated in FIG. 54, the first expert terminal displays a counseling record sheet screen seen by the expert 5400 corresponding to the selected counseling record sheet item 4740 (S620).

Thereafter, when the additional item is selected from the counseling record sheet screen seen by the expert displayed on the expert terminal 300, to store (or record) counseling content related to a specific user currently in counseling, the expert terminal 300 is linked with the server 200 to display the counseling record sheet input screen corresponding to the selected additional item. Here, the counseling record sheet input screen includes a session number and counseling topic item, a specific user's nickname item (or name item), an expert name item (or person in charge name/counseling name item), a current recording time item, a user's subjective item, an expert's objective item, a future plan item, a feedback item to a user, a temporary storage item for temporarily storing written content, a writing completion item for storing written content, etc. In this case, the expert's objective item may vary depending on whether the expert of the expert terminal 300 is a mentor expert, a psychological counseling expert, or a speech lesson expert. That is, when the expert of the expert terminal 300 is a mentor expert, examples of the expert's objective item include a common checklist item (e.g., including anxiety, assertiveness/confidence, mind control, communication skills, listening skills, sociability, situational judgment power, will to improve, strength/information for each item, brief description for each item, etc.), a mentoring checklist item (e.g., professionalism, interest/degree of interest, propensity coincidence, counseling purpose, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc. In addition, when the expert of the expert terminal 300 is a psychological counseling expert, examples of the expert's objective item include a common checklist item (e.g., anxiety, assertiveness/confidence, mind control, communication skills, listening skills, sociability, situational judgment power, will to improve, strength/information for each item, brief description for each item, etc.), a psychological state checklist item (e.g., social anxiety, depression/ anxiety, panic disorder, sleep disorder, bipolar disorder, alcoholic dementia, addiction (e.g., game addiction, drug addiction, gambling addiction, etc.), cognitive distortion, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc. In addition, when the expert of the expert terminal 300 is a speech lesson expert, examples of the expert's objective item include a common checklist item (e.g., anxiety, assertiveness/confidence, mind control, communication skills, listening skills, sociability, situational judgment power, will to improve, strength/information for each item, brief description for each item, etc.), a speech checklist item (e.g., including fluency, logic, speed/pace, vocalization/tone, leadership, etc.), a problem situation item (e.g., a chat situation, a presentation situation, an interview situation, etc.), an expert recommendation item (e.g., "I think you need to go to the hospital," "I think you would benefit from psychological counseling," "I think you would benefit from speech training," "I think you would benefit more from help from a specific mentor expert," etc.), a difficult target item (e.g., family, a romantic relationship, a friend, a workplace, others, etc.), a topic/situation required for training (e.g., a daily topic, a professional topic, etc.), an expert's opinion item, etc.

In addition, the expert terminal 300 receives counseling record information including a plurality of different input values corresponding to a plurality of different input items included in the counseling record sheet input screen displayed on the expert terminal 300. Here, the counseling record information includes session number and counseling topic information, nickname information (or name information) of a specific user, expert name information (or person in charge name/counselor name information), current record time information, a user's subjective information, an expert's objective information, future plan information, feedback information to a user, etc. In this case, the specific user's nickname information, the expert name information, the current recording time information, etc., may be automatically input under the control of the server 200.

In addition, the expert terminal 300 is linked with the server 200 to map the received counseling record information with the personal information corresponding to the corresponding specific user and the user information of the expert terminal 300 and store (or register) the mapped information in the server 200.

In addition, when the detail view item displayed on one side of a specific counseling record sheet case is selected from the counseling record sheet screen for the expert displayed on the expert terminal 300, the expert terminal 300 is linked with the server 200 to display the detailed counseling record sheet information on the specific counseling record sheet case related to the selected detail view item. Here, the detailed counseling record sheet information includes a counseling record sheet writing date item related to the corresponding specific counseling record sheet case, a modification item for modifying the content of the corresponding specific counseling record sheet, an output item for outputting the content of the corresponding specific counseling record sheet, a deletion item for deleting the content of the corresponding specific counseling record sheet, a session number and counseling topic item, an expert name item, a last modified date display item, a user's subjective item, an expert's objective item, a future plan item, a feedback item to a user, etc. In this case, as described above, the expert's objective item may vary depending on whether the expert of the expert terminal 300 is a mentor expert, a psychological counseling expert, or a speech lesson expert.

In addition, the expert terminal 300 may additionally perform a modification function, an output function, a deletion function, etc., on the content of the detailed counseling record sheet information being displayed on the expert terminal 300.

Figure 55:
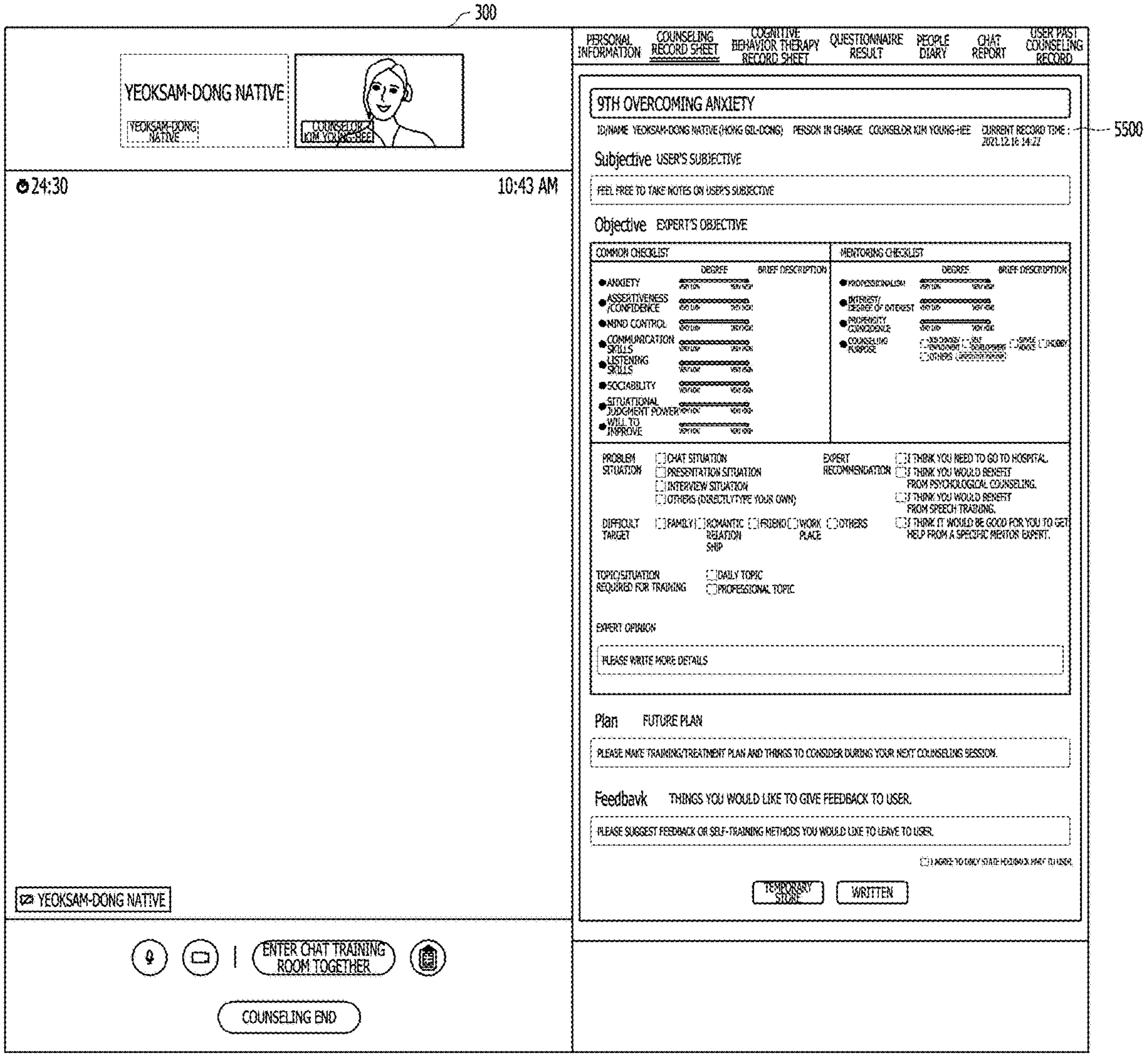

As another example, when the first expert is the mentor expert and an additional item 5410 is selected from the counseling record sheet screen seen by the expert 5400 displayed on the first expert terminal, as illustrated in FIG. 55, to record counseling content for the current date (e.g., Thursday, Dec. 16, 2021), the first expert terminal displays a counseling record sheet input screen 5500 corresponding to the selected additional item 5410.

In addition, the first expert terminal receives eleventh counseling record information that includes a 9th session and a topic (e.g., session 9, overcoming anxiety) according to the first expert input of the corresponding first expert terminal in the counseling record sheet input screen 5500 displayed on the corresponding first expert terminal, an eleventh user's nickname and name (e.g., Yeoksam-dong native, Hong Gil-dong), a first expert name (e.g., expert Kim Young-Hee), an eleventh current recording time (e.g., Dec. 16, 2021, 10: 5:10 AM), an eleventh user's subjective (e.g., "I'm planning to learn coding and change jobs," "I'm not sure if I'm right for the job," and "I want to get interview and qualification information"), an eleventh common checklist (e.g., including anxiety: very high, assertiveness/confidence: very low, mind control: very low, communication skills: average, listening skills: average, sociality: average, situational judgment power: average, will to improve: average, etc.) included in an eleventh expert's objective, an eleventh mentoring checklist included in an eleventh expert's objective (e.g., including professionalism: very low, interest/degree of interest: average, propensity coincidence: average, counseling purpose: others, etc.), an eleventh problem situation (e.g., including presentation situation-large scale, etc.) included in an eleventh expert's objective, an eleventh recommendation (e.g., "I think you need to go to the hospital," etc.) included in an eleventh expert's objective, an eleventh difficult target (e.g., including family-husband, etc.) included in an eleventh expert's objective, a topic (e.g., including a daily topic, etc.) necessary for eleventh training included in an eleventh expert's objective, an eleventh expert opinion (e.g., "There appears to be serious cognitive distortion and a lot of distrust toward her husband." "She wants to know how to speak nicely, but can't seem to overcome her distrust in her husband," etc.), an eleventh future plan (e.g., "We plan to give more advice to develop expertise in the field for this job change," "We also plan to transmit more information through various interviews and talk rooms on related topics," etc.), feedback to give to an eleventh user (e.g., "It is a good idea to prepare for certification in the second half of 2022"), etc.

In addition, the first expert terminal is linked with the server 200 to map the received eleventh counseling record information, the first user information corresponding to the first expert, the first personal information corresponding to the Yeoksam-dong native, etc., and store the mapped information.

Figure 56:
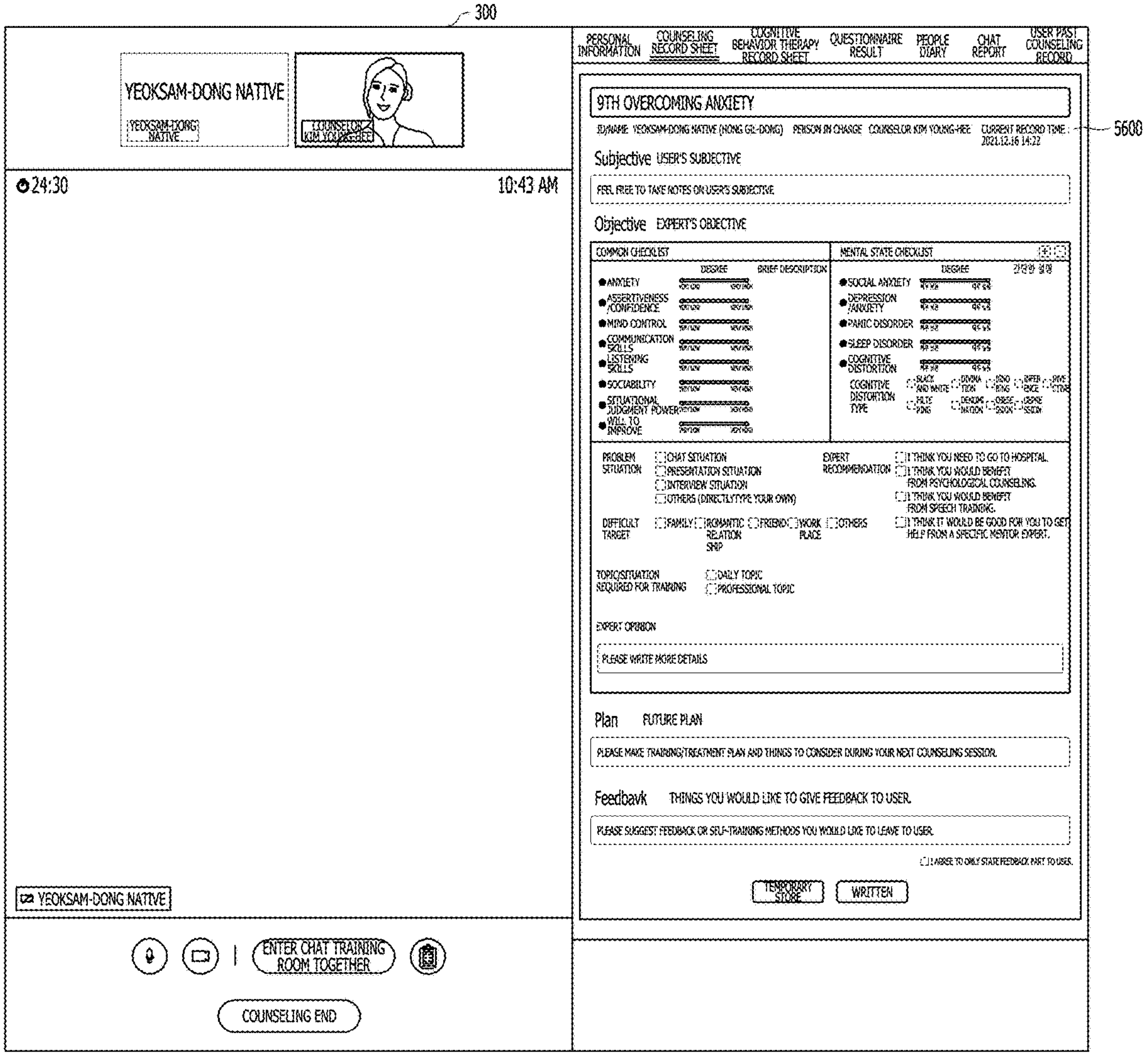

As another example, when the first expert is the psychological counseling expert and an additional item 5410 is selected from the counseling record sheet screen seen by the expert 5400 and displayed on the first expert terminal, as illustrated in FIG. 56, to record counseling content for the current date (e.g., Thursday, Dec. 16, 2021), the first expert terminal displays a counseling record sheet input screen 5600 corresponding to the selected additional item 5410. In this case, the counseling record sheet input screen 5600 may be in a state where the mentoring checklist has been changed to the content of the psychological state checklist items compared to the previous mentor expert.

Figure 57:
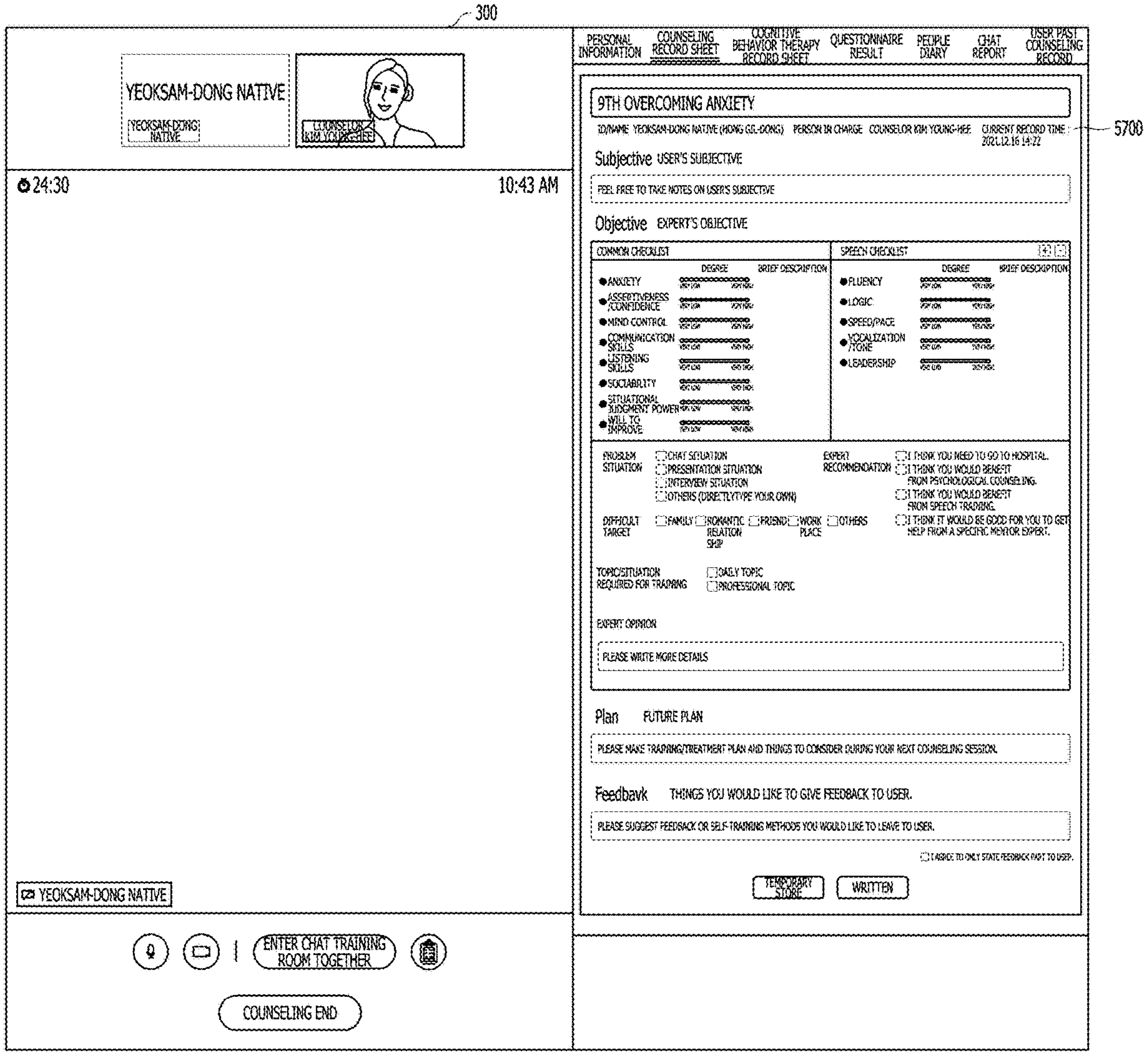

As another example, when the first expert is the speech lesson expert and an additional item 5410 is selected from the counseling record sheet screen seen by the expert 5400 and displayed on the first expert terminal, as illustrated in FIG. 57, to record counseling content for the current date (e.g., Thursday, Dec. 16, 2021), the first expert terminal displays a counseling record sheet input screen 5700 corresponding to the selected additional item 5410. In this case, the counseling record sheet input screen 5700 may be in a state where the mentoring checklist has been changed to the content of the speech checklist item compared to the previous mentor expert (S630).

In addition, when a cognitive behavior therapy record sheet item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected cognitive behavior therapy record sheet item in the corresponding additional detailed information display area.

That is, when the cognitive behavior therapy record sheet included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the cognitive behavior therapy record sheet screen seen by the expert corresponding to the selected cognitive behavior therapy record sheet in the corresponding additional detailed information display area. Here, the cognitive behavior therapy record sheet screen seen by the expert includes an additional item (or an adding item) for adding the cognitive behavior therapy record sheet related to the corresponding specific user, a deletion item for deleting the information on the specific cognitive behavior therapy record sheet displayed on the cognitive behavior therapy record sheet screen for the corresponding expert, a record sheet item written together during counseling for providing the list of the corresponding cognitive behavior therapy record sheets generated by the user in counseling, a record sheet item generated by the user alone for providing the list of the cognitive behavior therapy record sheets generated by the corresponding specific user, etc. In addition, examples of the record sheet item written together during the counseling include a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), etc. In addition, examples of the record sheet item written by the user alone include a date and time item, a record sheet title item by date and time, an item on whether to write the cognitive behavior therapy record sheet before training by date and time, an item on whether to write the cognitive behavior therapy record sheet after training by date and time, a detail view item for the counseling record sheet (or a detail view item for the cognitive behavior therapy record sheet), an item on whether to confirm the written cognitive behavior therapy record sheet (e.g., confirmation needed, confirmation not needed, confirmed, etc.), etc.

Figure 58:
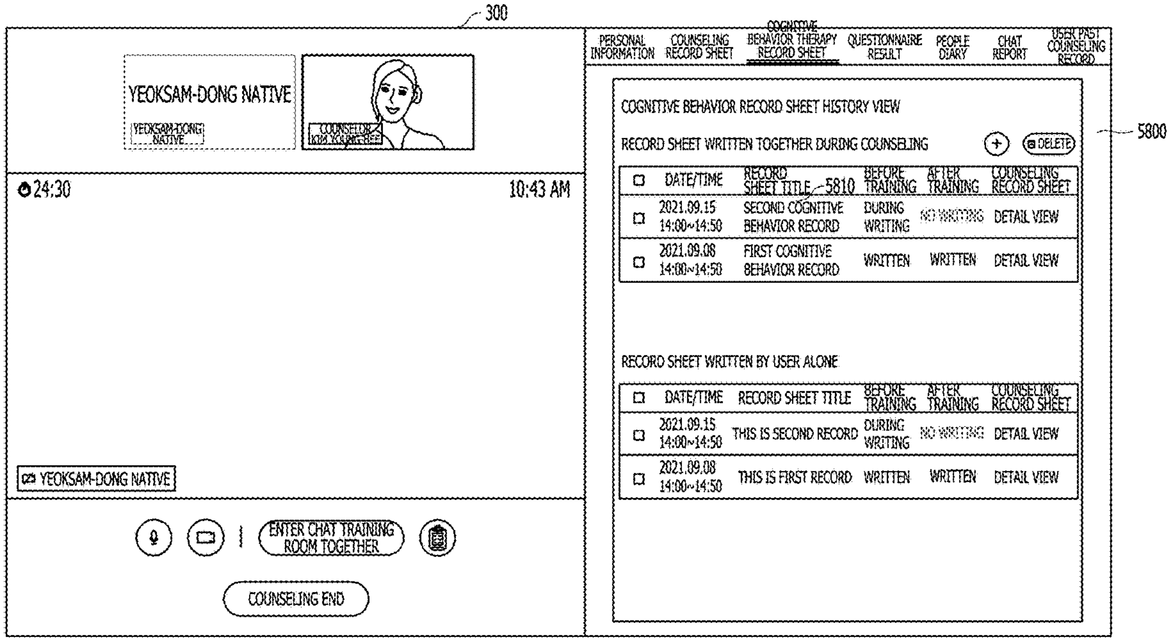

As an example, when a cognitive behavior therapy record sheet item 4750 included in the detailed member information display area in the XR counseling room screen 4700 is selected according to the first expert selection while the counseling function between the first expert, Kim Young-Hee, and the user, a Yeoksam-dong native, is being performed through the generated XR counseling room screen 4700, as illustrated in FIG. 58, the first expert terminal displays a cognitive behavior therapy record sheet screen seen by the expert 5800 corresponding to the selected cognitive behavior therapy record sheet item 4750 (S640).

Thereafter, when the specific cognitive behavior therapy record sheet is selected from the cognitive behavior therapy record sheet screen for the expert displayed on the expert terminal 300 (or when an item being written or an item written before/after the training related to the specific cognitive behavior therapy record sheet is selected), the expert terminal 300 is linked with the server 200 to display the detailed cognitive behavior therapy record sheet information on the specific cognitive behavior therapy record sheet case related to the selected specific cognitive behavior therapy record sheet. Here, the detailed cognitive behavior therapy record sheet information (or detailed cognitive behavior therapy record sheet information related to the selected specific cognitive behavior therapy record sheet) includes a displayed session number and counseling topics, a writer ID and name display item, a writing state display item before/after training (e.g., including not written, being written, written, etc.), a last modified date display item, a cognitive behavior information item for each item before training, a cognitive behavior information item for each item after training, etc. In addition, the cognitive behavior information item for each item before training includes an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for displaying "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, the cognitive behavior information item for each item after training includes an item (e.g., improvement-related item, anxiety-related item, etc.) for displaying "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/rage, irritation, disbelief, displeasure, disappointment, sadness/depression, anxiety, tiredness, fatigue, frustration, etc.) for selecting how one feels now, and an item for displaying "What did you learn?" etc.

In addition, the expert terminal 300 may additionally perform a modification function, an output function, a deletion function, etc., on the content of the detailed cognitive behavior therapy record sheet information being displayed on the expert terminal 300.

Figure 59:
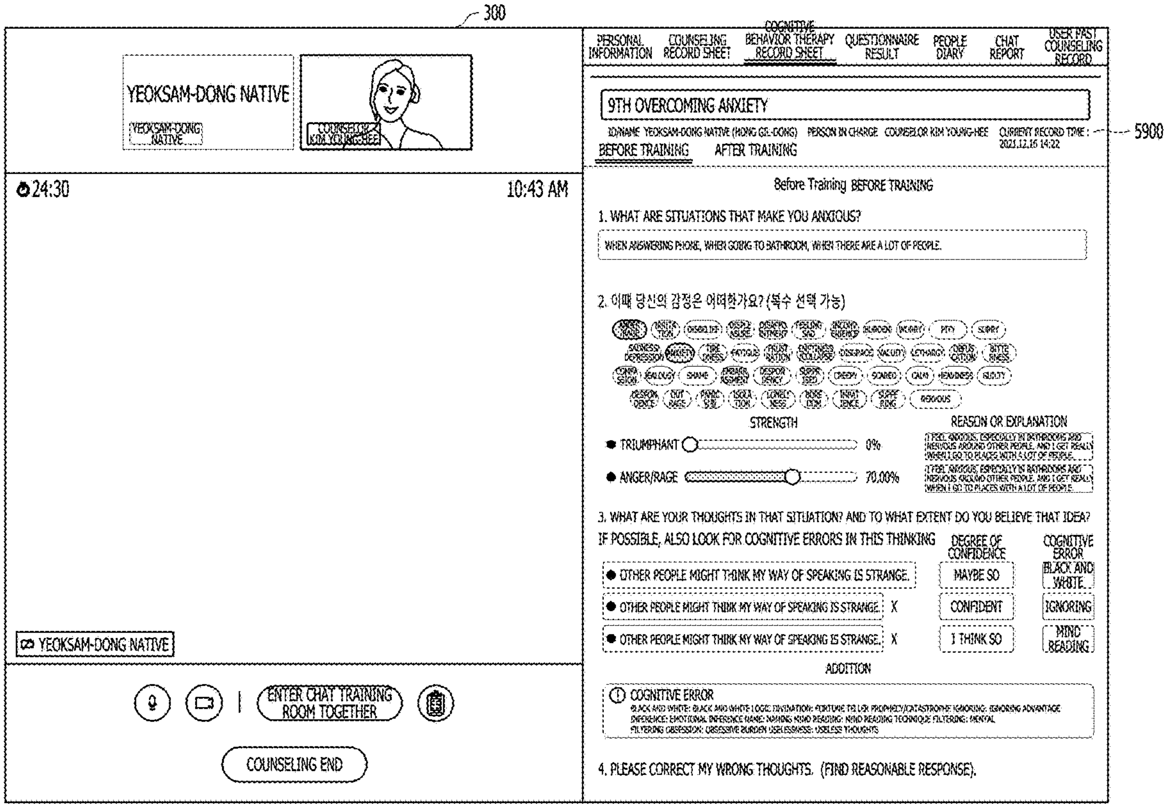

As an example, when a second cognitive behavior record case 5810 dated Sep. 15, 2021, is selected from the cognitive behavior therapy record sheet screen seen by the expert 5810 and displayed on the first expert terminal, as illustrated in FIG. 59, the first expert terminal displays second detailed cognitive behavior therapy record sheet information 5900 of the corresponding Yeoksam-dong native dated Sep. 15, 2021, that is related to the selected second cognitive behavior record case 5810.

In addition, when a questionnaire result item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected questionnaire result item in the corresponding additional detailed information display area.

That is, when the questionnaire result item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the questionnaire result screen viewed by the expert corresponding to the selected questionnaire result item in the corresponding additional detailed information display area. Here, the questionnaire result screen viewed by the expert includes the sorting item for providing the sorting function (including, for example, sorting by most recent, by format, etc.) in relation to one or more questionnaire cases performed by the corresponding specific user, the deletion item for deleting the selected questionnaire results (or selected questionnaire items), the file name item for each questionnaire, the last modified time item for each questionnaire, the format item for each questionnaire (or questionnaire type item), the result item (or detail view item) for each questionnaire, the memo item for recording simple memo content, etc.

Figure 60:
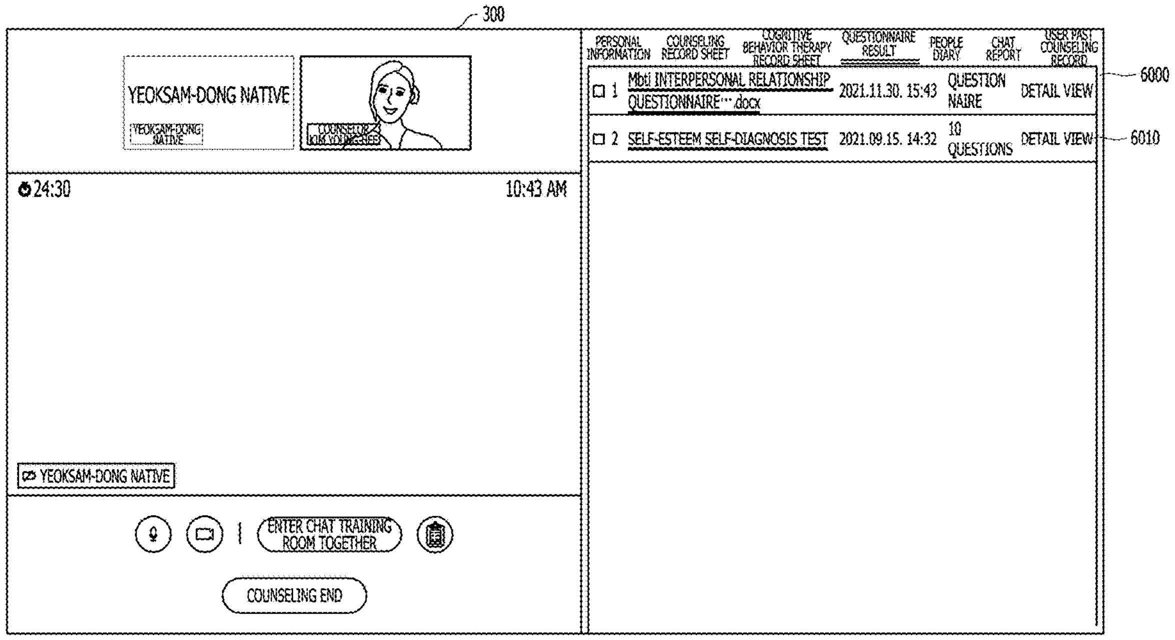

As an example, when the questionnaire result item 4760 included in the detailed member information display area in the XR counseling room screen 4700 is selected according to the first expert selection while the counseling function between the first expert, Kim Young-Hee, and the user, the Yeoksam-dong native, is being performed through the generated XR counseling room screen 4700, as illustrated in FIG. 60, the first expert terminal displays a questionnaire result screen seen by the expert 6000 corresponding to the selected questionnaire result item 4760 (S660).

Thereafter, when a specific file name (or specific file name item) is selected from one or more file names (or file name items) in the questionnaire result screen for the expert displayed on the expert terminal 300 or when a detailed item related to a specific file name is selected from one or more file names displayed on the questionnaire result screen viewed by the expert, the expert terminal 300 is linked with the server 200 to display detailed questionnaire information related to the selected specific file name or a specific file name corresponding to the selected detail view item. Here, the detailed questionnaire information is configured variously depending on the purpose of the questionnaire, and may include content of one or more questions for each questionnaire, answers/responses to the question content, etc.

Figure 61:
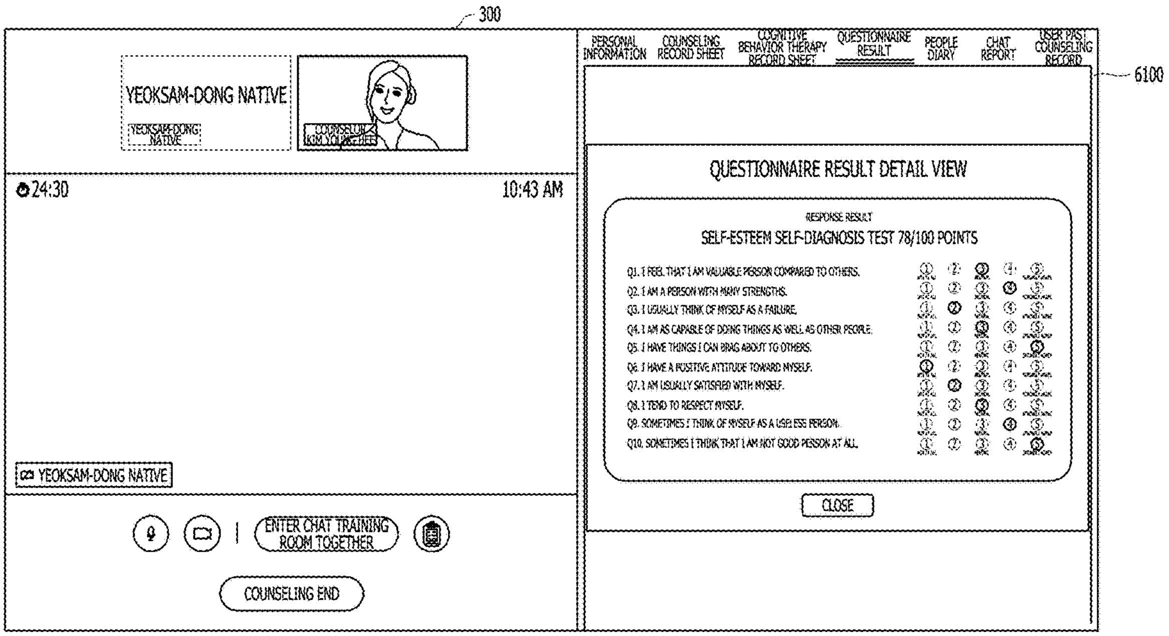

As an example, when a self-esteem self-diagnosis test questionnaire item 6010 is selected from the questionnaire result screen viewed by the expert 6000 and displayed on the first expert terminal, as illustrated in FIG. 61, the first expert terminal displays a self-esteem self-diagnosis test questionnaire result screen 6100 corresponding to the selected self-esteem self-diagnosis test questionnaire item 6010 in the form of a pop-up window (S670).

In addition, when the people diary item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected people diary item in the corresponding additional detailed information display area.

That is, when the people diary item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the people diary item viewed by the expert corresponding to the selected people diary item in the corresponding additional detailed information display area. Here, the people diary screen viewed by the expert includes a calendar screen, etc., including the emotional record state by date in preset period units (e.g., including 3 months, 6 months, etc.). In addition, when the calendar screen (or calendar item) is in a state where the emotional record information (e.g., including detailed emotional record information, simple emotional record information, etc.) is stored on a specific date, the calendar screen (or calendar item) includes an emotional record state (or mind state), such as images (or emoticon/avatar) representing feeling comfortable, normal, and uncomfortable, corresponding to mental state information, which is part of the information in the corresponding emotional record information on the corresponding specific date.

Figure 62:
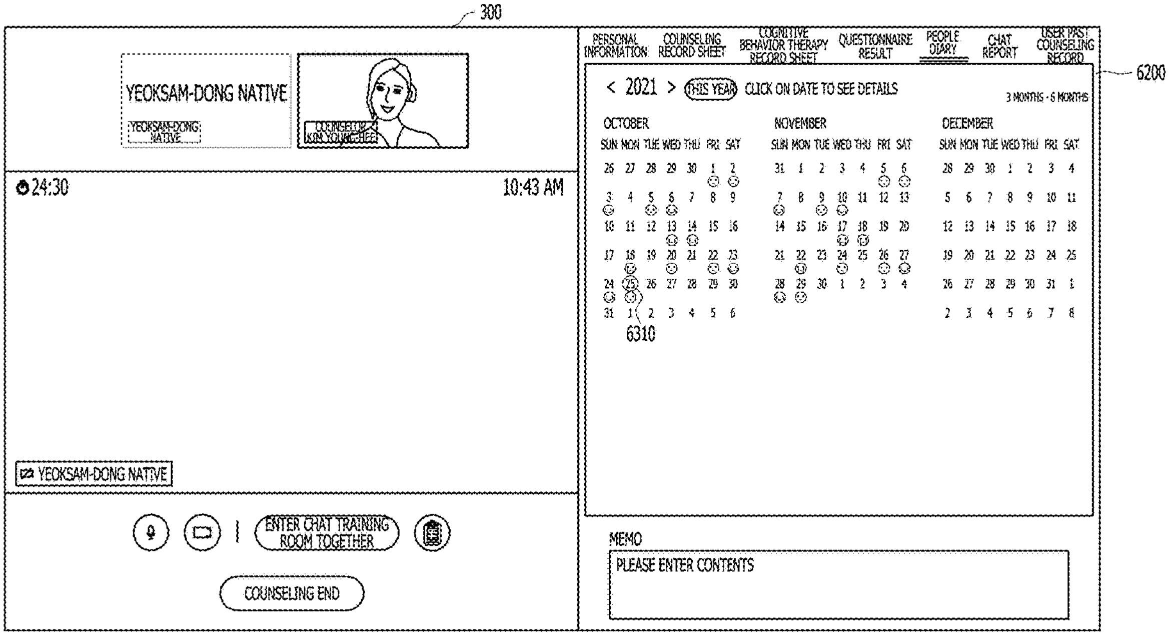

As an example, when the people diary item 4770 included in the detailed member information display area in the XR counseling room screen 4700 is selected according to the first expert selection while the counseling function between the first expert, Kim Young-Hee, and the user, the Yeoksam-dong native, is being performed through the generated XR counseling room screen 4700, as illustrated in FIG. 62, the first expert terminal displays a people diary screen viewed by the expert 6200 corresponding to the selected questionnaire result item 4770 (S680).

Thereafter, when a specific date including the emotional record state in the people diary screen viewed by the expert displayed on the expert terminal 300 is selected, the expert terminal 300 is linked with the server 200 to display the detailed people diary screen viewed by the expert related to the selected specific date. Here, the detailed people diary screen viewed by the expert includes a calendar screen (or calendar item) related to the corresponding specific date, an emotional record information item related to the corresponding specific date, an emotional pattern graph item for the corresponding month related to the corresponding specific date, an information display item related to the corresponding specific user's emotional record state for the corresponding week related to the corresponding specific date, etc.

In addition, examples of the emotional record information item include date information, situation information (e.g., including who else is there, a counterpart's actions, one's own actions, etc.), and emotional information (e.g., including one's emotional state, whether to express emotions, one's current emotions, etc.), review information (e.g., a comfort level in chat, future resolutions, personal notes, etc.), etc. In addition, examples of the information display item (or weekly emotional record information item) about the counseling requester's emotional record state include mental state items by day of the week (or date), a situation information item (e.g., who else is there, a counterpart's actions, one's own actions, etc.), an emotional information item (e.g., one's emotional state, whether to express emotions, one's current emotions, etc.), a review information item (e.g., a comfort level in chat, future resolutions, personal notes, etc.), a detail view item, etc.

Figure 63:
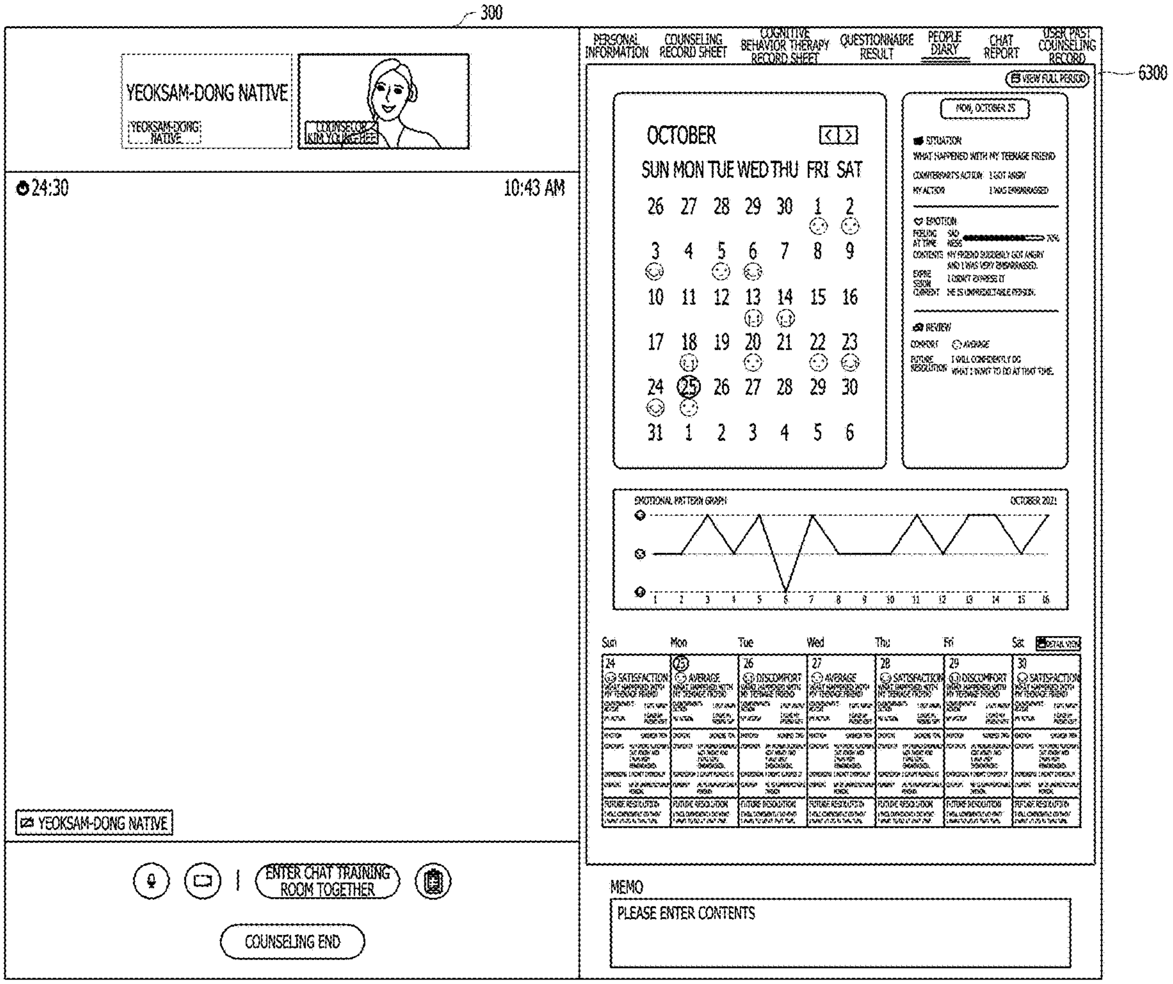

As an example, when Oct. 25, 2021, 6210 including the emotional record state in the people diary screen viewed by the expert 6200 and displayed on the first expert terminal is selected, as illustrated in FIG. 63, the first expert terminal displays a detailed people diary screen 6300 corresponding to the selected date (e.g., Oct. 25, 2021) 6210 (S690).

In addition, when a chart report item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected chart report item in the corresponding additional detailed information display area.

That is, when the chart report item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the chart report screen viewed by the expert corresponding to the selected chart report item in the corresponding additional detailed information display area. Here, the chat report screen viewed by the expert (or a "my report" screen used by the expert) includes an analysis result item for providing the analysis results according to the performance of the functions such as topic talk, role-playing, and theme practice in relation to the corresponding counseling requester, a participation list item for providing the participation list related to the chat list in which the corresponding user participates, a content display item (or a content display area) for displaying the detailed information according to the selection of the analysis result item or the participation list item, etc.

In addition, when a preset analysis result item is selected from the chat report screen viewed by the expert (or a "my report" screen used by the expert) displayed on the expert terminal 300, to provide the analysis results according to the performance of chat functions such as topic talk, role-playing, and theme practice in relation to the user of the terminal 100, the expert terminal 300 displays the detailed information corresponding to the selected analysis result menu in the content display area. In this case, when the preset chat report item is selected from the app execution result screen displayed on the expert terminal 300, the expert terminal 300 may display the analysis result screen (or the detailed information) corresponding to the analysis result item set by default in response to the selected chat report item in the content display area by default. Here, the analysis result item (or the analysis result screen/detailed information) includes a sort item for sorting functions related to all, topic talk, role-playing, theme practice, etc., a "number of times you've participated in the chat room" display item for displaying the number of times the user has participated in the chat room within a preset period, a period display item for displaying the corresponding preset period, a "number of times you've participated in the chat room by category" display item for displaying the number of times the user has participated in the chat room by category, a "free expression" index display item for displaying the "free expression" index calculated in relation to the user, an anxiety index display item for displaying the anxiety index calculated in relation to the user, a detailed score view item for displaying additional detailed information in relation to the "free expression" index or the anxiety index, a relative evaluation display item for displaying information on oneself as evaluated by other users who performed the chat function together, a "my 'free expression' score aspect" display item for displaying the "free expression" score aspect, a "my anxiety score pattern" display item for displaying the user's anxiety score pattern, a "my confidence/assertiveness, mind control, communication skills/logic/persuasive power, immersion, empathy/listening skills score aspect" display item for displaying the user's confidence/assertiveness, mind control, communication skills/logic/persuasive power, immersion, empathy/listening skills score aspect, a "topic I have practiced a lot" display item for displaying a topic that the user has practiced a lot in relation to the topic talk, a "keyword that I have practiced a lot" display item for displaying keywords that the user has practiced a lot in relation to the topic talk, a "target I've practiced a lot" display item for displaying what the user has practiced a lot in relation to role-playing, a "situation I've practiced a lot" display item for displaying situations in which the user has practiced a lot in relation to role-playing, a "What emotions am I sensitive to?" display item for displaying what emotions the user is sensitive to in relation to role-playing, a "Which experts I have practiced with a lot?" display item for a displaying indicating with which experts the user has practiced a lot in relation to the theme, a "theme I practiced a lot" display item for displaying a theme that the user has practiced a lot in relation to theme practice, etc. Here, the "free expression" index display item includes an overall rating display item, a "free expression" index overall average display item, a satisfaction graph display item for overall average, a "free expression" index change graph display item by day of the week, a score display item for each item (e.g., including confidence/assertiveness, mind control, communication skills/logic/persuasive power, immersion, empathy/listening skills, etc.), a graph display item of a score change for each item by day of the week, an exponential distribution display item for each topic and situation, a detailed score view item, etc. In addition, the anxiety index display item includes a total rating display item, an anxiety index overall average display item, an anxiety graph display item for the overall average, a graph display item of an anxiety index change by day of the week, etc. In this case, the "free expression" index can be calculated by adding up the average score of the user's self-evaluation after performing the chat function in the chat room (e.g., including the topic talk chat room, the role-playing chat room, the theme practice chat room, etc.) in which the user participates, in relation to one or more chat rooms in which the user of the corresponding terminal 100 participates for a preset period or all chat rooms in which the user of the corresponding terminal 100 participates, and results (or evaluation received) (e.g., +1 for affirmative evaluation/satisfied, −1 for negative evaluation/not great) of evaluation of the user by the counterpart in the chat room in which the user participates. In addition, the anxiety index represents the average value of the anxiety self-evaluated by the user after performing the chat function in the chat room (e.g., including the topic talk chat room, the role-playing chat room, the theme practice chat room, etc.) in which the user participates in relation to one or more chat rooms in which the user of the corresponding terminal 100 participates for a preset period or all chat rooms in which the user of the corresponding terminal 100 participates. In addition, examples of the relative evaluation display item include the reason for receiving a good evaluation, the reason for receiving a bad evaluation, and the satisfaction of chat evaluated by others. In addition, examples of the "my 'free expression' score aspect" display item include a "How many people am I with when my free expression score gets high?" item, a "What age group of people am I talking with when I have a high score in 'free expression'?" item, a "What MBTI type am I talking with when I have a high score in 'free expression'?" item, a "What gender is the person I'm talking with when I have a high score in 'free expression'?" item, a "When I talk in a certain place, do I have a high score in free expression?" item, etc. In addition, the "my anxiety score aspect" display item includes a "How many people am I with when my anxiety score gets high?" item, a "What age group of people am I talking with when I have a high score in anxiety?" item, a "What MBTI type am I talking with when I have a high score in anxiety?" item, a "What gender is the person I'm talking with when I have a high score in anxiety?" item, a "When I talk in a certain place, do I have a high score in anxiety?" item, etc. In addition, examples of the "topic that I have practiced a lot" display item include an interpersonal relationship item, a daily life item, an employment/workplace item, a knowledge sharing item, a well-being item, other items, etc. In addition, examples of the "keyword that I have practiced a lot" display item include a boss item, a soccer item, a job preparation item, a presentation preparation item, a health item, other items, etc. In addition, examples of the "target that I have practiced a lot" display item include a husband item, a boss item, a coworker item, a chairman item, a stranger item, other items, etc. In addition, examples of the "situation that I have practiced a lot" display item include a rejection expression item, an affection expression item, an opinion expression item, a gratitude/sorry expression item, a conflict item, other items, etc. In addition, examples of the "What emotions am I sensitive to?" display item include a joy/pleasure item, an empathy item, an appreciation item, a sorry item, a grief/hurt item, an anger/annoyance/rage item, etc. In addition, examples of the "Which experts I have practiced with a lot?" display item include a psychological counselor item, a speech trainer item, a mentor item, etc. In addition, examples of the "theme that I practiced a lot" display item include a blind date item, a phone item, an interview item, a business report item, a small-scale presentation item, a large-scale presentation item, a professional discussion item, a pros and cons discussion item, etc.

In addition, when a preset detailed score view item is selected from the detailed information included in the content display area displayed on the expert terminal 300, the expert terminal 300 is linked with the server 200 to display detailed score information corresponding to the selected detailed score view item. Here, the detailed score information (or detailed score screen) includes the sort items for sorting functions related to all, topic talk, role-playing, theme practice, etc., the "number of times you've participated in the chat room" display item, the period display item for displaying the corresponding preset period, the "number of times you've participated in the chat room for each category" display item, the "free expression" index display item, the anxiety index display item, the relative evaluation display item, the "my 'free expression' score aspect" display item, the "my anxiety score aspect" display item, the "my confidence/assertiveness, mind control, communication skills/logic/persuasive power, immersion, empathy/listening skills score pattern" display item, the "topic I have practiced a lot" display item, the "keyword that I have practiced a lot" display item, the "target that I have practiced a lot" display item, the "situation that I have practiced a lot" display item, the "Which emotions I am sensitive to?" display item, the "Which experts have I practiced with a lot?" display item, the "theme which I have practiced a lot" display item, etc. In this case, when the detailed score view item related to the "free expression" index is selected, the expert terminal 300 may display one or more pieces of information related to the "free expression" index among the information included in the detailed score information, and when the detailed score view item related to the anxiety index is selected, the expert terminal 300 may mainly display one or more other pieces of information related to the anxiety index among the information included in the detailed score information.

That is, when a preset detailed score view item is selected from the detailed information included in the content display area displayed on the expert terminal 300, the expert terminal 300 is linked with the server 200 to display the detailed score information corresponding to the selected detailed score view item instead of the "free expression" index display item or anxiety index display item displayed previously.

In addition, when a preset period display item (or date selection item/calendar item) is selected from the chat report screen viewed by the expert (or the "my report" screen used by the expert) displayed on the expert terminal 300, the expert terminal 300 displays a calendar screen corresponding to the selected period. Here, the calendar screen includes the information on the presence or absence of chat records by date recorded by the user of the terminal 100 within the corresponding period (or corresponding month).

In addition, when the specific date within the calendar screen is selected, if a chat record exists on the corresponding specific date, the expert terminal 300 displays the detailed score information related to the chat record and if no chat record exists on the corresponding specific date, the expert terminal 300 displays the information indicating that no chat record exists.

In addition, when a preset participation list item is selected from the chat report screen for the expert (or a "my report" screen used by the expert) displayed on the expert terminal 300, to provide the participation list related to the conversation list in which the user of the terminal 100 participates, the expert terminal 300 displays the participation list screen corresponding to the selected participation list item. Here, the participation list screen includes a sort item for sorting functions related to all, topic talk, role-playing, theme practice, etc., a change information display item for providing information on changes in self-evaluation results or other's evaluation results compared to a preset period (or last week), a "number of times you've participated in the chat room" display item for displaying the number of times the user has participated in the chat room within a preset period, an information display item for each chat participation case for providing information related to topic talk, role-playing, theme practice, etc., in which the user participates, etc. In this case, the information display item for each chat participation includes a date information display item of participation in the chat room, a detail view item for displaying the detailed information, a chat room type (or chat room category) display item (e.g., including topic talk, role-playing, theme practice, etc.) for displaying the type of chat room in which the user participates, a chat room topic display item for displaying the topic of the chat room, a chat room name display item for displaying the room title (or chat room name) of the chat room, a keyword display item for displaying the main keywords/hashtags related to the corresponding chat room, a self-evaluation information display item for displaying the self-evaluation results, a received evaluation information display item for displaying the evaluation information received from other users participating in the corresponding chat room, a chat recording display item for the re-listening function of chat content from the chat room, etc.

In addition, when a specific participation list (or a detail view item displayed on one side of the corresponding specific participation list) is selected from one or more participation lists displayed in the information display items for each chat participation in the participation list screen displayed on the expert terminal 300, the expert terminal 300 is linked with the server 200 to display the detail view item information related to the selected specific participation list. Here, the detail view item information includes a date information display item of participation in the chat room corresponding to the selected specific participation list, a chat room type (or chat room category) display item for displaying the type of chat room (e.g., including a topic talk chat room, a role-playing chat room, a theme practice chat room, etc.) in which someone is participating, a chat room topic display item for displaying the topic of the chat room, a chat room name display item for displaying the room title of the chat room, a keyword display item for displaying main keywords/hashtags related to the chat room, a chat participant information display item for displaying information (e.g., including a nickname) of other users participating in the corresponding chat room, a self-evaluation result display item (or self-evaluation information display item) for displaying self-evaluation results, a received evaluation result display item (or a received evaluation information display item) for displaying evaluation results received from other users participating in the chat room, a chat recording display item for re-listening to chat content from the chat room.

Figure 64:
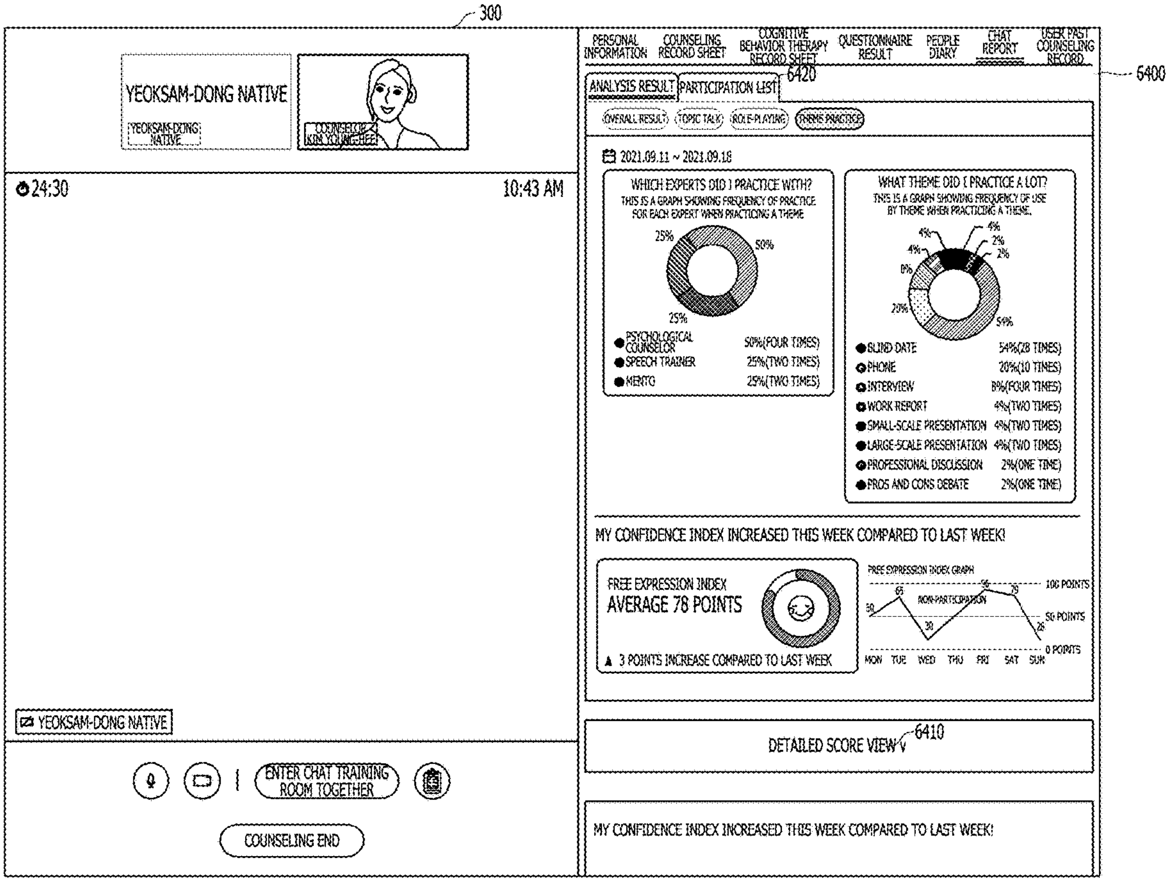

As an example, when a chat report item 4780 included in the detailed member information display area in the XR counseling room screen 4700 is selected according to the first expert selection while the counseling function between the first expert, Kim Young-Hee, and the user, the Yeoksam-dong native, is being performed through the generated XR counseling room screen 4700, as illustrated in FIG. 64, the first expert terminal displays a chat report screen seen by the expert 6400 including an analysis result screen corresponding to the analysis result item set as a default in response to the selected chat report item 4780.

Figure 65:
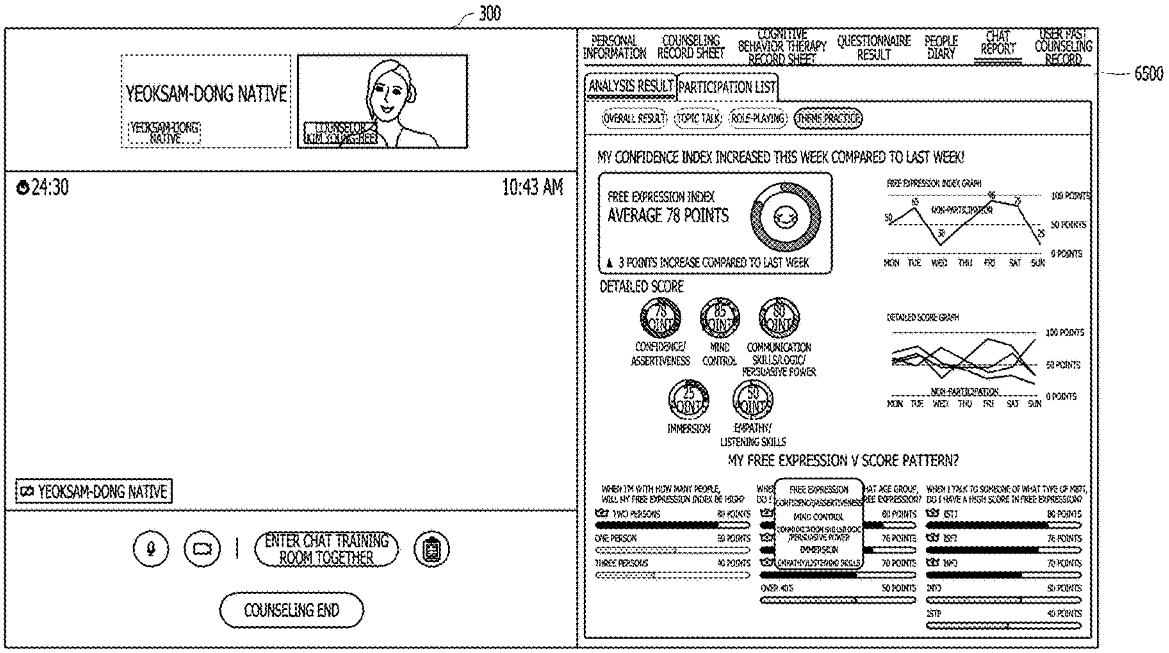

In addition, when a preset detailed score view item 6410 is selected from the chat report screen viewed by the expert 6400 and displayed on the first expert terminal, as illustrated in FIG. 65, the first expert terminal displays a detailed score screen (or a detailed score information screen) 6500 corresponding to the selected detailed score view item 6410 provided from the server 200.

Figure 66:
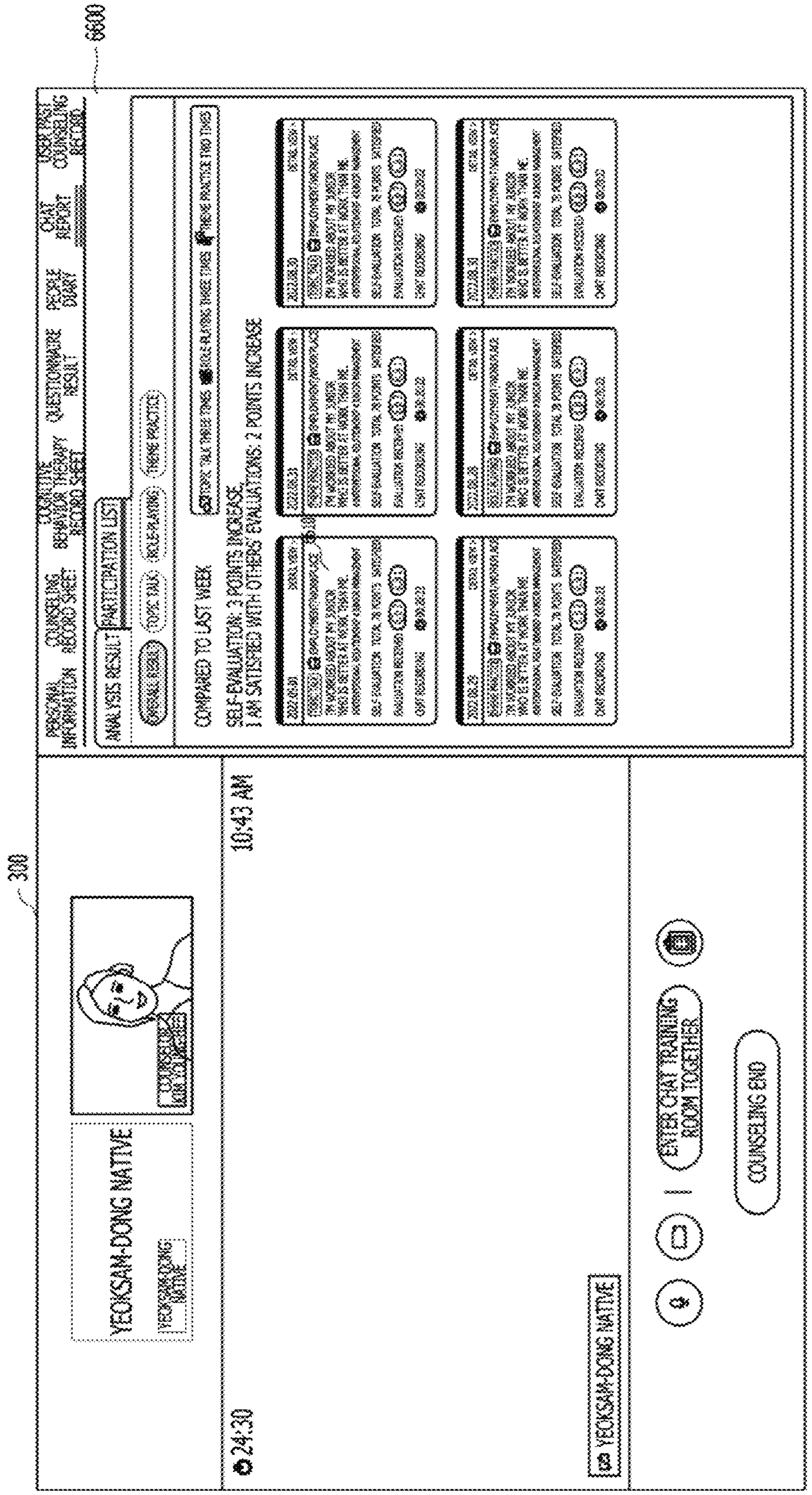

In addition, when a preset participation list item 6420 is selected from the chat report screen viewed by the expert 6400 and displayed on the first expert terminal, as illustrated in FIG. 66, the first expert terminal displays a participation list screen 6600 corresponding to the selected participation list item 6420.

Figure 67:
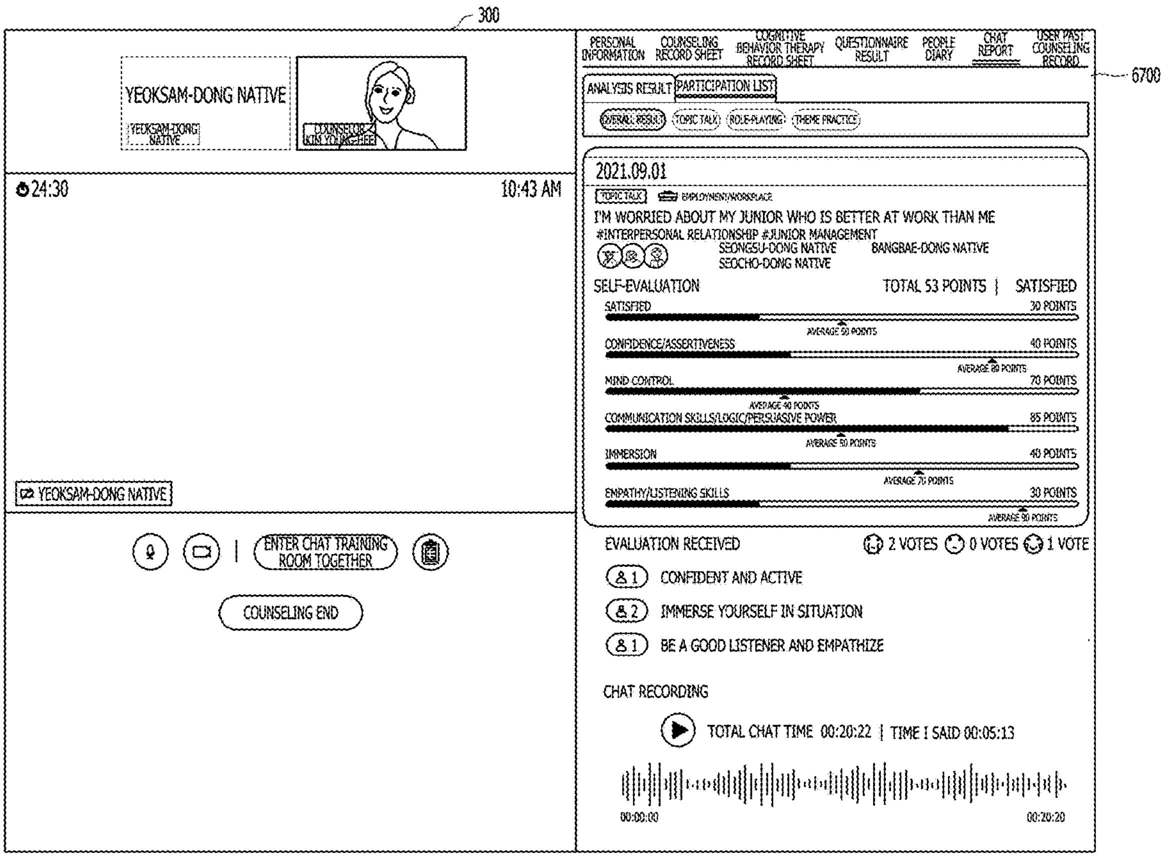

In addition, when a detail view item 6610 related to "I'm worried about my junior who is better at work than me," expressed on Sep. 1, 2021, in the participation list screen 6600 displayed on the first expert terminal is selected, as illustrated in FIG. 67, the first expert terminal displays detail view item information 6700 corresponding to the selected detail view item 6610 provided from the server 200 (S700).

In addition, when a past counseling record item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the detailed information related to the selected past counseling record item in the corresponding additional detailed information display area.

That is, when a past counseling record item included in the detailed member information display area in the corresponding XR counseling room screen is selected while the counseling function with the corresponding expert and the corresponding specific user is being performed through the XR counseling room screen displayed on the expert terminal 300, the expert terminal 300 is linked with the server 200 to display the past counseling record screen viewed by the expert corresponding to the selected past counseling record item in the corresponding additional detailed information display area. Here, the past counseling record screen viewed by the expert includes a participation list menu for providing the list of who has performed the psychological counseling function, the speech lesson function, or the mentoring function with the expert in relation to the specific topic or situation, a cognitive behavior therapy record menu for providing the cognitive behavior therapy record (or cognitive behavior therapy record sheet) written by the user according to the performance of the training function for the appropriate chat style in relation to the specific topic or situation, a content display area (or content display menu) for displaying the detailed information according to the selection of the participation list menu or the cognitive behavior therapy record menu, etc.

In addition, when a preset participation list menu (or other participation list menu) is selected from the past counseling record screen for the expert displayed on the expert terminal 300, to provide other participation lists in which the user of the terminal 100 performs a counseling function, a speech lesson function, a mentoring function, etc., with the expert of the expert terminal 300, the expert terminal 300 displays other participation list screens corresponding to the selected participation list menu in the content display area. Here, all the other participation list screens include another sorting item for sorting functions related to psychological counseling, speech, mentoring, etc., another sorting item for sorting functions related to most recent, highest score, lowest score, etc., other change information display items for providing information on changes in the number of counseling sessions, the number of times one has performed chat training with an expert, or a cognitive behavior therapy record compared to a preset period (or the last week), an item for displaying the number of times one has participated in other chat rooms for displaying the number of chat room participations within a preset period, an information display item for each expert chat participation case for providing information related to psychological counseling, speech, mentoring, etc., in which a user participates, etc. In this case, examples of the item for displaying the number of times one has participated in other chat rooms include an item for displaying the number of counseling sessions, an item for displaying the number of times one has performed chat training sessions with an expert, a cognitive behavior therapy record item, etc. In addition, examples of the information display item for each expert chat participation case include other chat room type (or chat room category) display items for displaying the type of chat room (e.g., including psychological counseling, speech, mentoring, etc.) in which one is participating, another chat room topic display item for displaying the topic of the chat room, a detail view item for displaying detailed information, an expert information display item for displaying an expert's photo and name, a counseling date display item for displaying a counseling date, other keyword display items for displaying main keywords/hashtags related to the corresponding chat room, an expert feedback item for providing expert feedback, a cognitive behavior therapy record sheet item for providing a cognitive behavior therapy record sheet, a written questionnaire item for providing questionnaire content written by a user, a chat room training display item for displaying chat room training content, etc. Here, when the psychological test result item included in the detailed member information display area in the corresponding XR counseling room screen is selected while the counseling function with the corresponding expert and the corresponding specific user is being performed through the XR counseling room screen displayed on the expert terminal 300, the expert terminal 300 may display other participation list screens corresponding to the participation list item preset by default in response to the selected past counseling record item in the additional detailed information display area by default.

Figure 68:
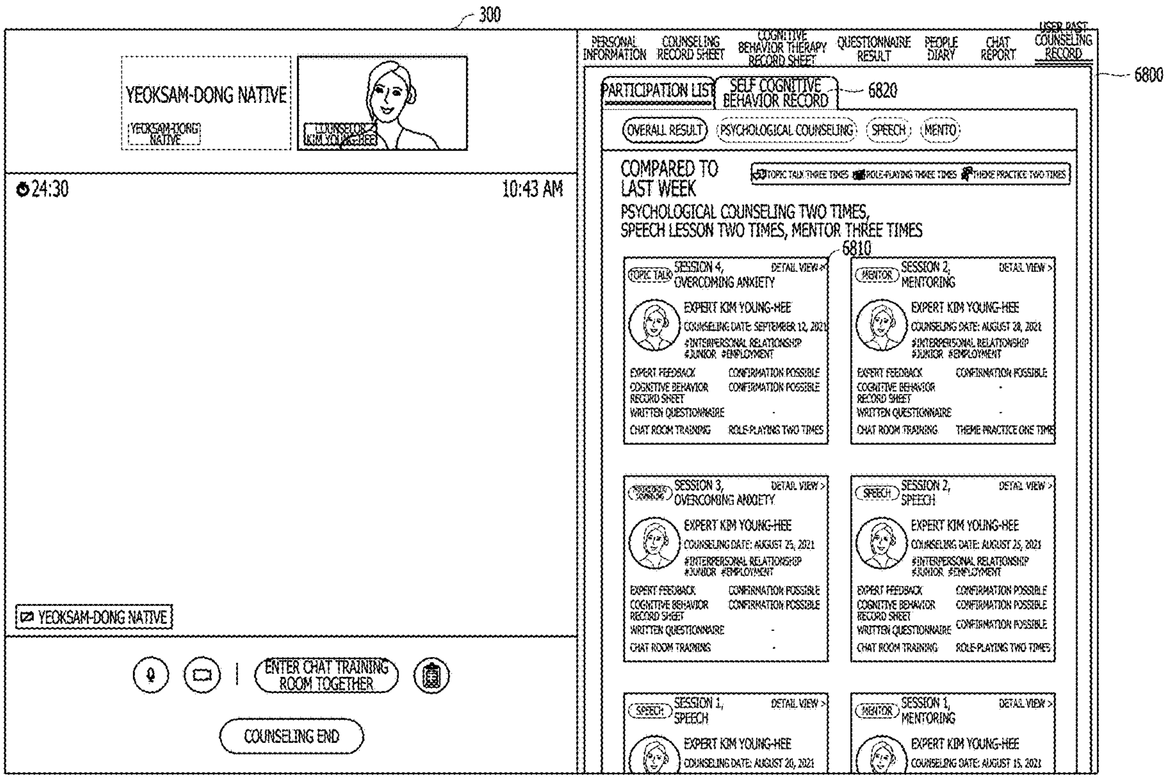

As an example, when a past counseling record item 4790 included in the detailed member information display area in the XR counseling room screen 4700 is selected according to the first expert selection while the counseling function between the first expert, Kim Young-Hee, and the user, the Yeoksam-dong native, is being performed through the generated XR counseling room screen 4700, as illustrated in FIG. 68, the first expert terminal displays other participation list screens 6800 corresponding to the participation list menu set as the default in response to the selected past counseling record item 4790 (S710).

Thereafter, when other specific participation lists (or detail view items displayed on one side of the corresponding other specific participation lists) are selected from one or more other participation lists being displayed in the information display items for each expert chat participation case in other participation list screens displayed on the expert terminal 300, the expert terminal 300 is linked with the server 200 to display the detailed information related to the selected other specific participation lists. Here, the detailed information (or detailed counseling result item screen) includes other chat room type (or chat room categories) display items for displaying the types of chat rooms (e.g., including psychological counseling, speech, mentoring, etc.) in relation to the other specific participation lists, other chat room topic display items for displaying the topic of the chat room, an expert information display item for displaying the expert's photo and name, a counseling date display item for displaying the counseling date, other keyword display items for displaying the main keywords/hashtags related to the corresponding chat room, an expert feedback display item for displaying the expert feedback, a cognitive behavior therapy record sheet item for providing the cognitive behavior therapy record sheet before and after training, a questionnaire item written during counseling for providing the type and results of the questionnaire written by the user, a chat room participation record display item for providing the chat room participation record, etc. In this case, examples of the questionnaire item written during counseling may include information on various types of tests (or questionnaires) such as a self-esteem self-diagnosis test, a communication type test, an anxiety test, etc. In addition, examples of the chat room participation record display item include a date information display item participating in the chat room, an expert state item for displaying whether the expert is participating in training or observing the expert, a chat room type (or chat room category) display item for displaying the type of a chat room (including, for example, a topic talk chat room, a role-playing chat room, a theme practice chat room, etc.) in which the user participates, a chat room topic display item for displaying the topic of the chat room, a chat room name display item for displaying the room title of the chat room, a chat participant information display item for displaying information (including, for example, nicknames) of other users participating in the corresponding chat room, a self-evaluation result display item (or self-evaluation information display item) for displaying the self-evaluation results, a received evaluation result display item (or received evaluation information display item) for displaying the evaluation results received from other users participating in the corresponding chat room, a chat recording display item for re-listening to the chat content from the chat room, etc.

Figure 69:
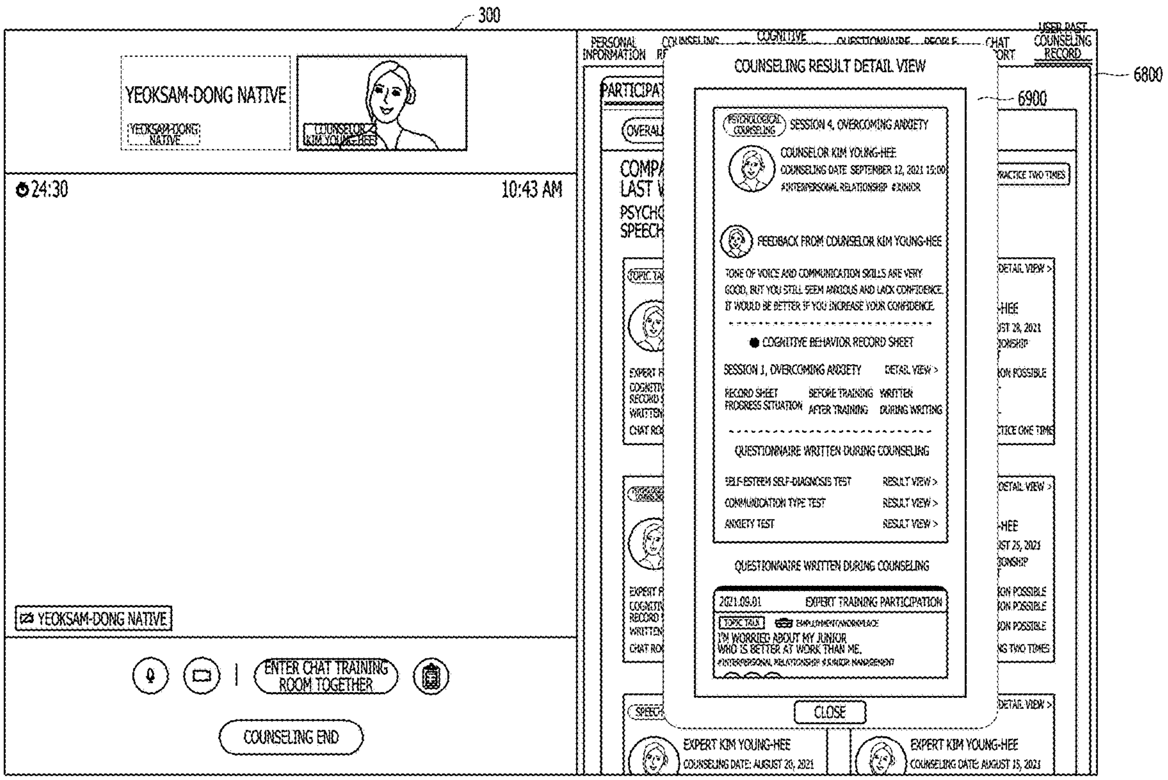

As an example, when a detail view item 6810 related to "session 4, overcoming anxiety" performed on Sep. 12, 2021, in the other participation list screens 6800 displayed on the first expert terminal is selected, as illustrated in FIG. 69, the first expert terminal displays detailed item information 6900 corresponding to the selected detail view item 6810 provided from the server 200 (S720).

In addition, when a preset cognitive behavior therapy record menu is selected from the past counseling record screen displayed on the expert terminal 300, to provide the information on the cognitive behavior therapy record sheet written by the user of the terminal 100 according to the user's performance of the training function for the appropriate chat style in relation to the specific topic or situation, the terminal 300 displays a cognitive behavior therapy record screen corresponding to the selected cognitive behavior therapy record menu. Here, the cognitive behavior therapy record screen (or cognitive behavior therapy record sheet screen) includes the cognitive behavior therapy record information display item for each chat participation case, etc., to provide the cognitive behavior therapy record (or cognitive behavior therapy record sheet) written before and after training in relation to the specific topic or situation in which the user of the terminal 100 participates. In addition, examples of the cognitive behavior therapy record information display item for each chat participation case include a cognitive behavior therapy record sheet title display item for displaying the title, a result view item for displaying the written cognitive behavior therapy record result, a record date display item for displaying the date when the cognitive behavior therapy record (or cognitive behavior therapy record sheet) was written, a record sheet progress situation display item for displaying the record sheet progress situation before/after training, a confirmed expert display item for displaying the expert who confirmed that the cognitive behavior therapy record sheet had been written by the user, etc.

Figure 70:
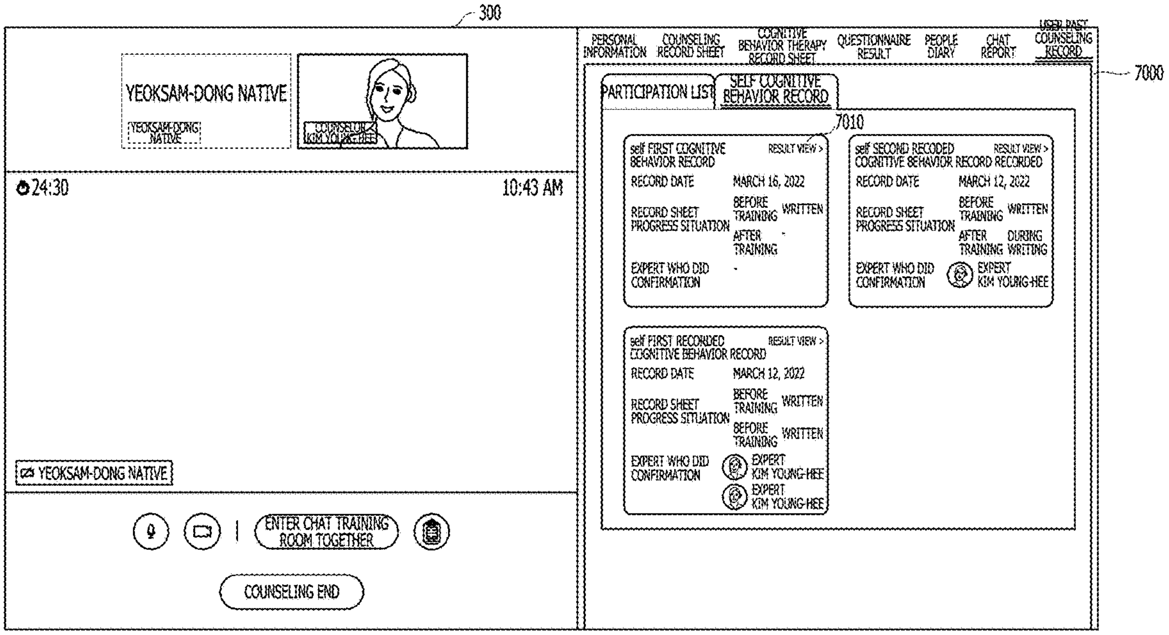

As an example, when a cognitive behavior therapy record menu 6820 is selected from the other participation list screens 6800 displayed on the first expert terminal, as illustrated in FIG. 70, the first expert terminal displays a cognitive behavior therapy record screen 7000 corresponding to the selected cognitive behavior therapy record menu 6820 (S730).

Thereafter, when the specific cognitive behavior therapy record is selected from one or more cognitive behavior therapy record cases being displayed in the cognitive behavior therapy record information display item for each chat participation in the cognitive behavior therapy record screen displayed on the expert terminal 300, the expert terminal 300 is linked with the server 200 to display other detailed information related to the selected specific cognitive behavior therapy record case. Here, the other detailed information (or cognitive behavior therapy record sheet/cognitive behavior therapy record sheet screen) includes a cognitive behavior therapy record sheet title display item to display the title, a last modified date display item, a writer ID and name display item, a writing state display item before and after training (e.g., not written, being written, written, etc.), a cognitive behavior information item for each item before training, a cognitive behavior information item for each item after training, etc. In addition, examples of the cognitive behavior information item for each item before training include an item for displaying "What are situations that make you anxious?" an item (e.g., anger/rage, irritation, disbelief, discomfort, disappointment, sadness/depression, anxiety, tiredness, fatigue, frustration, bitterness, compassion, jealousy, shame, embarrassment, despondence, outrage, panic, isolation, loneliness, boredom, etc.) for displaying "How are you feeling at this time?" an item (e.g., a confidence level, a cognitive error, etc.) for displaying "What are your thoughts in that situation?" an item (or reasonable response finding item) for "Please correct my wrong thoughts," a behavioral goal setting item, etc. In this case, the types of cognitive errors include black and white (or black and white logic), divination (or fortune teller/catastrophe), ignoring (or ignoring advantages), inference (or emotional inference), name (or naming), mind reading (or mind reading technique), filtering (or mental filtering), obsession (or obsessive burden), uselessness (or useless thoughts), etc. In addition, examples of the cognitive behavior information item for each item after training include an item for displaying (e.g., improvement-related item, anxiety-related item, etc.) "Please display any area that has improved slightly through training," an item for displaying "What actually happened related to an area I was worried about before training?" an item for displaying "Please re-evaluate your thoughts before training," an item (e.g., happiness, joy, vitality, confidence, courage, spirit, gratitude, appreciation, passion, inspiration, ecstasy, love, anger/rage, irritation, disbelief, displeasure, disappointment, sadness/depression, anxiety, tiredness, fatigue, frustration, etc.) for selecting how one feels now, an item for displaying "What did you learn?" etc. Here, the cognitive behavior information item for each item before the training and/or the cognitive behavior information item for each item after the training may be commonly preset or may be set differently for each expert.

Figure 71:
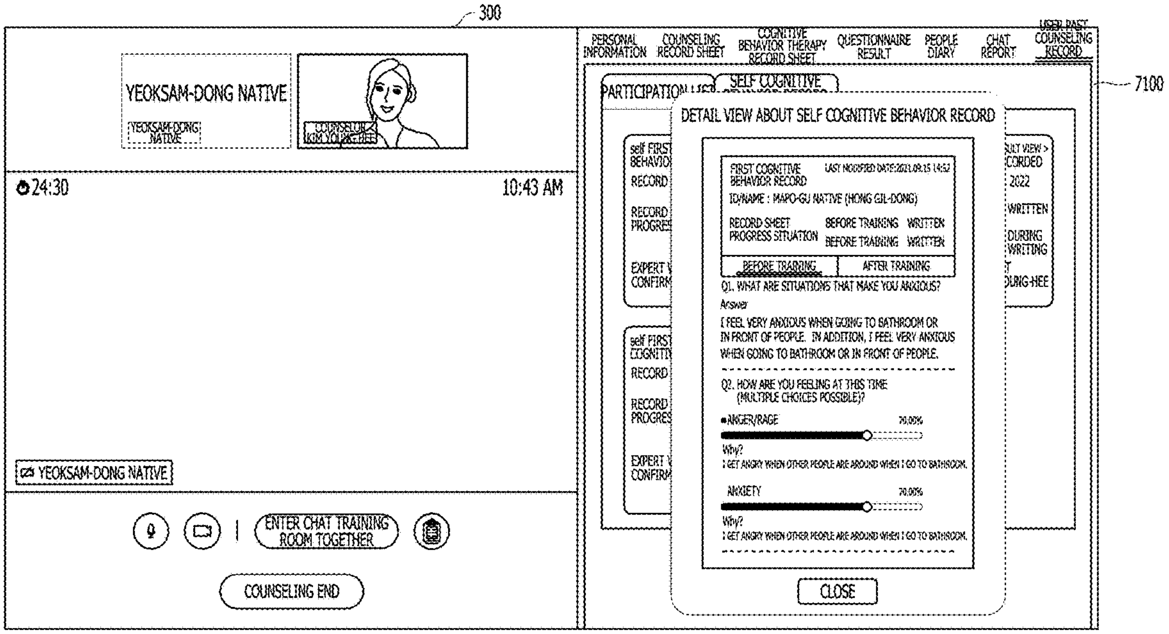

As an example, when a first cognitive behavior therapy record item 7010 is selected from the cognitive behavior therapy record screen 7000 displayed on the first expert terminal, as illustrated in FIG. 71, the first expert terminal displays a first cognitive behavior therapy record screen 7100 corresponding to the selected first cognitive behavior therapy record item 7010 (S740).

In addition, while other specific users are selected from the XR counseling room invitation client selection screen displayed on the expert terminal 300, when the corresponding other specific users are performing a chat function (e.g., including topic talk chatting, role-playing chatting, theme practice chatting, etc.) with another user, the expert terminal 300 is linked with the server 200 to enter (or participate in) the chat room in which the corresponding other specific users and another user who are performing the chat function in the spectator mode.

In addition, the expert terminal 300 (or an expert possessing the expert terminal 300) is linked with the server 200 to confirm (or monitor) the chat content shared between the corresponding other specific users and another user in the chat room who has entered in the spectator mode state. In this case, the expert terminal 300 may use artificial intelligence to check (or monitor/analyze) the chat content shared between the corresponding other specific users and another user in the chat room in the spectator mode state in which it has entered. Here, the spectator mode may perform only the function of confirming chat content between users participating in the corresponding chat room, and may not perform the chat function with the users participating in the corresponding chat room.

In this case, the expert terminal 300 displays the chat room in the spectator mode state related to the user of the terminal 100 on one side of the screen of the corresponding expert terminal 300, and to perform the counseling function with the expert in the XR, the expert terminal 300 is linked with the server 200 and the terminal 100 owned by the corresponding other selected specific users on the other side of the screen of the expert terminal 300 to display the XR counseling room screen.

That is, the expert terminal 300 uses a screen split function to display the chat room in the spectator mode state on one side and display the XR counseling room screen for performing the counseling function with the terminal 100 on the other side.

In this way, the expert terminal 300 can not only perform counseling within the XR counseling room through the exposure training during the cognitive behavior therapy performed on users with social anxiety, but also perform 1:1 training in a specific situation (e.g., role-playing, theme practice, etc.) with an expert, and also provides group therapy in which an expert may conduct counseling while simultaneously confirming the user's state, actions, and activities in a situation where the user is talking to other users.

As an example, while a Nowon-gu native 4620 is selected from the XR counseling room invitation client selection screen 4600 displayed on the first expert terminal, when the fourth user corresponding to the Nowon-gu native is performing the chat function with the fifth user in the eleventh topic talk chat room, the first expert terminal is linked with the server 200 to enter the eleventh topic talk chat room in which the fourth and fifth users are performing the chat function in the spectator mode.

Figure 72:
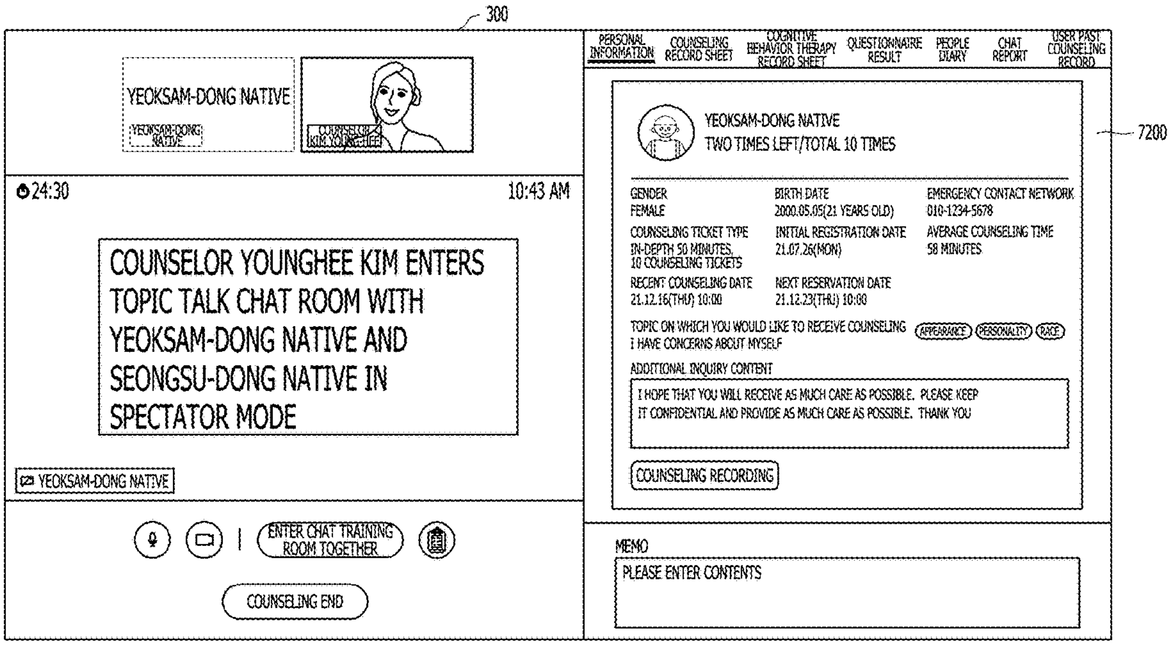

In addition, as illustrated in FIG. 72, to perform the counseling function with the expert in the XR, the first expert terminal is linked with the server 200 and the fourth terminal 100 owned by the fourth user to display an XR counseling room screen 7200 (S750).

Thereafter, while the corresponding other specific users are performing the chat function with another user or after the chat function ends, the expert terminal 300 is linked with the server 200 to transmit the customized advice information, the analysis information, etc., related to the corresponding other specific users according to the expert input of the corresponding expert terminal 300 to the terminal 100 owned by the other specific users.

In addition, the terminal 100 receives the customized advice information, the analysis information, etc., related to the corresponding other specific users transmitted from the expert terminal 300 via the server 200, and displays (or outputs) the received customized advice information, analysis information, etc., related to the corresponding other specific users. In this case, when the other specific users are performing the chat function with another user, the expert terminal 300 may be linked with the server 200 and the terminal 100 to display the customized advice information, the analysis information, etc., related to the corresponding other specific users in real time through the created XR counseling room screen.

As an example, while the corresponding fourth user is performing the chat function with the fifth user in real time, the first expert terminal displays first advice information related to the fourth user on the XR counseling room screen through the chat function (S760).

According to the present invention, as described above, when the preset XR room-creation menu is selected from the website screen, the expert of the expert terminal performs the psychological counseling function in the metaverse chat room with the specific user under management, and the user of the terminal and the expert of the expert terminal may participate in another metaverse chat room together while the counseling function is performed to perform the chat function, so that the expert may perform the psychological counseling function with the user in real-time and accordingly identify the user's psychological state and provide the appropriate coping measures, and may accurately identify the user's state as the user performs the chat function with another user in the metaverse chat room.

In addition, according to the present invention, as described above, by providing the user-related questionnaire or counseling record sheet while the user of the terminal and the expert of the expert terminal perform the counseling function through the metaverse chat room, it is possible for the expert to perform the psychological counseling function with the user in real time, identify the user's psychological state and provide the appropriate coping measures, and specifically confirm the user's state through the questionnaire or counseling record sheet.

In addition, according to the present invention, as described above, by providing the user-related cognitive behavior therapy record sheet while the user of the terminal and the expert of the expert terminal perform the counseling function through the metaverse chat room, it is possible for the expert to perform the psychological counseling function with the user in real time, identify the user's psychological state and provide the appropriate coping measures, and specifically confirm the user's state through the cognitive behavior therapy record sheet.

In addition, according to the present invention, as described above, by providing the user-related chat report or people diary while the user of the terminal and the expert of the expert terminal perform the counseling function through the metaverse chat room, it is possible for the expert to perform the psychological counseling function with the user in real time, identify the user's psychological state and provide the appropriate coping measures, and comprehensively confirm the user's state by considering the user-related data together.

In addition, according to the present invention, as described above, by providing the user-related past counseling record while the user of the terminal and the expert of the expert terminal perform the counseling function through the metaverse chat room, it is possible for the expert to perform the psychological counseling function with the user in real time, identify the user's psychological state and provide the appropriate coping measures, and comprehensively confirm the user's state by considering the user's past counseling record data together.

In addition, according to the present invention, as described above, when a preset people diary menu is selected from the website screen, the expert of the expert terminal confirms the information on the emotional state by date recorded by the specific user in a diary format in relation to the specific user under management, so it is possible for the expert to conveniently confirm the change in the user's emotional state by date.

In addition, according to the present invention, as described above, when a preset chat report menu is selected from the website screen, the expert of the expert terminal provides the "free expression" index, the anxiety index, etc., corresponding to the comprehensive psychological state of the specific user in relation to the specific user under management, so it is possible for the expert to conveniently confirm the information on the user's psychological state.

In addition, according to the present invention, as described above, when the preset XR room-creation menu is selected from the website screen, the expert of the expert terminal performs the psychological counseling function in the XR room with the specific user under management to perform the psychological counseling function with the user in real time, so it is possible to identify the user's psychological state and provide the appropriate coping measures.

The above-described content may be variously modified and altered by those skilled in the art to which the present invention pertains without departing from the essential features of the present invention. Accordingly, exemplary embodiments disclosed in the present invention are not to limit the spirit of the present invention, but are to describe the spirit of the present invention. The scope of the present invention is not limited to these exemplary embodiments. The scope of the present invention should be interpreted by the following claims and it should be interpreted that all spirits equivalent to the following claims fall within the scope of the present invention.

[Modes of the Invention]

Modes for carrying out the invention have been described together in the best mode for carrying out the present invention described above.

INDUSTRIAL APPLICABILITY

The present invention has industrial applicability in that, when a preset extended reality (XR) room-creation menu is selected from a website screen, an expert of an expert terminal performs a psychological counseling function in a metaverse chat room with a specific user under management and a user of a terminal and the expert of the expert terminal participate in another metaverse chat room together while performing a counseling function to perform a chat function, so that it is possible for the expert to perform a psychological counseling function with the user in real time, identify a user's psychological state and provide appropriate coping measures, and accurately identify a user's state as the user performs the chat function with other users in the metaverse chat room.

The invention claimed is:

1. A system for providing psychological counseling, comprising:

when a preset extended reality (XR) room-creation menu is selected from an initial screen displayed on an expert terminal, a server providing an XR counseling room invitation client selection screen corresponding to the selected XR room-creation menu to the expert terminal; and the expert terminal that is linked with the server and a terminal owned by a selected specific user to display an XR counseling room screen when the XR counseling room invitation client selection screen is displayed and the specific user is selected from the displayed XR counseling room invitation client selection screen, selects a specific metaverse chat room when an entry item with a chat training room displayed on one side of the XR counseling room screen is selected while a counseling function with an expert of the expert terminal and the specific user is performed through the XR counseling room screen displayed on the expert terminal, displays an expert's position selection screen to select whether the expert enters as a spectator or as chatter, and when a spectator item or a chatter item is selected from the expert's position selection screen displayed on the expert terminal according to the expert's selection, enters the metaverse chat room as a spectator corresponding to the selected spectator item or as chatter corresponding to the selected chatter item.

2. The system for providing psychological counseling of claim 1, wherein the XR counseling room screen includes a counseling screen area for displaying a counseling function performance state with the specific user of the terminal and a detailed member information display area for displaying detailed information on the specific user, the counseling screen area includes at least one of a video information display area for displaying video information related to the expert and the specific user, a counseling time display item for displaying a counseling time, a current time display item for displaying a current time, a microphone item for setting whether to output voice, a video item for setting whether to output the video information, the entry item with a chat training room for a counselor and the specific user to enter a new metaverse chat room related to a specific theme to perform a chat function, a questionnaire writing request item for requesting the specific user in counseling to fill out a questionnaire, a file item for sharing a file during the counseling, and a counseling end item for ending the counseling function, and the detailed member information display area includes at least one of a personal information item for displaying personal information on the specific user in counseling, a counseling record sheet item for displaying a counseling record sheet related to one or more counseling sessions performed by the specific user in counseling, a cognitive behavior therapy record sheet item for displaying a cognitive behavior therapy record sheet related to one or more counseling sessions performed by the specific user in counseling, a questionnaire result item for displaying a questionnaire result related to the questionnaire performed by the specific user in counseling, a people diary item for displaying an emotional state written by the specific user by date, a chat report item for displaying a chat report related to the specific user, a past counseling record item for displaying past counseling record performed by the specific user, and an additional detailed information display area for providing detailed information on a specific item selected from a plurality of items.

3. The system for providing psychological counseling of claim 1, wherein, when a room leader who opens the metaverse chat room selects a preset start menu while the number of people set in the metaverse chat room is satisfied, the expert terminal is the spectator or the chatter and is linked with the terminal, one or more other terminals owned by each of one or more other users who entered the metaverse chat room, and the server to perform or monitor a chat function related to a specific topic in the metaverse chat room, generate feedback information related to the specific user when the chat function in the metaverse chat room ends, and provide the generated feedback information to the terminal through the server.

4. A method of providing psychological counseling, comprising:

when a preset extended reality (XR) room-creation menu is selected from an initial screen displayed on an expert terminal, displaying, by the expert terminal linked with a server, an XR counseling room invitation client selection screen corresponding to the selected XR room-creation menu to select a client to be invited to the XR counseling room;

when a specific user is selected from the XR counseling room invitation client selection screen displayed on the expert terminal, displaying, by the expert terminal linked with the server and a terminal owned by the selected specific user, an XR counseling room screen;

while a counseling function with an expert of the expert terminal and the specific user is performed through the XR counseling room screen displayed on the expert terminal, to perform a monitoring function for the specific user through a chat function by participating in a metaverse chat room related to a specific theme, selecting, by the expert terminal, a specific metaverse chat room when an entry item with a chat training room displayed on one side of the XR counseling room screen is selected;

displaying, by the expert terminal, an expert's position selection screen for selecting whether the expert enters as a spectator or as a chatter; and when a spectator item or a chatter item is selected from the expert's position selection screen displayed on the expert terminal according to the expert's selection, entering, by the expert terminal linked with the server, the metaverse chat room as a spectator corresponding to the selected spectator item or as chatter corresponding to the selected chatter item.

5. The method of claim 4, wherein the selecting of the specific metaverse chat room includes any one of:

creating, by the expert terminal, a new metaverse chat room and selecting the created new metaverse chat room as the specific metaverse chat room; and selecting a specific metaverse chat room as the specific metaverse chat room according to the expert selection from one or more pre-created metaverse chat rooms.

6. The method of claim 4, wherein, in the entering of the metaverse chat room as the spectator corresponding to the selected spectator item or as the chatter corresponding to the selected chatter item, when the spectator item is selected from the expert's position selection screen displayed on the expert terminal according to the expert's selection, the expert terminal is linked with the server to enter the metaverse chat room as the spectator corresponding to the selected spectator item.

7. The method of claim 6, wherein, in the entering of the metaverse chat room as the spectator corresponding to the selected spectator item or as the chatter corresponding to the selected chatter item, when entering the metaverse chat room as the spectator from the expert terminal, an image or an emoticon indicating that the expert of the expert terminal is participating as the spectator is displayed on one side of the screen of the expert terminal and the terminal related to the specific user entering the metaverse chat room together.

8. The method of claim 4, wherein, in the entering of the metaverse chat room as the spectator corresponding to the selected spectator item or as the chatter corresponding to the selected chatter item, when the chatter item is selected from the expert's position selection screen displayed on the expert terminal according to the expert's selection, the expert terminal is linked with the server to enter the metaverse chat room as the spectator corresponding to the selected chatter item.

9. The method of claim 4, wherein, in the entering of the metaverse chat room as the spectator corresponding to the selected spectator item or as the chatter corresponding to the selected chatter item, the terminal corresponding to the specific user in counseling is also linked with the server to enter the metaverse chat room together with the expert terminal as the chatter.

10. The method of claim 4, further comprising:

when a room leader who opens the metaverse chat room selects a preset start menu while the number of people set in the metaverse chat room is satisfied, performing or monitoring, by the expert as the spectator or the chatter linked with the terminal, one or more other terminals owned by each of one or more other users who entered the metaverse chat room, and the server, a chat function related to a specific topic of the metaverse chat room;

when the chat function in the metaverse chat room ends, generating, by the expert terminal, feedback information related to the specific user; and providing, by the expert terminal, the generated feedback information to the terminal through the server.

* * * * *